US012797470B2

(12) United States Patent
Drummond et al.

(10) Patent No.: US 12,797,470 B2
(45) Date of Patent: *Nov. 17, 2026

(54) IONIZABLE LIPIDS AND LIPOSOMAL NANOPARTICLE COMPOSITIONS

(71) Applicant: Akagera Medicines, Inc., Waltham, MA (US)

(72) Inventors: Daryl C. Drummond, Lincoln, MA (US); Dmitri Kirpotin, San Francisco, CA (US); Mark E. Hayes, Mill Valley, CA (US); Ross Fulton, Southborough, MA (US); Alexander Koshkaryev, Norwood, MA (US)

(73) Assignee: Akagera Medicines, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/573,533

(22) Filed: Mar. 20, 2026

(65) Prior Publication Data

US 2026/0283973 A1 Sep. 24, 2026

Related U.S. Application Data

(60) Provisional application No. 64/007,071, filed on Mar. 16, 2026, provisional application No. 63/944,616, filed on Dec. 19, 2025, provisional application No. 63/869,090, filed on Aug. 22, 2025, provisional application No. 63/775,688, filed on Mar. 21, 2025.

(51) Int. Cl.
*A61K 9/51* (2006.01)
*A61K 31/7105* (2006.01)

(52) U.S. Cl.
CPC ........ *A61K 9/5123* (2013.01); *A61K 31/7105* (2013.01)

(58) Field of Classification Search
None
See application file for complete search history.

(56) References Cited

U.S. PATENT DOCUMENTS

| | | | |
|---|---|---|---|
| 4,394,448 | A | 7/1983 | Szoka, Jr. et al. |
| 4,438,052 | A | 3/1984 | Weder et al. |
| 4,515,736 | A | 5/1985 | Deamer |
| 4,598,051 | A | 7/1986 | Papahadjopoulos et al. |
| 4,897,355 | A | 1/1990 | Eppstein et al. |
| 5,013,556 | A | 5/1991 | Woodle et al. |
| 5,171,678 | A | 12/1992 | Behr et al. |
| 5,208,036 | A | 5/1993 | Eppstein et al. |
| 5,225,212 | A | 7/1993 | Martin et al. |
| 5,264,618 | A | 11/1993 | Feigner et al. |
| 5,279,833 | A | 1/1994 | Rose |
| 5,283,185 | A | 2/1994 | Epand et al. |
| 5,316,771 | A | 5/1994 | Barenholz et al. |
| 5,320,906 | A | 6/1994 | Eley et al. |
| 5,334,761 | A | 8/1994 | Gebeyehu et al. |
| 5,434,183 | A | 7/1995 | Larsson-Backstrom |
| 5,545,412 | A | 8/1996 | Eppstein et al. |
| 5,578,475 | A | 11/1996 | Jessee |
| 5,627,159 | A | 5/1997 | Shih et al. |
| 5,641,662 | A | 6/1997 | Debs et al. |
| 5,656,743 | A | 8/1997 | Busch et al. |
| 5,674,908 | A | 10/1997 | Haces et al. |
| 5,703,055 | A | 12/1997 | Feigner et al. |
| 5,705,385 | A | 1/1998 | Bally et al. |
| 5,736,392 | A | 4/1998 | Hawley-Nelson et al. |
| 5,800,833 | A | 9/1998 | Hope et al. |
| 5,820,873 | A | 10/1998 | Choi et al. |
| 5,877,220 | A | 3/1999 | Schwartz et al. |
| 5,885,613 | A | 3/1999 | Holland et al. |
| 5,958,901 | A | 9/1999 | Dwyer et al. |
| 5,976,567 | A | 11/1999 | Wheeler et al. |
| 5,981,501 | A | 11/1999 | Wheeler et al. |
| 6,020,202 | A | 2/2000 | Jessee |
| 6,020,526 | A | 2/2000 | Schwartz et al. |
| 6,034,135 | A | 3/2000 | Schwartz et al. |
| 6,051,429 | A | 4/2000 | Hawley-Nelson et al. |
| 6,075,012 | A | 6/2000 | Gebeyehu et al. |

(Continued)

FOREIGN PATENT DOCUMENTS

| | | |
|---|---|---|
| CA | 2 271 582 | 11/1989 |
| CA | 2 309 727 | 4/1999 |

(Continued)

OTHER PUBLICATIONS

Akinc et al., "Development of Lipidoid—siRNA Formulations for Systemic Delivery to the Liver" Molecular Therapy, vol. 17, No. 5, pp. 872-879, May 2009.

(Continued)

*Primary Examiner* — Bethany P Barham
*Assistant Examiner* — Judith Marie Kamm
(74) *Attorney, Agent, or Firm* — Greenberg Traurig, LLP; David J. Dykeman; Natalie Salem

(57) ABSTRACT

Aspects of the present disclosure provide for improved compositions of bioreducible and/or hydrolysable ionizable lipid compounds, useful in the preparation of lipid nanoparticles (LNP) for the delivery of therapeutic nucleic acids and other compounds to cells. Anionic phospholipids, including a phosphatidyl-L-serine (PS) or a phosphatidylglycerol (PG) can be included in the lipid nanoparticles to increase the transfection efficiency in human dendritic cells. In some examples, the LNP compositions are vaccine compositions comprising mRNA encapsulated in lipid nanoparticles formed from an ionizable cationic lipid compound, cholesterol, an anionic phospholipid and a PEG conjugated lipid.

21 Claims, 57 Drawing Sheets

Specification includes a Sequence Listing.

(56) References Cited

U.S. PATENT DOCUMENTS 6,110,491 A 8/2000 Kirpotin
6,165,501 A 12/2000 Tirosh et al.
6,172,049 B1 1/2001 Dwyer et al.
6,251,939 B1 6/2001 Schwartz et al.
6,284,267 B1 9/2001 Aneja
6,287,591 B1 9/2001 Semple et al.
6,339,173 B1 1/2002 Schwartz et al.
6,376,248 B1 4/2002 Hawley-Nelson et al.
6,534,484 B1 3/2003 Wheeler et al.
6,586,410 B1 7/2003 Wheeler et al.
6,638,529 B2 10/2003 Schwartz et al.
6,649,780 B1 11/2003 Eibl et al.
6,671,393 B2 12/2003 Hays et al.
6,689,779 B2 2/2004 Lee et al.
6,696,424 B1 2/2004 Wheeler
6,815,432 B2 11/2004 Wheeler et al.
6,858,224 B2 2/2005 Wheeler et al.
7,074,596 B2 7/2006 Darzynkiewicz
7,166,745 B1 1/2007 Chu et al.
7,422,902 B1 9/2008 Wheeler et al.
7,462,615 B2 12/2008 Guedat et al.
7,479,573 B2 1/2009 Chu et al.
7,601,872 B2 10/2009 Chu et al.
7,687,070 B2 3/2010 Gebeyehu et al.
7,744,921 B2 6/2010 Tardi et al.
7,745,651 B2 6/2010 Heyes et al.
7,799,565 B2 9/2010 Maclachlan et al.
7,803,397 B2 9/2010 Heyes et al.
7,807,815 B2 10/2010 Maclachlan et al.
7,816,379 B2 10/2010 Rhee et al.
7,838,658 B2 11/2010 Maclachlan et al.
7,901,708 B2 3/2011 Maclachlan et al.
7,915,450 B2 3/2011 Chu et al.
7,982,027 B2 7/2011 Maclachlan et al.
8,021,686 B2 9/2011 Semple et al.
8,058,068 B2 11/2011 Hawley-Nelson et al.
8,058,069 B2 11/2011 Yaworski et al.
8,101,741 B2 1/2012 Maclachlan et al.
8,147,867 B2 4/2012 Hong et al.
8,158,827 B2 4/2012 Chu et al.
8,188,263 B2 5/2012 Maclachlan et al.
8,227,443 B2 7/2012 Maclachlan et al.
8,278,036 B2 10/2012 Kariko et al.
8,283,333 B2 10/2012 Yaworski et al.
8,349,360 B2 1/2013 Bally et al.
8,455,455 B1 6/2013 Robbins et al.
8,492,359 B2 7/2013 Yaworski et al.
8,513,403 B2 8/2013 Maclachlan et al.
8,569,256 B2 10/2013 Heyes et al.
8,598,333 B2 12/2013 Maclachlan et al.
8,822,668 B2 9/2014 Yaworski et al.
9,061,063 B2 6/2015 Maier et al.
9,139,554 B2 9/2015 Hope et al.
9,220,683 B2 12/2015 Manoharan et al.
9,364,435 B2 6/2016 Yaworski et al.
9,404,127 B2 8/2016 Yaworski et al.
9,504,651 B2 11/2016 MacLachlan et al.
9,549,939 B2 1/2017 Weers
9,657,295 B2 5/2017 Schrum et al.
9,764,036 B2 9/2017 Manoharan et al.
10,072,057 B2 9/2018 Hoge et al.
10,221,127 B2 3/2019 Du et al.
10,369,226 B2 8/2019 Maier et al.
10,632,191 B2 4/2020 Reed et al.
10,653,780 B2 5/2020 Hope et al.
11,071,784 B2 7/2021 Maier et al.
11,141,378 B2 10/2021 Yaworski et al.
11,246,933 B1 2/2022 Maier et al.
11,590,229 B2 2/2023 Maier et al.
11,591,544 B2 2/2023 Drummond et al.
11,633,479 B2 4/2023 Maier et al.
11,633,480 B2 4/2023 Maier et al.
12,064,479 B2 8/2024 Drummond et al.
12,077,725 B2 9/2024 Drummond et al.
12,331,264 B2 6/2025 Drummond et al.
12,606,773 B2 4/2026 Drummond et al.
2001/0048940 A1 12/2001 Tousignant et al.
2003/0069173 A1 4/2003 Hawley-Nelson et al.
2003/0072794 A1 4/2003 Boulikas
2003/0077829 A1 4/2003 Maclachlan
2003/0143732 A1 7/2003 Fosnaugh et al.
2004/0009126 A1 1/2004 Pilkiewicz et al.
2004/0063654 A1 4/2004 Davis et al.
2004/0142892 A1 7/2004 Finn et al.
2004/0253723 A1 12/2004 Tachas et al.
2004/0258651 A1 12/2004 Pascaly et al.
2004/0258652 A1 12/2004 Pascaly et al.
2004/0259247 A1 12/2004 Tuschl et al.
2005/0000030 A1 1/2005 Dupont et al.
2005/0064595 A1 3/2005 Maclachlan et al.
2005/0118253 A1 6/2005 Maclachlan et al.
2005/0187218 A1 8/2005 Marinier et al.
2005/0260757 A1 11/2005 Gebeyehu et al.
2006/0008519 A1 1/2006 Davidsen et al.
2006/0008910 A1 1/2006 Maclachlan et al.
2006/0083780 A1 4/2006 Heyes et al.
2006/0147514 A1 7/2006 Gebeyehu et al.
2006/0228406 A1 10/2006 Chiou et al.
2006/0240093 A1 10/2006 Maclachlan et al.
2007/0042031 A1 2/2007 Maclachlan et al.
2007/0148220 A1 6/2007 Muller et al.
2007/0202598 A1 8/2007 Chu et al.
2007/0202600 A1 8/2007 Chu et al.
2008/0021071 A1 1/2008 Gravestock et al.
2008/0214849 A1 9/2008 Hansjorg et al.
2009/0023729 A1 1/2009 Nakamura et al.
2009/0117153 A1 5/2009 Hansen et al.
2009/0143583 A1 6/2009 Chu et al.
2009/0291131 A1 11/2009 Maclachlan et al.
2010/0130588 A1 5/2010 Yaworski et al.
2010/0159593 A1 6/2010 Chu et al.
2010/0192814 A1 8/2010 Herzog et al.
2011/0060032 A1 3/2011 MacLachlan et al.
2011/0262527 A1 10/2011 Heyes et al.
2012/0058188 A1 3/2012 Maclachlan et al.
2012/0095075 A1 4/2012 Manoharan et al.
2012/0136073 A1 5/2012 Zhiwei et al.
2012/0183581 A1 7/2012 Yaworski et al.
2012/0238747 A1 9/2012 Chu et al.
2012/0276209 A1 11/2012 Cullis et al.
2014/0065228 A1 3/2014 Yaworski et al.
2016/0106842 A1 4/2016 Baryza et al.
2016/0317676 A1 11/2016 Hope et al.
2018/0064807 A1 3/2018 Manoharan et al.
2018/0125985 A1 5/2018 Manoharan
2018/0170866 A1 6/2018 Payne et al.
2018/0353434 A1 12/2018 Hatanaka et al.
2018/0369143 A1 12/2018 Bally et al.
2019/0083593 A1 3/2019 Sahin et al.
2019/0262448 A1 8/2019 Brito et al.
2019/0380963 A1 12/2019 Chen et al.
2020/0078345 A1 3/2020 Rhee et al.
2020/0121809 A1 4/2020 Hope et al.
2020/0206362 A1 7/2020 Besin et al.
2020/0254086 A1 8/2020 Hoge et al.
2020/0282060 A1 9/2020 Heyes et al.
2020/0289638 A1 9/2020 Ciaramella et al.
2021/0290756 A1 9/2021 Sullivan et al.
2021/0323914 A1 10/2021 Payne et al.
2022/0105187 A1 4/2022 Maier et al.
2022/0111053 A1 4/2022 Maier et al.
2022/0162521 A1 5/2022 Drummond et al.
2022/0175928 A1 6/2022 Maier et al.
2022/0175929 A1 6/2022 Maier et al.
2022/0175930 A1 6/2022 Maier et al.
2022/0218622 A1 7/2022 Bushmann et al.
2022/0370624 A1 11/2022 Rajappan et al.
2022/0389422 A1 12/2022 Rajappan et al.
2022/0411394 A1 12/2022 Drummond et al.
2023/0081530 A1 3/2023 Frederick et al.
2023/0126953 A1 4/2023 Drummond et al.
2023/0256098 A1 8/2023 Maier et al.
2023/0381303 A1 11/2023 Drummond et al.
2024/0309291 A1 9/2024 Drummond et al.

(56) References Cited

U.S. PATENT DOCUMENTS

| | | | |
|---|---|---|---|
| 2024/0325525 A1 | 10/2024 | Drummond et al. |
| 2024/0343701 A1 | 10/2024 | Cen et al. |
| 2026/0055335 A1 | 2/2026 | Drummond et al. |
| 2026/0069684 A1 | 3/2026 | Drummond et al. |
| 2026/0077038 A1 | 3/2026 | Drummond et al. |
| 2026/0125614 A1 | 5/2026 | Drummond et al. |

FOREIGN PATENT DOCUMENTS

| | | |
|---|---|---|
| CA | 2 330 741 | 11/1999 |
| CA | 2 397 016 | 7/2001 |
| CN | 110974954 A | 4/2020 |
| EP | 2 350 043 | 3/2014 |
| EP | 2 554 988 | 10/2015 |
| JP | 03-126211 | 5/1991 |
| JP | 2002522442 A | 7/2002 |
| JP | 2002525063 | 8/2002 |
| JP | 2003524349 | 2/2003 |
| JP | 2005-202085 | 7/2005 |
| JP | 2006-080560 | 3/2006 |
| JP | 2009-051827 | 3/2009 |
| JP | 2009-051828 | 3/2009 |
| WO | WO1990001405 | 2/1990 |
| WO | WO1991016024 | 10/1991 |
| WO | WO1993005162 | 3/1993 |
| WO | WO1993012240 | 6/1993 |
| WO | WO1993012756 | 7/1993 |
| WO | WO1993024640 | 12/1993 |
| WO | WO1993025673 | 12/1993 |
| WO | WO1995002698 | 1/1995 |
| WO | WO1995018863 | 7/1995 |
| WO | WO1995035301 | 12/1995 |
| WO | WO1996002655 | 2/1996 |
| WO | WO1996010390 | 4/1996 |
| WO | WO1996040964 | 12/1996 |
| WO | WO1996041873 | 12/1996 |
| WO | WO1998051285 | 11/1998 |
| WO | WO2000003683 | 1/2000 |
| WO | WO2000008031 | 2/2000 |
| WO | WO2000015820 | 3/2000 |
| WO | WO2000062813 | 10/2000 |
| WO | WO2001005374 | 1/2001 |
| WO | WO2001005873 | 1/2001 |
| WO | WO2001075164 | 10/2001 |
| WO | WO2001093836 | 12/2001 |
| WO | WO2002020492 | 3/2002 |
| WO | WO2002034236 | 5/2002 |
| WO | WO2002040614 | 5/2002 |
| WO | WO2002087541 | 11/2002 |
| WO | WO2003097805 | 11/2003 |
| WO | WO2004039409 | 5/2004 |
| WO | WO2004041752 | 5/2004 |
| WO | WO2004065546 | 8/2004 |
| WO | WO2004072069 | 8/2004 |
| WO | WO2004087117 | 10/2004 |
| WO | WO2004110499 | 12/2004 |
| WO | WO2005007196 | 1/2005 |
| WO | WO2005026372 | 3/2005 |
| WO | WO2005035764 | 4/2005 |
| WO | WO2005115992 | 12/2005 |
| WO | WO2005120152 | 12/2005 |
| WO | WO2006002538 | 1/2006 |
| WO | WO2006053430 | 5/2006 |
| WO | WO2006124687 | 11/2006 |
| WO | WO2007015877 | 2/2007 |
| WO | WO2007036366 | 4/2007 |
| WO | WO2007048046 | 4/2007 |
| WO | WO2007056861 | 5/2007 |
| WO | WO2007066200 | 6/2007 |
| WO | WO2007088999 | 8/2007 |
| WO | WO2007095976 | 8/2007 |
| WO | WO2007116922 | 10/2007 |
| WO | 2008010096 A1 | 1/2008 |
| WO | WO2008037635 | 4/2008 |
| WO | WO2008038136 | 4/2008 |
| WO | WO2008127714 | 4/2008 |
| WO | WO2008064317 | 5/2008 |
| WO | WO2008064318 | 5/2008 |
| WO | WO2008091681 | 7/2008 |
| WO | WO2008101029 | 8/2008 |
| WO | WO2008101905 | 8/2008 |
| WO | WO2009024221 | 2/2009 |
| WO | WO2009025983 | 2/2009 |
| WO | WO2009086558 | 7/2009 |
| WO | WO2009103064 | 8/2009 |
| WO | WO2009105782 | 8/2009 |
| WO | WO2009111658 | 9/2009 |
| WO | WO2009114763 | 9/2009 |
| WO | WO2009132131 | 10/2009 |
| WO | WO2009156535 | 12/2009 |
| WO | WO2010006432 | 1/2010 |
| WO | WO2010042877 | 4/2010 |
| WO | WO2010048228 | 4/2010 |
| WO | WO2010048536 | 4/2010 |
| WO | WO2010054406 | 5/2010 |
| WO | WO2010074327 | 7/2010 |
| WO | WO2010088537 | 8/2010 |
| WO | WO2010105209 | 9/2010 |
| WO | WO2010129709 | 11/2010 |
| WO | WO2010138652 | 12/2010 |
| WO | WO2010138659 | 12/2010 |
| WO | WO2010138685 | 12/2010 |
| WO | WO2010138695 | 12/2010 |
| WO | WO2010138706 | 12/2010 |
| WO | WO2010138758 | 12/2010 |
| WO | WO2010148422 | 12/2010 |
| WO | WO2011000106 | 1/2011 |
| WO | WO2011000107 | 1/2011 |
| WO | WO2011000108 | 1/2011 |
| WO | WO2011011447 | 1/2011 |
| WO | WO2011017548 | 1/2011 |
| WO | WO2011021218 | 2/2011 |
| WO | WO2011045415 | 4/2011 |
| WO | WO2011050168 | 4/2011 |
| WO | WO2011066651 | 6/2011 |
| WO | WO2011079315 | 6/2011 |
| WO | WO2011103189 | 8/2011 |
| WO | WO2011140627 | 11/2011 |
| WO | WO2013086354 | 6/2013 |
| WO | WO2013149140 | 10/2013 |
| WO | WO2014089239 | 6/2014 |
| WO | WO2015130584 | 9/2015 |
| WO | WO2016176330 | 3/2016 |
| WO | WO2016118697 | 7/2016 |
| WO | WO2017066964 | 4/2017 |
| WO | WO2017070624 | 4/2017 |
| WO | WO2017112865 | 6/2017 |
| WO | WO2017172890 | 10/2017 |
| WO | WO2017173054 | 10/2017 |
| WO | WO2017201346 | 11/2017 |
| WO | WO2017218704 | 12/2017 |
| WO | WO2018064755 | 4/2018 |
| WO | WO2018075592 | 4/2018 |
| WO | WO2018078053 | 5/2018 |
| WO | WO2018081480 | 5/2018 |
| WO | WO2018081638 | 5/2018 |
| WO | WO2018089540 | 5/2018 |
| WO | WO2018109220 | 6/2018 |
| WO | WO2018119514 | 7/2018 |
| WO | WO2018126084 | 7/2018 |
| WO | WO2018170306 | 9/2018 |
| WO | WO2018170336 | 9/2018 |
| WO | WO2018200613 | 11/2018 |
| WO | WO2018208856 | 11/2018 |
| WO | WO2018213789 | 11/2018 |
| WO | WO2018232120 | 12/2018 |
| WO | WO2018232357 | 12/2018 |
| WO | WO2019046809 | 3/2019 |
| WO | WO2019051289 | 3/2019 |
| WO | WO2019067992 | 4/2019 |
| WO | WO2019089828 | 5/2019 |
| WO | WO2019126593 | 6/2019 |
| WO | WO2019141814 | 7/2019 |
| WO | WO2019147749 | 8/2019 |

(56) References Cited

FOREIGN PATENT DOCUMENTS

| | | |
|---|---|---|
| WO | WO2019200171 | 10/2019 |
| WO | WO2019202035 | 10/2019 |
| WO | WO2019210394 | 11/2019 |
| WO | WO2020028133 | 2/2020 |
| WO | WO2020056304 | 3/2020 |
| WO | WO2020061332 | 3/2020 |
| WO | WO2020061367 | 3/2020 |
| WO | WO2020061457 | 3/2020 |
| WO | WO2020069169 | 4/2020 |
| WO | WO2020069718 | 4/2020 |
| WO | WO2020070040 | 4/2020 |
| WO | WO2020077007 | 4/2020 |
| WO | 2020106903 A1 | 5/2020 |
| WO | WO2020089342 | 5/2020 |
| WO | WO2020102172 | 5/2020 |
| WO | WO2020123300 | 6/2020 |
| WO | WO2020160397 | 8/2020 |
| WO | WO2020191103 | 9/2020 |
| WO | WO2020198697 | 10/2020 |
| WO | WO2020198706 | 10/2020 |
| WO | WO2020201383 | 10/2020 |
| WO | WO2020205644 | 10/2020 |
| WO | WO2020210901 | 10/2020 |
| WO | WO2020219941 | 10/2020 |
| WO | WO2020227510 | 11/2020 |
| WO | WO2020252589 | 12/2020 |
| WO | WO2020263985 | 12/2020 |
| WO | WO2021000041 | 1/2021 |
| WO | WO2021016430 | 1/2021 |
| WO | WO2021022173 | 2/2021 |
| WO | WO2021026358 | 2/2021 |
| WO | WO2021030701 | 2/2021 |
| WO | WO2021046265 | 3/2021 |
| WO | WO2021050986 | 3/2021 |
| WO | WO2021055833 | 3/2021 |
| WO | WO2021055835 | 3/2021 |
| WO | WO2021055849 | 3/2021 |
| WO | WO2021076805 | 4/2021 |
| WO | WO2021077066 | 4/2021 |
| WO | WO2021077067 | 4/2021 |
| WO | WO2021102411 | 5/2021 |
| WO | WO2021123332 | 6/2021 |
| WO | WO2021142336 | 7/2021 |
| WO | WO2021148511 | 7/2021 |
| WO | WO2021155274 | 8/2021 |
| WO | WO2021156267 | 8/2021 |
| WO | WO2021159130 | 8/2021 |
| WO | WO2021168305 | 8/2021 |
| WO | WO2021178510 | 9/2021 |
| WO | WO2021178725 | 9/2021 |
| WO | WO2021183563 | 9/2021 |
| WO | WO2021191265 | 9/2021 |
| WO | WO2021195529 | 9/2021 |
| WO | WO2021198157 | 10/2021 |
| WO | WO2021207020 | 10/2021 |
| WO | WO2021207710 | 10/2021 |
| WO | WO2021207712 | 10/2021 |
| WO | WO2021214204 | 10/2021 |
| WO | WO2021216743 | 10/2021 |
| WO | WO2021222287 | 11/2021 |
| WO | WO2021222801 | 11/2021 |
| WO | WO2021231901 | 11/2021 |
| WO | WO2022011092 | 1/2022 |
| WO | WO2022015662 | 1/2022 |
| WO | WO2022081750 | 4/2022 |
| WO | WO2022115645 | 6/2022 |
| WO | WO2022140404 | 6/2022 |
| WO | WO2023031392 | 3/2023 |
| WO | WO2023036960 | 3/2023 |
| WO | WO2023230587 | 11/2023 |
| WO | WO2024027910 | 2/2024 |
| WO | WO2024028445 | 2/2024 |
| WO | WO2024036303 | 2/2024 |
| WO | WO2024054020 | 3/2024 |
| WO | WO2024138121 | 6/2024 |
| WO | WO2024138134 | 6/2024 |
| WO | WO2024184500 | 9/2024 |
| WO | WO2024213776 | 10/2024 |
| WO | WO2024216212 | 10/2024 |
| WO | WO2024216214 | 10/2024 |
| WO | WO2024243480 | 11/2024 |
| WO | WO2025117732 | 6/2025 |
| WO | 2025146125 A1 | 7/2025 |
| WO | 2025264937 A1 | 12/2025 |
| WO | 2025265101 A1 | 12/2025 |
| WO | WO2026044248 | 2/2026 |

OTHER PUBLICATIONS

Allen et al., "Pharmacokinetics and Anti-Tumor Activity of Vincristine Encapsulated in Sterically Stabilized Liposomes", Int. J. Cancer, vol. 62, No. 2, pp. 199-204, Jul. 17, 1995.

Anderluzzi et al., "Investigating the Impact of Delivery System Design on the Efficacy of Self-Amplifying RNA Vaccines," Vaccines, vol. 8, No. 2, pp. 212-233, May 8, 2020.

Anderson et al., "Safety and Immunogenicity of SARS-CoV-2 mRNA-1273 Vaccine in Older Adults," New England Journal of Medicine, vol. 383, No. 25, pp. 2427-2438, Sep. 29, 2020.

Arpicco et al., "Preparation and Characterization of Novel Cationic Lipids Developed for Gene Transfection," Proceed. Int'I Symp. Control. Rel. Bioact. Mater. (Controlled Release Society, Inc.), 1999, vol. 26, pp. 759-760.

Arpicco et al., "Synthesis, characterization and transfection activity of new saturated and unsaturated cationic lipids," IL Farmaco, vol. 59, No. 11, pp. 869-878, Nov. 2004.

Ballas et al., "Liposomes bearing a quaternary ammonium detergent as an efficient vehicle for functional transfer of TMV-RNA into plant protoplasts," Biochimica et Biophysica Acta, vol. 939, No. 1, pp. 8-18, Mar. 22, 1988.

Barinaga, M., "Step Taken Toward Improved Vectors for Gene Transfer," Science, vol. 266, Issue 5189, pp. 1326-1327, Nov. 25, 1994.

Bass, "The Short Answer," Nature, vol. 411, No. 6836, pp. 428-429, May 24, 2001.

Beale et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System, " Journal of Drug Targeting, vol. 11, No. 7, pp. 449-456, Aug. 1, 2003.

Behr, J.-P., "Synthetic Gene-Transfer Vectors," Acc. Chem. Res., vol. 26, No. 5, pp. 274-278, May 1, 1993.

Birkkholz et al., "Targeting of DEC-205 on Human Dendritic Cells Results in Efficient MHC Class II-Restricted Antigen Presentation," Blood, vol. 116, No. 13, pp. 2277-2286, Sep. 2010.

Bloom et al., "Self-Amplifying RNA Vaccines for Infectious Diseases," Gene Therapy, vol. 28, pp. 117-129, Oct. 22, 2020.

Bonifaz et al., "In Vivo Targeting of Antigens to Maturing Dendritic Cells via the DEC-205 Receptor Improves T Cell Vaccination," J. Exp. Med., vol. 199, No. 6, pp. 815-824, Mar. 15, 2004.

Brigham et al., "Rapid Communication: In vivo Transfection of Murine Lungs with a Functioning Prokaryotic Gene Using a Liposome Vehicle," The American Journal of the Medical Sciences, vol. 298, No. 4, pp. 278-281, Oct. 1, 1989.

Brummelkamp et al., "A System for Stable Expression of Short Interfering RNAs in Mammalian Cells," Science, vol. 296, No. 5567, pp. 550-553, Mar. 21, 2002.

Certificate of Analysis, Retest date: Mar. 2021, [online] [found on Jun. 19, 2025].

Cevc, G., "How Membrane Chain-Melting Phase-Transition Temperature is Affected by the Lipid Chain Asymmetry and Degree of Unsaturation: An Effective Chain-Length Model," Biochemistry, vol. 30, No. 29, pp. 7186-7193, Jul. 23, 1991.

Check, "RNA to the Rescue", Nature, vol. 425:10-12 (2003), https://222.nature.com/articles/425010a.

Chonn et al., "Recent Advances in Liposomal Drug-Delivery Systems," Current Opinion in Biotechnology, vol. 6, No. 6, pp. 698-708, Jan. 1, 1995.

(56) References Cited

OTHER PUBLICATIONS

Chung et al., "COVID-19 Vaccine Frontrunners and Their Nanotechnology Design," ACS Nano, vol. 14, No. 10, pp. 12522-12537, Oct. 2020.
Corbett et al., "Evaluation of the mRNA-1273 Vaccine Against SARS-CoV-2 in Nonhuman Primates", New England Journal of Medicine, vol. 383, Issue 16, pp. 1544-1555, Jul. 28, 2020.
Corbett et al., "SARS-CoV-2 mRNA Vaccine Development Enabled by Prototype Pathogen Preparedness" bioRvix.org Jun. 11, 2020, https://www.biorxiv.org/content/10.1101/2020.06.11.145920v1.full.
Cortesi et al., "Effect of cationic liposome composition on in vitro cytotoxicity and protective effect on carried DNA," International Journal of Pharmaceutics, vol. 139, No. 1-2, pp. 69-78, Aug. 9, 1996.
COVID-19 Vaccinations in the United States, CDC (last visited Feb. 25, 2022) https://covid.cdc.gov/covid-data-tracker/#vaccinations_vacc-total-admin-rate-total.
Cross, Ryan, "Without These Lipid Shells, There Would be no mRNA Vaccines for COVID-19", Chemical & Engineering News, Mar. 6, 2021, https://cen.acs.org/pharmaceuticals/drugdelivery/Without-lipid-shells-mRNA-vaccines/99/18.
Cruz et al., "Targeting Nanoparticles fo CD40, DEC-205 or CD11c Molecules on Dendritic Cells for Efficient CD8+ T Cell Response: A Comparative Study," Journal of Controlled Release, vol. 192, pp. 209-218 (2004).
Crystal, R., "Transfer of Genes to Humans: Early Lessons and Obstacles to Success," Science, vol. 270, No. 5235, pp. 404-410, Oct. 20, 1995.
Culver K., "The First Human Gene Therapy Experiment," Gene Therapy: A Handbook for Physicians, pp. 33-40, 1994.
Delaware Environmental Public Health Tracking Network, Vaccine Tracker, https:/myhealthycommunity.dhss.delaware.gove/locations/state/vaccine-tracker.
Dhodapkar et al., "Induction of Antigen-Specific Immunity with a Vaccine Targeting NY-ESO-1 to the Dendritic Cell Receptor DEC-205," Sci. Transl. Med., vol. 6(232), pp. 1-22, Apr. 16, 2014.
Dolgin, "Startups Set Off New Wave of mRNA Therapeutics," Nature Biotechnology, vol. 39, No. 9, pp. 1029-1031, Sep. 2021.
Dolgin, "The Tangled History of MRNA Vaccines," Nature, vol. 597, pp. 318-324, Sep. 16, 2021.
Duzgunes, N., "Membrane Fusion," Subcellular Biochemistry, vol. 11, pp. 195-286, 1985.
Dwarki et al., "Cationic Liposome-Mediated RNA Transfection," Methods in Enzymology, vol. 217, pp. 644-654, 1993.
Elbashir, et al., "Duplexes of 21-nucleotide RNAs Mediate RNA Interference in Cultured Mammalian Cells," Nature, vol. 411, No. 6836, pp. 494-498, May 2001.
Enoch et al., "Formation and Properties of 1000-A-Diameter, Single-Bilayer Phospholipid Vesicles," Proc. Natl. Acad. Sci., vol. 76, No. 1, pp. 145-149, Jan. 1, 1979.
Fadok et al., "Apoptosis: Giving Phosphatidylserine Recognition an Assist—With a Twist", Curr Biol. vol. 13, No. 16, pp. R655-R657, Aug. 19, 2003.
Fahey et al., "A Comprehensive Classification System for Lipids," J. Lipid Res. vol. 46, No. 5, pp. 839-861, May 1, 2005.
Felgner et al., "Cationic Lipid-Mediated Transfection in Mammalian Cells: 'Lipofection,'" J. Tiss. Cult. Meth., vol. 15, No. 2, pp. 63-68, Jun. 1, 1993.
Felgner et al., "Enhanced Gene Delivery and Mechanism Studies with a Novel Series of Cationic Lipid Formulations," The Journal of Biological Chemistry, vol. 269, No. 4, pp. 2550-2561, Jan. 28, 1994.
Felgner et al., "Lipofection: A Highly Efficient, Lipid-Mediated DNA-Transfection Procedure," Proc. Natl. Acad. Sci. vol. 84, No. 21, pp. 7413-7417, Nov. 1, 1987.
Felgner et al., "Cationic Liposome Mediated Transfection," Proc. West. Pharmacol. Soc., vol. 32, pp. 115-121, 1989.
Filion et al., "Toxicity and Immunomodulatory Activity of Liposomal Vectors Formulated with Cationic Lipids Toward Immune Effector Cells, " Biochim Biophys Acta. vol. 1329, No. 2, pp. 345-356, Oct. 23, 1997.
Fossom et al., "Targeting Antigens to Different Receptors on Conventional Type 1 Dendritic Cells Impacts the Immune Response," J. Immnol., vol. 205, pp. 661-673, Jun. 26, 2020.
Gao, X., et al., "A Novel Cationic Liposome Reagent for Efficient Transfection of Mammalian Cells," Biochem. Biophys. Res. Comm., vol. 179, No. 1, pp. 280-285, Aug. 30, 1991.
Gauthier et al., "Quantification of Surface GalNAc Ligands Decorating Nanostructured Lipid Carriers by UPLC-ELSD," J Mol Sci. vol. 20, No. 22, pp. 5669-5684, Nov. 12, 2019.
Gershon, H., et al., "Mode of Formation and Structural Feature of DNA-Cationic Liposome Complexes Used forTransfection," Biochemistry, vol. 32, No. 28, pp. 7143-7151, Jul. 1, 1993.
Global Newswire, retrieved from http://globalnewswire.com on Feb. 27, 2013, Tekmira sues Alnylam Pharmaceuticals for repeated misuse of tradesecrets and confidential information, Mar. 16, 2011, pp. 1-3.
Guy-Caffey et al., "Novel Polyaminolipids Enhance the Cellular Uptake of Oligonucleotides," The Journal of Biological Chemistry, vol. 270, No. 52, pp. 31391-31396, Dec. 29, 1995.
Han et al., "An Ionizable Lipid Toolbox for RNA Delivery", Nature Communications, vol. 12, No. 1, pp. 7233 (1-6), Dec. 2021.
Han et al., "Profiling patent compounds in lipid nanoparticle formulations of siRNA", Molecular Therapy: Nucleic Acids, vol. 35, pp. 1-11, Dec. 2024.
Hassett et al., "Optimization of Lipid Nanoparticles for Intramuscular Administration of mRNA Vaccines", Molecular Therapy: Nucleic Acids, vol. 15, Issue 1, pp. 1-11, Apr. 2019.
Hauser et al., "Crystallization of Phosphatidylserine Bilayers Induced by Lithium," The Journal of Biological Chemistry, vol. 256, No. 22, pp. 11377-11380, Nov. 25, 1981.
Hawley-Nelson et al., "LipofectAmine™ Reagent: A New, Higher Efficiency Polycationic Liposome Transfection Reagent," Focus, vol. 15, No. 3, pp. 73-79, 1993.
Heinz et al., "Distinguishing Features of Current COVID-19 Vaccines: Knowns and Unknowns of Antigen Presentation and Modes of Action," npj Vaccines, vol. 6, No. 1, pp. 1-13, Aug. 16, 2021.
Heyes et al., "Cationic lipid saturation influences intracellular delivery of encapsulated nucleic acids," Journal of Controlled Release, 2005, vol. 107, pp. 276-287.
Heyes et al., "Synthesis of novel cationic lipids: effect of structural modification on the efficiency of gene transfer," J. Med. Chem., vol. 45, No. 1, pp. 99-114, Jan. 3, 2002.
Hoge, Stephen, "Turns Out, Designing a COVID Vaccine Was Easy", UCSF Alumni, https://alumni.ucsf.edu/stories/stephen-hoge.
Hou et al., "Lipid Nanoparticles for mRNA Delivery", Nature, vol. 6, pp. 1078-1094, Dec. 2021.
Huang et al., "Thiocholesterol-Based Lipids for Ordered Assembly of Bioresponsive Gene Carriers," Molecular Therapy, vol. 11, No. 3, pp. 409-417, Mar. 2005.
Hyde, S., et al., "Correction of the Ion Transport Defect in Cystic Fibrosis Transgenic Mice by Gene Therapy," Nature, vol. 362, pp. 250-255, Mar. 18, 1993.
Jackson et al., "An mRNA Vaccine Against SARS-CoV-2—Preliminary Report," New Engl. J. Med., vol. 383, No. 20, pp. 1920-1931, Nov. 12, 2020.
Jayaraman et al., "Maximizing the Potency of siRNA Lipid Nanoparticles for Hepatic Gene Silencing In Vivo**," Angew. Chem. Int. Ed., vol. 51, No. 34, pp. 8529-8533, Aug. 20, 2012.
Jiang, L., et al., "Comparison of protein precipitation methods for sample preparation prior to proteomic analysis," Journal of Chromatography A, vol. 1023, No. 2, pp. 317-320, Jan. 16, 2004.
John et al., "Chemistry and Art of Developing Lipid Nanoparticles for Biologics Delivery: Focus on Development and Scale-Up", Pharmaceutics, vol. 16, No. 1, p. 131, 34 pages, Jan. 19, 2024.
Jorgensen et al., "Biodegradable Cationic and Ionizable Cationic Lipids: A Roadmap for Safer Pharmaceutical Excipients", Nano-Micro Small Journal, vol. 19, No. 17, p. 2206968, 24 pages, Apr. 2023.

(56) References Cited

OTHER PUBLICATIONS

Joyce et al., "Iterative Structure-Based Improvement of a Respiratory Syncytial Virus Fusion Glycoprotein Vaccine", Nat Struct Mol Biol., vol. 23, No. 9, pp. 811-820, Sep. 2016.
Juliano et al., "The Effect of Particle Size and Charge on the Clearance Rates of Liposomes and Liposome Encapsulated Drugs," Biochem. Biophys. Res. Commun., vol. 63, No. 3, pp. 651-658, Apr. 7, 1975.
Keough, K., "Influence of Chain Unsaturation and Chain Position on Thermotropism and Intermolecular Interactions in Membranes," Biochem. Soc. Transactions, vol. 18, No. 5, pp. 835-837, 1990.
Krichevsky et al., "RNAi Functions in Cultured Mammalian Neurons," PNAS, vol. 99, No. 18, pp. 11926-11929, Sep. 3, 2002.
Lawrence et al. "The formation, characterization and stability of non-ionic surfactant vesicles," S.T.P. Pharma Sciences, vol. 6, No. 1, pp. 49-60, 1996.
Lawrence et al., "Synthesis and Aggregation Properties of Dialkyl Polyoxyethylene Glycerol Ethers," Chemistry and Physics of Lipids, vol. 82, No. 2, pp. 89-100, Aug. 19, 1996.
Legendre et al., "Delivery of Plasmid DNA into Mammalian Cell Lines Using pH-Sensitive Liposomes: Comparison with Cationic Liposomes," Pharm. Res., vol. 9, No. 10, pp. 1235-1242, Oct. 9, 1992.
Leventis et al., "Interactions of mammalian cells with lipid dispersions containing novel metabolizable cationic amphiphiles," Biochem. Biophys. Acta, vol. 1023, No. 1, pp. 124-132, Mar. 30, 1990.
Li et al., "A Review on Phospholipids and Their Main Applications in Drug Delivery Systems," Asian J. Pharm. Sci. vol. 10, pp. 81-98, 2015.
Li, et al., "Tailoring Combinatorial Lipid Nanoparticles for Intracellular Delivery of Nucleic Acids, Proteins, and Drugs," Acta Pharm. Scinica, vol. 12, No. 6, pp. 2624-2639, 2022.
Liu et al., "Cationic Liposome-Mediated Intravenous Gene Delivery", J. Biol. Chem., vol. 270, No. 42, pp. 24864-24870, Oct. 20, 1995.
Liu, et al., "An inhalable nanoparticulate STING agonist synergizes with radiotherapy to confer long-term control of lung metastases", Nature Communication, 10, 5108 (2019). https://doi.org/10.1038/s41467-019-13094-5.
Liu, et al., "Development of mRNA Lipid Nanoparticles: Targeting and Therapeutic Aspects", International Journal of Molecular Sciences, 2024, 25, 10166. https://doi.org/10.3390/ijms251810166.
Loh, Tim, "Lipids are Delivering the Vaccine Revolution", Bloomberg, Mar. 6, 2021, https://www.bloomberg.com/news/newsletters/2021-03-06/lipids-are-delivering-the-vaccine-revolution.
Lo Presti et al., "The Replacement of Helper Lipids with Charged Alternatives in Lipid Nanoparticles Facilitates Targeted mRNA Delvery to the Spleen and Lungs" Journal of Controlled Release, vol. 345, pp. 819-831, May 1, 2022.
Lotter et al., "Incorporation of Phosphatidylserine Improves Efficiency of Lipid Based Gene Delivery Systems" European Journal of Pharmaceutics and Biopharmaceutics, vol. 172, pp. 134-143, Mar. 2022.
Luozhong et al., "Phosphatidylserine Lipid Nanoparticles Promote Systemic RNA Delivery to Secondary Lymphoid Organs" Nano Letters, vol. 22, No. 20, pp. 8304-8311, Oct. 4, 2022. https://doi.org/10.1021/acs.nanolett.2c03234.
Maloy et al., "Intralymphatic Immunization Enhances DNA Vaccination," Proc Natl Acad Sci USA, vol. No. 6, pp. 3299-3033, Mar. 13, 2001.
Marshall, E., "Gene Therapy's Growing Pains," Science, vol. 269, No. 5227, pp. 1050-1055, Aug. 25, 1995.
Mrksich et al., "Breaking the Final Barrier: Evolution of Cationic and Ionizable Lipid Structure in Lipid Nanoparticles to Escape the Endosome", Adv. Drug Deliv. Rev., vol. 214, p. 115446, 32 pages, Nov. 2024.
Murahashi et al., "Synthesis and Evaluation of Neoglycolipid for Liposome Modification," Biol. Pharm. Bull., vol. 20, No. 6, pp. 704-707, Jun. 15, 1997.
Nellis et al., "Preclinical Manufacture of an Anti-HER2 scFv-PEG-DSPE, Liposome-Inserting Conjugate. 1. Gram-Scale Production and Purification," Biotechnol Prog., vol. 21, pp. 205-220, Jan. 2005.
Nellis et al., "Preclinical Manufacture of Anti-HER2 Liposome-Inserting, scFv-PEG-Lipid Conjugate. 2. Conjugate Micelle Identity, Purity, Stability, and Potency Analysis," Biotechnol Prog., vol. 21, pp. 221-232, Jan. 2005.
Oberli et al., "Lipid Nanoparticle Assisted mRNA for Potent Cancer Immunotherapy", Nano Letters, vol. 17, No. 3, pp. 1326-1335, Mar. 8, 2017.
Offutt-Powell et al., "Delaware's My Healthy Community Data Platform: At the Intersection of Public Health Informatics and Epidemiology" Delaware Journal of Public Health, vol. 7, No. 3, p. 58, Jul. 2021.
Orkin, S., et al., NIH Report, Report and Recommendations of the Panel to Assess the NIH Investment in Research on Gene Therapy, vol. 7, Dec. 7, 1995.
Pardi, et al., "mRNA Vaccines—A New Era in Vaccinology," Nat. Rev. Drug Discov. vol. 17, No. 4, pp. 261-279, Apr. 19, 2018.
Parr et al., "Factors Influencing the Retention and Chemical Stability of Polly (Ethylene Glycol)-Lipid Conjugates Incorporated into Large Unilamellar Vesicles," Biochimica et Biophysica Acta, vol. 1195, No. 1, pp. 21-30, Oct. 12, 1994.
Paul, C., et al., "Effective Expression of Small Interfering RNA in Human Cells," Nature Biotech., vol. 20, No. 5, pp. 505-508, May 2002.
Press Release, Moderna and Baxter Announce Agreement for Fill/Finish Manufacturing of the Moderna COVID-19 Vaccine in the U.S. https://investors.modernatx.com/news-releases/news-release-details/baxter-biopharma-solutions-and-moderna-announce-agreement.
Press Release, Moderna and Lonza Announce Worldwide Strategic Collaboration to Manufacture Moderna's Vaccine (mRNA-1273) Against Novel Coronavirus (May 1, 2020), https://investors.modernatx.com/news-releases/news-release-details/moderna-and-lonza-announce-worldwide-strategic-collaboration.
Press Release, Moderna Announces Initiation of Rolling Submission of Biologics License Application (BLA) with U.S. FDA for the Moderna COVID-19 Vaccine (Jun. 1, 2021) https://investors.modernatx.com/news-releases/news-release-details/moderna-announces-initiation-rolling-submission-biologics.
Press Release, Moderna Receives Full U.S. FDA Approval for COVID 19 Vaccine Spikevax 2022.
Press Release, Moderna, Moderna Reports Fourth Quarter and Fiscal Year 2021 Financial Results and Provides Business Updates, Feb. 24, 2022, https://investors.modernatx.com/news/news-details/2022/Moderna-Reports-Fourth-Quarter-and-Fiscal-Year-2021-Financial-Results-and-Provides-Business-Updates/default.aspx.
Press Release, Moderna, Vaccine Exports from U.S. Accelerate as Moderna Ships Abroad, Bloomberg.com, May 20, 2021, https://www.bloomberg.com/news/articles/2021-05-20/moderna-starts-shipping-vaccine-from-us-boosting-shot-exports.
Puyal, C., et al., "A New Cationic Liposome Encapsulating Genetic Material: A Potential Delivery System for Polynucleotides," Eur. J. Biochem., vol. 228, No. 3, pp. 697-703, Mar. 1995.
Rahn et al., "Isoprenoid CARTs: In Vitro and In Vivo mRNA Delivery by Charge-Altering Releasable Transporters Functionalized with Archaea-Inspired Branched Lipids", Biomacromolecules, vol. 25, pp. 4305-4316, May 30, 2024.
Regalado, Antonio, "None of Us Were Ready to Manufacture Genetic Vaccines for a Billion People", MIT Technology Review, Dec. 17, 2020, https://www.technologyreview.com/2020/12/17/1014989/moderna-vaccine-availability-stephane-bancel-ceo/.
Ren et al., "Impact of ionizable lipid type on the pharmacokinetics and biodistribution of mRNA-lipid nanoparticles after intravenous and subcutaneous injection", Journal of Controlled Release, vol. 384, 113945, 14 pages, Aug. 10, 2025.
Sabnis et al., "A Novel Amino Lipid Series for mRNA Delivery: Improved Endosomal Escape and Sustained Pharmacology and Safety in Non-Human Primates," Molecular Ther., vol. 26, No. 6, pp. 1509-1519, Jun. 2018.

(56) References Cited

OTHER PUBLICATIONS

Sahin et al., "Personalized RNA Mutanome Vaccines Mobilize Poly-Specific Therapeutic Immunity Against Cancer," Nature, vol. 547, pp. 222-240, Jul. 13, 2017.
Sawada et al., "Microemulsions in Supercritical CO2 Utilizing the Polyethyleneglycol Dialkylglycerol and Their Use for the Solubilization of Hydrophiles," Dyes and Pigments, vol. 65, No. 1, pp. 67-74, Apr. 1, 2005.
Semple et al., "Rational Design of Cationic Lipids for siRNA Delivery," Nature Biotechnology, vol. 28, No. 2, pp. 172-178, Feb. 2010.
Sharma, et al., "A Review of the Progress and Challenges of Developing a Vaccine for COVID-19," Frontiers in Immunology, vol. 11, pp. 1-17, Oct. 2020.
Shin, et al. "Acid-Triggered Release via dePEGylation of DOPE Liposomes Containing Acid-Labile Vinyl Ether PEG-lipids," Journal of Controlled Release, vol. 91, No. 1-2, pp. 187-200, Aug. 28, 2003.
Shirley et al., "Amikacin Liposome Inhalation Suspension: A Review in *Mycobacterium avium* Complex Lung Disease", Drugs, vol. 79, No. 5, pp. 555-562, Apr. 2019.
Shurin, et al., "Recognition of Live Phosphatidylserine-Labeled Tumor Cells by Dendritic Cells: A Novel Approach to Immunotherapy of Skin Cancer," Cancer Res. vol. 69, No. 6, pp. 2487-2496, Mar. 15, 2009.
Song et al., "Characterization of the Inhibitory Effect of PEG-lipid Conjugates on the Intracellular Delivery of Plasmid and Antisense DNA Mediated by Cationic Lipid Liposomes," Biochimica et Biophysica Acta, vol. 1558, No. 1, pp. 1-13, Jan. 2, 2002.
Sorensen, et al., "Gene Silencing by Systemic Delivery of Synthetic siRNAs in Adult Mice", J. Biol. Chem., vol. 327, No. 4, pp. 761-766, Apr. 4, 2003.
Spagnou, S., et al., "Lipidic Carriers of siRNA: Differences in the Formulation, Cellular Uptake, and Delivery with Plasmid DNA," Biochemistry, vol. 43, No. 42, pp. 13348-13356, Oct. 26, 2004.
Stamatatos, L., et al., "Interactions of Cationic Lipid Vesicles with Negatively Charged Phospholipid Vesicles and Biological Membranes," Biochemistry, vol. 27, No. 11, pp. 3917-3925, May 1, 1988.
Sun et al., "Structure and Function of Cationic and Ionizable Lipids for Nucleic Acid Delivery", Pharmaceutical Research, vol. 40, No. 1, pp. 27-46, Jan. 2023.
Swadling et al., "Pre-Existing Polymerase-Specific T Cells Expand in Abortive Seronegative SARS-CoV2," Nature, vol. 601, pp. 110-142, Jan. 6, 2022.
Szoka, F., et al., "Comparative Properties and Methods of Preparation of Lipid Vesicles (Liposomes)," Ann. Rev. Biophys. Bioeng., vol. 9, No. 1, pp. 467-508, Jun. 1980.
Szoka et al., "Procedure for preparation of liposomes with large internal aqueous space and high capture by reverse-phase evaporation," Proc. Natl. Acad. Sci., vol. 75, No. 9, pp. 4194-4198, Sep. 1, 1978.
Tada, et al., "Comparison of Neutralizing Antibody Titers Elicited by mRNA and Adenoviral Vector Vaccine Against SARS-CoV-2 Variants," Biorxiv, Jan. 2021.
Tang et al., "Ionizable Lipid Nanoparticles for mRNA Delivery", Advanced NanoBiomed Research, vol. 3, No., 8, pp. 2300006 (1-21), Aug. 2023.
Templeton, "Cationic Liposome-mediated Gene Delivery In vivo", Bioscience Reports, vol. 22, No. 2, pp. 283-295, Apr. 2002.
Tenchov et al., "Lipid Nanoparticles—From Liposomes to mRNA Vaccine Delivery, a Landscape of Research Diversity and Advancement", ACS Nano, vol. 15, No. 11, pp. 16892-17015, Jun. 28, 2021.
Vanderwoude, I., et al., "Parameters influencing the introduction of plasmid DNA into cells by the use of synthetic amphiphiles as a carrier system," Biochimica et Biophysica Acta, vol. 1240, No. 1, pp. 34-40, Nov. 22, 1995.
Vardi, Nathan, "Moderna's Mysterious Coronavirus Vaccine Delivery System", Forbes.com, Jul. 29, 2020, www.forbes.com/sites/nathanvardi/2020/7/29/modernas-mysterious-coronavirus-vaccine-delivery-system/.
Vasileva, et al., "Composition of lipid nanoparticles for targeted delivery: application to mRNA therapeutics", Frontiers in Pharmacology, 15:1466337. doi: 10.3389/fphar.2024.1466337.
Walsh, et al., "Safety and Immunogenicity of Two RNA-Based Covid-19 Vaccine Candidates," N. Engl. J. Med., vol. 383, No. 25, pp. 2439-2450, Dec. 17, 2020.
Wheeler, et al., "Stabilized Plasmid-lipid Particles: Constructions and Characterization," Gene Therapy, vol. 6, No. 2, pp. 271-281, Feb. 5, 1999.
Wilson, R., et al., "Counterion-Induced Condensation of Deoxyribonucleic Acid," A Light-Scattering Study, Biochemistry, vol. 18, No. 11, pp. 2192-2196, May 1, 1979.
Witten et al., Recent Advances in Nanoparticulate RNA Delivery Systems, PNAS, vol. 121, No. 11, pp. e2307798120 (1-9), Mar. 2024.
Woodle, M.C., et al., "Versatility in lipid compositions showing prolonged circulation with sterically stabilized liposomes," Biochimica et Biophysica Acta, vol. 1105, pp. 193-200, Apr. 13, 1992.
Wu, et al., "Engineering an intracellular pathway for major histocompatibility complex class II presentation of antigens", Proc. Natl. Acad. Sci., vol. 92, pp. 11671-11675, Dec. 1995.
Xu, et al., "Lipid-Mediated Targeting with Membrane Wrapped Nanoparticles in the Presence of Corona Formation", ACS Nano, vol. 10, No. 1, pp. 1189-1200, Jan. 26, 2016.
Yang et al., "DS2 Designer Pre-Fusion F Vaccine Induces Strong and Protective Antibody Response Against RSV Infection", NPJ Vaccines, vol. 9, No. 1, p. 258, 12 pages, Dec. 31, 2024.
Yihunie et al., "Recent Advances in Messenger Ribonucleic Acid (mRNA) Vaccines and Their Delivery Systems: A Review", Clinical Pharmacology: Advances and Applications, vol. 14, pp. 77-98, 2023.
Yu et al., "RNA Drugs and RNA Targets for Small Molecules: Principles, Progress, and Challenges," Pharmacological Reviews, vol. 72, pp. 862-898, Oct. 2020.
YUSUKE Sato, "Development of Lipid Nanoparticles for the Delivery of Macromolecules Based on the Molecular Design of pH-Sensitive Cationic Lipids", Chem. Pharm. Bulletin, vol. 69, No. 12, pp. 1141-1159, 2021.
Zhang et al., "Modification of Lipid-Based Nanoparticles: An Efficient Delivery System for Nucleic Acid-Based Immunotherapy", Molecules, vol. 27, No. 6, pp. 1943 (1-29), Mar. 2022.
Zhu, N., et al., "Systemic Gene Expression After Intravenous DNA Delivery into Adult Mice," Science, vol. 261, No. 5118, pp. 209-211, Jul. 9, 1993.
Pilkington et al., "From Influenza to COVID-19: Lipid Nanoparticla mRNA Vaccines at the Frontiers of Infectious Diseases", Acta Biomaterialia, vol. 131, pp. 16-40, 2021.
Zhang et al., "Lipids and Lipid Derivatives for RNA Delivery", Chem Rev, vol. 121, No. 20, pp. 12181-12277, Oct. 27, 2021.

Scheme 1.

Scheme 2.

4

KC3-X1-PH12

| Compound | Analytical Characterization |
|---|---|
| <br>KC2-X1-G | LCMS: CAD, m/z, M+H+=738.8<br>HRMS (ESI) m/z: [M + H]+ Calcd for C45H88NO6+ 738.6606, found 738.6638.<br>$^1$H NMR (400 MHz, CHLOROFORM-d, EW58397-228-P1A1) δ 4.14 - 3.98 (m, 6H), 3.52 - 3.43 (m, 1H), 2.47 - 2.35 (m, 1H), 2.34 - 2.26 (m, 5H), 2.23 (s, 6H), 1.89 - 1.75 (m, 1H), 1.73 - 1.53 (m, 12H), 1.41 - 1.20 (m, 48H), 0.89 (t, *J* = 6.8 Hz, 6H). |
| <br>KC3-X1-G | $^1$H NMR (400 MHz, CHLOROFORM-d, EW53829-397-P1A) δ = 4.10 - 3.95 (m, 6H), 3.51 - 3.40 (m, 1H), 2.32-2.25 (m, 6H), 2.23 (s, 6H), 1.61 (br d, *J* = 6.8 Hz, 15H), 1.39 - 1.20 (m, 47H), 0.89 (s, 6H)<br>Special MS (EW58397-397-P1A): CAD m/z, M+H=752.8<br>Special MS (EW58397-397-P1a1):ELSD m/z, M+H=752.9<br>HRMS (EW53829-397-P1B , ESI) *m/z*:<br>$[M + H]^+$ Calcd for $C_{46}H_{90}NO_6^+$ 752.6763, found.752.6789. |

| | |
|---|---|
|  KC3-X1-J | LCMS (EW58397-234-P1B2): CAD, m/z, $M+H^+$=780.9<br>HRMS (ESI) m/z: [M + H]+ Calcd for $C_{48}H_{94}NO_6^+$ 780.7076, found 780.7105.<br>$^1$H NMR (400 MHz, CHLOROFORM-d, EW58397-234-P1A2) δ 4.17 - 3.97 (m, 6H), 3.51 - 3.39 (m, 1H), 2.29 (t, *J* = 7.6 Hz, 6H), 2.22 (s, 6H), 1.67 - 1.52 (m, 15H), 1.40 - 1.24 (m, 53H), 0.88 (t, *J* = 6.8 Hz, 6H). |
|  KC2-X1-K | LCMS (EW58397-345-P1A1): CAD, m/z, $M + H^+$ = 794.9.<br>HRMS (ESI) *m/z*: $[M + H]^+$ Calcd for $C_{49}H_{96}NO_6^+$ 794.7232, found 794.7251.<br>$^1$H NMR (400 MHz, CHLOROFORM-d, EW58397-345-P1A1) δ 4.11 - 4.01 (m, 6H), 3.49 (t, *J* = 7.2 Hz, 1H), 2.47 - 2.38 (m, 1H), 2.29 (t, *J* = 7.6 Hz, 5H), 2.24 (s, 6H), 1.89 - 1.76 (m, 1H), 1.69 - 1.50 (m, 13H), 1.41 - 1.19 (m, 56H), 0.89 (t, *J* = 6.8 Hz, 6H) |

| | |
|---|---|
| <br>KC3-X1-K | 1H NMR (400 MHz, CHLOROFORM-d, EW58397-252-P1A2) δ 4.14 - 3.97 (m, 6H), 3.52 - 3.39 (m, 1H), 2.29 (t, *J* = 7.6 Hz, 6H), 2.23 (s, 6H), 1.67 - 1.46 (m, 16H), 1.37 - 1.24 (m, 56H), 0.89 (t, *J* = 6.8 Hz, 6H).<br><br>LCMS (EW58397-252-P1A1): CAD, m/z, $M+H^+$=808.9<br><br>HRMS (ESI) m/z: $[M + H]^+$ Calcd for $C_{50}H_{98}NO_6^+$ 808.7389, found 808.7421. |
| <br>KC3-X1-L | 1H NMR (400 MHz, $CDCl_3$) δ = 4.10 - 4.00 (m, 6H), 3.49 - 3.42 (m, 1H), 2.29 (t, *J* = 7.6 Hz, 6H), 2.23 (s, 6H), 1.68 - 1.48 (m, 16H), 1.40 - 1.28 (m, 31H), 1.27 - 1.23 (m, 13H), 0.89 (t, *J* = 6.8 Hz, 6H)<br>LCMS (EW58397-249-P1A1): CAD, m/z, $M+H^+$ = 752.8<br>HRMS (ESI) m/z: $[M + H]^+$ Calcd for $C_{46}H_{90}NO_6^+$ 752.6790, found 752. 6763. |

| | |
|---|---|
|  KC3-X1-M | LCMS (EW58311-235-P1C1): CAD, m/z, M+H=780.9. HRMS (ESI) *m/z*: $[M + H]^+$ Calcd for $C_{48}H_{94}NO_6^+$ 780.7076, found 780.7109. $^1$H NMR (400 MHz, CHLOROFORM-d, EW58311-235-P1A1) δ 4.03 - 3.94 (m, 6H), 3.45 - 3.34 (m, 1H), 2.28 - 2.14 (m, 12H), 1.59 - 1.45 (m, 16H), 1.21 (br d, $J$ = 8.2 Hz, 52H), 0.82 (t, $J$ = 6.8 Hz, 6H). |
|  KC3-X1-N | LCMS (EW58311-262-P1C1): CAD, m/z, M+H=752.9. HRMS (ESI) *m/z*: $[M + H]^+$ Calcd for $C_{46}H_{90}NO_6^+$ 752.6763, found 752.6794. $^1$H NMR (400 MHz, CHLOROFORM-d, EW58311-262-P1A1) δ 4.05 - 3.91 (m, 6H), 3.42 - 3.34 (m, 1H), 2.23 (br t, $J$ = 7.6 Hz, 6H), 2.16 (s, 6H), 1.59 - 1.40 (m, 16H), 1.34 - 1.16 (m, 48H), 0.82 (br t, $J$ = 6.4 Hz, 6H). |

| | |
|---|---|
|  KC3-X1-O | LCMS (EW58311-263-P1C1): CAD, m/z, M+H=808.9. HRMS (ESI) *m/z*: $[M + H]^+$ Calcd for $C_{50}H_{98}NO_6^+$ 808.7389, found 808.7420. $^1$H NMR (400 MHz, CHLOROFORM-d, EW58311-263-P1A1) δ 4.03 - 3.94 (m, 6H), 3.41 - 3.35 (m, 1H), 2.23 (br t, *J* = 7.6 Hz, 6H), 2.16 (s, 6H), 1.61 - 1.47 (m, 16H), 1.31 - 1.17 (m, 56H), 0.82 (t, *J* = 6.8 Hz, 6H). |
|  KC3-X1-P | LCMS (EW58397-277-P1A1): CAD, m/z, $M+H^+$=752.9 HRMS (ESI) *m/z*: $[M + H]^+$ Calcd for $C_{46}H_{90}NO_6^+$ 752.6763, found 752.6791. $^1$H NMR (400 MHz, CHLOROFORM-d, EW58397-277-P1A1) δ 4.11 - 3.98 (m, 6H), 3.49 - 3.39 (m, 1H), 2.35 - 2.26 (m, 6H), 2.23 (s, 6H), 1.68 - 1.53 (m, 15H), 1.40 - 1.22 (m, 50H), 0.89 (t, *J* = 6.8 Hz, 6H) |

| | |
|---|---|
|  KC3-X1-Q | $^1$H NMR (400 MHz, CHLOROFORM-d EW53829-488-P1C) δ 4.11 - 4.00 (m, 6H), 3.49 - 3.39 (m, 1H), 2.29 (d, *J* = 7.6 Hz, 6H), 2.22 (s, 6H), 1.69 - 1.53 (m, 15H), 1.44 - 1.20 (m, 59H), 0.92 - 0.85 (m, 6H)<br><br>LC-MS(EW53829-488-P1E) CAD m/z, M + $H^+$=808.9<br>LC-MS(EW53829-492-P1A1) ELSD m/z, M + $H^+$=809.0<br>HRMS (ESI) m/z: $[M + H]^+$ Calcd for $C_{50}H_{98}NO_6^+$ 808.7389, found 808.7419. |
|  KC3-X1-R | LCMS (EW58311-317-P1B1): CAD, m/z, M + $H^+$ = 865.0.<br><br>HRMS (ESI) *m/z*: $[M + H]^+$ Calcd for $C_{54}H_{106}NO_6^+$ 864.8015, found 864.8048.<br><br>$^1$H NMR (400 MHz, CHLOROFORM-d, EW58311-317-P1A2) δ 4.04 - 3.94 (m, 6H), 3.46 (t, *J* = 7.2 Hz, 1H), 2.22 (t, *J* = 7.6 Hz, 6H), 2.16 (s, 6H), 1.59 - 1.46 (m, 15H), 1.29 - 1.17 (m, 65H), 0.82 (t, *J* = 6.8 Hz, 6H). |

| | |
|---|---|
| <br>KC3-X1-T | LCMS (EW58311-315-P1B1): CAD, m/z, M + $H^+$ = 921.1.<br>HRMS (ESI) *m/z*: $[M + H]^+$ Calcd for $C_{58}H_{114}NO_6^+$ 920.8641, found 920.8662.<br>$^1$H NMR (400 MHz, CHLOROFORM-d EW58311-315-P1A2) δ 4.11 - 4.01 (m, 6H), 3.46 (t, *J* = 7.2 Hz, 1H), 2.36 - 2.23 (m, 12H), 1.67 - 1.53 (m, 15H), 1.33 - 1.22 (m, 73H), 0.87 (t, *J* = 6.8 Hz, 6H). |
| <br>KC3-X1-U | LCMS (EW53829-534-P1A): CAD, m/z, M + $H^+$ = 808.9.<br>LCMS (EW53829-534-P1A1): ELSD, m/z, M + $H^+$ = 808.9<br>HRMS (ESI) *m/z*: $[M + H]^+$ Calcd for $C_{50}H_{98}NO_6^+$ 808.7389, found 808.7421<br>$^1$H NMR (400 MHz, CHLOROFORM-d EW53829-534-P1A1) δ 4.12 - 3.98 (m, 6H), 3.46 (t, *J* = 6.8 Hz, 1H), 2.29 (t, *J* = 7.6 Hz, 6H), 2.23 (s, 6H), 1.68 - 1.48 (m, 16H), 1.27 (s, 57H), 0.89 (t, *J* = 6.8 Hz, 6H) |

| | |
|---|---|
|  KC3-X1-V | LCMS (EW53829-550-P1A): CAD, m/z, M + $H^+$ = 865.0.<br>LCMS (EW53829-550-P1B): ELSD, m/z, M + $H^+$ = 865.0<br>HRMS (ESI) *m/z*: $[M + H]^+$ Calcd for: $C_{54}H_{106}NO_6^+$: 864.8015, found 864.8044.<br>1H NMR (400 MHz, CHLOROFORM-d EW53829-550-P1B) δ 4.12 - 4.00 (m, 6H), 3.46 (t, *J* = 7.2 Hz, 1H), 2.29 (t, *J* = 7.6 Hz, 6H), 2.24 (s, 6H), 1.69 - 1.53 (m, 19H), 1.27 (s, 67H), 0.89 (t, *J* = 6.8 Hz, 6H) |
|  KC3-X1-W | Special MS (EW58397-360-P1A1) : CAD, m/z, M+H=528.5<br>HRMS (ESI) *m/z*: $[M + H]^+$ Calcd for: $C_{30}H_{58}NO_6^+$ 528.4259, found 528.4281.<br>$^1$H NMR (400 MHz, CHLOROFORM-d, EW58397-360-P1A1) δ 4.21 - 3.97 (m, 6H), 3.45 (t, *J* = 6.8 Hz, 1H), 2.28 (t, *J* = 7.6 Hz, 6H), 2.22 (s, 6H), 1.69 - 1.44 (m, 12H), 1.37 - 1.21 (m, 26H). |

| | |
|---|---|
| 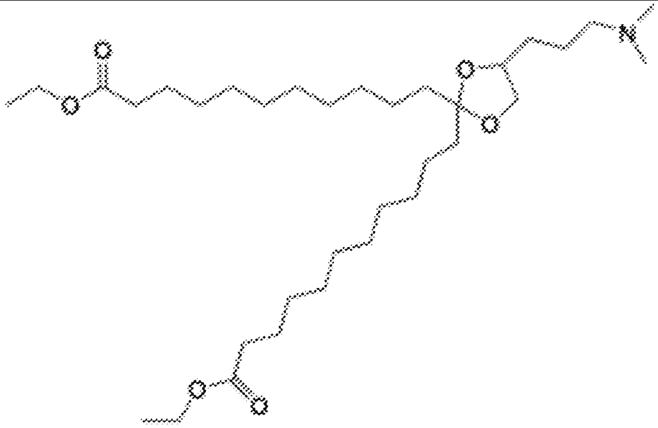<br>KC3-X1-Y | **$^{1}$H NMR** (400 MHz, CHLOROFORM-d EW53829-577-P1A1) δ 4.13 (d, *J* = 7.2 Hz, 4H), 4.09 - 4.01 (m, 2H), 3.47 (t, *J* = 1.2 Hz, 1H), 2.29 (t, *J* = 7.6 Hz, 6H), 2.24 (s, 6H), 1.62 (m, 13H), 1.39 - 1.20 (m, 33H)<br>**LCMS** (EW53829-577-P1A): CAD, m/z, $M+H^{+}$ = 584.6<br>**LCMS** (EW53829-577-P1A1): ELSD, m/z, $M+H^{+}$ = 584.6<br>**HRMS** (ESI) m/z: $[M + H]^{+}$ Calcd for $C_{34}H_{66}NO_{6}^{+}$ 584.4885, found 584.4906 |
| 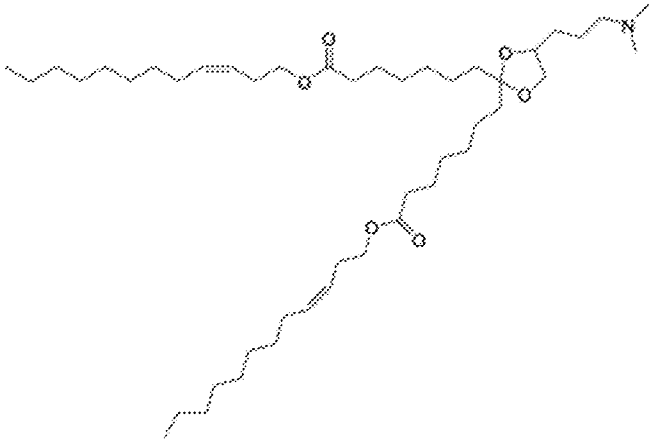<br>KC3-X1-E | **LCMS** (EW58311-175-P1C1): CAD, m/z, M+H=748.8.<br><br>**HRMS** (ESI) *m/z*: $[M + H]^{+}$ Calcd for $C_{46}H_{86}NO_{6}^{+}$ 748.6450, found 748.6466.<br><br>**$^{1}$H NMR** (400 MHz, CHLOROFORM-*d*, EW58311-175-P1A1) δ 5.48 - 5.39 (m, 2H), 5.31 - 5.22 (m, 2H), 4.03 - 3.93 (m, 6H), 3.43 - 3.34 (m, 1H), 2.30 (q, *J* = 6.8 Hz, 4H), 2.21 (br t, *J* = 7.6 Hz, 6H), 2.16 (s, 6H), 1.96 (q, *J* = 6.8 Hz, 4H), 1.59 - 1.35 (m, 14H), 1.28 - 1.17 (m, 34H), 0.84 - 0.78 (m, 6H).<br><br>**$^{13}$C NMR** (CHLOROFORM-*d*, EW58311-175-P1A2): δ 173.9, 133.0, 124.3, 112.0, 70.0, 63.8, 59.6, 45.4, 37.8, 37.5, 34.3, 31.9, 31.3, 29.6, 29.5, 29.3, 29.2, 29.2, 27.3, 26.9, 25.0, 25.0, 24.0, 23.9, 23.6, 22.7, 14.1. |

FIGURE 1C (continued)

| | |
|---|---|
| 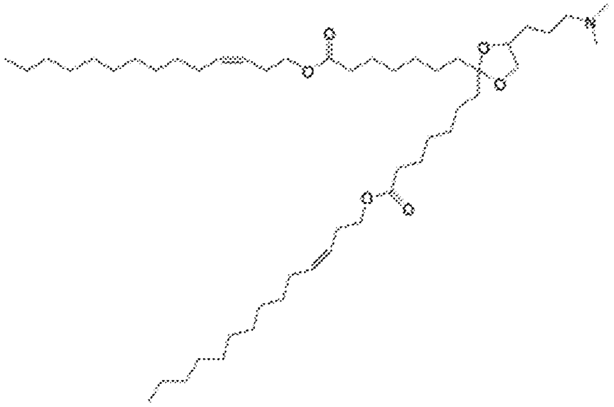 KC3-X1-F | **LCMS** (EW58311-181-P1C1): CAD, m/z, M+H$^+$=804.8<br><br>**HRMS** (EW58311-181-P1C3): ESI+, m/z: [M + H]$^+$ Calcd for $C_{50}H_{94}NO_6^+$, 804.7076, found 804.7101.<br><br>**$^1$H NMR** (400 MHz, CHLOROFORM-d, EW58311-181-P1A1) δ 5.48 - 5.38 (m, 2H), 5.31 - 5.22 (m, 2H), 4.03 - 3.95 (m, 6H), 3.41 - 3.34 (m, 1H), 2.30 (q, *J* = 7.2 Hz, 4H), 2.21 (t, *J* = 7.6 Hz, 6H), 2.17 (s, 6H), 1.96 (q, *J* = 6.8 Hz, 4H), 1.58 - 1.42 (m, 12H), 1.29 - 1.18 (m, 44H), 0.81 (t, *J* = 6.8 Hz, 6H).<br><br>**$^{13}$C NMR** (CHLOROFORM-d, EW58311-181-P1A2): δ 173.9, 133.0, 124.3, 112.0, 70.0, 63.8, 59.6, 45.3, 37.8, 37.5, 34.3, 31.9, 31.2, 29.6, 29.5, 29.2, 29.2, 27.3, 26.9, 25.0, 25.0, 23.9, 23.9, 23.6, 22.7, 14.2. |
| 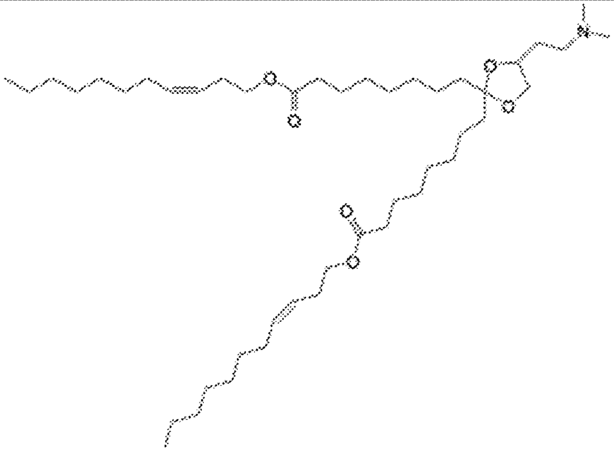 KC2-X1-H | **$^1$H NMR** (400 MHz, CHLOROFORM-d EW53829-515-P1A) δ 5.57 - 5.44 (m, 2H), 5.41-5.29 (m, 2H), 4.06 (t, *J* = 6.8 Hz, 6H), 3.48 (t, *J*=7.6, 1H), 2.37 (q, *J* = 7.2 Hz, 5H), 2.29 (t, *J* = 7.6 Hz, 5H), 2.23 (s, 6H), 2.04 (q, *J* = 7.2 Hz, 4H), 1.89 - 1.76 (m, 1H), 1.69 - 1.50 (m, 9H), 1.41 - 1.20 (m, 37H), 0.88 (t, *J* = 6.8 Hz, 6H)<br><br>**$^{13}$C NMR** (CHLOROFORM-d EW53829-515-P1A1): δ 173.9, 132.9, 124.3, 112.0, 77.2, 74.8, 70.0, 63.8, 56.3, 45.5, 37.8, 37.5, 34.3, 31.9, 31.9, 29.8, 29.8, 29.6, 29.3, 29.3, 29.2, 29.1, 27.3, 26.9, 25.0, 24.0, 23.7, 22.7, 14.1<br><br>**LCMS** (EW58397-515-P1A): CAD, m/z, M+H$^+$=734.8<br>**LCMS** (EW58397-515-P1A1): ELSD, m/z, M+H$^+$=734.8<br>**HRMS** (ESI) m/z: [M + H]$^+$ Calcd for $C_{45}H_{84}NO_6^+$ 734.6293, found 734.6325. |

FIGURE 1C (continued)

| | |
|---|---|
|  KC3-X1-H | LCMS (EW58397-208-P1A7): CAD, m/z, $M+H^+$=748.8<br><br>HRMS (ESI) m/z: [M + H]+ Calcd for $C_{46}H_{86}NO_6^+$ 748.6450, found 748.6478.<br>$^{13}$C NMR (CHLOROFORM-d, EW58397-208-P1A2): δ 173.9, 132.9, 124.3, 112.0, 70.0, 63.8, 59.6, 45.4, 37.8, 37.5, 34.3, 31.9, 31.3, 29.8, 29.6, 29.3, 29.2, 29.2, 27.3, 25.0, 24.0, 26.9, 23.7, 22.7, 14.1<br><br>$^1$H NMR (400 MHz, CHLOROFORM-d, EW58397-208-P1A1) δ 5.55 - 5.45 (m, 2H), 5.38 - 5.28 (m, 2H), 4.12 - 3.97 (m, 6H), 3.50 - 3.41 (m, 1H), 2.37 (q, *J* = 7.0 Hz, 4H), 2.29 (t, *J* = 7.6 Hz, 6H), 2.22 (s, 6H), 2.04 (q, *J* = 7.2 Hz, 4H), 1.67 - 1.45 (m, 12H), 1.41 - 1.18 (m, 37H), 0.89 (t, *J* = 6.8 Hz, 6H). |

| | |
|---|---|
| <br>KC4-X1-H | $^{1}$H NMR (400 MHz, CHLOROFORM-d EW53829-513-P1A) δ 5.49 (s, 2H), 5.35 (s, 2H), 4.10 - 3.95 (m, 6H), 3.46-3.40 (m, 1H), 2.42 - 2.34 (m, 4H), 2.32 - 2.25 (m, 6H), 2.22 (s, 6H), 2.08 - 1.99 (m, 4H), 1.73 - 1.42 (m, 14H), 1.39 - 1.20 (m, 38H), 0.88 (t, $J$ = 6.8 Hz, 6H).<br><br>$^{13}$C NMR (CHLOROFORM-d EW53829-513-P1B): δ 173.9, 132.9, 124.3, 111.9, 77.2, 76.2, 70.0, 63.8, 59.7, 45.5, 37.8, 37.5, 34.3, 33.4, 31.9, 29.8, 29.6, 29.2, 29.2, 29.1, 27.8, 27.3, 25.0, 26.9, 23.8, 23.7, 22.7, 14.1<br><br>LCMS (EW58397-513-P1B): CAD, m/z, $M+H^{+}$=762.9<br>LCMS (EW58397-513-P1A1): ELSD, m/z, $M+H^{+}$=762.9<br>HRMS (ESI) m/z: $[M + H]^{+}$ Calcd for $C_{47}H_{88}NO_{6}^{+}$ 762.6606, found 762.6636. |

| | |
|---|---|
| <br>KC3-X1-I | ¹H NMR (400 MHz, $CDCl_3$ EW53829-421-P1B1) δ 5.57 - 5.45 (m, 2H), 5.41 - 5.28 (m, 2H), 4.13 - 3.98 (m, 6H), 3.51 - 3.40 (m, 1H), 2.38 (dd, *J* = 7.2 Hz, 4H), 2.29 (t, *J* = 7.6 Hz, 6H), 2.23 (s, 6H), 2.04 (dd, *J* = 7.2 Hz, 4H), 1.68 - 1.46 (m, 12H), 1.41 - 1.21 (m, 44H), 0.89 (t, *J* = 6.8 Hz, 6H).<br><br>¹³C NMR ($CDCl_3$ EW53829-421-P1B): δ 173.9, 133.0, 124.3, 112.0, 63.8, 59.6, 45.4, 37.8, 37.5, 34.4, 31.3, 29.8, 29.8, 29.6, 29.6, 29.4, 29.3, 29.2, 29.6, 26.9, 25.0, 24.0, 23.7, 22.7, 14.1<br><br>LCMS (EW58397-421-P1C1): CAD, m/z, $M+H^+$ = 804.9<br><br>LCMS (EW58397-421-P1C): ELSD, m/z, $M+H^+$ = 804.9<br><br>HRMS (ESI) m/z: $[M + H]^+$ Calcd for $C_{50}H_{94}NO_6^+$ 804.7076, found 804.7112. |

| | |
|---|---|
| 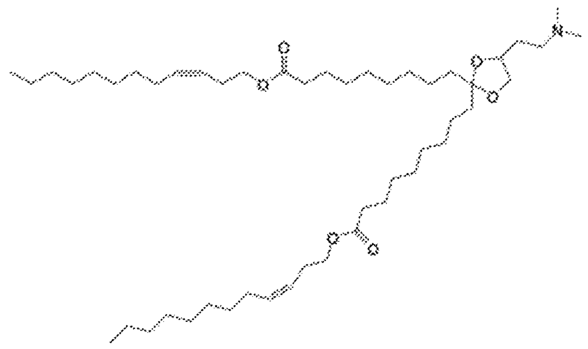<br>KC2-X1-S | **Special MS** (EW58397-375-P1A1) : CAD, m/z, M+H=790.9<br>**Special MS** (EW58397-375-P1A2) : CAD, m/z, M+H=790.9<br><br>**HRMS** (ESI) *m/z*: $[M + H]^+$ Calcd for: $C_{49}H_{92}NO_6^+$ 790.6920, found 790.6933<br><br>**1H NMR** (400 MHz, CHLOROFORM-d EW58397-375-P1A1) δ 5.58 - 5.43 (m, 2H), 5.40 - 5.21 (m, 2H), 4.14 - 3.95 (m, 6H), 3.48 (t, *J* = 7.2 Hz, 1H), 2.48 - 2.34 (m, 5H), 2.33 - 2.18 (m, 11H), 2.04 (q, *J* = 7.2 Hz, 4H), 1.89 - 1.76 (m, 1H), 1.72 - 1.50 (m, 9H), 1.39 - 1.22 (m, 44H), 0.92 - 0.84 (m, 6H)<br><br>$^{13}$**C NMR** (CHLOROFORM-d, EW58397-375-P1B1): δ 173.9, 132.9, 124.3, 112.1, 74.8, 70.0, 63.8, 56.3, 45.5, 37.8, 37.5, 34.4, 31.9, 31.8, 29.9, 29.6, 29.5, 29.3, 29.4, 29.2, 27.3, 26.9, 25.0, 24.0, 23.7, 22.7, 14.1 |
| 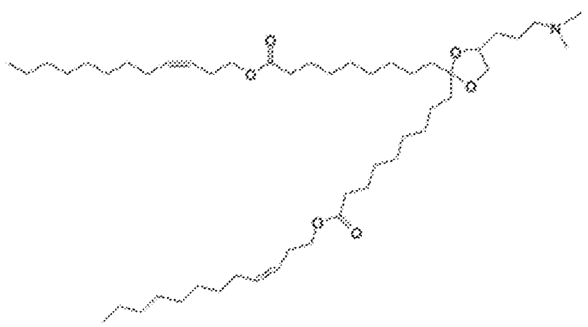<br>KC3-X1-S | **LCMS** (EW58397-317-P1B1): CAD, m/z, $M+H^+$=804.9.<br>**HRMS** (ESI) *m/z*: $[M + H]^+$ Calcd for $C_{50}H_{94}NO_6^+$ 804.7076, found 804.7088.<br><br>$^1$**H NMR** (400 MHz, CHLOROFORM-d, EW58397-317-P1B1) δ 8.54 (s, 1H), 5.59 – 5.41 (m, 2H), 5.39 – 5.29 (m, 2H), 4.16 – 3.97 (m, 6H), 3.49 – 3.41 (m, 1H), 2.37 (td,*J*= 6.8, 14.0 Hz, 6H), 2.32 – 2.22 (m, 10H), 2.04 (q,*J*= 6.8 Hz, 4H), 1.69 – 1.47 (m, 12H), 1.42 – 1.20 (m, 44H), 0.89 (t,*J*= 6.8 Hz, 6H)<br><br>$^{13}$**C NMR** (CHLOROFORM-d, EW58397-317-P1B2): δ 173.9, 133.0, 124.3, 112.1, 76.1, 76.0, 70.0, 63.8, 59.4, 45.2, 45.2, 37.9, 31.9, 34.4, 29.5, 29.3, 29.6, 27.3, 26.9, 25.0, 24.0, 23.8, 23.7, 22.7, 14.1 |

FIGURE 1C (continued)

| | |
|---|---|
| 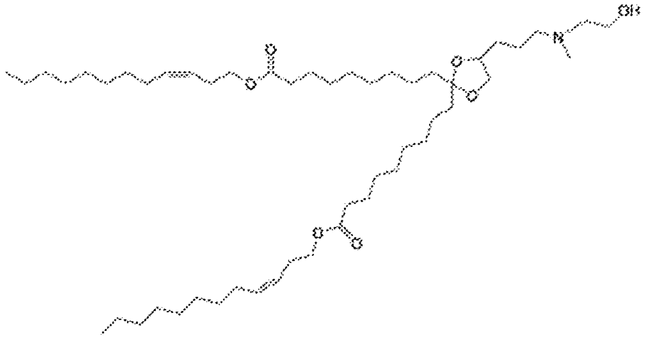<br>KC3A-X1-S | **$^1$H NMR** (400 MHz, CHLOROFORM-d, EW58311-363-P1A1) δ 5.56 - 5.44 (m, 2H), 5.39 - 5.29 (m, 2H), 4.11 - 4.00 (m, 6H), 3.63 (t, $J$ = 5.4 Hz, 2H), 3.50 - 3.41 (m, 1H), 2.60 (t, $J$ = 5.2 Hz, 2H), 2.52 (br t, $J$ = 6.8 Hz, 2H), 2.38 (q, $J$ = 6.8 Hz, 4H), 2.32 - 2.25 (m, 8H), 2.04 (q, $J$ = 7.0 Hz, 4H), 1.67 - 1.50 (m, 12H), 1.37 - 1.24 (m, 44H), 0.93 - 0.85 (m, 6H).<br>**$^{13}$C NMR** (CHLOROFORM-d EW58311-363-P1A3): δ 173.9, 132.9, 124.3, 112.2, 76.0, 69.9, 63.8, 58.8, 58.1, 57.5, 41.4, 37.8, 37.5, 34.4, 31.9, 31.0, 29.9, 29.9, 29.6, 29.5, 29.5, 29.3, 29.2, 29.2, 27.3, 26.9, 25.0, 24.0, 23.7, 23.3, 22.7, 14.1.<br>**LCMS** (EW58311-363-P1C1): CAD, m/z, $M+H^+$ = 834.9<br>**LCMS** (EW58311-363-P1C2): ELSD, m/z, $M+H^+$ = 835.0<br>**HRMS** (ESI) m/z: $[M + H]^+$ Calcd for $C_{51}H_{96}NO_7^+$ 834.7182, found 834.7202 |
| 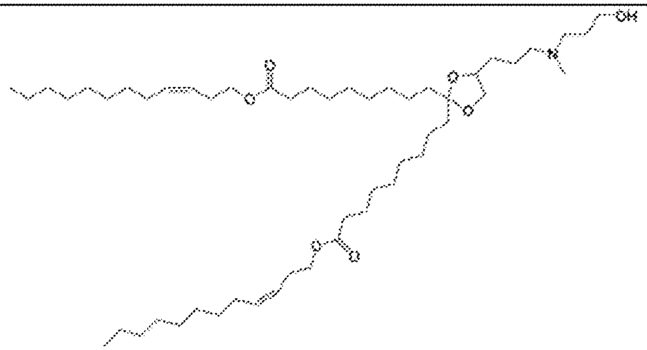<br>KC3B-X1-S | **$^1$H NMR** (400 MHz, CHLOROFORM-d EW53829-584-P1B) δ 5.57 - 5.45 (m, 2H), 5.40 - 5.29 (m, 2H), 4.14 - 3.97 (m, 6H), 3.80 (t, $J$ = 1.2 Hz, 2H), 3.51 - 3.40 (m, 1H), 2.68 (t, $J$ = 1.2 Hz, 2H), 2.49 (br t, $J$ = 6.8 Hz, 2H), 2.42 - 2.35 (m, 4H), 2.34 - 2.26 (m, 7H), 2.04 (q, $J$ = 6.8 Hz, 4H), 1.79 - 1.69 (m, 3H), 1.68 - 1.49 (m, $J$ = 7.2, 12.4 Hz, 12H), 1.40 - 1.22 (m, $J$ = 5.6 Hz, 45H), 0.89 (t, $J$ = 6.8 Hz, 6H)<br>**$^{13}$C NMR** (CHLOROFORM-d EW53829-584-P1B1): δ 173.9, 133.0, 124.3, 112.2, 76.0, 69.9, 64.0, 63.8, 57.9, 57.8, 41.6, 37.8, 37.5, 34.4, 31.9, 31.0, 29.9, 29.9, 29.6, 29.5, 29.5, 29.3, 29.2, 27.6, 27.3, 26.9, 25.0, 24.0, 23.7, 23.2, 22.7, 14.1<br>**LCMS** (EW53829-584-P1A1): CAD, m/z, $M+H^+$ = 848.9<br>**LCMS** (EW53829-584-P1A2): ELSD, m/z, $M+H^+$ = 849.0<br>**HRMS** (ESI) m/z: $[M + H]^+$ Calcd for $C_{52}H_{98}NO_7^+$ 848.7338, found 848.7358 |

FIGURE 1C (continued)

| | |
|---|---|
| 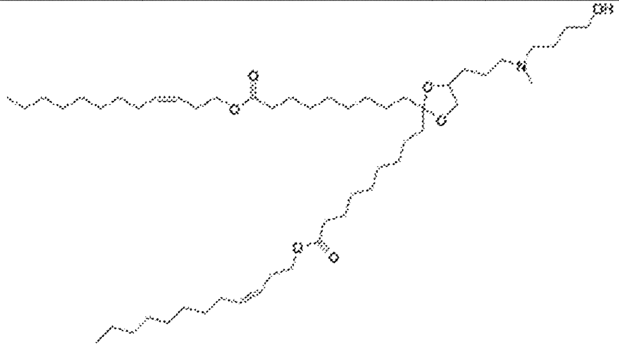<br>KC3C-X1-S | **$^1$H NMR** (400 MHz, CHLOROFORM-d EW53829-586-P1B2)δ 8.54 (s, 1H), 5.56 - 5.44 (m, 2H), 5.39 - 5.30 (m, 2H), 4.12 - 4.00 (m, *J* = 6.9, 6.9 Hz, 6H), 3.61 - 3.54 (m, 2H), 3.45 (t, *J* = 1.0 Hz, 1H), 2.50 - 2.42 (m, 4H), 2.41 - 2.34 (m, 4H), 2.33 - 2.26 (m, 7H), 2.08 - 1.98 (m, , 4H), 1.74 - 1.49 (m, 16H), 1.40 - 1.19 (m, 44H), 0.89 (t, *J* = 6.8 Hz, 6H)<br>**$^{13}$C NMR** (CHLOROFORM-d EW53829-586-P1B): δ 173.9, 133.0, 124.3, 112.2, 76.0, 69.9, 64.0, 63.8, 57.9, 57.8, 41.6, 37.8, 37.5, 34.4, 31.9, 31.0, 29.9, 29.9, 29.6, 29.5, 29.5, 29.3, 29.2, 27.6, 27.3, 26.9, 25.0, 24.0, 23.7, 23.2, 22.7, 14.1<br>**LCMS** (EW53829-586-P1A1): CAD, m/z, M+H$^+$ = 862.9<br>**LCMS** (EW53829-586-P1A2): ELSD, m/z, M+H$^+$ = 863.0<br>**HRMS** (ESI) m/z: $[M + H]^+$ Calcd for $C_{53}H_{100}NO_7^+$ 862.7495, found 862.7517 |
| 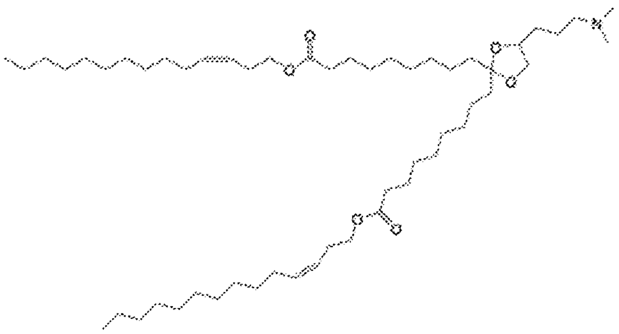<br>KC3-X1-Z | **LCMS** (EW58311-370-P1C1): CAD, m/z, M+H=861.0.<br><br>**HRMS** (ESI) *m/z*: $[M + H]^+$ Calcd for $C_{54}H_{102}NO_6^+$ 860.7702, found 860.7722.<br><br>**$^1$H NMR** (400 MHz, CHLOROFORM-d, EW58311-370-P1A1) δ 8.54 (s, 0.183 H, FA salt), 5.59 - 5.44 (m, 2H), 5.42 - 5.24 (m, 2H), 4.12 - 3.96 (m, 6H), 3.53 - 3.38 (m, 1H), 2.46 - 2.27 (m, 18H), 2.04 (q, *J* = 7.2 Hz, 4H), 1.70 - 1.50 (m, 12H), 1.36 - 1.23 (m, 50H), 0.89 (t, *J* = 6.8 Hz, 6H).<br><br>**$^{13}$C NMR** (CHLOROFORM-d, EW58311-P1A2) δ 173.9, 132.9, 124.3, 112.2, 75.9, 69.9, 63.8, 59.0, 44.7, 37.8, 37.5, 34.4, 31.9, 31.2, 29.9, 29.9, 29.6, 29.6, 29.5, 29.3, 29.3, 29.3, 29.2, 29.2, 27.3, 26.9, 25.0, 24.0, 23.7, 23.4, 22.7, 14.1. |

FIGURE 1C (continued)

| | |
|---|---|
| <br>KC4-X1-Z | $^1$H NMR (300 MHz, DMSO-d$_6$) δ 5.34 (m, 4H), 4.12 (t, J = 7.1 Hz, 4H), 3.87–3.62 (m, 3H), 2.46 (t, J = 7.1 Hz, 2H), 2.32 (t, J = 7.1 Hz, 4H), 2.24–2.15 (m, 12H), 2.15 (s, 6H), 1.66–1.51 (m, 8H), 1.38–1.21 (m, 40H), 0.88 (t, J = 8.0 Hz, 6H). |
| <br>KC3-X1-AA | $^1$H NMR (400 MHz, CHLOROFORM-d EW53829-581-P1A) δ 5.57 - 5.45 (m, 2H), 5.40 - 5.29 (m, 2H), 4.07 (t, *J* = 6.8 Hz, 6H), 3.50 - 3.42 (m, 1H), 2.38 (br d, *J* = 6.8 Hz, 6H), 2.33 - 2.26 (m, 10H), 2.04 (q, *J* = 6.8 Hz, 4H), 1.69 - 1.50 (m, 12H), 1.39 - 1.21 (m, 54H), 0.92 - 0.85 (m, 6H)<br><br>$^{13}$C NMR (CHLOROFORM-d EW53829-581-P1A1): δ 173.9, 132.9, 124.4, 112.2, 76.0, 69.9, 63.8, 59.4, 45.0, 45.0, 37.9, 37.5, 34.4, 31.2, 30.0, 30.0, 29.5, 29.5, 29.3, 29.2, 29.6, 26.9, 25.0, 24.1, 23.8, 22.7, 14.1<br><br>LCMS (EW53829-581-P1A): CAD, m/z, M+H$^+$=860.9<br>LCMS (EW53829-581-P1A1): ELSD, m/z, M+H$^+$=861.0<br>HRMS (ESI) m/z: $[M + H]^+$ Calcd for: $C_{54}H_{102}NO_6^+$ 860.7702, found 860.7731. |

| | |
|---|---|
|  KC2-X1-PH1 | LCMS (EW58397-293-P1A1): CAD, m/z, M+H$^+$=823.0.<br><br>HRMS (ESI) *m/z*: [M + H]$^+$ Calcd for $C_{51}H_{100}NO_6^+$ 822.7545, found 822.7576.<br><br>$^1$H NMR (400 MHz, CHLOROFORM-d, EW58397-293-P1A4) δ 4.15 - 4.02 (m, 6H), 3.48 (t, *J* = 7.2 Hz, 1H), 2.46 - 2.35 (m, 1H), 2.34 - 2.26 (m, 5H), 2.23 (s, 6H), 1.88 - 1.76 (m, 1H), 1.72 - 1.51 (m, 15H), 1.44 - 1.20 (m, 30H), 1.18 - 1.04 (m, 10H), 0.93 - 0.83 (m, 24H). |
|  KC3-X1-PH1 | LCMS (EW58311-197-P1C1): CAD, m/z, M+H$^+$=836.9<br><br>HRMS (ESI) m/z: [M + H]+ Calcd for $C_{52}H_{102}NO_6^+$ , 836.7702, found 836.7712<br><br>$^1$H NMR (400 MHz, CHLOROFORM-d, EW58311-197-P1A1) δ 4.15 - 4.02 (m, 6H), 3.50 - 3.43 (m, 1H), 2.34 - 2.28 (m, 6H), 2.24 (s, 6H), 1.74 - 1.50 (m, 20H), 1.49 - 1.20 (m, 34H), 1.19 - 1.03 (m, 11H), 0.95 - 0.82 (m, 26H). |

| | |
|---|---|
|  KC4-X1-PH1 | LCMS (EW58397-310-P1A1): CAD, m/z, M+H$^+$=851.0.<br>HRMS (ESI) *m/z*: [M + H]$^+$ Calcd for $C_{53}H_{104}NO_6^+$ 850.7858, found 850.7887.<br><br>$^1$H NMR (400 MHz, CHLOROFORM-d, EW58397-310-P1A1) δ 4.19 - 4.07 (m, 4H), 4.05 - 3.98 (m, 2H), 3.47 - 3.37 (m, 1H), 2.33 - 2.25 (m, 6H), 2.22 (s, 6H), 1.72 - 1.45 (m, 19H), 1.43 - 1.21 (m, 31H), 1.19 - 1.04 (m, 10H), 0. 93 - 0.82 (m, 24H). |
|  KC3-X1-PH2 | LCMS (EW58311-286-P1C1): CAD, m/z, M+H=752.9.<br><br>HRMS (ESI) *m/z*: [M + H]$^+$ Calcd for $C_{46}H_{90}NO_6^+$ 752.6763, found 752.6793.<br><br>$^1$H NMR (400 MHz, CHLOROFORM-d, EW58311-286-P1A1) δ 4.17 - 4.02 (m, 6H), 3.52 - 3.42 (m, 1H), 2.35 - 2.28 (m, 6H), 2.25 (s, 6H), 1.78 (br s, 3H), 1.71 - 1.51 (m, 16H), 1.44 - 1.26 (m, 27H), 1.19 - 1.05 (m, 6H), 0.95 - 0.82 (m, 18H). |

| | |
|---|---|
|  KC3-X1-PH3 | LCMS (EW58311-200-P1C1): CAD, m/z, M+H=780.9.<br><br>HRMS (ESI) *m/z*: $[M + H]^+$ Calcd for $C_{48}H_{94}NO_6^+$ 780.7076, found 780.7104.<br><br>$^1$H NMR (400 MHz, CHLOROFORM-d) δ 4.09 - 3.92 (m, 6H), 3.44 - 3.30 (m, 1H), 2.27 - 2.18 (m, 6H), 2.15 (s, 6H), 1.63 - 1.41 (m, 18H), 1.39 - 1.25 (m, 10H), 1.24 - 1.14 (m, 12H), 1.10 - 0.96 (m, 10H), 0.84 - 0. 75 (m, 24H) |
|  KC2-X1-PH4 | LCMS (EW58397-306-P1A1): CAD, m/z, $M+H^+$=907.1.<br>HRMS (ESI) *m/z*: $[M + H]^+$ Calcd for $C_{57}H_{112}NO_6^+$ 906.8484, found 906.8516.<br><br>$^1$H NMR (400 MHz, CHLOROFORM-d, EW58397-306-P1A1) δ 4.15 - 4.01 (m, 6H), 3.52 - 3.42 (m, 1H), 2.44 - 2.35 (m, 1H), 2.30 (br t, *J* = 7.6 Hz, 5H), 2.24 (s, 6H), 1.86 - 1.75 (m, 1H), 1.71 - 1.49 (m, 17H), 1.44 - 1.33 (m, 11H), 1.29 - 1.21 (m, 17H), 1.18 - 1.01 (m, 15H), 0.92 - 0.81 (m, 30H) |

| | |
|---|---|
| <br>KC3-X1-PH4 | $^1$H NMR (400 MHz, CHLOROFORM-d, EW53829-441-P1A) δ 4.17 - 3.99 (m, 6H), 3.44 (t, *J* = 7.2 Hz, 1H), 2.35 - 2.26 (m, 6H), 2.23 (s, 6H), 1.71 - 1.48 (m, 18H), 1.47 - 1.18 (m, 34H), 1.17 - 1.00 (m, 15H), 0.93 - 0.82 (m, 31H)<br><br>LCMS (EW58397-441-P1B): CAD, m/z, M+H=921.1<br><br>LCMS (EW58397-25-P1A): ELSD, m/z, M+H=921.1<br><br>HRMS (ESI) *m/z*: $[M + H]^+$ Calcd for $C_{58}H_{114}NO_6^+$ 920.8641, found 920.8646. |
| <br>KC4-X1-PH4 | LCMS (EW58397-321-P1A1): CAD, m/z, $M + H^+ = 935.1$.<br><br>HRMS (ESI) *m/z*: $[M + H]^+$ Calcd for $C_{59}H_{116}NO_6^+$ 934.8797, found 934.8825.<br><br>$^1$H NMR (400 MHz, CHLOROFORM-d, EW58397-321-P1A2) δ 4.15 - 4.06 (m, 4H), 4.06 - 3.99 (m, 2H), 3.46 - 3.38 (m, 1H), 2.33 - 2.25 (m, 6H), 2.22 (s, 6H), 1.70 - 1.00 (m, 72H), 0.93 - 0.83 (m, 32H) |

| | |
|---|---|
|  KC3-X1-PH5 | LCMS (EW58311-226-P1C1): CAD, m/z, M+H=865.0.<br><br>HRMS (ESI) *m/z*: $[M + H]^+$ Calcd for $C_{54}H_{106}NO_6^+$ 864.8015, found 864.8044.<br><br>$^1$H NMR (400 MHz, CHLOROFORM-d, EW58311-226-P1A1) δ 4.20 - 3.98 (m, 6H), 3.52 - 3.41 (m, 1H), 2.35 - 2.17 (m, 12H), 1.75 - 1.49 (m, 18H), 1.48 - 1.20 (m, 34H), 1.19 - 0.98 (m, 10H), 0.95 - 0.83 (m, 24H). |
|  KC4-X1-PH4 | LCMS (EW58311-383-P1C1): CAD, m/z, M+H=879.1.<br>HRMS (ESI) *m/z*: $[M + H]^+$ Calcd for $C_{55}H_{108}NO_6^+$ 878.8171, found 878.8173.<br><br>$^1$H NMR (400 MHz, CHLOROFORM-d, EW58311-383-P1A1) δ 4.17 - 3.99 (m, 6H), 3.54 - 3.34 (m, 1H), 2.35 - 2.17 (m, 12H), 1.69 - 1.44 (m, 24H), 1.38 - 1.23 (m, 30H), 1.17 - 1.03 (m, 10H), 0.94 - 0.82 (m, 24H). |

| | |
|---|---|
| <br>KC2-X1-PH6 | $^{1}$H NMR (400 MHz, CHLOROFORM-d EW58397-406-P1A2) δ 4.21 - 3.95 (m, 6H), 3.48 (t, *J* = 7.2 Hz, 1H), 2.47 - 2.36 (m, 1H), 2.29 (t, *J* = 7.6 Hz, 5H), 2.23 (s, 6H), 1.88 - 1.76 (m, 1H), 1.73 - 1.50 (m, 19H), 1.43 - 1.21 (m, 34H), 1.18 - 1.00 (m, 10H), 0.95 - 0.79 (m, 24H)<br>LCMS (EW58397-406-P1A1): CAD, m/z, M + $H^+$ = 879.0<br>LCMS (EW58397-406-P1A2): ELSD, m/z, M + $H^+$ = 879.1<br>HRMS (ESI) *m/z*: $[M + H]^+$ Calcd for: $C_{55}H_{108}NO_6^+$ 878.8172, found 878.8174 |

| | |
|---|---|
| <br>KC3-X1-PH6 | LCMS (EW58397-333-P1A1): CAD, m/z, $M+H^+$=893.0.<br><br>HRMS (ESI) *m/z*: $[M + H]^+$ Calcd for $C_{56}H_{110}NO_6^+$ 892.8328, found 892.8357.<br><br>$^1$H NMR (400 MHz, CHLOROFORM-d, EW58397-333-P1A2) δ 4.16 - 4.00 (m, 6H), 3.52 - 3.40 (m, 1H), 2.29 (t, *J* = 7.6 Hz, 6H), 2.23 (s, 6H), 1.71 - 1.48 (m, 19H), 1.42 - 1.21 (m, 37H), 1.18 - 1.04 (m, 10H), 0.95 - 0.81 (m, 24H) |

| | |
|---|---|
|  KC4-X1-PH6 | $^1$H NMR (400 MHz, CHLOROFORM-d, EW58397-405-P1A4) δ 4.23 - 3.96 (m, 6H), 3.49 - 3.39 (m, 1H), 2.33 - 2.24 (m, 6H), 2.22 (s, 6H), 1.71 - 1.44 (m, 22H), 1.38 - 1.23 (m, 36H), 1.19 - 1.04 (m, 10H), 0.94 - 0.82 (m, 24H)<br><br>LCMS (EW58397-405-P1B1): CAD, m/z, M + H$^+$ = 907.0<br><br>LCMS (EW58397-405-P1B2): ELSD, m/z, M + H$^+$ = 907.1<br>HRMS (ESI) *m/z*: $[M + H]^+$ Calcd for: $C_{57}H_{112}NO_6^+$ 906.8485, found 906.8505 |

| | |
|---|---|
|  KC3-X1-PH7 | LCMS (EW58311-326-P1C1): CAD, m/z, M+H=808.9.<br><br>HRMS (ESI) *m/z*: $[M + H]^+$ Calcd for $C_{50}H_{98}NO_6^+$ 808.7389, found 808.7413.<br><br>$^1$H NMR (400 MHz, CHLOROFORM-d, EW58311-326-P1A1) δ 8.48 (s, 0.141H, FA salt), 4.04 - 3.93 (m, 6H), 3.43 - 3.34 (m, 1H), 2.32 (br t, *J* = 7.2 Hz, 2H), 2.24 - 2.11 (m, 12H), 1.60 - 1.42 (m, 18H), 1.31 - 1.16 (m, 32H), 1.10 - 0.97 (m, 8H), 0.84 - 0.75 (m, 18H). |
|  KC3-X1-PH8 | LCMS (EW58311-328-P1C1): CAD, m/z, M+H=959.1.<br><br>HRMS (ESI) *m/z*: $[M + H]^+$ Calcd for $C_{60}H_{118}NO_6^+$ 948.8954, found 948.8976.<br><br>$^1$H NMR (400 MHz, CHLOROFORM-d, EW58311-328-P1A1) δ 4.09 - 3.94 (m, 6H), 3.45 - 3.35 (m, 1H), 2.26 - 2.19 (m, 6H), 2.16 (s, 6H), 1.64 - 1.42 (m, 20H), 1.41 - 1.18 (m, 49H), 1.10 - 0.96 (m, 10H), 0.86 - 0.76 (m, 24H). |

| | |
|---|---|
| 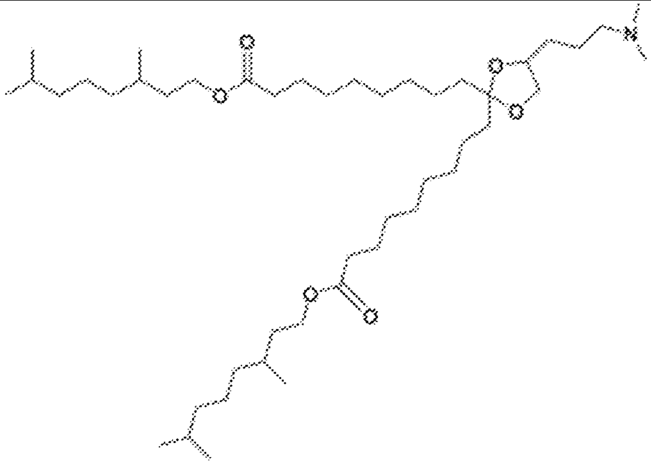 KC3-X1-PH9 | **Special MS** (EW53829-526-P1A2): CAD, m/z, M + $H^+$ = 752.9.<br><br>**Special MS** (EW53829-526-P1A1): ELSD, m/z, M + $H^+$ = 752.9.<br><br>**HRMS** (ESI) *m/z*: $[M + H]^+$ Calcd for: $C_{46}H_{90}NO_6^+$ 752.6763, found 752.6792.<br><br>**$^1$H NMR** (400 MHz, CHLOROFORM-d EW53829-526-P1A) δ 4.18 - 3.98 (m, 6H), 3.46 (t, *J* = 7.2 Hz, 1H), 2.28 (t, *J* = 7.6 Hz, 6H), 2.22 (s, 6H), 1.72 - 1.49 (m, 17H), 1.48 - 1.39 (m, 3H), 1.38 - 1.22 (m, 26H), 1.20 - 1.10 (m, 6H), 0.92 - 0.84 (m, 18H) |
| 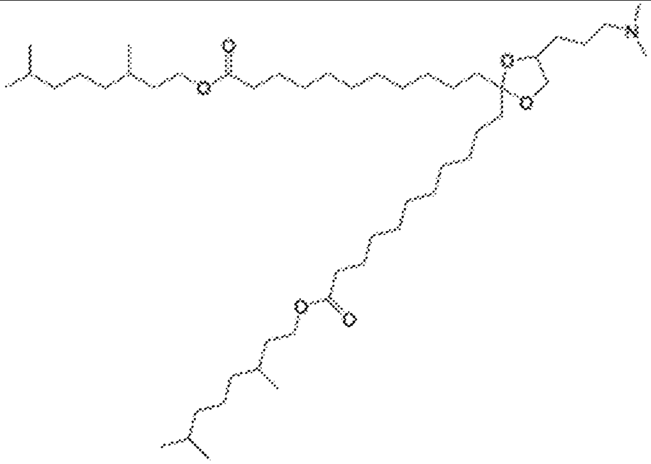 KC3-X1-PH10 | **$^1$H NMR** (400 MHz, CHLOROFORM-d EW53829-549-P1A1) δ 4.18 - 3.97 (m, 6H), 3.46 (t, *J* = 7.2 Hz, 1H), 2.29 (t, *J* = 7.6 Hz, 6H), 2.23 (s, 6H), 1.71 - 1.39 (m, 21H), 1.38 - 1.22 (m, 34H), 1.19 - 1.09 (m, 6H), 0.93 - 0.85 (m, 18H)<br><br>**Special MS** (EW53829-549-P1A): CAD, m/z, M + $H^+$ = 808.9<br><br>**Special MS** (EW53829-549-P1A1): ELSD, m/z, M + $H^+$ = 808.9<br><br>**HRMS** (ESI) m/z: $[M + H]^+$ Calcd for: $C_{50}H_{98}NO_6^+$ 808.7389, found 808.7415. . |

FIGURE 1C (continued)

| | |
|---|---|
| <br>KC3-X1-PH11 | LCMS (EW58397-361-P1C1): CAD, m/z, M + $H^+$ = 949.1.<br>HRMS (ESI) *m/z*: $[M + H]^+$ Calcd for $C_{60}H_{118}NO_6^+$ 948.8954, found 948.8982.<br><br>$^1$H NMR (400 MHz, CHLOROFORM-d, EW58397-361-P1A2) δ 8.54 (s, 0.118 eq FA salt), 4.14 - 3.91 (m, 6H), 3.46 (t, *J* = 7.2 Hz, 1H), 2.39 (t, *J* = 7.2 Hz, 2H), 2.35 - 2.23 (m, 10H), 1.69 - 1.46 (m, 19H), 1.44 - 1.19 (m, 44H), 1.18 - 0.99 (m, 12H), 0.91 - 0.79 (m, 24H). |
| <br>KC3-X1-PH12 | LCMS (EW58311-340-P1C1): CAD, m/z, M+H=865.0.<br><br>HRMS (ESI) *m/z*: $[M + H]^+$ Calcd for $C_{54}H_{106}NO_6^+$ 864.8015, found 864.8044.<br><br>$^1$H NMR (400 MHz, CHLOROFORM-d, EW58311-340-P1A1) δ 8.55 (s, 0.094H, FA salt), 4.15 - 3.98 (m, 6H), 3.52 - 3.40 (m, 1H), 2.36 (br t, *J* = 7.2 Hz, 2H), 2.32 - 2.26 (m, 10H), 1.67 - 1.47 (m, 18H), 1.41 - 1.19 (m, 39H), 1.16 - 1.00 (m, 8H), 0.93 - 0.76 (m, 18H). |

| | |
|---|---|
| 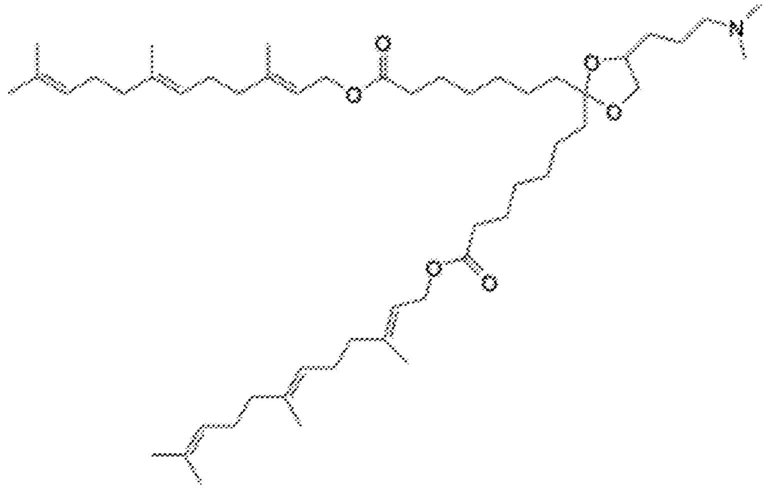<br>KC3-X1-PH1B | **LCMS** (EW58397-65-P1A1): CAD, m/z, M+H$^+$=824.8.<br><br>**HRMS** (ESI) *m/z*: [M + H]$^+$ Calcd for $C_{52}H_{90}NO_6^+$ 824.6763, found 824.6788.<br><br>**$^1$H NMR** (400 MHz, CHLOROFORM-d) δ 5.35 (br t, *J* = 7.2 Hz, 2H), 5.16 - 5.04 (m, 4H), 4.59 (d, *J* = 7.2 Hz, 4H), 4.10 - 4.01 (m, 2H), 3.49 - 3.42 (m, 1H), 2.30 (t, *J* = 7.6 Hz, 6H), 2.23 (s, 6H), 2.17 - 2.02 (m, 13H), 2.02 - 1.95 (m, 4H), 1.70 (d, *J* = 9.6 Hz, 13H), 1.66 - 1.43 (m, 21H), 1.31 (br d, *J* = 2.0 Hz, 13H).<br>**$^{13}$C NMR** (CHLOROFORM-d): δ 173.9, 142.1, 135.5, 131.3, 124.3, 123.7, 118.5, 112.0, 77.2, 76.2, 70.0, 61.2, 59.6, 45.4, 39.7, 39.6, 37.8, 37.5, 34.4, 31.3, 29.6, 29.2, 29.2, 26.7, 26.2, 25.7, 25.0, 25.0, 24.0, 23.9, 23.6, 17.7, 16.5, 16.0. |
| 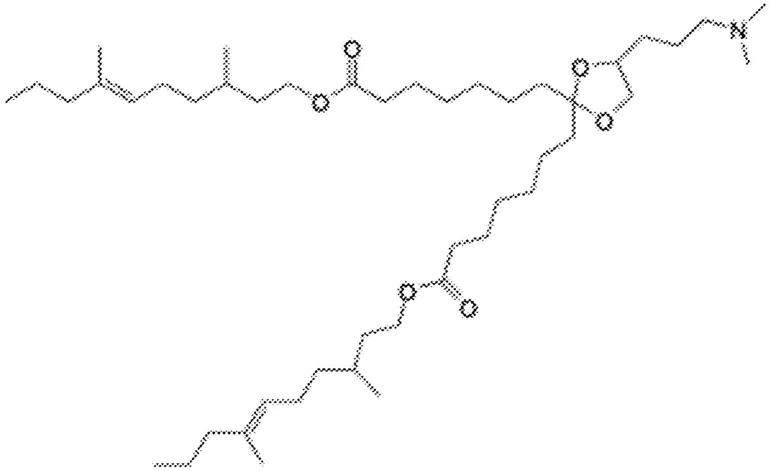<br>KC3-X1-PH2B | **LCMS** (EW58311-266-P1C1): CAD, m/z, M+H=748.8.<br>**HRMS** (ESI) *m/z*: [M + H]$^+$ Calcd for $C_{46}H_{86}NO_6^+$ 748.6450, found 748.6482.<br>**$^1$H NMR** (400 MHz, CHLOROFORM- d, EW58311-266-P1B1) δ 8.48 (s, 0.056H, FA salt), 5.02 (br t, *J* = 6.8 Hz, 2H), 4.10 - 3.93 (m, 6H), 3.43 - 3.35 (m, 1H), 2.31 (br t, *J* = 7.2 Hz, 2H), 2.26 - 2.16 (m, 10H), 2.00 - 1.83 (m, 8H), 1.64 - 1.43 (m, 22H), 1.40 - 1.23 (m, 19H), 1.17 - 1.07 (m, 2H), 0.88 - 0.75 (m, 12H). |

FIGURE 1C (continued)

| | |
|---|---|
| 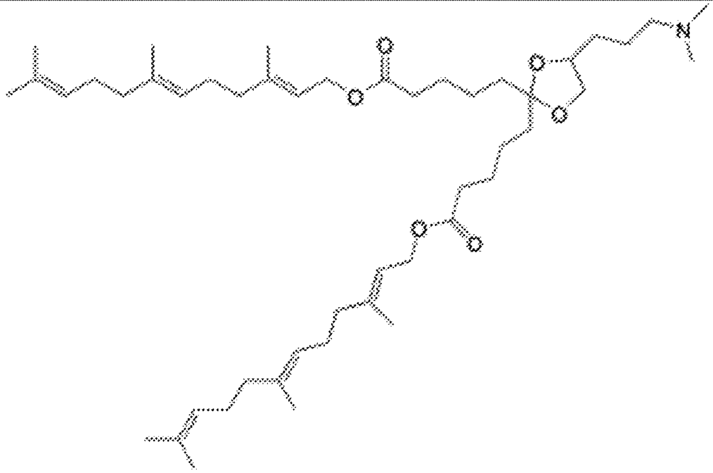<br>KC3-X1-PH3B | **LCMS** (EW58397-221-P1A4): CAD, m/z, M+H$^+$=768.8<br><br>**HRMS** (ESI) *m/z*: [M + H]$^+$ Calcd for $C_{48}H_{82}NO_6^+$ 768.6137, found 768.6164<br><br>**$^1$H NMR** (400 MHz, CHLOROFORM-d, EW58397-221-P1A2) δ 5.34 (br t, *J* = 7.2 Hz, 2H), 5.14-5.03 (m, 4H), 4.59 (d, *J* = 7.2 Hz, 4H), 4.12 - 3.94 (m, 2H), 3.53 - 3.36 (m, 1H), 2.35 - 2.26 (m, 6H), 2.22 (s, 6H), 2.16 - 2.02 (m, 12H), 2.01 - 1.93 (m, 4H), 1.69 (d, *J* = 9.2 Hz, 12H), 1.66 - 1.55 (m, 21H), 1.53 - 1.30 (m, 6H).<br><br>**$^{13}$C NMR** (CHLOROFORM-d, EW58397-221-P1A3) δ 173.68, 173.68, 142.15, 142.15, 135.46, 131.33, 124.34, 123.67, 118.41, 111.60, 70.02, 61.26, 59.58, 45.42, 39.72, 39.57, 37.44, 37.14, 34.38, 34.38, 31.28, 26.74, 26.25, 25.72, 25.26, 24.02, 23.64, 23.31, 17.71, 16.51, 16.05 |
| 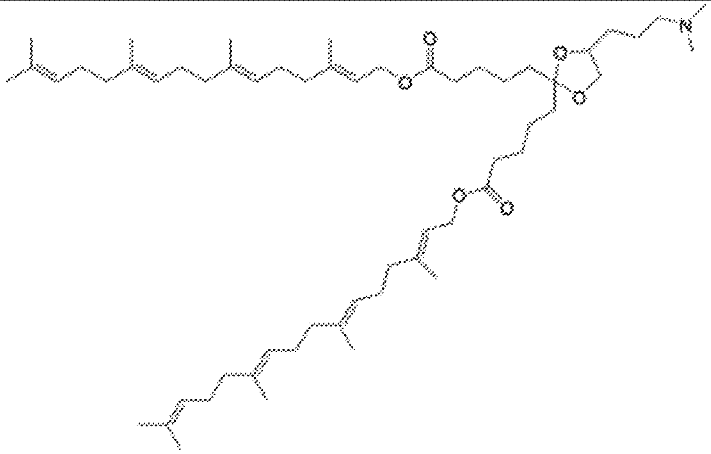<br>KC3-X1-PH4B | **LCMS** (EW58311-211-P1C1): CAD, m/z, M+H=905.0.<br><br>**HRMS** (ESI) *m/z*: [M + H]$^+$ Calcd for $C_{58}H_{98}NO_6^+$ 904.7389, found 904.7421.<br><br>**$^1$H NMR** (400 MHz, CHLOROFORM-d, EW58311-211-P1A1) δ 27 (br t, *J* = 6.8 Hz, 2H), 5.03 (br s, 6H), 4.51 (d, *J* = 7.2 Hz, 4H), 4.01 - 3.91 (m, 2H), 3.40 - 3.33 (m, 1H), 2.27 - 2.19 (m, 6H), 2.15 (s, 6H), 2.07 - 1.88 (m, 24H), 1.62 (d, *J* = 8.4 Hz, 12H), 1.58 - 1.49 (m, 27H), 1.38 - 1.18 (m, 6H), 0.82 - 0.73 (m, 1H)<br>**$^{13}$C NMR** (CHLOROFORM-d): δ 173.7, 142.2, 135.5, 135.0, 131.3, 124.4, 124.2, 123.7, 118.4, 111.6, 70.0, 61.2, 59.6, 45.4, 39.7, 39.7, 39.6, 37.1, 34.4, 34.3, 26.8, 26.6, 26.3, 25.7, 25.2, 24.0, 23.6, 23.3, 17.7, 16.5, 16.0 |

FIGURE 1C (continued)

| | |
|---|---|
| <br>KC3-X1-PH5B | $^{1}$H NMR (400 MHz, CHLOROFORM-d, EW53829-451-P1A) δ 5.35 (br t, *J* = 7.2 Hz, 2H), 5.10 (br s, 4H), 4.59 (d, *J* = 7.2 Hz, 4H), 4.12 - 3.98 (m, 2H), 3.50 - 3.41 (m, 1H), 2.30 (t, *J* = 7.6 Hz, 6H), 2.22 (s, 6H), 2.16 - 2.02 (m, 12H), 1.99 (br d, *J* = 8.4 Hz, 4H), 1.70 (d, *J* = 10.0 Hz, 12H), 1.66 - 1.42 (m, 22H), 1.42-1.20 (m, 16H)<br><br>$^{13}$C NMR (CHLOROFORM-d, EW53829-454-P1A): δ 173.9, 142.1, 135.5, 131.3, 124.3, 123.7, 118.5, 112.0, 70.0, 61.2, 59.7, 45.5, 39.7, 39.6, 37.8, 34.4, 29.3, 29.5, 26.7, 26.2, 25.7, 25.0, 24.0, 24.0, 23.7, 17.7, 16.5, 16.0<br><br>HRMS (EW53829-454-P1B , ESI+) *m/z*: $[M + H]^+$ Calcd for $C_{54}H_{94}NO_6^+$ 852.7076, found 852.7103.<br>Special LCMS (EW58397-454-P1A): CAD, m/z, M+H=852.9<br>Special LCMS (EW58397-454-P1A1): ELSD, m/z, M+H=852.9 |

Scheme 3

Scheme 4

1
2
3
4
5
6

7

KC3-X2-PH12

| Compound | Analytical Characterization |
| --- | --- |
|  KC3-X2-PH6 | LCMS (EW58397-469-P1C1): CAD, m/z, $M+H^+$=808.9. HRMS (ESI) *m/z*: $[M + H]^+$ Calcd for $C_{50}H_{98}NO_6^+$ 808.7389, found 808.7411. $^1$H NMR (400 MHz, CHLOROFORM-d, EW58397-469-P1A1) δ 4.15 - 3.96 (m, 6H), 3.52 - 3.39 (m, 1H), 2.36 - 2.22 (m, 10H), 2.14 - 2.05 (m, 2H), 2.00 - 1.90 (m, 2H), 1.68 - 1.44 (m, 14H), 1.40 - 1.02 (m, 38H), 0.93 (d, *J* = 6.8 Hz, 6H), 0.89 - 0.81 (m, 18H) |
|  KC3-X2-PH7 | $^1$H NMR (400 MHz, CHLOROFORM-d, EW53829-706-P1A) δ4.06 (t, *J* = 6.8 Hz, 6H), 3.46 (t, *J* = 1.2 Hz, 1H), 2.38 (t, *J* = 1.2 Hz, 2H), 2.34 - 2.26 (m, 8H), 2.15 - 2.06 (m, 2H), 1.94 (m, 6H), 1.69 - 1.46 (m, 12H), 1.45 - 1.02 (m, 40H), 0.94 (d, *J* = 6.8 Hz, 6H), 0.90 - 0.82 (m, 18H)<br>LCMS (EW53829-706-P1A): CAD, m/z, $M+H^+$= 837.0<br>HRMS (ESI) m/z: $[M + H]^+$ Calcd for $C_{52}H_{102}NO_6^+$ 836.7702, found 836.7725 |

| | |
|---|---|
|  KC3-X2-PH8 | LCMS (EW58397-430-P1A2): CAD, m/z, M+H$^+$=865.0 . HRMS (ESI) *m/z*: [M + H]$^+$ Calcd for $C_{54}H_{106}NO_6^+$ 864.8015, found 864.8026. $^1$H NMR (400 MHz, CHLOROFORM-d) δ 4.12 - 3.98 (m, 6H), 3.50 - 3.41 (m, 1H), 2.34 - 2.25 (m, 4H), 2.22 (s, 6H), 2.15 - 2.04 (m, 2H), 2.01 - 1.89 (m, 2H), 1.66 - 1.47 (m, 14H), 1.40 - 1.20 (m, 36H), 1.18 - 1.02 (m, 10H), 0.93 (d, J = 6.6 Hz, 6H), 0.89 - 0.81 (m, 18H) |
|  KC3-X2-PH9 | $^1$H NMR (400 MHz, CHLOROFORM-d EW53829-630-P1B1) δ 4.06 (t, *J* = 6.8 Hz, 6H), 3.46 (t, *J* = 1.2 Hz, 1H), 2.34 - 2.26 (m, 4H), 2.23 (s, 6H), 2.15 - 2.07 (m, 2H), 2.01 - 1.89 (m, 2H), 1.71 - 1.46 (m, 16H), 1.43 - 1.21 (m, 38H), 1.16 (m, 10H), 0.94 (d, *J* = 6.8 Hz, 6H), 0.90 - 0.82 (m, 18H) LCMS (EW53829-630-P1A): CAD, m/z, M+H$^+$ = 893.0 LCMS (EW53829-630-P1B1): ELSD, m/z, M+H$^+$ = 893.1 HRMS (ESI) m/z: [M + H]$^+$ Calcd for: $C_{56}H_{110}NO_6^+$, 892.8328, found 892.8345 |

| | |
|---|---|
| <br>KC3-X2-PH10 | LCMS (EW58397-482-P1B1): CAD, m/z, M+H$^+$=809.0.<br>HRMS (ESI) *m/z*: [M + H]$^+$ Calcd for $C_{50}H_{98}NO_6^+$ 808.7389, found 808.7406.<br>$^1$H NMR (400 MHz, CHLOROFORM-d) δ 4.06 (t, *J* = 6.8 Hz, 6H), 3.52 - 3.40 (m, 1H), 2.35 - 2.26 (m, 6H), 2.23 (s, 6H), 1.66 - 1.46 (m, 18H), 1.45 - 1.19 (m, 34H), 1.17 - 1.02 (m, 8H), 0.91 - 0.80 (m, 18H) |
| <br>KC3-X2-PH11 | $^1$H NMR (400 MHz, CHLOROFORM-d EW53829-721-P1A1) δ 4.12 - 4.02 (m, 6H), 3.46 (t, *J* = 1.2 Hz, 1H), 2.41 (t, *J* = 7.2 Hz, 2H), 2.34 - 2.27 (m, 10H), 1.70 - 1.47 (m, 18H), 1.45 - 1.19 (m, 38H), 1.18 - 1.00 (m, 8H), 0.94 - 0.78 (m, 18H)<br>LCMS (EW53829-721-P1A): CAD, m/z, M+H$^+$ = 837.0<br>HRMS (ESI) m/z: [M + H]$^+$ Calcd for $C_{52}H_{102}NO_6^+$ 836.7702, found 836.7691 |

| | |
|---|---|
| <br>KC3-X2-PH12 | LCMS (EW58311-481-P1C1): CAD, m/z, M+H=865.0.<br><br>HRMS (ESI) *m/z*: $[M + H]^+$ Calcd for $C_{54}H_{106}NO_6^+$ 864.8015, found 864.8032.<br><br>$^1$H NMR (400 MHz, CHLOROFORM-d, EW58311-481-P1A1) δ 4.13 - 3.99 (m, 6H), 3.52 - 3.40 (m, 1H), 2.44 - 2.21 (m, 12H), 1.67 - 1.48 (m, 18H), 1.39 - 1.19 (m, 42H), 1.17 - 1.04 (m, 8H), 0.92 - 0.82 (m, 18H). |
| <br>KC3-X2-K | LCMS (EW58311-348-P1C1): CAD, m/z, $M + H^+ = 808.9$.<br><br>HRMS (ESI) *m/z*: $[M + H]^+$ Calcd for $C_{50}H_{98}NO_6^+$ 808.7389, found 808.7417.<br><br>$^1$H NMR (400 MHz, CHLOROFORM-d, EW58311-348-P1A1) δ 4.10 - 4.02 (m, 6H), 3.46 (t, $J$ = 7.2 Hz, 1H), 2.43 - 2.20 (m, 12H), 1.64 - 1.55 (m, 24H), 1.32 - 1.25 (m, 48H), 0.89 (t, $J$ = 6.8 Hz, 6H). |

| | |
|---|---|
|  KC3-X2-R | LCMS (EW58311-351-P1C1): CAD, m/z, M + H$^+$ = 865.0.<br><br>HRMS (ESI) *m/z*: [M + H]$^+$ Calcd for $C_{54}H_{106}NO_6^+$ 864.8015, found 864.8048.<br><br>$^1$H NMR (400 MHz, CHLOROFORM-d, EW58311-315-P1A1) δ 4.05 (t, *J* = 6.8 Hz, 6H), 3.49 - 3.42 (m, 1H), 2.52 (br s, 2H), 2.41 (br s, 6H), 2.29 (t, *J* = 7.6 Hz, 4H), 1.75 - 1.53 (m, 16H), 1.41 - 1.21 (m, 64H), 0.89 (t, *J* = 6.8 Hz, 6H). |
|  KC3-X2-R9 | $^1$H NMR (400 MHz, CHLOROFORM-d EW53829-617-P1A) δ 4.13 – 3.97 (m, 6H), 3.46 (t, *J* = 6.8 Hz, 1H), 2.37 - 2.21 (m, 12H), 1.62 (m, 18H), 1.38 - 1.22 (m, 62H), 0.89 (t, *J* = 7.2 Hz, 6H)<br><br>LCMS (EW53829-617-P1A): CAD, m/z, M + H$^+$ = 865.0<br>LCMS (EW53829-617-P1A1): ELSD, m/z, M + H$^+$ = 865.0<br><br>HRMS (ESI) *m/z*: [M + H]$^+$ Calcd for: $C_{54}H_{106}NO_6^+$ 864.8015, found 864.8041 |

| | |
|---|---|
|  KC3-X2-S9 | $^1$H NMR (400 MHz, CHLOROFORM-d, EW53829-691-P1A) δ 5.47 - 5.38 (m, 2H), 5.37 - 5.29 (m, 2H), 4.10 - 4.00 (m, 6H), 3.46 (t, *J* = 1.2 Hz, 1H), 2.39 - 2.30 (m, 10H), 2.24 (s, 6H), 2.04 (q, *J* = 6.8 Hz, 4H), 1.68 - 1.50 (m, 12H), 1.39 - 1.23 (m, 48H), 0.92 - 0.85 (m, 6H)<br><br>$^{13}$C NMR (CHLOROFORM-d EW53829-691-P1A2): δ 173.4, 131.5, 127.4, 112.1, 77.2, 76.1, 69.9, 64.5, 59.5, 45.3, 37.8, 37.5, 34.5, 31.9, 31.3, 29.9, 29.9, 29.6, 29.6, 29.5, 29.3, 29.3, 29.3, 28.7, 27.2, 25.9, 24.0, 23.9, 23.7, 22.9, 22.7, 14.1<br><br>LCMS (EW53829-691-P1A): CAD, m/z, $M+H^+$ = 832.9<br>LCMS (EW53829-691-P1B): ELSD, m/z, $M+H^+$ = 835.0<br>HRMS (ESI) m/z: $[M + H]^+$ Calcd for: $C_{52}H_{98}NO_6^+$ 832.7389, found 832.7400 |

FIGURE 3A

| Name | R1, R2 | Z | X1, X2 | A1, A2 | Y1, Y2 |
|---|---|---|---|---|---|
| KC2-OA-C | -CH3 | $-(CH_2)_2-$ | $-(CH_2)_2-$ | -C(=O)-O- | $-(CH_2)_8-CH=CH-(CH_2)_8-H$ |
| KC2-X1 | -CH3 | $-(CH_2)_2-$ | $-(CH_2)_4-$ | -C(=O)-O- | $-(CH_2)_2-CH=CH-(CH_2)_8-H$ |
| KC2-X1-G | -CH3 | $-(CH_2)_2-$ | $-(CH_2)_7-$ | -C(=O)-O- | $-(CH_2)_{11}-H$ |
| KC2-X1-H | -CH3 | $-(CH_2)_2-$ | $-(CH_2)_7-$ | -C(=O)-O- | $-(CH_2)_2-CH=CH-(CH_2)_7-H$ |
| KC2-X1-K | -CH3 | $-(CH_2)_2-$ | $-(CH_2)_8-$ | -C(=O)-O- | $-(CH_2)_{12}-H$ |
| KC2-X2 | -CH3 | $-(CH_2)_2-$ | $-(CH_2)_3-$ | -O-C(=O)- | $-(CH_2)_2-CH=CH-(CH_2)_9-H$ |
| KC3-HA-A | -CH3 | $-(CH_2)_3-$ | $-(CH_2)_2-$ | -C(=O)-O- | $-(CH_2)_{16}-H$ |
| KC3-OA-A | -CH3 | $-(CH_2)_3-$ | $-(CH_2)_1-$ | -O-C(=O)- | $-(CH_2)_7-CH=CH-(CH_2)_8-H$ |
| KC3-OA-B | -CH3 | $-(CH_2)_3-$ | $-(CH_2)_1-$ | -C(=O)-O- | $-(CH_2)_8-CH=CH-(CH_2)_8-H$ |
| KC3-OA-C | -CH3 | $-(CH_2)_3-$ | $-(CH_2)_2-$ | -C(=O)-O- | $-(CH_2)_8-CH=CH-(CH_2)_8-H$ |
| KC3-PA-A | -CH3 | $-(CH_2)_3-$ | $-(CH_2)_2-$ | -C(=O)-O- | $-(CH_2)_8-CH=CH-(CH_2)_6-H$ |
| KC3-X1 | -CH3 | $-(CH_2)_3-$ | $-(CH_2)_7-$ | -C(=O)-O- | $-(CH_2)_9-H$ |
| KC3-X1-A | -CH3 | $-(CH_2)_3-$ | $-(CH_2)_4-$ | -C(=O)-O- | $-(CH_2)_{12}-H$ |
| KC3-X1-B | -CH3 | $-(CH_2)_3-$ | $-(CH_2)_6-$ | -C(=O)-O- | $-(CH_2)_{10}-H$ |
| KC3-X1-C | -CH3 | $-(CH_2)_3-$ | $-(CH_2)_4-$ | -C(=O)-O- | $-(CH_2)_2-CH=CH-(CH_2)_8-H$ |
| KC3-X1-D | -CH3 | $-(CH_2)_3-$ | $-(CH_2)_6-$ | -C(=O)-O- | $-(CH_2)_2-CH=CH-(CH_2)_6-H$ |
| KC3-X1-E | -CH3 | $-(CH_2)_3-$ | $-(CH_2)_6-$ | -C(=O)-O- | $-(CH_2)_2-CH=CH-(CH_2)_8-H$ |
| KC3-X1-F | -CH3 | $-(CH_2)_3-$ | $-(CH_2)_6-$ | -C(=O)-O- | $-(CH_2)_2-CH=CH-(CH_2)_{10}-H$ |
| KC3-X1-G | -CH3 | $-(CH_2)_3-$ | $-(CH_2)_7-$ | -C(=O)-O- | $-(CH_2)_{11}-H$ |
| KC3-X1-H | -CH3 | $-(CH_2)_3-$ | $-(CH_2)_7-$ | -C(=O)-O- | $-(CH_2)_2-CH=CH-(CH_2)_7-H$ |
| KC3-X1-I | -CH3 | $-(CH_2)_3-$ | $-(CH_2)_7-$ | -C(=O)-O- | $-(CH_2)_2-CH=CH-(CH_2)_9-H$ |
| KC3-X1-J | -CH3 | $-(CH_2)_3-$ | $-(CH_2)_7-$ | -C(=O)-O- | $- (CH_2)_{12}-H$ |
| KC3-X1-K | -CH3 | $-(CH_2)_3-$ | $-(CH_2)_8-$ | -C(=O)-O- | $-(CH_2)_{12}-H$ |
| KC3-X1-L | -CH3 | $-(CH_2)_3-$ | $-(CH_2)_8-$ | -C(=O)-O- | $- (CH_2)_{10}-H$ |
| KC3-X1-M | -CH3 | $-(CH_2)_3-$ | $-(CH_2)_8-$ | -C(=O)-O- | $-(CH_2)_{11}-H$ |
| KC3-X1-N | -CH3 | $-(CH_2)_3-$ | $-(CH_2)_5-$ | -C(=O)-O- | $-(CH_2)_{13}-H$ |
| KC3-X1-O | -CH3 | $-(CH_2)_3-$ | $-(CH_2)_5-$ | -C(=O)-O- | $-(CH_2)_{15}-H$ |
| KC3-X1-P | -CH3 | $-(CH_2)_3-$ | $-(CH_2)_4-$ | -C(=O)-O- | $-(CH_2)_{14}-H$ |
| KC3-X1-Q | -CH3 | $-(CH_2)_3-$ | $-(CH_2)_4-$ | -C(=O)-O- | $-(CH_2)_{16}-H$ |
| KC3-X1-R | -CH3 | $-(CH_2)_3-$ | $-(CH_2)_8-$ | -C(=O)-O- | $-(CH_2)_{14}-H$ |
| KC3-X1-S | -CH3 | $-(CH_2)_3-$ | $-(CH_2)_8-$ | -C(=O)-O- | $-(CH_2)_2-CH=CH-(CH_2)_8-H$ |
| KC3-X1-T | -CH3 | $-(CH_2)_3-$ | $-(CH_2)_8-$ | -C(=O)-O- | $-(CH_2)_{16}-H$ |
| KC3-X1-U | -CH3 | $-(CH_2)_3-$ | $-(CH_2)_{10}-$ | -C(=O)-O- | $-(CH_2)_{10}-H$ |
| KC3-X1-V | -CH3 | $-(CH_2)_3-$ | $-(CH_2)_{10}-$ | -C(=O)-O- | $-(CH_2)_{12}-H$ |
| KC3-X2 | -CH3 | $-(CH_2)_3-$ | $-(CH_2)_7-$ | -O-C(=O)- | $-(CH_2)_9-H$ |
| KC3-X2-A | -CH3 | $-(CH_2)_3-$ | $-(CH_2)_3-$ | -O-C(=O)- | $-(CH_2)_{13}-H$ |
| KC3-X2-B | -CH3 | $-(CH_2)_3-$ | $-(CH_2)_5-$ | -O-C(=O)- | $-(CH_2)_{11}-H$ |

| | | | | | |
|---|---|---|---|---|---|
| KC3-X2-C | -CH3 | $-(CH_2)_3-$ | $-(CH_2)_3-$ | -O-C(=O)- | $-(CH_2)_2$-CH=CH-$(CH_2)_9$-H |
| KC3-X2-D | -CH3 | $-(CH_2)_3-$ | $-(CH_2)_5-$ | -O-C(=O)- | $-(CH_2)_2$-CH=CH-$(CH_2)_7$-H |
| KC3-X2-G | -CH3 | $-(CH_2)_3-$ | $-(CH_2)_7-$ | -O-C(=O)- | $-(CH_2)_{11}$-H |
| KC3-X2-K | -CH3 | $-(CH_2)_3-$ | $-(CH_2)_8-$ | -O-C(=O)- | $-(CH_2)_{12}$-H |
| KC3-X2-R | -CH3 | $-(CH_2)_3-$ | $-(CH_2)_8-$ | -O-C(=O)- | $-(CH_2)_{14}$-H |
| KC4-OA-C | -CH3 | $-(CH_2)_4-$ | $-(CH_2)_2-$ | -C(=O)-O- | $-(CH_2)_8$-CH=CH-$(CH_2)_8$-H |
| KC4-X1 | -CH3 | $-(CH_2)_4-$ | $-(CH_2)_4-$ | -C(=O)-O- | $-(CH_2)_2$-CH=CH-$(CH_2)_8$-H |
| KC4-X1-H | -CH3 | $-(CH_2)_4-$ | $-(CH_2)_7-$ | -C(=O)-O- | $-(CH_2)_2$-CH=CH-$(CH_2)_7$-H |
| KC4-X2 | -CH3 | $-(CH_2)_4-$ | $-(CH_2)_3-$ | -O-C(=O)- | $-(CH_2)_2$-CH=CH-$(CH_2)_9$-H |

FIGURE 3A (continued)

FIGURE 3B

| Name | R1, R2 | Z | X1, X2 | A1, A2 | Y1, Y2 |
|---|---|---|---|---|---|
| KC2-X1-PH1 | -CH3 | $-(CH_2)_2-$ | $-(CH_2)_6-$ | -C(=O)-O- | $-(CH_2-CH_2-CH(-CH_3)-CH_2)_3-H$ |
| KC3-X1-PH1 | -CH3 | $-(CH_2)_3-$ | $-(CH_2)_6-$ | -C(=O)-O- | $-(CH_2-CH_2-CH(-CH_3)-CH_2)_3-H$ |
| KC3-X1-PH1-B | -CH3 | $-(CH_2)_3-$ | $-(CH_2)_6-$ | -C(=O)-O- | $-(CH_2-CH=C(-CH_3)-CH_2)_3-H$ |
| KC4-X1-PH1 | -CH3 | $-(CH_2)_4-$ | $-(CH_2)_6-$ | -C(=O)-O- | $-(CH_2-CH_2-CH(-CH_3)-CH_2)_3-H$ |
| KC3-X1-PH2 | -CH3 | $-(CH_2)_3-$ | $-(CH_2)_6-$ | -C(=O)-O- | $-CH_2-CH_2-CH(-CH_3)-CH_2)_2-CH_2-CH_3$ |
| KC3-X1-PH2-B | -CH3 | $-(CH_2)_3-$ | $-(CH_2)_6-$ | -C(=O)-O- | $-(CH_2-CH_2-CH(-CH_3)-CH_2-CH_2-CH=C(-CH_3)-CH_2-CH_2)-H$ |
| KC3-X1-PH3 | -CH3 | $-(CH_2)_3-$ | $-(CH_2)_4-$ | -C(=O)-O- | $-(CH_2-CH_2-CH(-CH_3)-CH_2)_3-H$ |
| KC3-X1-PH3-B | -CH3 | $-(CH_2)_3-$ | $-(CH_2)_4-$ | -C(=O)-O- | $-(CH_2-CH=C(-CH_3)-CH_2)_3-H$ |
| KC3-X1-PH4 | -CH3 | $-(CH_2)_3-$ | $-(CH_2)_4-$ | -C(=O)-O- | $-(CH_2-CH_2-CH(-CH_3)-CH_2)_4-H$ |
| KC3-X1-PH4-B | -CH3 | $-(CH_2)_3-$ | $-(CH_2)_4-$ | -C(=O)-O- | $-(CH_2-CH=C(-CH_3)-CH_2)_4-H$ |
| KC2-X1-PH5 | -CH3 | $-(CH_2)_2-$ | $-(CH_2)_7-$ | -C(=O)-O- | $-(CH_2-CH_2-CH(-CH_3)-CH_2)_3-H$ |
| KC3-X1-PH5 | -CH3 | $-(CH_2)_3-$ | $-(CH_2)_7-$ | -C(=O)-O- | $-(CH_2-CH_2-CH(-CH_3)-CH_2)_3-H$ |
| KC3-X1-PH5-B | -CH3 | $-(CH_2)_3-$ | $-(CH_2)_7-$ | -C(=O)-O- | $-(CH_2-CH=C(-CH_3)-CH_2)_3-H$ |
| KC2-X1-PH6 | -CH3 | $-(CH_2)_2-$ | $-(CH_2)_8-$ | -C(=O)-O- | $-(CH_2-CH_2-CH(-CH_3)-CH_2)_3-H$ |
| KC3-X1-PH7 | -CH3 | $-(CH_2)_3-$ | $-(CH_2)_8-$ | -C(=O)-O- | $- CH_2-CH_2 -(CH_2-CH_2-CH(-CH_3)-CH_2)_2-H$ |
| KC3-X1-PH8 | -CH3 | $-(CH_2)_2-$ | $-(CH_2)_{10}-$ | -C(=O)-O- | $-(CH_2-CH_2-CH(-CH_3)-CH_2)_3-H$ |
| KC3-X1-PH9 | -CH3 | $-(CH_2)_2-$ | $-(CH_2)_8-$ | -C(=O)-O- | $-(CH_2-CH_2-CH(-CH_3)-CH_2)_2-H$ |
| KC3-X1-PH10 | -CH3 | $-(CH_2)_2-$ | $-(CH_2)_{10}-$ | -C(=O)-O- | $-(CH_2-CH_2-CH(-CH_3)-CH_2)_2-H$ |
| KC3-X1-PH11 | -CH3 | $-(CH_2)_3-$ | $-(CH_2)_8-$ | -C(=O)-O- | $- CH_2-CH_2 -(CH_2-CH_2-CH(-CH_3)-CH_2)_3-H$ |
| KC3-X1-PH12 | -CH3 | $-(CH_2)_3-$ | $-(CH_2)_{10}-$ | -C(=O)-O- | $- CH_2-CH_2 -(CH_2-CH_2-CH(-CH_3)-CH_2)_2-H$ |

FIGURE 6A

| Group # | mRNA constructs | LNP formulation | mol % ICL | N/P | vaccine schedule | Dose per mRNA (ug) H1/H3/Bvic/RSVpreF |
|---|---|---|---|---|---|---|
| 1 | H1/H3/BVictoria RSV | KC3-X1-PH12 | 52 | 5.25 | Intramuscular prime/boost<br><br>boost on day 28 | 0.03/0.045/0.03/0.3 (high) |
| 2 | | | | | | 0.01/0.015/0.01/0.1 (low) |
| 3 | H1/H3/Bvic/RSV | KC3-X1-PH12 (lyo) | 52 | 5.25 | | 0.03/0.045/0.03/0.3 (high) |
| 4 | | | | | | 0.01/0.015/0.01/0.1 (low) |
| 5 | H1/H3/Bvic/RSV | KC3-X1-PH12 | 56 | 5.25 | | 0.03/0.045/0.03/0.3 (high) |
| 6 | | | | | | 0.01/0.015/0.01/0.1 (low) |
| 7 | H1/H3/Bvic/RSV | KC3-X1-PH12 (lyo) | 56 | 5.25 | | 0.03/0.045/0.03/0.3 (high) |
| 8 | | | | | | 0.01/0.015/0.01/0.1 (low) |
| 9 | H1/H3/Bvic/RSV | KC3-X2-PH12 | 56 | 4.5 | | 0.03/0.045/0.03/0.3 (high) |
| 10 | | | | | | 0.01/0.015/0.01/0.1 (low) |
| 11 | H1/H3/Bvic/RSV | KC3-X2-PH12 | 56 | 5.25 | | 0.03/0.045/0.03/0.3 (high) |
| 12 | | | | | | 0.01/0.015/0.01/0.1 (low) |
| 13 | H1/H3/Bvic/RSV | KC3-X2-PH12 | 52 | 5.25 | | 0.03/0.045/0.03/0.3 (high) |
| 14 | | | | | | 0.01/0.015/0.01/0.1 (low) |
| 15 | H5 | KC3-X1-PH12 | 52 | 5.25 | | 0.1 |
| 16 | | | | | | 0.02 |
| 17 | | KC3-X1-PH12 | 56 | 5.25 | | 0.1 |
| 18 | | | | | | 0.02 |

IONIZABLE LIPIDS AND LIPOSOMAL NANOPARTICLE COMPOSITIONS

RELATED APPLICATIONS

This patent application claims the benefit of and priority to U.S. Provisional Patent Application No. 63/775,688, filed on Mar. 21, 2025, U.S. Provisional Patent Application No. 63/869,090, filed Aug. 22, 2025, U.S. Provisional U.S. Provisional Patent Application No. 63/944,616, filed Dec. 19, 2025, and U.S. Provisional Patent Application No. 64/007,071, filed Mar. 16, 2026, the entire content of each of which is hereby incorporated herein by reference in their entirety.

REFERENCE TO SEQUENCE LISTING

The application contains a Sequence Listing which has been submitted electronically in XML file format and is hereby incorporated by reference in its entirety. Said XML copy, created on Mar. 20, 2026, is titled 191016-011610_US_SL.xml and is 394,185 bytes in size.

FIELD

Aspects of the present disclosure relate to ionizable lipids useful for the preparation of lipid nanoparticles (LNP) encapsulating a nucleic acid.

BACKGROUND

Lipid nanoparticles (LNP) are used for the delivery of therapeutic nucleic acids to cells, including vaccines to deliver mRNA therapeutics. LNP formulations typically include an ionizable lipid, a sterol, and a phospholipid. Ionizable lipids in LNP compositions facilitate delivery of encapsulated nucleic acid by remaining mostly neutral at physiological pH, but becoming protonated in the acidic environment of endosomes after cellular uptake. Ionizable lipids that are hydrolysable or bioreducible offer desirable in vivo clearance properties for vaccine-focused lipid nanoparticle (LNP) delivery systems by enhancing both efficacy and safety. Hydrolysable lipids, which break down through controlled chemical or enzymatic cleavage, and bioreducible lipids, which degrade in response to intracellular reducing conditions, promote timely LNP disassembly after delivering the vaccine payload. There remains a need for ionizable lipids that are hydrolysable and/or bioreducible for use in the preparation of LNP formulations for therapeutic delivery of nucleic acids.

SUMMARY

In some embodiments, this disclosure provides ionizable cationic lipid compounds with significantly improved hydrolysis (Example 4) with significantly improved mRNA transfection efficiency in dendritic cells from LNPs encapsulating the mRNA (Example 5). In some embodiments, an ionizable lipid compound consists of a dioxolane ring covalently bound to both (x) an alkylamine head group having a pKa of 6-7.5, and (y) a pair of identical geminal functionalized aliphatic chains at the 2-position of the dioxolane ring, each having 18-25 total carbon atoms and each consisting of (i) a 7-10 carbon linear aliphatic group covalently bound to the dioxolane ring and to (ii) an ester functional group, and (iii) a 10-20 carbon aliphatic chain covalently bound to the ester functional group. In some embodiments, the dioxolane ring is a 1,3-dioxolane ring and each of the functionalized aliphatic chains comprises two or more branched $C_5$ hydrocarbon monomer units such as isopentane (IPN) or 2-methylbut-2-ene (2 MB). For example, in some embodiments, the ionizable lipid is selected from the group consisting of:

(KC3-X1-PH12)

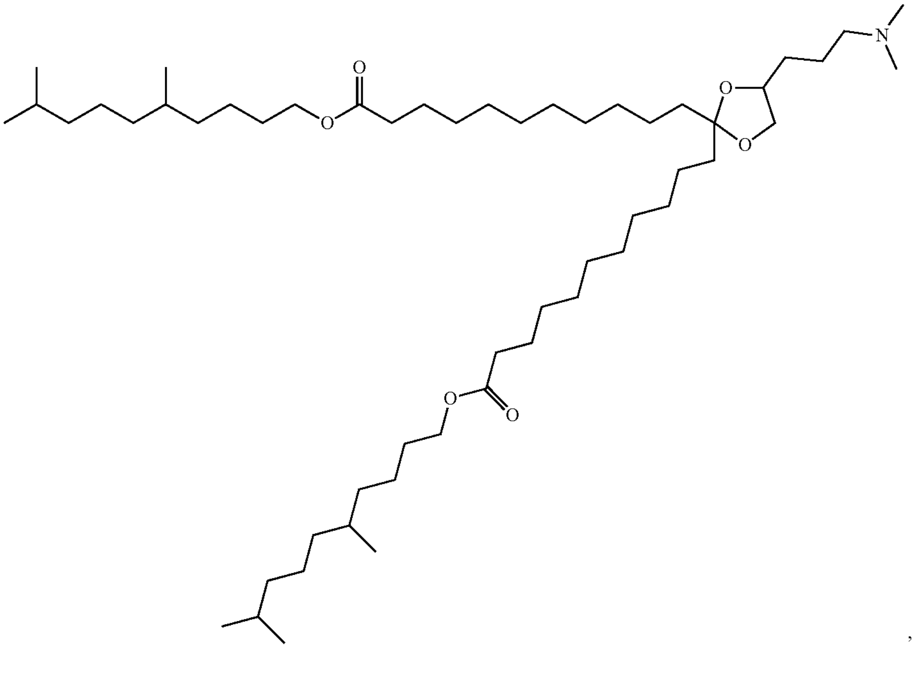

,

-continued (KC3-X2-PH12)

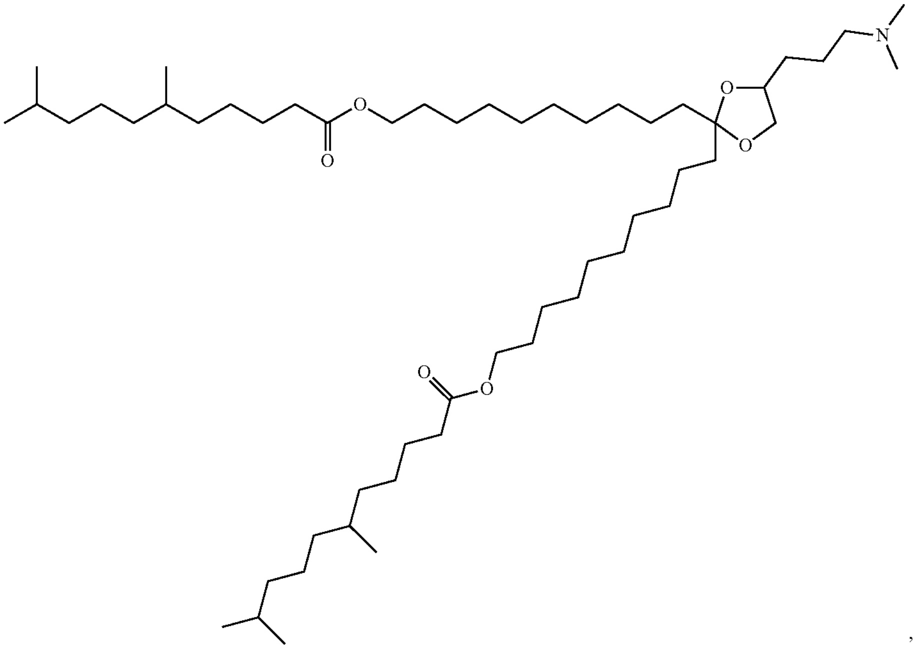

, or a salt thereof.

In some embodiments, a lipid nanoparticle (LNP) composition comprises a mRNA nucleic acid encapsulated in lipidic nanoparticles formed from the ionizable lipid disclosed herein at a N/P ratio of 3.5 to 8 relative to the mRNA nucleic acid in a total amount of 40-65 mol % of the total lipid content of the LNP composition; a sterol in a total amount of 25-45 mol % of the total lipid content of the LNP composition; one or more phospholipids in a total amount of phospholipids of 5-25 mol % of the total lipid content of the LNP composition; and a PEG-containing conjugated lipid in a total amount of 0.5-5.0 mol % of the total lipid content of the LNP composition. In some embodiments, the two or more phospholipids in the LNP composition comprise a total of 5 mol % of a phosphatidyl-L-serine (PS). In some embodiments, the LNP composition comprises the conjugated lipid in a total amount of 0.5-2.5 mol % of the total lipid content of the LNP composition. In some embodiments, the phospholipids consist of: 1,2-distearoyl-sn-glycero-3-phosphocholine (DSPC) in a total amount of 5 mol % of the total lipid content of the LNP composition, and a phosphatidyl-L-serine (DPPS), such as dipalmitoylphosphatidyl-L-serine (DPPS) or distearoylphosphatidyl-L-serine (DSPS), in a total amount of 5 mol % of the total lipid content of the LNP composition. In some embodiments, the PEG-containing conjugated lipid in the LNP is PEG(2000)-dimyristoylglycerol (PEG-DMG) or PEG(2000)-dilauroylglycerol (PEG-DLG).

In some embodiments, a lipid nanoparticle (LNP) composition comprises a mRNA nucleic acid encoding an antigenic protein encapsulated at a N/P ratio of 3.25-8 in lipidic nanoparticles consisting of: a KCn-X1 or KCn-X2 ionizable cationic lipid disclosed herein and cholesterol in a molar ratio of the ionizable cationic lipid to the cholesterol of from 65:35 to 45:55, X mol % of an anionic phospholipid such as DPPS (wherein X is 2.5-7.5 mol %), (10–X) mol % phosphocholine phospholipid such as DSPC, and 1.5-4 mol % of a PEG conjugated lipid such as PEG-DMG. In some embodiments, a lipid nanoparticle (LNP) composition comprises a mRNA nucleic acid encapsulated at a N/P ratio of 5.25 in lipidic nanoparticles consisting of: 56 mol % of the KC3-X1-PH12 ionizable cationic lipid, 5 mol % DPPS, 5 mol % DSPC, 1.5 mol % PEG-DMG and 32.5 mol % cholesterol. In some embodiments, a lipid nanoparticle (LNP) composition comprises a mRNA nucleic acid encapsulated at a N/P ratio of 5.25 in lipidic nanoparticles consisting of: 52 mol % of the KC3-X1-PH12 ionizable cationic lipid, 5 mol % DPPS, 5 mol % DSPC, 1.5 mol % PEG-DMG and 36.5 mol % cholesterol.

BRIEF DESCRIPTION OF THE DRAWINGS

FIG. 3A is a table of various ionizable cationic lipids of Formula (I).

FIG. 3B is a table of various ionizable cationic lipids of Formula (I).

FIGS. 6A-6E are figures describing an experiment comparing B cell responses in BALB/c after prime/boost vaccination with mRNA encoding an influenza A subtypes H1, H3, and B/Victoria and RSV preF mRNA (Example 10). The mRNA was formulated with LNPs comprised with different ionizable lipids. FIG. 6A is a table summarizing the experimental design. FIG. 6B is a graph showing the anti-H1 IgG titers 21 days after vaccination with a high (0.03 mcg) dose. FIG. 6C is a graph showing the anti-H1 IgG titers 21 days after vaccination with a low (0.01 mcg) dose. FIG. 6D is a graph showing the anti-H3 IgG titers 21 days after vaccination with a high (0.045 mcg) dose; FIG. 6E is a graph showing the anti-H3 IgG titers 21 days after vaccination with a low (0.015 mcg) dose.

DETAILED DESCRIPTION

Figure 1A:
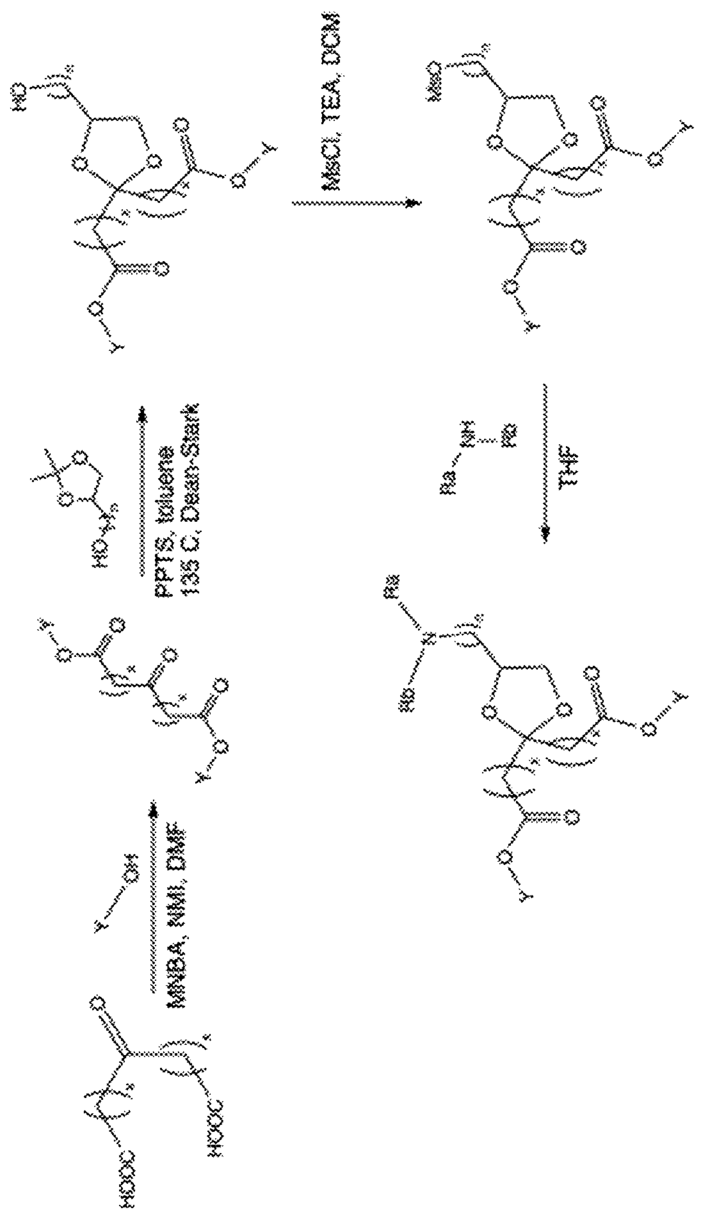
FIG. 1A is a synthetic scheme for preparing certain ionizable cationic lipids.
Figure 1A:
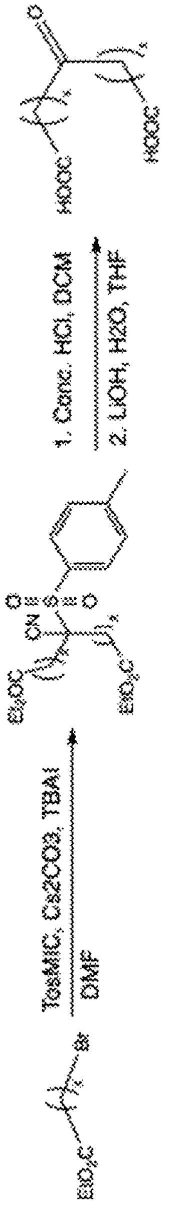

In some embodiments, the present disclosure provides ionizable cationic lipid compounds of Formula (I):

(I)

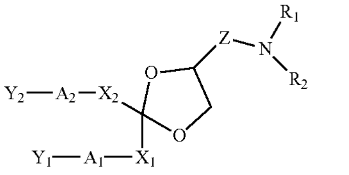

or a pharmaceutically acceptable salt thereof, wherein $R_1$ and $R_2$ are each independently $C_{1-4}$ alkyl optionally substituted with hydroxyl;

Z is $*—(CH_2)_n—**$, wherein * is a covalent bond to the 1,3-dioxolane ring and ** is a covalent bond to $—NR_1R_2$, and n is 2, 3 or 4;

$—X_1—$ and $—X_2—$ are the same of different and are each independently $—(CH_2)_{(x)}—$, wherein (x) is 7-10;

$-A_1-$ and $-A_2-$ are the same or different and are each independently ester groups;

$—Y_1—$ and $—Y_2—$ are the same or different and are each an aliphatic chain having (y) total carbon atoms, optionally comprising two or more branched $C_5$ hydrocarbon monomer units, wherein (y) is 10-17; and the sum of (x)+(y) is 18-25.

In some embodiments, ionizable lipid is a compound of Formula (I-A):

(I-A)

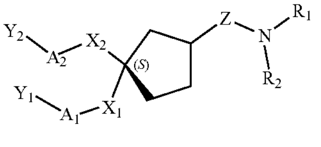

or a pharmaceutically acceptable salt thereof, wherein $R_1$, $R_2$, Z, $X_1$, $X_2$, $A_1$, $A_2$, $Y_1$ and $Y_2$ are as defined with respect to Formula (I).

In some embodiments, $R_1$ and $R_2$ are each methyl and n is 2, 3 or 4. In some embodiments, n is 2 and $R_1$ and $R_2$ are each methyl. In some embodiments, n is 3 and $R_1$ and $R_2$ are each methyl.

In some embodiments, n is 4 and $R_1$ and $R_2$ are each methyl. In some embodiments, $*—Z—N(R_1)(R_2)$ is selected from $—(CH_2)_{2-4}—N(CH_3)_2$, and $—(CH_2)_{2-4}—N(CH_3)—(CH_2)_{2-4}—OH$, wherein * is a covalent bond to the 1,3-dioxolane ring in Formula (I).

In some embodiments, $—X_1—$ and $—X_2—$ are both $—(CH_2)_{(x)}—$, wherein (x) is 7, 8, 9 or 10; $A_1$ and $A_2$ are the same and are both independently $*—C(O)—O—**$ or $*—O—C(O)—**$, wherein * is a covalent bond to $Y_1$ and $Y_2$, respectively, and ** is a covalent bond to $X_1$ and $X_2$, respectively; and $—Y_1—$ and $—Y_2—$ are each an aliphatic chain having (y) total carbon atoms, comprising two or more branched $C_5$ hydrocarbon monomer units, wherein (y) is 12, 13, 14, or 15; and wherein the sum of (x)+(y) is 22. In some embodiments, $—Y_1$ and $—Y_2$ are each independently $*—(CH_2)_{0-2}—(R_y)_{2-4}—H$ wherein each $R_y$ is independently an isopentane (IPN) or a 2-methylbut-2-ene (2 MB) hydrocarbon monomer unit, and * is a covalent bond to $A_1$ or $A_2$. In some embodiments, $R_y$ is $—CH_2—CH(—CH_3)—CH_2—CH_2—$ or $—CH_2—C(—CH_3)=CH—CH_2—$. In some embodiments, the ionizable lipid is a compound of Formula (I), wherein $X_1$-$A_1$-$Y_1$ and $—X_2$-$A_2$-$Y_2$ are identical.

In some embodiments, the compound is a compound of Formula (I), wherein $R_1$ and $R_2$ are each methyl and n is 2, 3 or 4. In some embodiments, the compound is a compound of Formula (I), wherein n is 2 and $R_1$ and $R_2$ are each methyl. In some embodiments, the compound is a compound of Formula (I), wherein n is 3 and $R_1$ and $R_2$ are each methyl. In some embodiments, the compound is a compound of Formula (I), wherein n is 4 and $R_1$ and $R_2$ are each methyl. In some embodiments, the compound is a compound of Formula (I), wherein n is 2, 3 or 4, $R_1$ is $—(CH_2)_2—OH$ and $R_2$ is methyl. In some embodiments, the compound is a compound of Formula (I), wherein n is 2, $R_1$ is $—(CH_2)_2—OH$ and $R_2$ is methyl. In some embodiments, the compound is a compound of Formula (I), wherein n is 3, $R_1$ is $—(CH_2)_2—OH$ and $R_2$ is methyl. In some embodiments, the compound is a compound of Formula (I), wherein n is 4, $R_1$ is $—(CH_2)_2—OH$ and $R_2$ is methyl. In some embodiments, the compound is a compound of Formula (I), wherein $R_1$ and $R_2$ are each $C_{1-4}$ alkyl optionally substituted with hydroxyl. In some embodiments, the compound is a compound of Formula (I), wherein $R_1$ is $C_{1-4}$ alkyl and $R_2$ is $C_{1-4}$ alkyl optionally substituted with hydroxyl. In some embodiments, the compound is a compound of Formula (I), wherein $R_1$ is methyl and $R_2$ is $—(CH_2)_{2-4}—OH$. In some embodiments, the compound is a compound of Formula (I), wherein $R_1$ is methyl and $R_2$ is $—(CH_2)_2—OH$. In some embodiments, the compound is a compound of Formula (I), wherein $R_1$ is methyl and $R_2$ is $—(CH_2)_3—OH$. In some embodiments, the compound is a compound of Formula (I), wherein $R_1$ is methyl and $R_2$ is $—(CH_2)_4—OH$.

In some embodiments, the compound is a compound of Formula (I), wherein $—X_1—$ and $—X_2—$ are each independently $—(CH_2)_{(x)}—$, wherein (x) is 7, 8, 9 or 10; $-A_1-$ and $-A_2-$ are the same or different and are each independently hydrolysable or bioreducible groups; $—Y_1—$ and $—Y_2—$ are the same or different and are each an aliphatic chain comprising two or more branched $C_5$ hydrocarbon monomer units and having (y) total carbon atoms, wherein (y) is 10, 11, 12, 13, 14, 15, 16 or 17; and the sum of (x)+(y) is 18-25.

In some embodiments, the compound is a compound of Formula (I), wherein each of $A_1$ and $A_2$ is a hydrolysable group such as an ester, carbonate, carbamate, acetal, ketal, orthoester, acid-labile dioxolane, phosphoester or phosphoramidate. In some embodiments, the compound is a compound of Formula (I), wherein —$Y_1$ and —$Y_2$ comprise one or more branched $C_5$ hydrocarbon monomer units, such as n-pentane, isopentane, neopentane, 1-pentene, cis-2-pentene, trans-2-pentene, 3-methyl-1-butene, 2-methylbut-2-ene, 2-methylbut-1-ene, 3-methylbut-1-ene (isopentane), isoprene, 1,4-pentadiene, 1,5-pentadiene, 1,3-pentadiene (cis, trans or cis/trans), 2-methyl-1,3-pentadiene, 3-methyl-1,3-pentadiene, 1-pentyne, 2-pentyne, 3-methyl-1-butyne, or 3-methyl-2-butyne (isopentyne). In some embodiments, the compound is a compound of Formula (I), wherein —$Y_1$ and —$Y_2$ comprise two, three or four $C_5$ hydrocarbon monomer units in a configuration forming a covalent bond from the $C_1$ carbon of a $C_5$ hydrocarbon monomer to the $C_4$ carbon of an adjacent $C_5$ hydrocarbon monomer, such as IPN (—$CH_2$—CH(—$CH_3$)—$CH_2$—$CH_2$—) and/or 2 MB (—$CH_2$—C(—$CH_3$)=CH—$CH_2$—). In some embodiments, the compound is a compound of Formula (I), wherein —$X_1$-$A_1$-$Y_1$ and —$X_2$-$A_2$-$Y_2$ are identical; —$X_1$— and —$X_2$— are each independently —$(CH_2)_{(x)}$—, wherein (x) is 7, 8, 9 or 10; each of $A_1$ and $A_2$ is independently *—C(O)—O—** or *—O—C(O)—**, wherein * is a covalent bond to $Y_1$ and $Y_2$, respectively, and ** is a covalent bond to $X_1$ and $X_2$, respectively; —$Y_1$ and —$Y_2$ are each *—$(CH_2)_{0-2}$—$(R_y)_{2-4}$—$(CH_2)_{0-2}$—H wherein each $R_y$ is independently a $C_5$ hydrocarbon monomer unit such as an IPN or a 2 MB hydrocarbon monomer unit, and * is a covalent bond to $A_1$ or $A_2$; (y) is 12, 13, 14 or 15; and the sum of (x)+(y) is 22.

Some aspects of the disclosure relate to bioreducible ionizable cationic lipids of Formula (I) or (I-A), wherein each $R_1$ is independently linear hydrocarbon alkyl chains each comprising a hydrolysable or bioreducible group, such as an ester group (e.g., —O—CO— or —CO—O—); and $R_2$ and $R_3$ are each independently ($C_1$-$C_4$) alkyl optionally substituted with hydroxyl; and n is an integer equal to 2, 3 or 4.

In some embodiments, a bioreducible or hydrolysable ionizable cationic lipid comprises a compound of Formula (I) or Formula (I-A) wherein each of $R_2$ and $R_3$ is methyl, —Z— is —$(CH_2)_n$— and n is 3 or 4 and each $R_1$ is the same. In some embodiments, a bioreducible or hydrolysable ionizable cationic lipid comprises a compound of Formula (I) or Formula (I-A) wherein each of $R_2$ and $R_3$ is methyl and each $R_1$ is a hydrocarbon chain comprising a single ester group with a total 15-22 atoms, and optionally comprising one or two olefin groups. In some embodiments, a bioreducible or hydrolysable ionizable cationic lipid comprises a compound of Formula (I) or Formula (I-A) wherein each of $R_2$ and $R_3$ is methyl and each $R_1$ is a hydrocarbon chain comprising a single ester group with a total 15-22 atoms, and optionally comprising one olefin group. In some embodiments, a bioreducible or hydrolysable ionizable cationic lipid comprises a compound of Formula (I) or Formula (I-A) wherein each of $R_2$ and $R_3$ is methyl and each $R_1$ is a hydrocarbon chain comprising a single ester group with a total 15-22 atoms, and optionally comprising two olefin groups separated by at least two methylene groups.

In some embodiments, a bioreducible or hydrolysable ionizable cationic lipid comprises a compound of Formula (I) or Formula (I-A) wherein each of $R_1$ and $R_2$ is methyl, —Z— is —$(CH_2)_n$—, n is 3 or 4 and each of —$X_1$-$A_1$-$Y_1$ and —$X_2$-$A_2$-$Y_2$ is the same or different and each comprises an ester joining a proximal saturated $C_{7-8}$ hydrocarbon at —$X_1$— and —$X_2$— and a distal $C_{12-15}$ hydrocarbon at —$Y_1$ and —$Y_2$ each optionally comprising one or more olefins and one or more methyl substituents.

In some embodiments, a bioreducible or hydrolysable ionizable cationic lipid comprises a compound of Formula (I) or Formula (I-A) wherein each of $R_1$ and $R_2$ is methyl, Z is —$(CH_2)_n$— and n is 3 or 4 and each of —$X_1$-$A_1$-$Y_1$ and —$X_2$-$A_2$-$Y_2$ is the same or different and each comprises an ester at -$A_1$- and -$A_2$- joining a proximal saturated $C_{4-10}$ hydrocarbon at —$X_1$— and —$X_2$— and a distal $C_{10-20}$ hydrocarbon at —$Y_1$ and —$Y_2$ optionally comprising one or more olefins and one or more methyl substituents.

In some embodiments, a bioreducible or hydrolysable ionizable cationic lipid comprises a compound of Formula (I) or Formula (I-A) wherein each of $R_1$ and $R_2$ is methyl, —Z— is —$(CH_2)_n$—, n is 3 or 4 and each of —$X_1$-$A_1$-$Y_1$ and —$X_2$-$A_2$-$Y_2$ is the same and each comprises a proximal $C_{7-10}$ hydrocarbon at —$X_1$— and —$X_2$— and a distal saturated isoprenoid alkane group at —$Y_1$ and -$Y_2$ joined by an ester at -$A_1$- and -$A_2$-. In some embodiments, a bioreducible or hydrolysable ionizable cationic lipid comprises a compound of Formula (I) or Formula (I-A) wherein each of $R_1$ and $R_2$ is methyl, —Z— is —$(CH_2)_n$—, n is 3 or 4 and each of —$X_1$-$A_1$-$Y_1$ and —$X_2$-$A_2$-$Y_2$ is the same and each comprises a proximal $C_{7-10}$ hydrocarbon at —$X_1$— and —$X_2$— and a distal saturated phytane group at —$Y_1$ and —$Y_2$ joined by an ester at -$A_1$- and -$A_2$-. In some embodiments, a bioreducible or hydrolysable ionizable cationic lipid comprises a compound of Formula (I) or Formula (I-A) wherein each of $R_1$ and $R_2$ is methyl, —Z— is —$(CH_2)_n$—, n is 3 or 4 and each of —$X_1$-$A_1$-$Y_1$ and -$X_2$-$A_2$-$Y_2$ is the same and each comprises a proximal $C_{7-10}$ hydrocarbon at —$X_1$— and —$X_2$— and a distal unsaturated phytane group at —$Y_1$ and —$Y_2$ comprising one or more olefins joined by an ester at -$A_1$- and -$A_2$-.

In some embodiments, a bioreducible or hydrolysable ionizable cationic lipid comprises a compound of Formula (I) or Formula (I-A) wherein each of $R_1$ and $R_2$ is methyl, —Z— is —$(CH_2)_n$—, n is 3 and each of —$X_1$-$A_1$-$Y_1$ and —$X_2$-$A_2$-$Y_2$ is the same and each comprises a proximal $C_{7-10}$ hydrocarbon at —$X_1$— and —$X_2$— joined by an ester at -$A_1$- and -$A_2$- to a distal branched hydrocarbon chain comprising two or three isoprene or isopentane monomer groups at —$Y_1$ and —$Y_2$. In some embodiments, a bioreducible or hydrolysable ionizable cationic lipid comprises a compound of Formula (I) or Formula (I-A) wherein each of $R_1$ and $R_2$ is methyl, Z— is —$(CH_2)_n$—, n is 3 or 4 and each —$X_1$-$A_1$-$Y_1$ and —$X_2$-$A_2$-$Y_2$ are each —$(CH_2)_{7-10}$-A-Y, wherein A is —C(=O)—O— or —O—C(=O)—, and Y is —($CH_2$—$CH_2$—CH(—$CH_3$)—$CH_2$)$_3$—H or —($CH_2$—$CH_2$—CH(—$CH_3$)—$CH_2$)$_3$—H or —$CH_2$—$CH_2$—($CH_2$—$CH_2$—CH(—$CH_3$)—$CH_2$)$_2$—H. In some embodiments, a bioreducible or hydrolysable ionizable cationic lipid comprises a compound of Formula (I) or Formula (I-A) wherein each of $R_1$ and $R_2$ is methyl, Z— is —$(CH_2)_n$—, n is 3 or 4 and each —$X_1$-$A_1$-$Y_1$ and —$X_2$-$A_2$-$Y_2$ is —$(CH_2)_7$-A-Y, wherein A is —C(=O)—O— or —O—C(=O)—, and Y is —($CH_2$—$CH_2$—CH(—$CH_3$)—$CH_2$)$_3$—H. In some embodiments, a bioreducible or hydrolysable ionizable cationic lipid comprises a compound of Formula (I) or Formula (I-A) wherein each of $R_2$ and $R_3$ is methyl, Z— is —$(CH_2)_n$—, n is 3 or 4 and each —$X_1$-$A_1$-$Y_1$ and —$X_2$-$A_2$-$Y_2$ is —$(CH_2)_8$-A-Y, wherein A is —C(=O)—O— or —O—C(=O)—, and Y is —($CH_2$—$CH_2$—CH(—$CH_3$)—$CH_2$)$_3$—H or —$(CH_2)_2$—CH=CH—$(CH_2)_8$—H or —$(CH_2)_{12}$—H. In some embodiments, a bioreducible or hydrolysable ionizable cationic lipid comprises a compound of Formula (I) or Formula (I-A) wherein each of $R_2$ and $R_3$ is methyl, Z— is —$(CH_2)_n$—, n is 3 or 4 and each —$X_1$-$A_1$-$Y_1$ and —$X_2$-$A_2$-$Y_2$ is —$(CH_2)_{10}$-A-Y, wherein A is —C(=O)—O— or —O—C(=O)—, and Y is —$CH_2$—$CH_2$—($CH_2$—$CH_2$—CH(—$CH_3$)—$CH_2$)$_2$—H.

In some embodiments, a bioreducible or hydrolysable ionizable cationic lipid comprises a compound of Formula (I) or Formula (I-A) wherein each of $R_1$ and $R_2$ is methyl, Z— is —$(CH_2)_n$—, n is 3 and each —$X_1$-$A_1$-$Y_1$ and —$X_2$-$A_2$-$Y_2$ are each —$(CH_2)_{7-10}$-A-Y, wherein A is —C(═O)—O— or —O—C(═O)—, and Y is —$(CH_2$—$CH_2$—CH(—$CH_3$)—$CH_2)_3$—H or —$(CH_2$—$CH_2$—CH(—$CH_3$)—$CH_2)_3$—H or —$CH_2$—$CH_2$—$(CH_2$—$CH_2$—CH(—$CH_3$)—$CH_2)_2$—H. In some embodiments, a bioreducible or hydrolysable ionizable cationic lipid comprises a compound of Formula (I) or Formula (I-A) wherein each of $R_1$ and $R_2$ is methyl, Z— is —$(CH_2)_n$—, n is 3 and each —$X_1$-$A_1$-$Y_1$ and —$X_2$-$A_2$-$Y_2$ is —$(CH_2)_7$-A-Y, wherein A is —C(═O)—O— or —O—C(═O)—, and Y is —$(CH_2$—$CH_2$—CH(—$CH_3$)—$CH_2)_3$—H. In some embodiments, a bioreducible or hydrolysable ionizable cationic lipid comprises a compound of Formula (I) or Formula (I-A) wherein each of $R_2$ and $R_3$ is methyl, Z— is —$(CH_2)_n$—, n is 3 and each —$X_1$-$A_1$-$Y_1$ and —$X_2$-$A_2$-$Y_2$ is —$(CH_2)_8$-A-Y, wherein A is —C(═O)—O— or —O—C(═O)—, and Y is —$(CH_2$—$CH_2$—CH(—$CH_3$)—$CH_2)_3$—H or —$(CH_2)_2$—CH═CH—$(CH_2)_8$—H or —$(CH_2)_{12}$—H. In some embodiments, a bioreducible or hydrolysable ionizable cationic lipid comprises a compound of Formula (I) or Formula (I-A) wherein each of $R_2$ and $R_3$ is methyl, Z— is —$(CH_2)_n$—, n is 3 and each —$X_1$-$A_1$-$Y_1$ and —$X_2$-$A_2$-$Y_2$ is —$(CH_2)_{10}$-A-Y, wherein A is —C(═O)—O— or —O—C(═O)—, and Y is —$CH_2$—$CH_2$—$(CH_2$—$CH_2$—CH(—$CH_3$)—$CH_2)_2$—H. In some embodiments, a bioreducible or hydrolysable ionizable cationic lipid comprises a compound of Formula (I) or Formula (I-A) as described in the table in FIG. 3A or the table in FIG. 3B.

In some embodiments, a lipid nanoparticle (LNP) vaccine composition, comprises a mRNA nucleic acid encoding one or more immunogenic proteins, encapsulated in lipidic nanoparticles consisting of:

a. an ionizable cationic lipid of Formula (I) at a N/P ratio of 3.25-8 relative to the mRNA nucleic acid, or a pharmaceutically acceptable salt thereof, wherein $R_1$ and $R_2$ are each independently $C_{1-4}$ alkyl optionally substituted with hydroxyl; Z is *—$(CH_2)_n$—**, wherein * is a covalent bond to the 1,3-dioxolane ring and ** is a covalent bond to —$NR_1R_2$, and n is 2, 3 or 4; —$X_1$— and —$X_2$— are the same of different and are each independently —$(CH_2)_{(x)}$—, wherein (x) is 7-10; -$A_1$- and -$A_2$- are the same or different and are each independently ester groups; —$Y_1$ and —$Y_2$ comprise one or more branched $C_5$ hydrocarbon monomer units having a total of (y) carbon atoms each, wherein (y) is 10-17; wherein —$Y_1$— and —$Y_2$— each comprise a total of one, two or three isopentane (IPN) or 2-methylbut-2-ene (2 MB) branched $C_5$ hydrocarbon monomer units; and the sum of (x)+(y) is 20-25;
b. a phosphocholine phospholipid in a total amount of phospholipids of (10-X) mol % of the total lipid content of the LNP composition;
c. an anionic phospholipid in a total amount of phospholipids of X mol % of the total lipid content of the LNP composition, wherein X is 2.5-7.5;
d. a PEG-containing conjugated lipid in a total amount of 1.5-4.0 mol % of the total lipid content of the LNP composition; and
e. cholesterol, in a molar ratio of the ionizable cationic lipid to the cholesterol of from 65:35 to 45:55.

In some embodiments, the disclosure provides certain compounds useful as ionizable lipids in the preparation of lipid nanoparticles encapsulating a nucleic acid such as mRNA. Aspects of the disclosure are based in part on the discovery of ionizable lipids containing one or more functionalized aliphatic tails interrupted by ester linkages with certain defined ratios of aliphatic chain length on either side of the ester emerged from systematic structure-activity relationship studies aimed at improving nucleic acid delivery while enhancing biodegradability. Applicants discovered that positioning an ester within the lipid tail, rather than only at the headgroup-tail junction, allowed control over certain properties of the ionizable lipids. The ionizable lipids with ester-containing, asymmetrically segmented lipid tails are useful in preparing lipid nanoparticle formulations for the delivery of nucleic acids, such as in mRNA vaccine and therapeutic applications.

An August 2025 study shows the biodistribution patterns of ionizable cationic lipid components of FDA-approved vaccines, including ALC-0315 and SM-102 (Yuxiang R, et al., "Impact of ionizable lipid type on the pharmacokinetics and biodistribution of mRNA-lipid nanoparticles after intravenous and subcutaneous injection," *Journal of Controlled Release*, v. 384, 2025, 113945, ISSN 0168-3659). The publication WO2022/115645 (PCT/US2021/060877) discloses ionizable cationic lipids including KC3-OA.

Figure 4A:
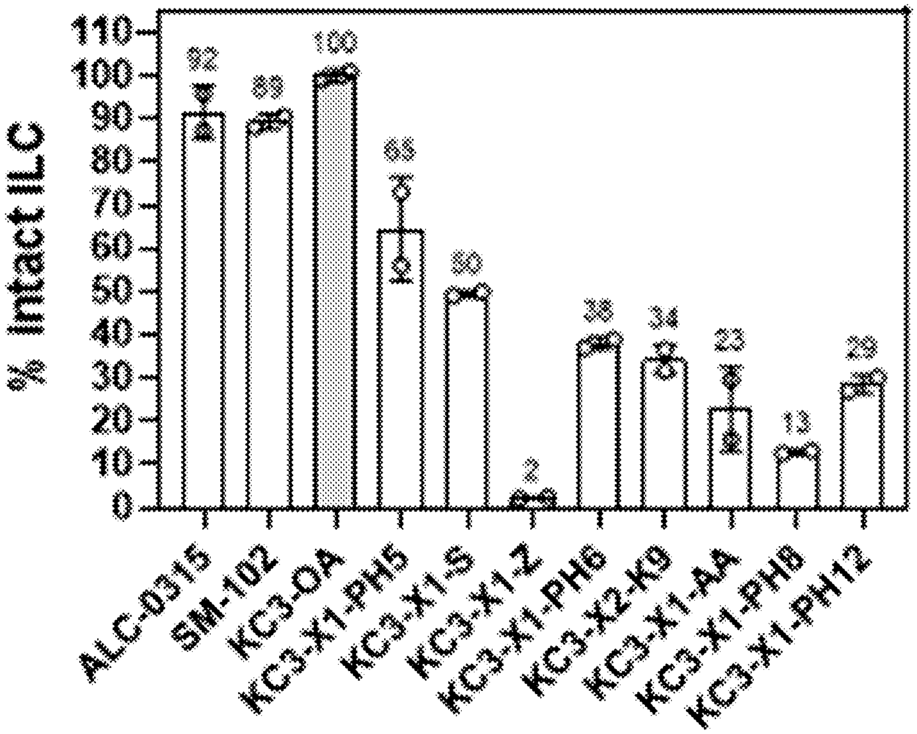
FIG. 4A is a graph of the biodegradability of ionizable cationic lipids (ICLs) measured after 15 minutes in the presence of pancreatin enzymes (including trypsin, amylase and lipase) measured according to the assay of Example 4.
Figure 4B:
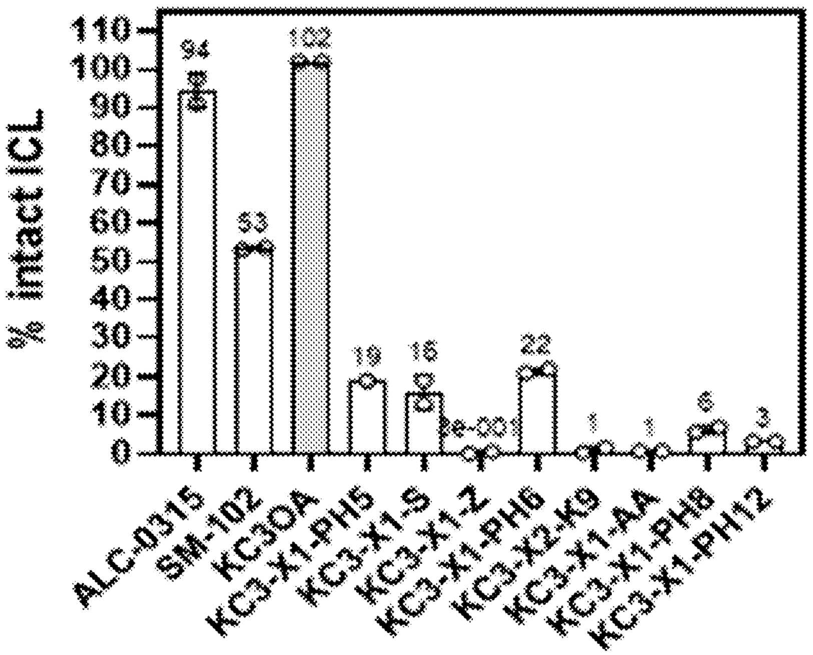
FIG. 4B is a graph of the biodegradability of ionizable cationic lipids (ICLs) measured after 3 hours in the presence of pancreatin enzymes (including trypsin, amylase and lipase) measured according to the assay of Example 4.
Figure 4C:
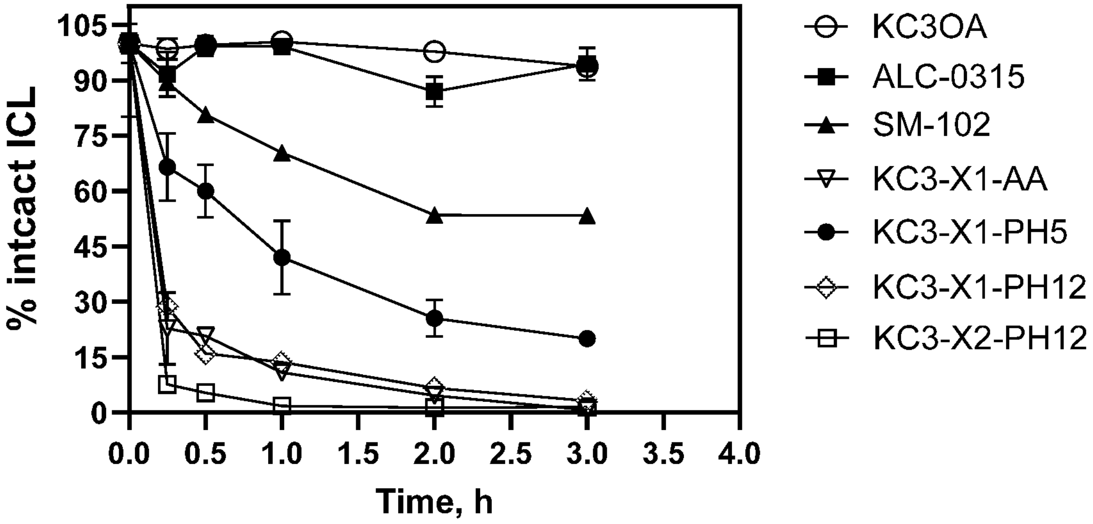
FIG. 4C is a graph showing the enzymatic degradation of various ionizable lipids.

The hydrolysis of various ionizable lipids were evaluated in the pancreatin enzyme assay of Example 4. Pancreatin contains a mixture of digestive enzymes, including lipases and esterases, that mimic the enzymatic environment encountered by LNPs after administration and cellular uptake. FIG. 4A is a graph of the biodegradability of ionizable cationic lipids (ICLs) measured after 15 minutes in the presence of pancreatin enzymes (including trypsin, amylase and lipase) measured according to the assay of Example 4. In FIG. 4A, the compounds of Formula (I) were hydrolyzed about 29%-98% more than ALC-0315, about 27%-98% more than SM-102 and about 35%-98% faster than KC3-OA. FIG. 4B is a graph of the biodegradability of ionizable cationic lipids (ICLs) measured after 3 hours in the presence of pancreatin enzymes (including trypsin, amylase and lipase) measured according to the assay of Example 4. In FIG. 2B, the compounds of Formula (I) were hydrolyzed about 77-99% more than ALC-0315, about 58-99% more than SM-102 and about 81-99% faster than KC3-OA. FIG. 4C is a graph showing the enzymatic degradation of various ionizable cationic lipids. The ionizable lipids of Formula (I) were hydrolyzed significantly faster than ALC-0315 and SM-102 in the assay of Example 4. The hydrolysis of the ionizable lipids of Formula (I) was significantly greater and more rapid than comparator ionizable lipids ALC-0315, SM102 and KC3-OA, when evaluated in an assay incorporating pancreatin enzymes in Example 4.

In some embodiments, the disclosure provides certain LNP compositions comprising one or more ionizable lipids disclosed herein, such as the ionizable lipids of Formula (I). In some aspects, the LNP compositions comprise a nucleic acid encapsulated in lipid nanoparticles formed from: (x) an ionizable lipid of Formula (I) at a N/P ratio of 3 to 8 relative to the nucleic acid in a total amount of 40-65 mol % of the total lipid content of the LNP composition; (y) a sterol in a total amount of 0.5-50 mol % of the total lipid content of the LNP composition; (c) one or more phospholipids in a total amount of phospholipids of 5-50 mol % of the total lipid content of the LNP composition; and (d) a conjugated lipid in a total amount of 0.5-2.5 mol % of the total lipid content of the LNP composition. Unless explicitly indicated otherwise, the isomer form of the phosphatidylserine (PS) lipids used in the Examples is phosphatidyl-L-serine. In some aspects, the LNP composition is further characterized in that: the nucleic acid is mRNA; the ionizable cationic lipid is present in the LNP composition at a N/P ratio of 4 to 7 relative to the nucleic acid; the one or more phospholipids in the LNP comprise a phosphatidylserine (PS) lipid in a total amount of 2.5-10 mol % of the total lipid content of the LNP composition; and the conjugated lipid is a PEG-containing conjugated lipid. In some embodiments, the LNP is a vaccine composition comprising lipid nanoparticles encapsulating mRNA encoding a vaccine antigen (e.g., Tables 5A and 5B), and formed from (x) the ionizable lipid of Formula (I) (e.g., 45-55 mol % KC3-X1-PH5, KC3-X1-PH12, or KC3-X2-PH12), (y) the sterol (e.g., 25-45 mol % cholesterol), (c) a phosphocholine phospholipid (e.g., 1,2-distearoyl-sn-glycero-3-phosphocholine (DSPC), hydrogenated soy phosphatidylcholine (HSPC), or egg sphingomyelin (SM)), (d) a phosphatidyl-L-serine or phosphatidylglycerol phospholipid selected to target dendritic cells (e.g., 2.5-10 mol %, 2.5-7.5 mol %, or 5 mol % dipalmitoylphosphatidyl-L-serine (DPPS), distearoylphosphatidyl-L-serine (DSPS) or (1,2-Distearoyl-sn-glycero-3-phosphoglycerol (DSPG)), and (e) a PEG-conjugated lipid (e.g., 0.5-4.0 mol %, 1.0-4.0 mol %, 1.5-4.0 mol %, 1.5-2.5 mol %, 0.5 mol %, 1.0 mol %, 1.5 mol %, 2.0 mol %, or 2.5 mol % PEG(2000)-dimyristoylglycerol (PEG-DMG) or 1,2-dimyristoyl-rac-glycero-3-methoxypolyethylene glycol-2000 (PEG-DLG)).

In some embodiments, the LNP comprises a phospholipid. A phospholipid is a lipid that comprises a phosphate group and at least one alkyl, alkenyl, or heteroalkyl chain. A phospholipid may be naturally occurring or non-naturally occurring (e.g., a synthetic phospholipid). A phospholipid may comprise an amine, amide, ester, carboxyl, choline, hydroxyl, acetal, ether, carbohydrate, sterol, or a glycerol. In some embodiments, a phospholipid may comprise a phosphocholine, phosphosphingolipid, or a plasmalogen. Exemplary phospholipids include 1,2-distearoyl-sn-glycero-3-phosphocholine (DSPC), 1,2-dipalmitoyl-sn-glycero-3-phosphocholine (DPPC), dipalmitoylphosphatidyl-L-serine (DPPS), distearoylphosphatidyl-L-serine (DSPS), hydrogenated soy phosphatidylcholine (HSPC), and/or sphingomyelin (SM). Additional phospholipids that may be included in an LNP described herein are disclosed in Li, J. et al. (Asian J. Pharm. Sci. 10:81-98 (2015)), which is incorporated herein by reference in its entirety.

Figure 5A:
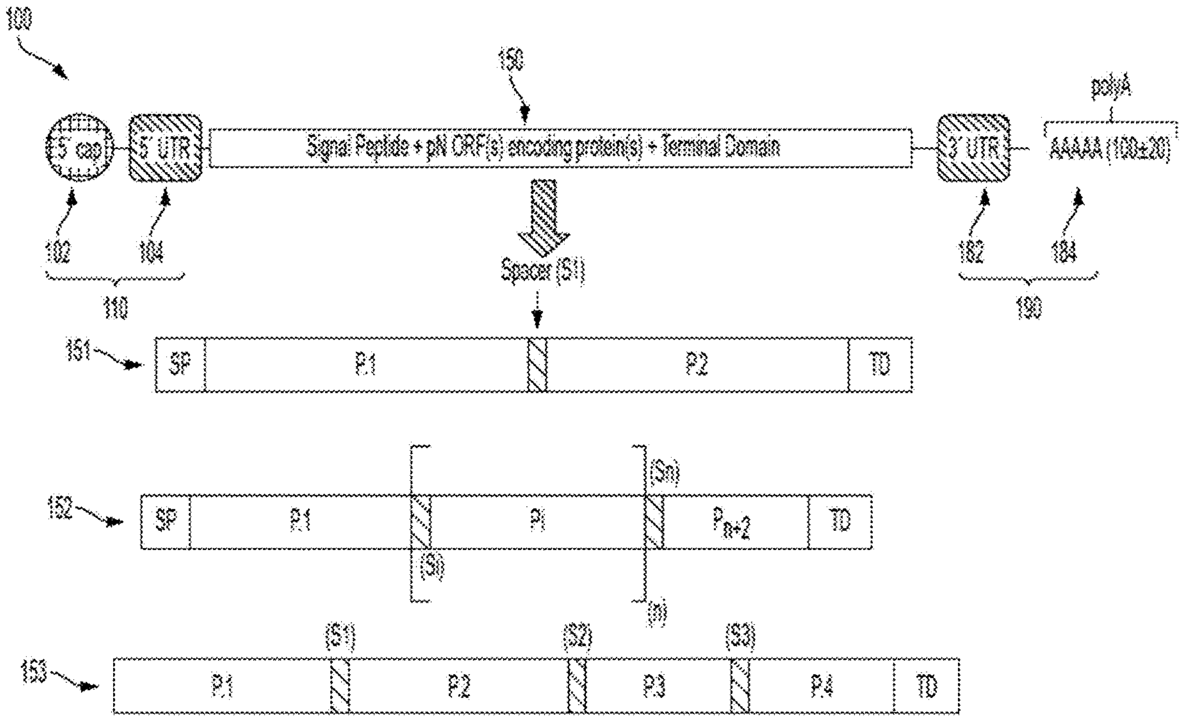
FIG. 5A-5B are each schematics of a mRNA construct comprising a 5'-cap, a 5'-UTR, a cassette comprising a signal peptide, an open reading frame and a terminal domain encoding a synthetic polypeptide, a 3'-UTR and a poly-A region.

In some embodiments, LNP compositions comprising lipid nanoparticles comprising the ionizable lipid(s) disclosed herein and encapsulating mRNA. FIG. 5A is a schematic of a mRNA construct comprising a 5'-cap, a 5'-UTR, a coding sequence (CDS) that encodes a polypeptide antigen, a 3'-UTR and a poly-A region. The CDS can encode a natural or synthetic polypeptide antigen. In some embodiments, the mRNA (100) is a single mRNA comprising a 5' region (110) and a 3' region (190) flanking a CDS (150). The 5' region of the mRNA (110) can comprise a 5' cap and a 5' UTR region. The 3' region of the mRNA (190) can comprise a 3'UTR (182) and a polyA sequence (184). In one embodiment, the mRNA CDS (150) comprises (from 5' to 3') a secreted protein consisting of a signal peptide (SP), and one or more unique polypeptides optionally connected by a spacer. In another embodiment, the mRNA CDS (150) comprises (from 5' to 3') a type I single-pass membrane protein consisting of a signal peptide (SP), one or more unique polypeptide optionally connected by a spacer, and a terminal domain comprising a transmembrane and optionally a cytoplasmic domain. In another embodiment, the mRNA CDS (150) comprises (from 5' to 3') a type II single-pass membrane protein consisting of a transmembrane domain and one or more unique polypeptides optionally connected by a spacer. In another embodiment, the mRNA CDS (150) comprises (from 5' to 3') a type III single-pass membrane protein consisting of an extracellular domain, one or more unique polypeptides optionally connected by a spacer, a transmembrane domain and a intracellular domain comprised of one or more unique polypeptides optionally connected by a spacer. In another embodiment, the mRNA CDS (150) comprises (from 5' to 3') a glycosylphosphatidylinositol (GPI)-anchored membrane protein consisting of a SP, one or more unique polypeptides optionally connected by a spacer, and GPI anchor domain. In another embodiment, the mRNA CDS (150) comprises (from 5' to 3') a multi-pass membrane protein comprised of one or more unique polypeptides optionally connected by a spacer, and two or more transmembrane domains.

The mRNA CDS (150) can be configured to encode one or more covalently-linked unique polypeptides and comprises one or more spacers between each unique antigen protein. For example, a concatenated mRNA CDS (151) can be constructed that encodes for a polypeptide comprising a signal peptide (SP), a first antigen protein (P.1) and a second antigen protein (P.2) separated by a spacer (S1). A concatenated mRNA CDS of various lengths (152) can be constructed that encodes for a polypeptide with a signal peptide (SP), a first antigen protein (P.1), a spacer (Si) between the first antigen protein (P.1) and each subsequent antigen protein (Pi), and a third or subsequent antigen protein (Pn+2), where each consecutive antigen protein is separated by a spacer (Sn). Another CDS (153) can be constructed that encodes for a polypeptide that comprises a signal peptide (SP), a first antigen protein (P.1), a second antigen protein (P.2), a third antigen protein (P.3), and a fourth antigen protein (P.4), wherein each antigen protein is separated by a spacer (S1), (S2) and (S3) respectively. The mRNA spacer CDSs can encode polypeptides comprised of G/P (gly-pro), G/S (gly-ser) or AAY that are positioned between concatenated antigen proteins. In some embodiments, the mRNA polynucleotide sequence of the CDS (150) further encodes (x) a LAMP-1 signal peptide and a LAMP-1 transmembrane and cytoplasmic domain; or (y) a human HLA Class I signal peptide and a LAMP-1 transmembrane and cytoplasmic domain. SEQ ID NO: 35 is the N-terminal signal peptide of human LAMP-1 (Uniprot ID P11279, amino acids 1-28); SEQ ID NO: 36 is the C-terminal domain of human LAMP-1, including the transmembrane and cytoplasmic domains.

The RNA according to aspects of the disclosure may have modified ribonucleotides in order to increase its stability and/or decrease cytotoxicity. For example, in some embodiments, 5-methylcytidine in the RNA is substituted partially or completely, for cytidine. In some embodiments, 5-methylcytidine in the RNA is substituted completely for cytidine. Alternatively or additionally, in some embodiments, pseudouridine in the RNA used is substituted partially or completely, for uridine. In some embodiments, pseudouridine in the RNA used is substituted completely for uridine. In some aspects, the LNP comprises nucleic acid comprising a 5' untranslated region (UTR) and 3' UTR, polyA tail of about 80 to about 140 nucleotides in length, and (i) a 5' enzymatic or (ii) a 5' clean cap. In some aspects, the LNP comprises a chemically modified mRNA, wherein the chemically modified mRNA comprises N1-methylpseudouridine. In other embodiments, the mRNA does not include N1-methyl-pseudouridine.

Figure 5B:
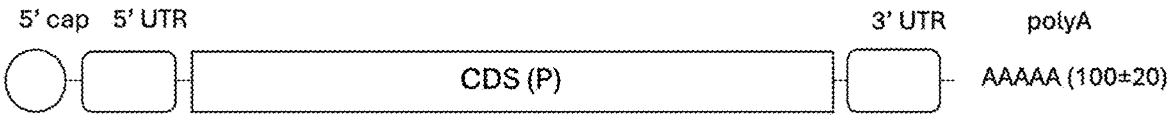
Figure 5B:
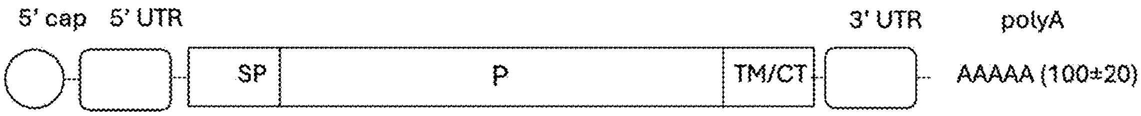
Figure 5B:
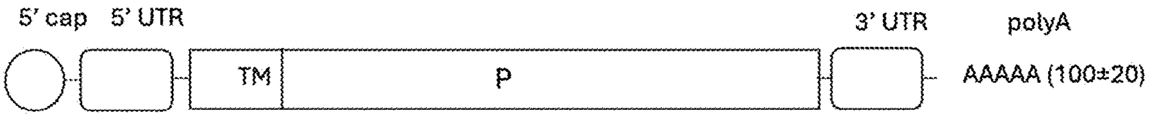
Figure 5B:
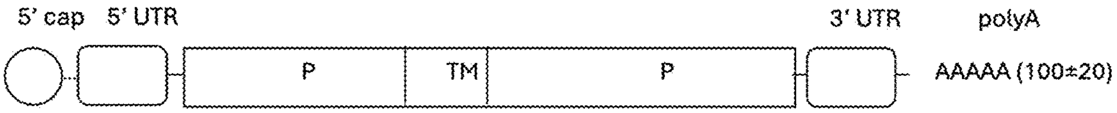
Figure 5B:
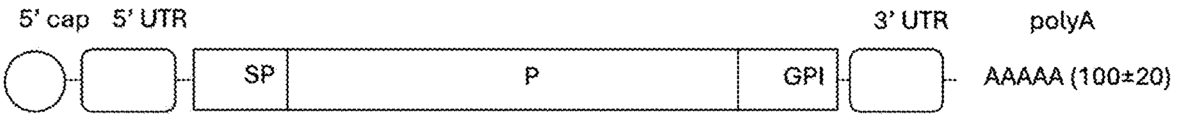
Figure 5B:
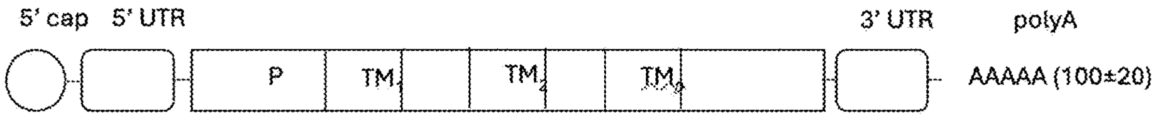
Figure 5B:
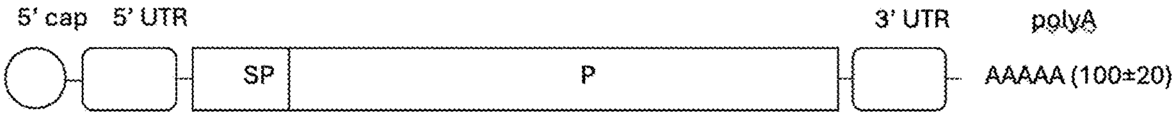
Figure 5B:
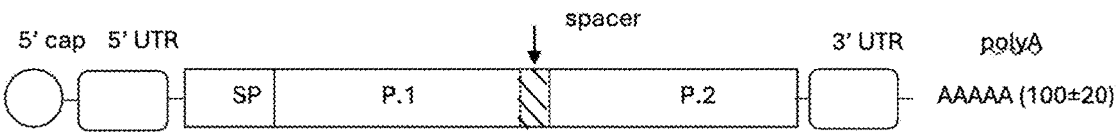
Figure 5B:
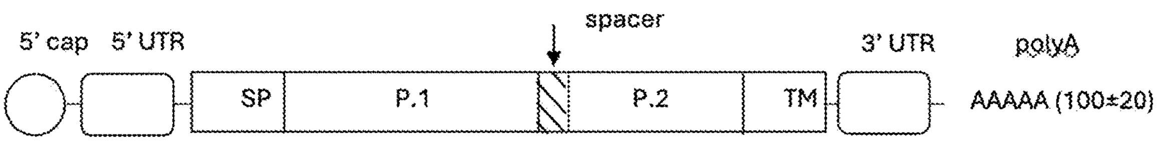

FIG. 5B is a schematic of a mRNA construct (200) comprising a 5' cap, 5' UTR, a polypeptide coding sequence (CDS), 3' UTR, polyA tail. The CDS encodes a polypeptide antigen (P). A Type I single-pass membrane protein mRNA construct (210) encodes a signal peptide encoded at the 5' end (N-terminus of the protein). The transmembrane domain TM with or without a cytoplasmic tail (CT) is encoded at the 3' end (C-terminus of the protein). Most Type I membrane proteins contain a cleavable SP, but it is not an absolute requirement. A Type II single-pass membrane protein mRNA construct (220) encodes a TM encoded at the 5' end (N-terminus of the protein). A Type III single-pass membrane protein mRNA construct (230) encodes the N-terminus of the encoded polypeptide is on the extracellular side of the membrane, followed by a TM domain, followed by an intracellular portion at the C-terminus. There is nosignal peptide. A Glycosylphosphatidylinositol (GPI)-anchored protein mRNA construct (240) encodes a SP at the 5' end (N-terminus), and a GPI-anchor sequence that attaches the polypeptide to a lipid bilayer membrane is located at the 3' end of the CDS (C-terminus of the polypeptide). A multi-pass membrane protein mRNA construct (250) encodes a CDS containing multiple transmembrane domains. A secreted protein mRNA construct (260) encodes signal peptide is encoded at the 5' end (N-terminus of the protein) and there is no transmembrane domain. An example of a secreted antigen mRNA construct (270) consists of two concatenated polypeptides. A CDS encoding a polypeptide comprising an N-terminal SP and two unique polypeptides connected with a short polypeptide spacer. An example of a type I membrane protein mRNA construct (280) contains two concatenated polypeptides. A CDS encoding a polypeptide comprising an N-terminal SP, two unique polypeptides connected with a short polypeptide spacer, and a C-terminal TM domain.

The RNA according to aspects of the disclosure may have modified ribonucleotides in order to increase its stability and/or decrease cytotoxicity. For example, in some embodiments, 5-methylcytidine in the RNA is substituted partially or completely, for cytidine. In some embodiments, 5-methylcytidine in the RNA is substituted completely for cytidine. Alternatively or additionally, in some embodiments, pseudouridine in the RNA used is substituted partially or completely, for uridine. In some embodiments, pseudouridine in the RNA used is substituted completely for uridine. In some aspects, the LNP comprises nucleic acid comprising a 5' untranslated region (UTR) and 3' UTR, polyA tail of about 80 to about 140 nucleotides in length, and (i) a 5' enzymatic or (ii) a 5' clean cap. In some aspects, the LNP comprises a chemically modified mRNA, wherein the chemically modified mRNA comprises N1-methylpseudouridine. In other embodiments, the mRNA does not include Nu-methyl-pseudouridine.

Exemplary LNP formulations can deliver mRNA encoding any protein antigen derived from an infectious pathogen or disease that can be targeted with the immune system. Listed in Tables 5A and 5B is a non-exhaustive list of vaccine antigens that could be encoded by mRNA and encapsulated in LNPs to comprise a vaccine using the lipids, methods, and formulations described in the Examples.

TABLE 5A

Examples of antigens that could be encoded by mRNA and encapsulated in LNPs to comprise a novel vaccine.

| Infectious pathogen/disease | vaccine antigen description | Reference (PMID) |
|---|---|---|
| respiratory syncytial | Prefusion stabilized F (DS-Cav1) and subsequent iterative structural improvements. E.g. sc9-10 DS-Cav1 A149C Y458C, DS-Cav1-153-50A SEQ ID NO: 9 | 24179220, 27478931, |
| virus (RSV) | RSV-G antigen SEQ ID NO: 509 SEQ ID NO: 510 SEQ ID NO: 511 SEQ ID NO: 512 SEQ ID NO: 513 SEQ ID NO: 515 | 30849373, 37689061 |
| Influenza virus (IAV, IBV) | HA (e.g., SEQ ID NO: 5, SEQ ID NO: 12, SEQ ID NO: 14, SEQ ID NO: 915 , SEQ ID NO: 905-907, and/or SEQ ID NO: 18); HA stabilized stem (Group 1 and 2), neuraminidase (NA) (e.g. SEQ ID NO: 37, SEQ ID NO: 38, SEQ ID NO: 39); M2; stabilized H5 (e.g., SEQ ID NO: 15), | 26301691, 26303961, 30808695, 36356572, 35869085, 35383176, A Dosey et al. bioRxiv 2025.07.30.667762 |
| Lassa virus (LASV) | stabilized LASV GPC; nucleoprotein; NP-GPC chimeric fusion protein (e.g., SEQ ID NO: 801 or SEQ ID NO: 803) | 38177144, 32269122, 32142546 |
| human immunodeficiency virus (HIV) | gp120 eOD-GT-based immunogens (e.g. eOD-GT8), stabilized Env trimers (e.g. BG505 DS-SOSPI), conserved protease cleavage sites, gp41 fusion peptide, HLA-E-restricted epitopes | 23539181, 31515132, 27174988, 37098956, 38997302, 33766848, 26687358 |
| *Mycobacterium tuberculosis* (tuberculosis) | individual Mtb proteins (e.g. ESAT-6, CFP10, Ag85B, Ag85A Esx family proteins), SEQ ID NO: 444 | 31114037, 36604540, 15187142, 24349004, 22133873, 34795205, 29263854, 29996082; N |

TABLE 5A-continued

Examples of antigens that could be encoded by mRNA and encapsulated in LNPs to comprise a novel vaccine.

| Infectious pathogen/disease | vaccine antigen description | Reference (PMID) |
|---|---|---|
| | SEQ ID NO: 445<br>SEQ ID NO: 447<br>SEQ ID NO: 449<br>SEQ ID NO: 450<br>synthetic fusion proteins (e.g. M72, H4, H56, H65, H107, CysVac2, BNT164B1/2)<br>SEQ ID NO: 401<br>SEQ ID NO: 403<br>SEQ ID NO: 405<br>SEQ ID NO: 407<br>SEQ ID NO: 409<br>SEQ ID NO: 411<br>SEQ ID NO: 413<br>SEQ ID NO: 415<br>SEQ ID NO: 417<br>SEQ ID NO: 419<br>SEQ ID NO: 421<br>SEQ ID NO: 423<br>SEQ ID NO: 425<br>SEQ ID NO: 427<br>SEQ ID NO: 429<br>SEQ ID NO: 431<br>SEQ ID NO: 437<br>SEQ ID NO: 438<br>SEQ ID NO: 440<br>SEQ ID NO: 442<br>SEQ ID NO: 451 | Agrawal et al. 2025, bioRxiv 2025.09.30.679428 |
| *Plasmodium falciparim* (malaria) | circumsporozoite protein (CPS), RTS,S, R21, CSP-HBsAg fusion (hepatitis B surface Ag); Pfs25; PfGARP; CelTOS, RH5.1, RH5.2 | 27355532, 33964223, 37168860, 35822551, 27457156, 39019011, 39025972, |

TABLE 5B

Examples of antigens that could be encoded by mRNA and encapsulated in LNPs to comprise a novel vaccine.

| Infectious pathogen/disease | vaccine antigen description | Reference (PMID) |
|---|---|---|
| respiratory syncytial virus (RSV) | RSVpreF (DS-Cav1) and subsequent iterative structural improvements. E.g. sc9-10 DS-Cav1 A149C Y458C, DS-Cav1-153-50A | 24179220, 27478931, 30849373, 37689061 |
| Influenza virus (IAV, IBV) | HA, HA stabilized stem, NA, M2 | 26301691, 26303961, 30808695, 36356572, 35869085, 35383176, 3480945 |
| Lassa virus (LASV) | stabilized LASV GPC, nucleoprotein | 38177144, 32269122, 32142546 |
| SARS-COV-2, betacoronaviruses | spike (S) protein, nucleocapsid, membrane, ORF3a, ORF1ab | 33128877 |
| Middle East respiratory syndrome coronavirus (MERS-COV) | spike (S) glycoprotein | 28807998 |
| Ebola virus (EBOV) | glycoprotein (GP), nucleoprotein (NP) | 32418798, 31589088, 32234486 |
| Marburg virus (MARV) | glycoprotein (GP), nucleoprotein (NP) | 31589088, 32234486 |
| human metapneumovirus (HMPV) | F glycoprotein | 34551978 |
| parainfluenza virus | Type 1 and type 4. Prefusion stabilized fusion proteins (e.g. prefusion PIV3 F) | 30420505 |

TABLE 5B-continued

Examples of antigens that could be encoded by mRNA and encapsulated in LNPs to comprise a novel vaccine.

| Infectious pathogen/disease | vaccine antigen description | Reference (PMID) |
|---|---|---|
| human immunodeficiency virus (HIV) | gp120 eOD-GT-based immunogens (e.g. eOD-GT8), stabilized Env trimers (e.g. BG505 DS-SOSPI), conserved protease cleavage sites, gp41 fusion peptide | 23539181, 31515132, 27174988 |
| human papilloma viruses (HPV) | L1 capsid protein, E7, glycoprotein D, gDE7 fusion | 38462683, 36867683 |
| Zika virus (ZIKV) | prM-E | 28222903 |
| Powassan virus (POWV) | prM, prE | 30566864 |
| MPox virus | A35, B6, M1, H3 | 38366591 |
| norovirus | capsid protein VP1 | 38811605 |
| human cytomegalovirus (HCMV) | glycoprotein B (gB), gH, gL, UL128, UL130, UL131 | 38324766, 29456015 |
| Ebstein Barr virus (EBV) | glycoprotein gp350, gp42, gH/gL (gp42/gp350) | 38479361, 38926438 |
| human varicella-zoster virus (VZV) | envelope glycoprotein E (gE) | 25916341 |
| Rabies virus (RABV) | glycoprotein (G) | 37349310 |
| West Nile virus (WNV) | premembrane (prM), envelope (E) | 37125778 |
| Dengue virus (DENV) | envelope protein (E), premembrane (prM), NS1, NS3, NS5, NS4B | 35608749 |
| Chikungunya virus (CHIKV). other Alphaviruses of the *Togaviridae* family (RRV, ONNV, BFV, MAYV, SINV, EEEV, WEEV, VEEV) | E1, E2, E3 glycoproteins | 23670192, 38005854, 36474012 |
| Nipah virus (NiV) | glycoprotein (G) | 38726013 |
| *Mycobacterium tuberculosis* (tuberculosis) | individual Mtb proteins (e.g. ESAT-6, CFP10, Ag85B, Esx family proteins), synthetic fusion proteins (e.g. M72) | 31114037, 36604540 |
| *Plasmodium falciparim*(malaria) | circumsporozoite protein (CPS); RTS,S; CSP-HBsAg fusion (hepatitus B surface Ag); Pfs25; PfGARP; CelTOS | 27355532, 33964223, 37168860 |
| *Borrelia burgdorferi*(Lyme disease) | outer surface protein A (OspA) | 37533256 |
| cancer | cancer neoantigens | 37165196, 28678784, 35970920, 38538867 |
| *A. americanum* (alpha-gal hypersensitivity), *I. scapularis* | Salivary proteins (e.g. Salp-family proteins, TSLPI) | 34788080, 37407406 |
| Mumps (MuV) | Fusion glycoprotein F, prefusion F variants, HN | 39527740, PCT/US2020/064619, WO2021119497A1 |
| Measles (MeV) | Fusion glycoprotein F, prefusion F | PCT/US2020/064619, WO2021119497A1 |

In some embodiments, the mRNA is a nucleic acid comprising or consisting of SEQ ID NOS: 3, 4, 6, 8, 10, 13, 16, 17, 402, 404, 406, 408, 410, 412, 414, 416, 418, 420, 422, 424, 426, 428, 430, 432, 439, 441, 443, 446, 448, 452, 501, 502, 505, 506, 507, 508, 514, 516, 802, 804, 901, 902, 903, 904, 909, or 914.

In some embodiments, the mRNA encodes a peptide or a protein comprising or consisting of SEQ ID NOS: 2, 5, 7, 9, 12, 14, 15, 18, 36, 37, 38, 39, 401, 403, 405, 407, 409, 411, 413, 415, 417, 419, 421, 423, 425, 427, 429, 431, 433, 434, 437, 438, 440, 442, 444, 445, 447, 449, 450, 451, 509, 510, 511, 512, 513, 515, 801, 803,905, 906, 907, 908, 910, 911, 912 or 915.

Figure 6B:
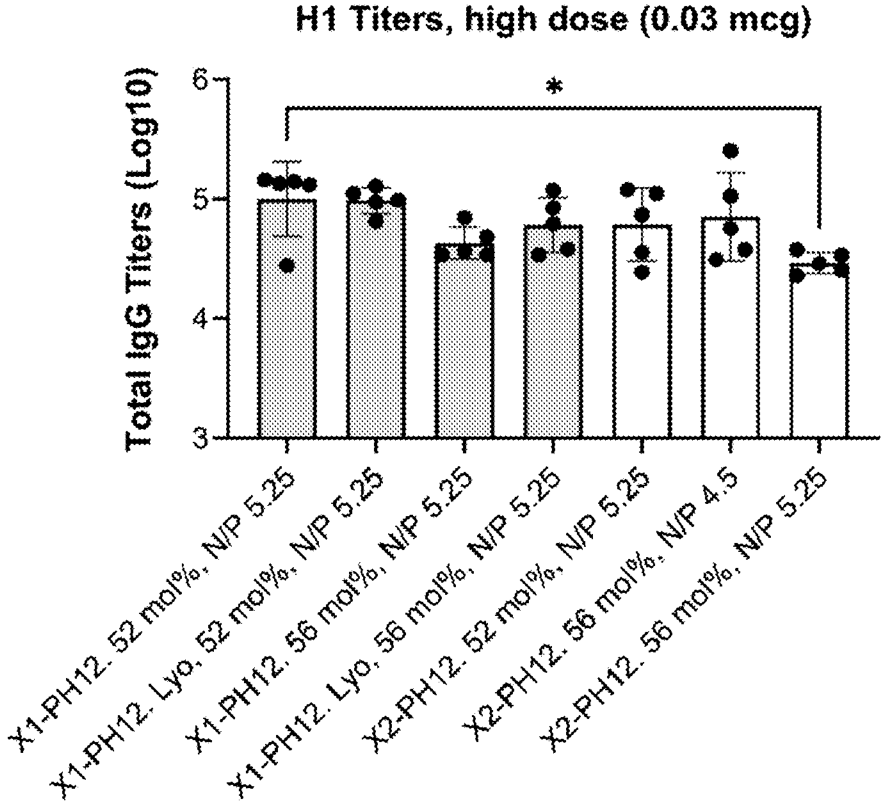
Figure 6C:
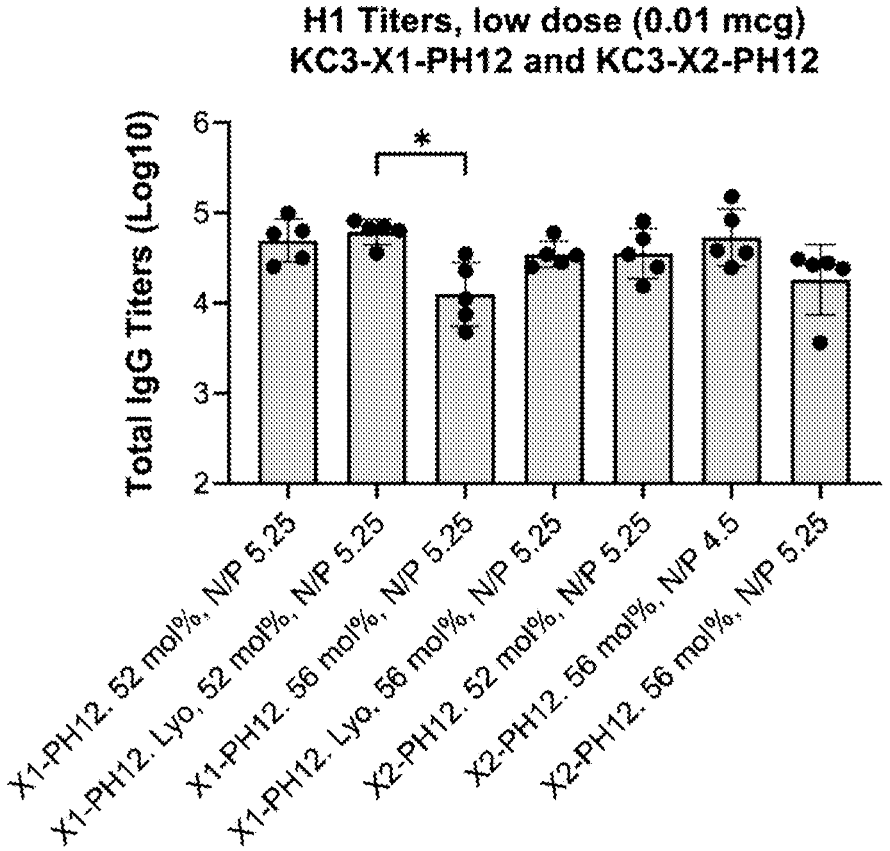
Figure 6D:
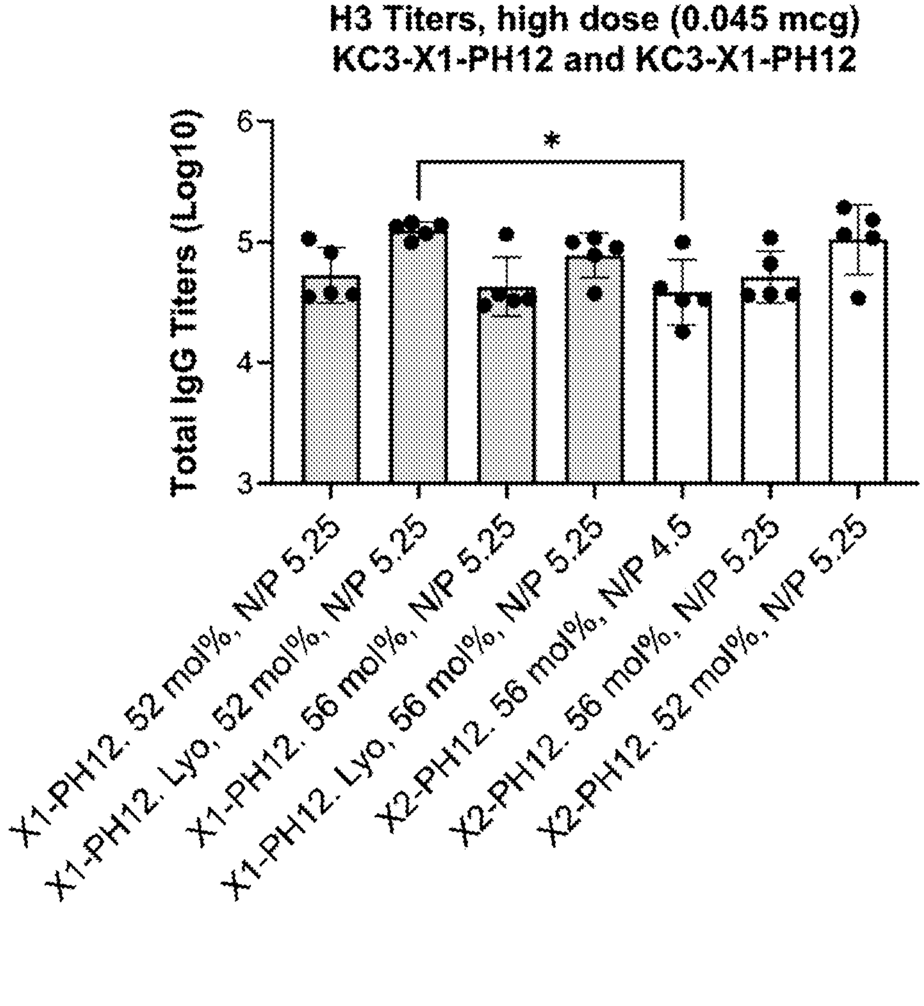
Figure 6E:
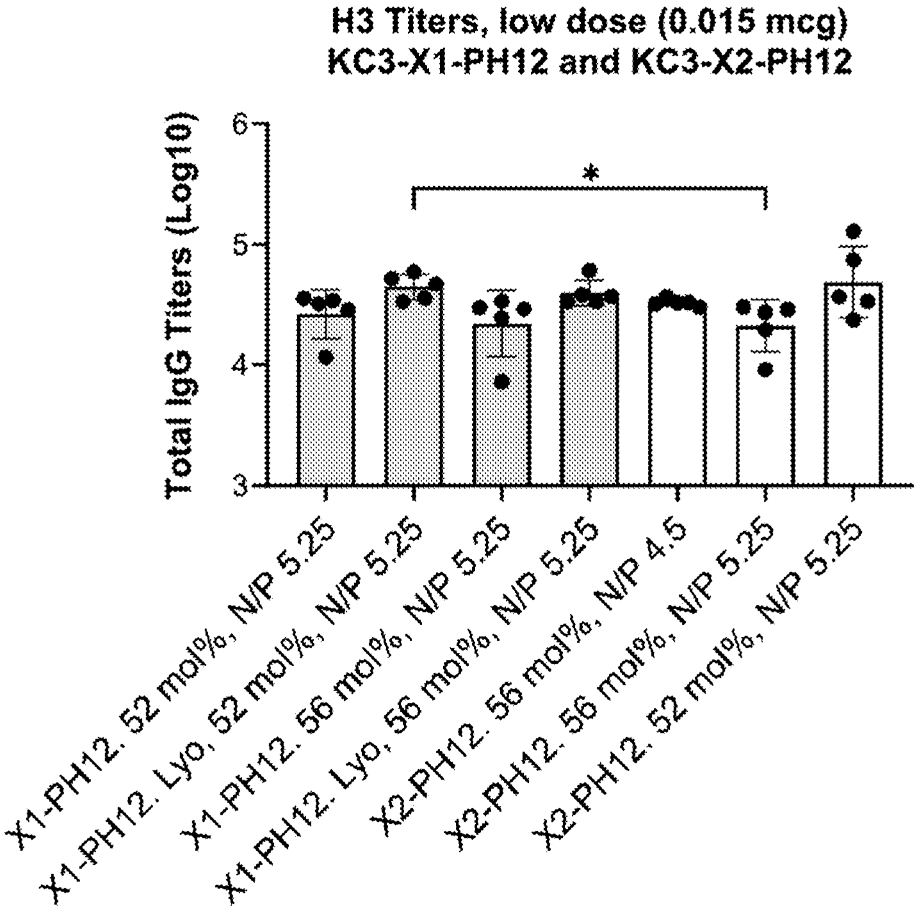

The mRNAs encoding antigens for influenza A subtypes H1 (SEQ ID NO:13 encoding SEQ ID NO:12), H3 (SEQ ID NO:914 encoding SEQ ID NO:14), influenza B/Victoria (SEQ ID NO:17 encoding SEQ ID NO:915), and RSVpreF (SEQ ID NO:10 encoding SEQ ID NO:9) were combined at equal weight ratios and encapsulated into LNPs comprising ionizable lipids of Formula (I) as described in Example 2. To measure the ability of these mRNA-LNPs to induce antibodies, BALB/c mice were immunized at a high and 3-fold lower dose in the caudal thigh in a volume of 50 μL. The experimental design and dosing schema is shown in FIG. 6A. Twenty-one days post vaccination, serum was collected and stored at −80° C. until analysis. Mouse IgG endpoint antibody titers against the matching H1, H3, B-Victora, RSVpreF or H5 antigens were determined by standard ELISA. For H1-specific Ab titers, we found for KC3-X1-PH12 that immunogenicity of freeze-dried material was not deleterious for biological activity (FIG. 6B and FIG. 6C). This was true for 52 and 56 mol % ICL with N/P=5.25. Second, Ab titers were comparable between LNPs comprised of KC3-X1-PH12 and KC3-X2-PH12, showing that either orientation of the biodegradable ester bond can be used for PH12 with a KC3 headgroup. Third, we found for KC3-X1-PH12 that either 52 or 56 mol % with N/P=5.25 elicited similar immune responses; the same was true for X2-PH12. For H3-specific Ab titers (FIG. 6D and FIG. 6E), results were similar to H1 titers: lyophilization of the mRNA-LPN was not deleterious to biological activity (H3 titers elicited by lyophilized material trended higher than for non-lyophilized, X1-PH12 and X2-PH12 were comparably immunogenic, and these ICLs can be used with either 52 or 56 mol % without impacting antibody titers.

The method of making a LNP can comprise mixing a first solution with a second solution. Mixing can be achieved using standard liquid mixing techniques, such as propellor mixing, vortexing solutions or preferably through microfluidic mixing or high efficiency T-mixing. In some embodiments, the first solution comprises a lipid or a plurality of lipids and a nucleic acid, where all components are solubilized, in water/solvent system. The solvent may be any water miscible solvent (e.g., ethanol, methanol, isopropanol, acetonitrile, dimethylformamide, dimethylsulfoxide, dioxane or tetrahydrofuran). In some embodiments, the first solution comprises a small percentage of water or pH buffered water. In some embodiments, the first solution comprises a single type of lipid, for example, an ionizable lipid, a phospholipid, a sterol, or a PEG-containing lipid. In some embodiments, the first solution comprises a plurality of lipids. In some embodiments, the plurality comprises an ionizable lipid, a phospholipid, a sterol, or a PEG-containing lipid. In some embodiments, the second solution is water. In some embodiments, the second solution is an aqueous buffer with a pH between 3-6 (e.g., a pH of about 3, about 4, about 5, or about 6). The second solution may comprise a load component, e.g., a nucleic acid (e.g., mRNA). The second solution may comprise a small percentage of water-miscible organic solvent. In some embodiments, the solution comprising a mixture of the first and second solutions comprising the LNP suspension can be diluted. In some embodiments, the pH of the solution comprising a mixture of the first and second solutions comprising the LNP suspension can be adjusted. Dilution or adjustment of the pH of the LNP suspension can be achieved with the addition of water, acid, base or aqueous buffer. In some embodiments, no dilution or adjustment of the pH of the LNP suspension is carried out. In some embodiments, both dilution and adjustment of the pH of the LNP suspension is carried out. In some embodiments, excess reagents, solvents, unencapsulated nucleic acid maybe removed from the LNP suspension by tangential flow filtration (TFF) (e.g., diafiltration). The organic solvent (e.g., ethanol) and buffer may also be removed from the LNP suspension with TFF. In some embodiments, the LNP suspension is subjected to dialysis and not TFF. In some embodiments, the LNP suspension is subjected to TFF and not dialysis. In some embodiments, the LNP suspension is subjected to both dialysis and TFF. In one aspect, the present disclosure features a method comprising treating a sample of LNPs comprising nucleic acid, with a fluid comprising a detergent (e.g., Triton X-100, or anionic detergents (such as, but not limited to, sodium dodecyl sulfate (SDS), or non-ionic detergent, such as but not limited to β-octylglucoside, or Zwittergent 3-14) for a period of time suitable to degrade the lipid layer and thereby release the encapsulated and/or entrapped nucleic acid(s). In an embodiment, the method further comprises analyzing the sample for the presence, absence, and/or amount of the released nucleic acid(s).

Methods of making lipid nanoparticle (LNP) compositions encapsulating mRNA are provided in Example 7 (Preparing ligand-targeted LNPs) and Example 9 (Preparation of lipidic nanoparticles) of Patent Cooperation Treaty Patent Application PCT/US2021/060877 (WO2022/115645), are incorporated herein by reference in their entirety. Methods of making lipid nanoparticle (LNP) compositions encapsulating mRNA are provided in Example 7 (Preparing ligand-targeted LNPs) and Example 9 (Preparation of lipidic nanoparticles) of Patent Cooperation Treaty Patent Application PCT/US2023/067517 (WO2023/230587), are incorporated herein by reference in their entirety. Methods of characterizing lipid nanoparticle (LNP) compositions encapsulating mRNA are provided in Example 10 (LNP Characterization) and Example 11 (Determination of transfection efficiency in murine dendritic cells of LNPs using mCherry mRNA) of Patent Cooperation Treaty Patent Application PCT/US2021/060877 (WO2022/115645), are incorporated herein by reference in their entirety. Methods of making lipid nanoparticle (LNP) compositions encapsulating mRNA are provided in Example 10 (LNP Characterization) and Example 11 (Determination of transfection efficiency in murine dendritic cells of LNPs using mCherry mRNA) of Patent Cooperation Treaty Patent Application PCT/US2023/067517 (WO2023/230587), are incorporated herein by reference in their entirety. These methods can be modified by using a microfluidics chip from ChipShop (187) to make LNPs at flow rates of 18 mL/min instead of the Nanoprecision Systems microfluidics cassette at 6 ml/min whilst keeping downstream processing and analytical procedures the same as described in the published patents referenced above. Additional disclosure of methods for the manufacture of mRNA lipid nanoparticle compositions are provided in: S. J. Shepherd, X. Han, A. J. Mukalel, R. El-Mayta, A. S. Thatte, J. Wu, M. S. Padilla, M. Alameh, N.

Srikumar, D. Lee, D. Weissman, D. Issadore, & M. J. Mitchell, Throughput-scalable manufacturing of SARS-CoV-2 mRNA lipid nanoparticle vaccines, Proc. Natl. Acad. Sci. U.S.A. 120 (33) e2303567120, doi.org/10.1073/pnas.2303567120 (2023), incorporated by reference herein in its entirety.

EXAMPLES

Certain examples are provided below to illustrate various embodiments of the embodiments disclosed herein. One of ordinary skill in the art will recognize that the various embodiments disclosed herein are not limited to these specific illustrative examples.

Example 1: Synthesis of Ionizable Cationic Lipids

Synthesis of KC3-X1 Ionizable Cationic Lipids

FIG. 1A is a general synthesis for compounds of Formula (I) wherein $W_1$ and $W_2$ are each *—O—C(O)—**, * is a covalent bond to $Y_1$ or $Y_2$ and ** is a covalent bond to $X_1$ or $X_2$ (respectively), $X_1$ or $X_2$ are each —$(CH_2)_x$—, and $Y_1$ or $Y_2$ are each identical linear or branched hydrocarbon chains with (y) total carbons (i.e., "KCn-X1" ionizable cationic lipids). A general synthesis for compounds of formula (I) shown in Scheme 1 involves i) esterification of the ketone dicarboxylic acid, ii) acid catalyzed trans ketal formation, iii) Mesylation of the primary alcohol, and finally iv) displacement of the mesyl group using dialkylamine resulting in a tertiary amine. A general synthesis of ketone dicarboxylic acid starting material in Scheme 1 is presented below in Scheme 2. A general synthesis of ketone dicarboxylic acid starting material shown in Scheme 2 involves i) treatment of suitable bromo alkyl carboxylate with toluenesulfonylmethyl isocyanide in the presence of a base, ii) conversion of the TosMIC adduct to ketone in the presence of HCl, and finally iv) hydrolysis of the ethyl carboxylate to ketone dicarboxylic acid.

Figure 1B:
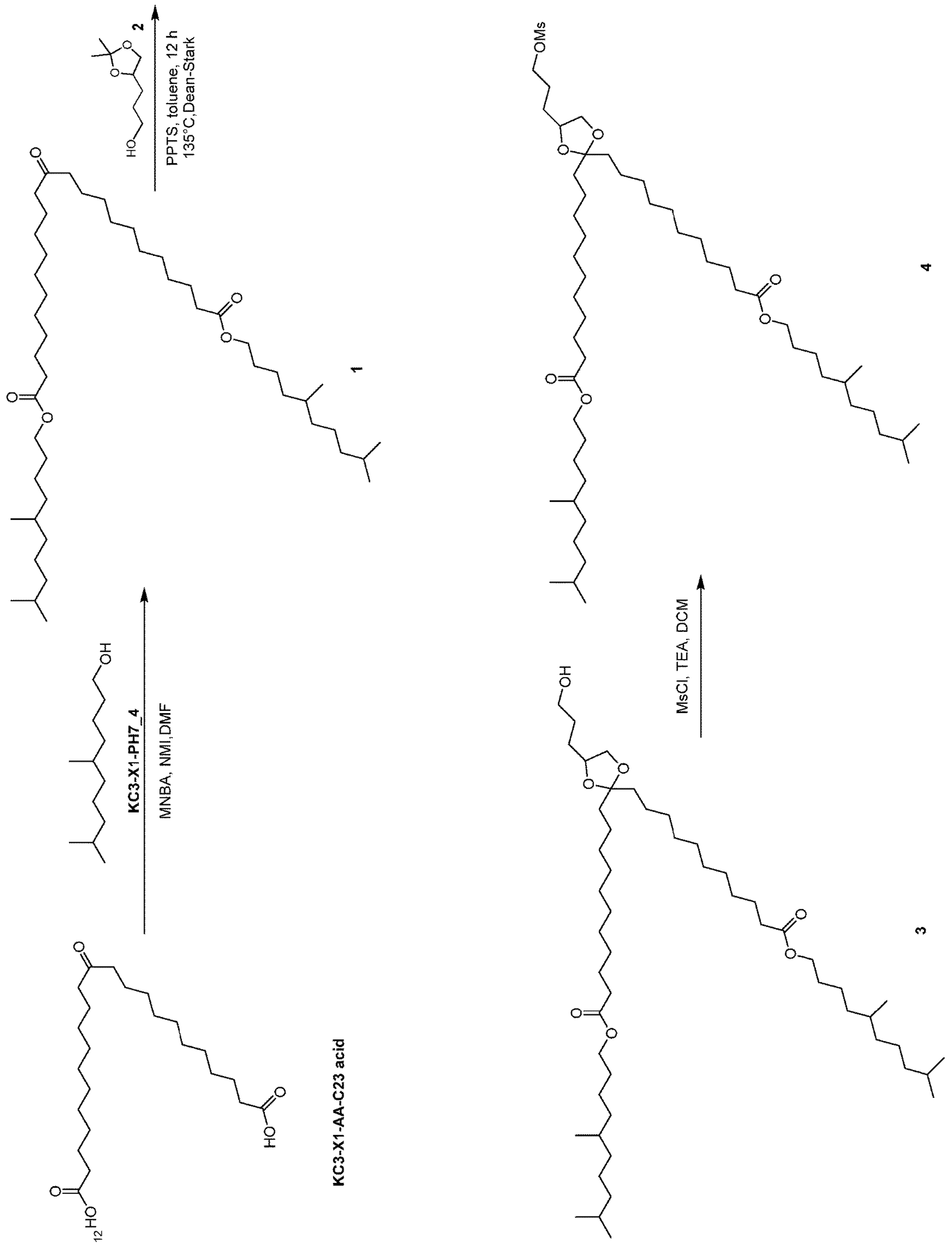
FIG. 1B is a synthetic scheme for preparing an exemplary ionizable cationic lipid designated KC3-X1-PH12.
Figure 1B:
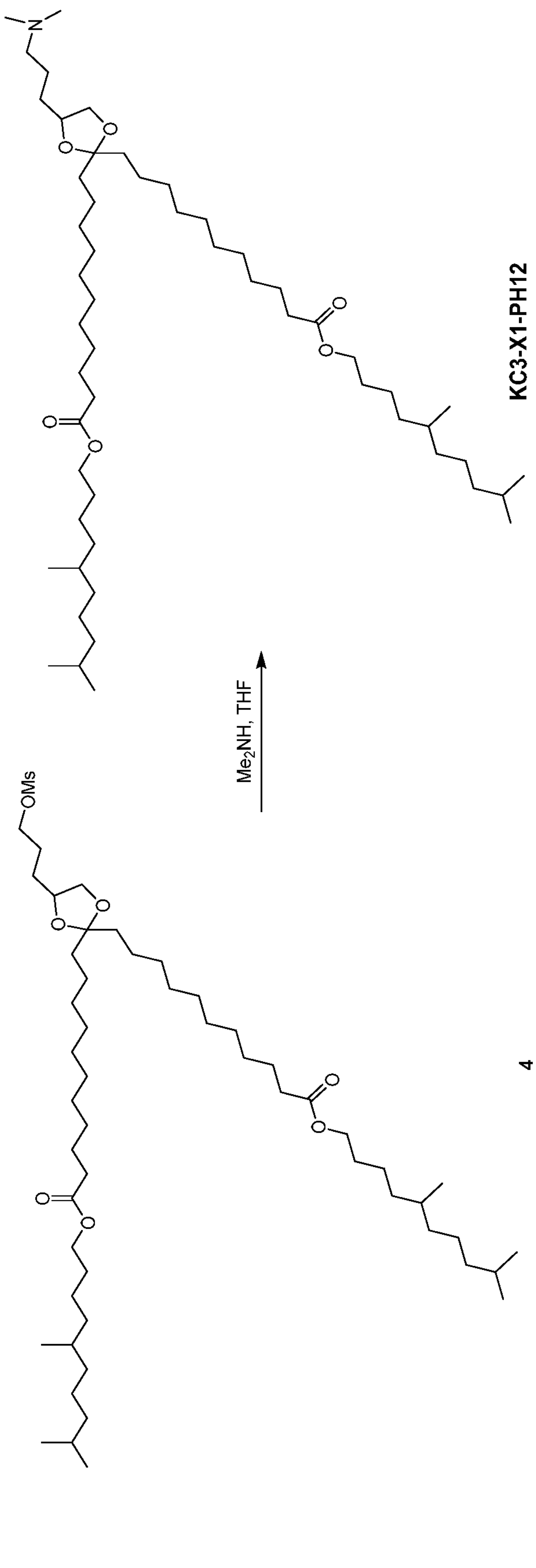

FIG. 1B is a chemical synthesis for preparing an ionizable cationic lipid of Formula (I) designated KC3-X1-PH12, as described below.

To a solution of KC3-X1-AA-C23 acid (800 mg, 2.01 mmol, 1 eq) and KC3-X1-PH7_4 (1.12 g, 6.02 mmol, 3 eq) in DMF (10 mL) was added NMI (1.65 g, 20.07 mmol, 1.60 mL, 10 eq) and MNBA (2.07 g, 6.02 mmol, 3 eq). The mixture was stirred at 70° C. for 12 hr. The reaction mixture was quenched by addition aq.$NaHCO_3$ (sat. 30 mL) at 25° C., and extracted with EtOAc (10 mL*3). The combined organic layers were washed with brine (10 mL*3), dried over $Na_2SO_4$, filtered and concentrated under reduced pressure to give a residue. The residue was purified by flash silica gel chromatography (ISCO®; 40 g SepaFlash® Silica Flash Column, Eluent of 0~3% Ethylacetate/Petroleum ethergradient @60 mL/min) to give compound 1 (1.5 g, 1.43 mmol, 71.2% yield, 70.1% purity) as a white solid. $^1H$ NMR (400 MHz, CHLOROFORM-d, EW58311-330-P1A1) δ 4.00 (t, J=6.8 Hz, 4H), 2.31 (t, J=7.4 Hz, 4H), 2.22 (t, J=7.6 Hz, 4H), 1.58-1.42 (m, 16H), 1.32-1.19 (m, 36H), 1.09-1.00 (m, 8H), 0.81-0.78 (m, 18H).

A mixture of compound 1 (1.5 g, 2.04 mmol, 1 eq), PPTS (256.36 mg, 1.02 mmol, 0.5 eq) and compound 2 (588.36 mg, 3.67 mmol, 1.8 eq) in Tol. (20 mL) was heated to reflux and remove water by Dean-Stark trap. The mixture was stirred at 135° C. for 12 hr. The reaction mixture was quenched by addition aq.$NaHCO_3$ (sat. 60 mL) at 25° C., and extracted with EtOAc (30 mL*3). The combined organic layers were washed with brine (20 mL*3), dried over $Na_2SO_4$, filtered and concentrated under reduced pressure to give a residue. The residue was purified by flash silica gel chromatography (ISCO®; 40 g SepaFlash® Silica Flash Column, Eluent of 0~10% Ethyl acetate/Petroleum ether gradient @60 mL/min) to give compound 3 (1 g, 1.19 mmol, 58.5% yield) as a yellow oil. $^1H$ NMR (400 MHz, CHLOROFORM-d, EW58311-334-P1A1) δ 4.13-4.05 (m, 6H), 3.75-3.66 (m, 2H), 3.52-3.45 (m, 1H), 2.31 (t, J=7.6 Hz, 4H), 1.74-1.48 (m, 20H), 1.41-1.26 (m, 41H), 1.18-1.08 (m, 8H), 0.90-0.85 (m, 18H).

To a solution of compound 3 (1 g, 1.19 mmol, 1 eq) in DCM (10 mL) was added TEA (604.23 mg, 5.97 mmol, 831.13 μL, 5 eq) and MsCl (630 mg, 5.50 mmol, 425.68 μL, 4.61 eq). The mixture was stirred at 0° C. for 1 hr. The reaction mixture was quenched by addition ice-water (30 mL) at 0° C., and extracted with EtOAc (10 mL*3). The combined organic layers were washed with brine (10 mL*3), dried over $Na_2SO_4$, filtered and concentrated under reduced pressure to give a residue. The residue was purified by flash silica gel chromatography (ISCO®; 12 g SepaFlash® Silica Flash Column, Eluent of 0~15% Ethyl acetate/Petroleum ether gradient @40 mL/min) to give compound 4 (1 g, 1.09 mmol, 91.5% yield) as a yellow oil. $^1H$ NMR (400 MHz, CHLOROFORM-d, EW58311-335-P1A1) δ 4.36-4.24 (m, 2H), 4.12-4.03 (m, 6H), 3.54-3.44 (m, 1H), 3.03 (s, 3H), 2.31 (t, J=7.6 Hz, 4H), 1.99-1.79 (m, 2H), 1.69-1.52 (m, 20H), 1.40-1.27 (m, 38H), 1.19-1.06 (m, 8H), 0.94-0.83 (m, 18H).

A solution of compound 4 (900 mg, 983.14 mol, 1 eq) in $Me_2NH$/THF (2 M, 20 mL, 40.69 eq) was stirred at 55° C. for 12 hr. The mixture was concentrated in vacuo to give a residue. The residue was purified by flash silica gel chromatography (ISCO®; 20 g SepaFlash® Silica Flash Column, Eluent of 0~8% Ethyl acetate/(Petroleum ether/Dichloromethane=3/1, 0.1% TEA as eluant) @40 mL/min) and followed by reversed-phase HPLC(column: PHS XP Phenyl-Hexyl 150*25 mm*7 um; mobile phase: [$H_2O$ (0.225% FA)-EtOH]; gradient: 65%-95% B over 15.0 min). KC3-X1-PH12 (0.094 eq. FA salt, 435.5 mg, 495.75 μmol, 53.6% yield, 98.4% purity) was obtained as a colorless oil. LCMS (EW58311-340-P1C1): CAD, m/z, M+H=865.0. HRMS (ESI) m/z: $[M+H]^+$ Calcd for $C_{54}H_{106}NO_6^+$ 864.8015, found 864.8044. $^1H$ NMR (400 MHz, CHLOROFORM-d, EW58311-340-P1A1) δ 8.55 (s, 0.094H, FA salt), 4.15-3.98 (m, 6H), 3.52-3.40 (m, 1H), 2.36 (br t, J=7.2 Hz, 2H), 2.32-2.26 (m, 10H), 1.67-1.47 (m, 18H), 1.41-1.19 (m, 39H), 1.16-1.00 (m, 8H), 0.93-0.76 (m, 18H).

Figure 1C:
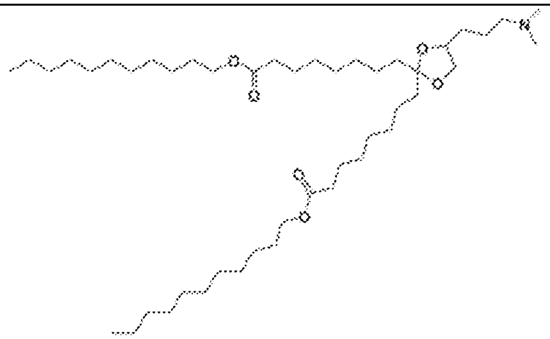
FIG. 1C is a table of ionizable cationic lipids.
Figure 1C:
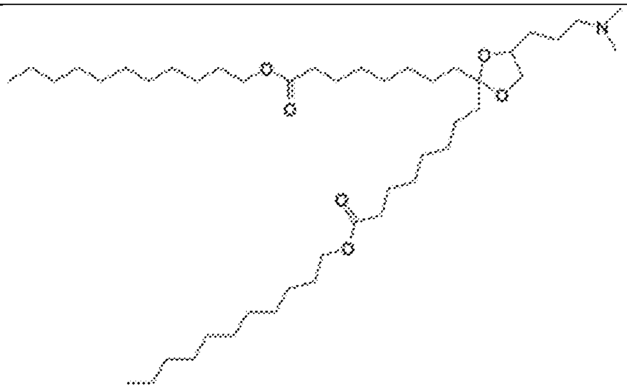
Figure 1C:
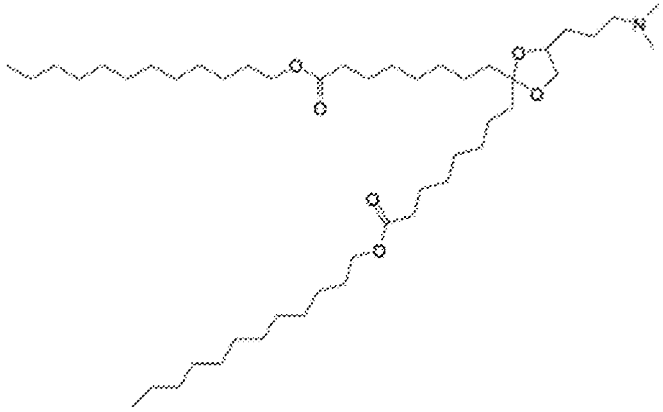
Figure 1C:
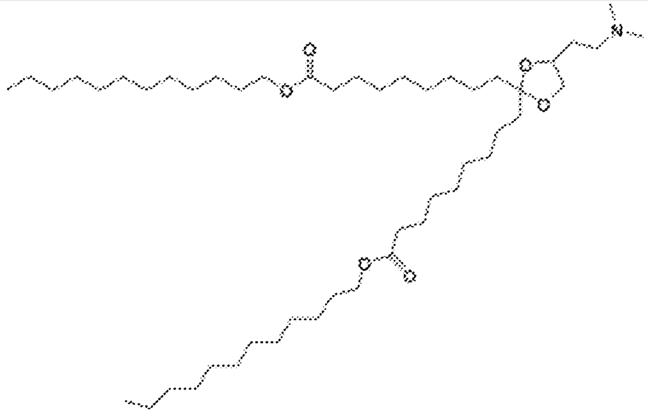
Figure 1C:
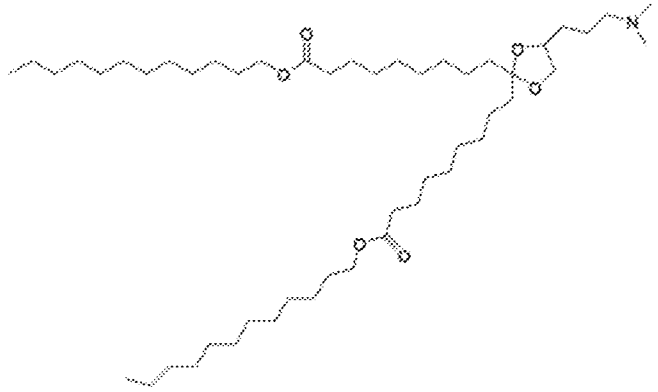
Figure 1C:
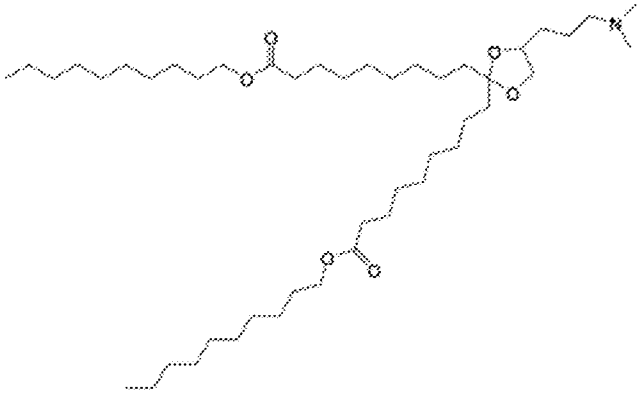
Figure 1C:
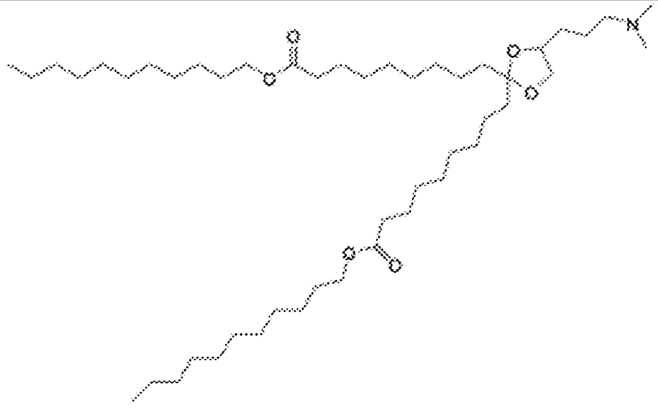
Figure 1C:
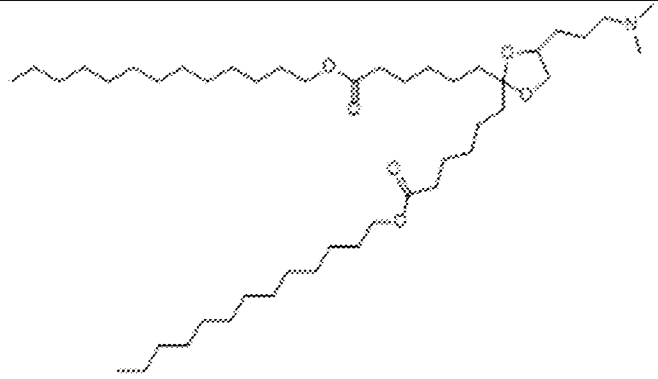
Figure 1C:
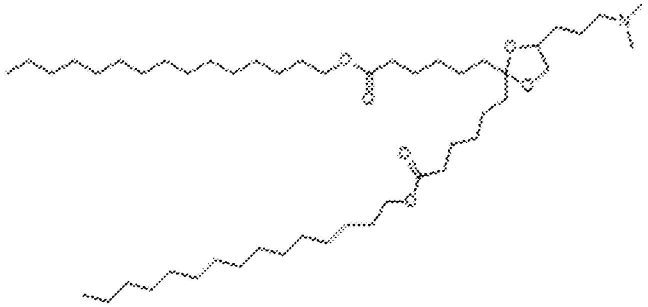
Figure 1C:
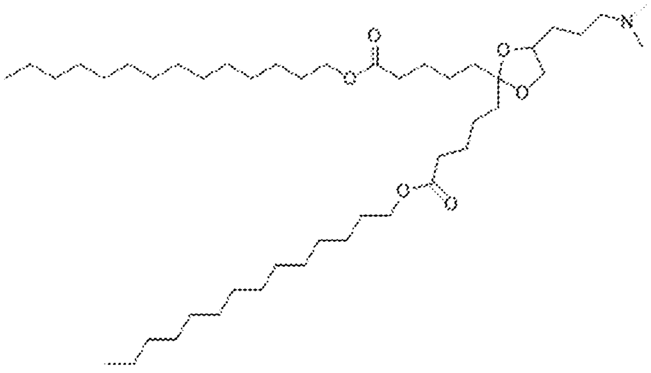
Figure 1C:
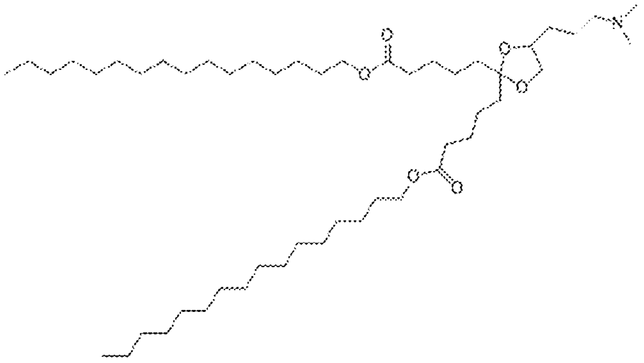
Figure 1C:
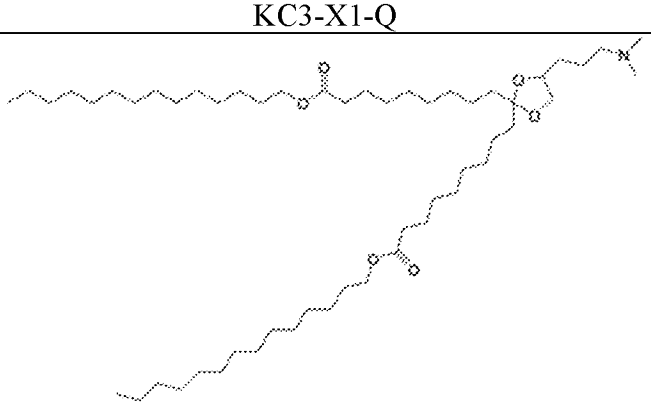
Figure 1C:
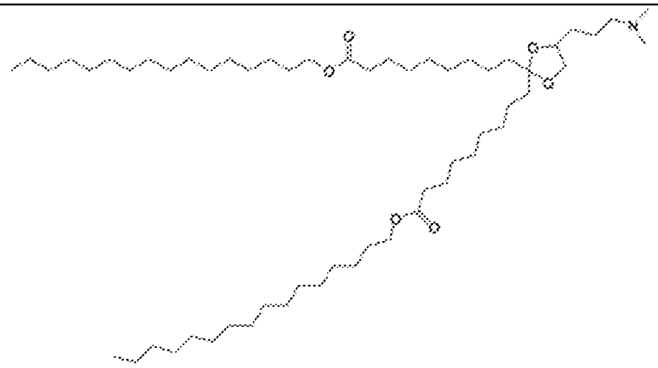
Figure 1C:
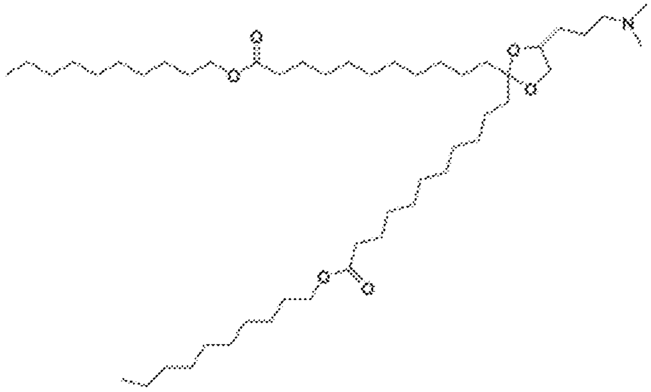
Figure 1C:
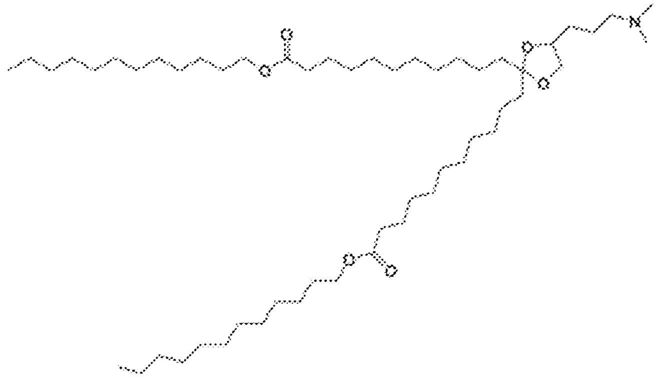
Figure 1C:
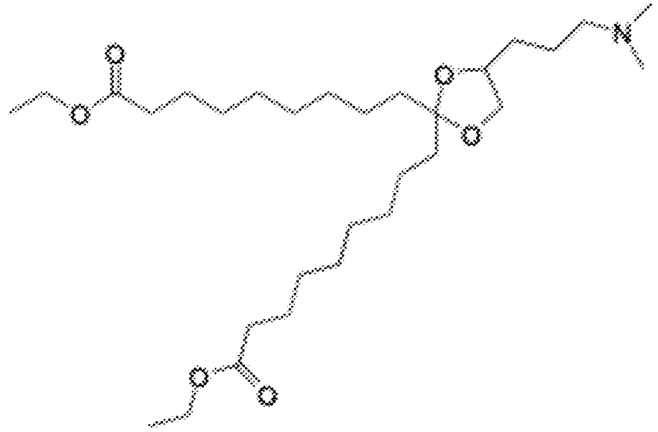
Figure 1C:
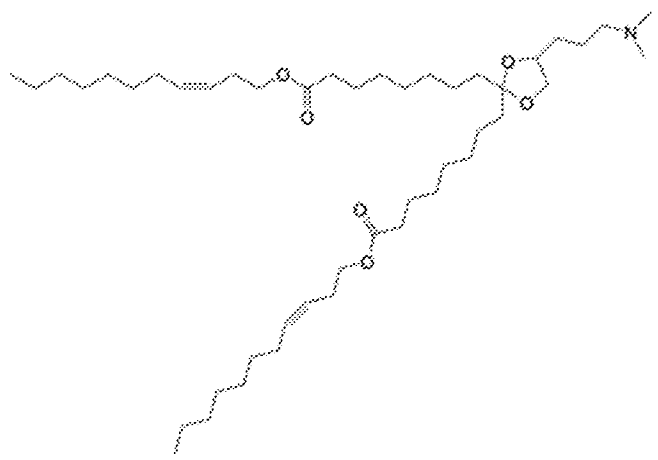
Figure 1C:
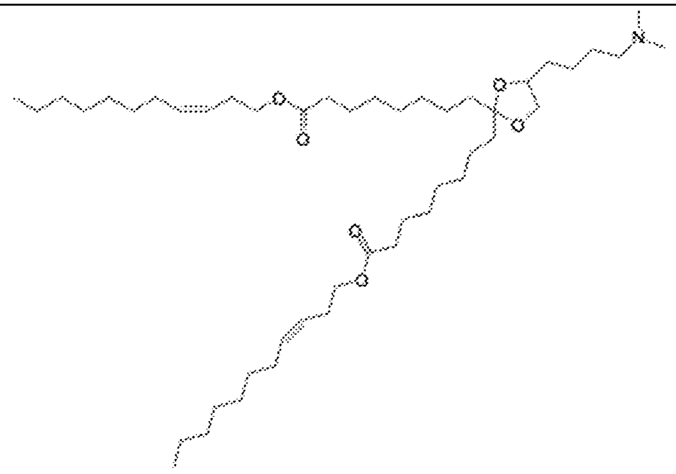
Figure 1C:
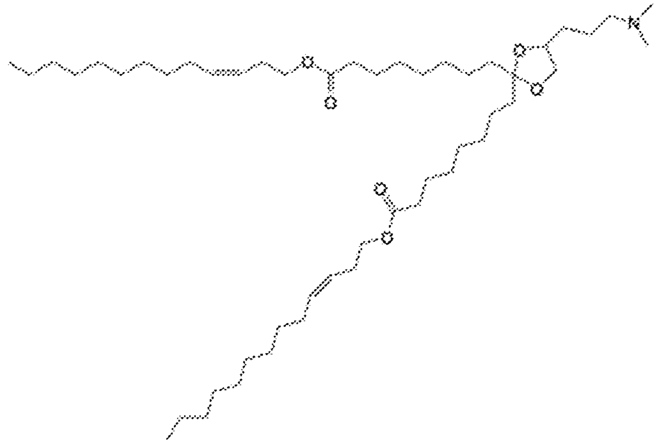
Figure 1C:
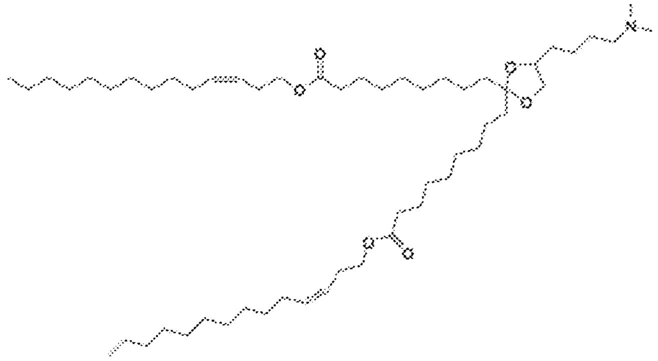
Figure 1C:
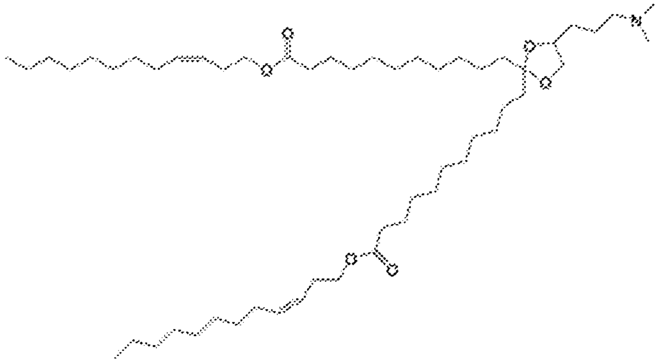
Figure 1C:
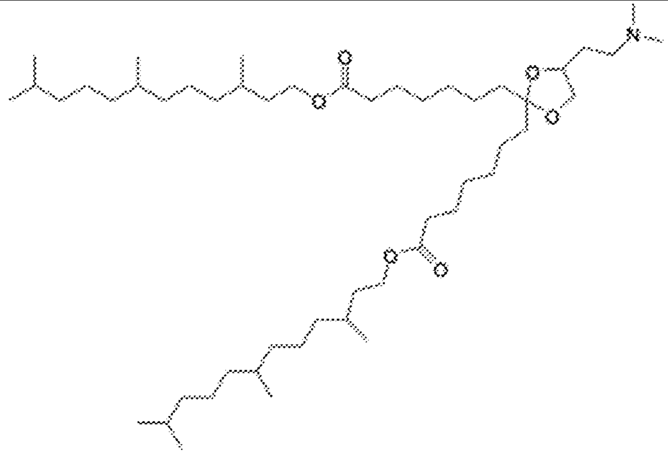
Figure 1C:
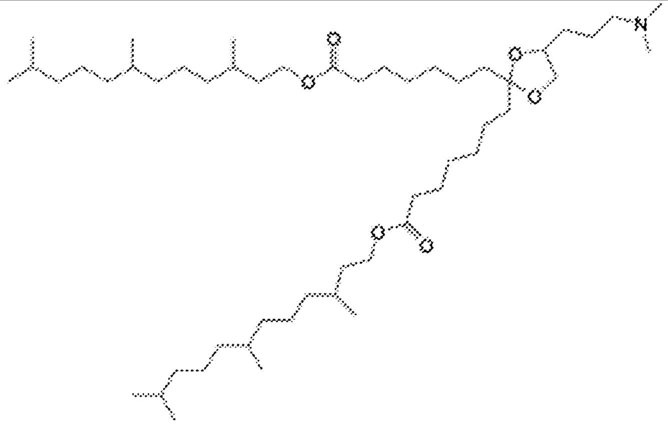
Figure 1C:
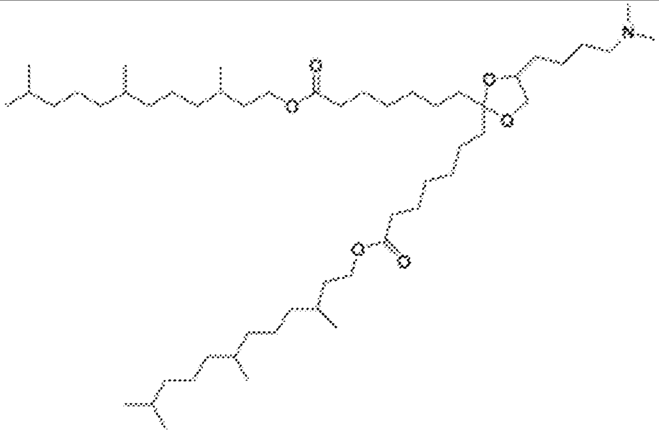
Figure 1C:
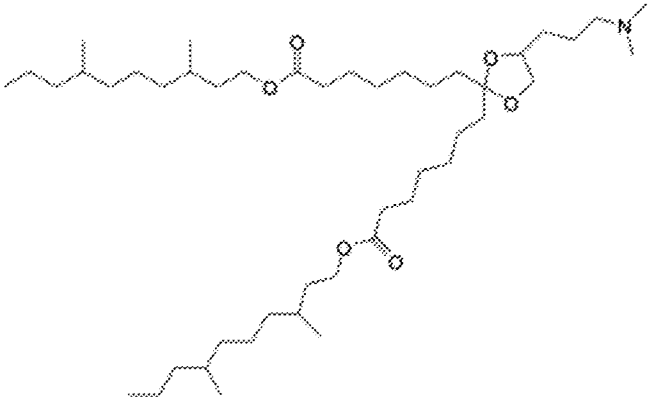
Figure 1C:
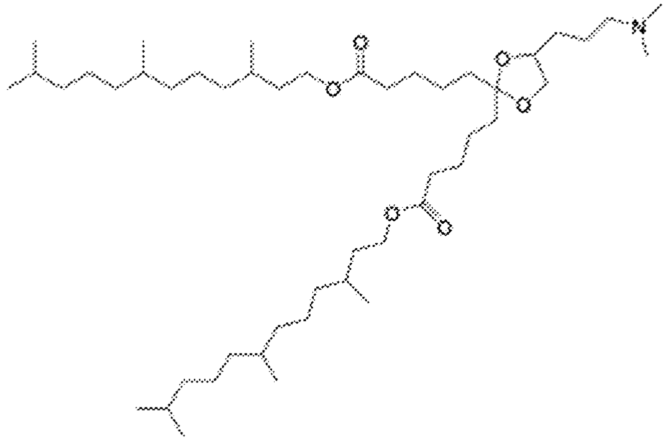
Figure 1C:
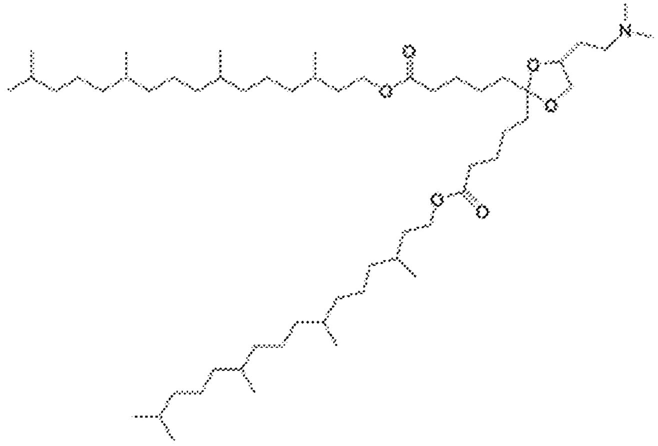
Figure 1C:
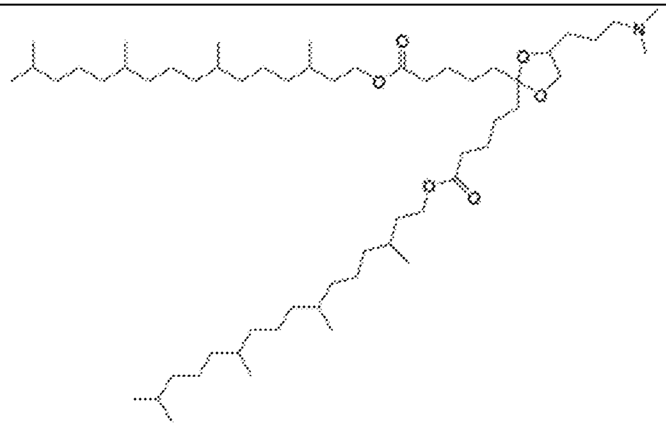
Figure 1C:
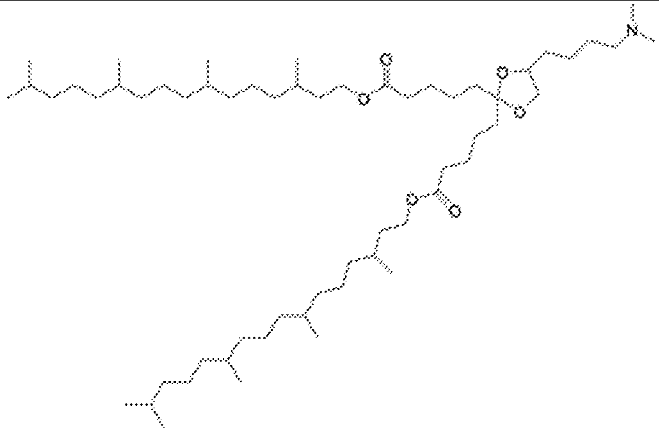
Figure 1C:
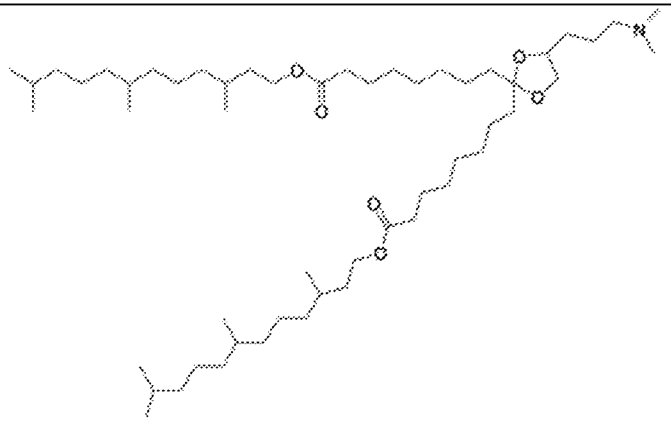
Figure 1C:
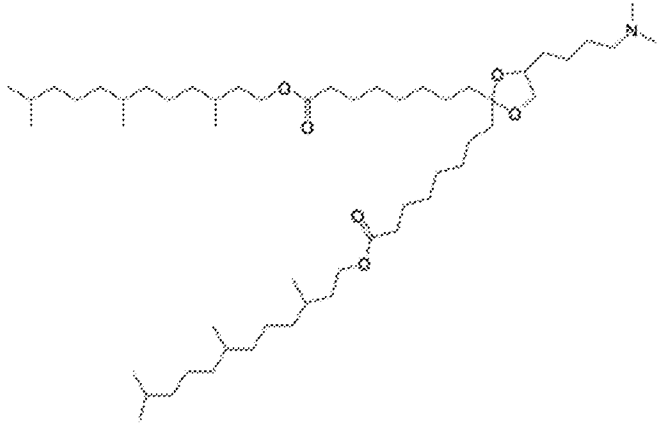
Figure 1C:
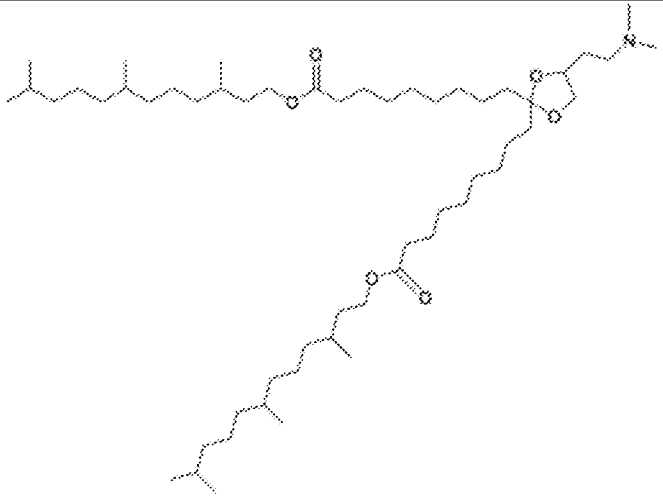
Figure 1C:
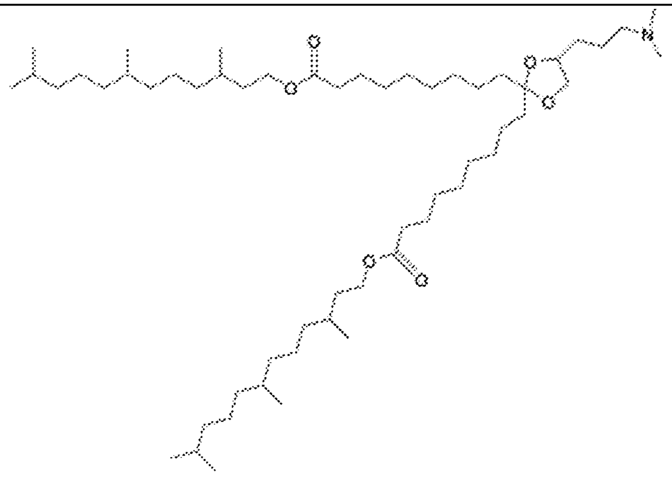
Figure 1C:
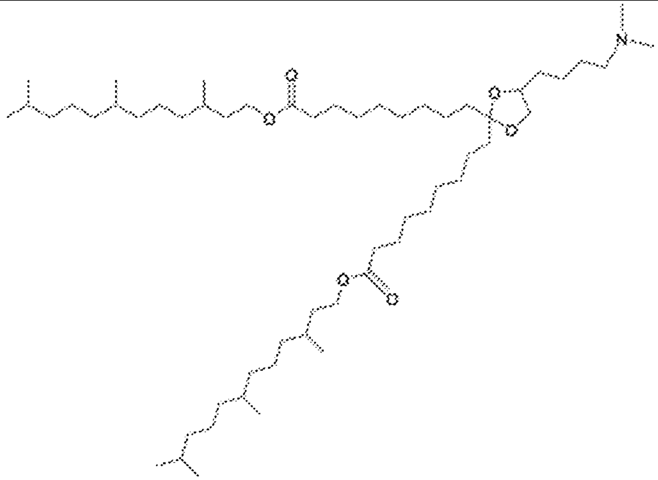
Figure 1C:
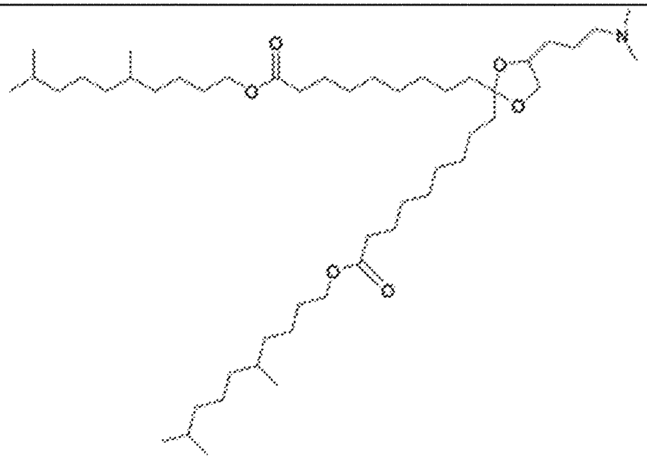
Figure 1C:
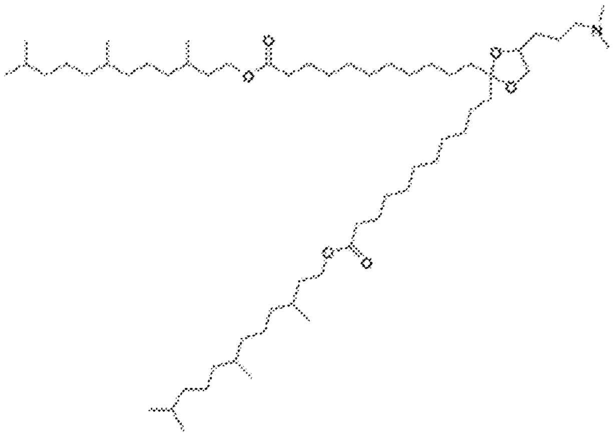
Figure 1C:
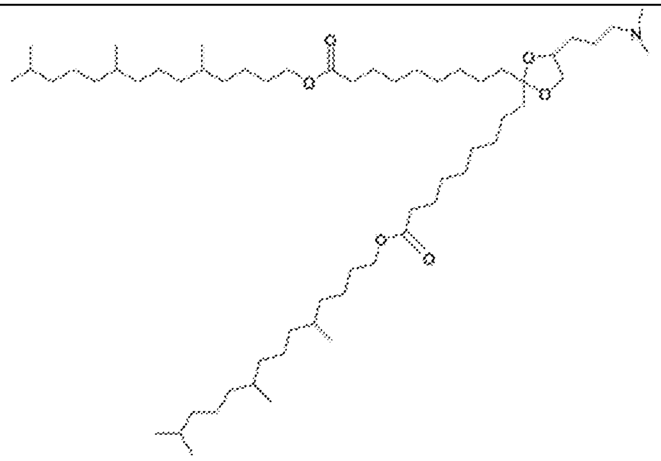
Figure 1C:
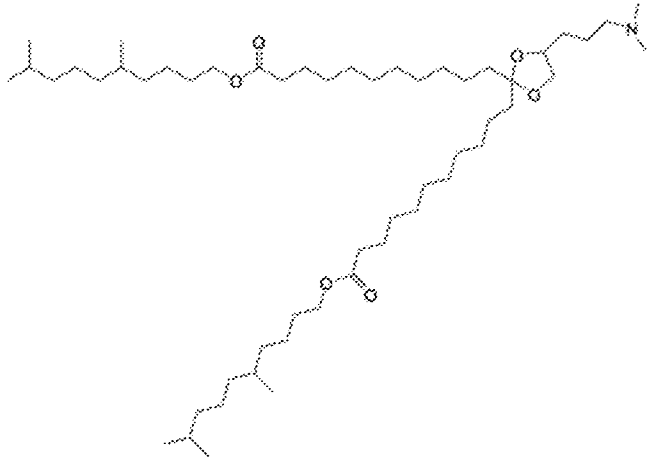
Figure 1C:
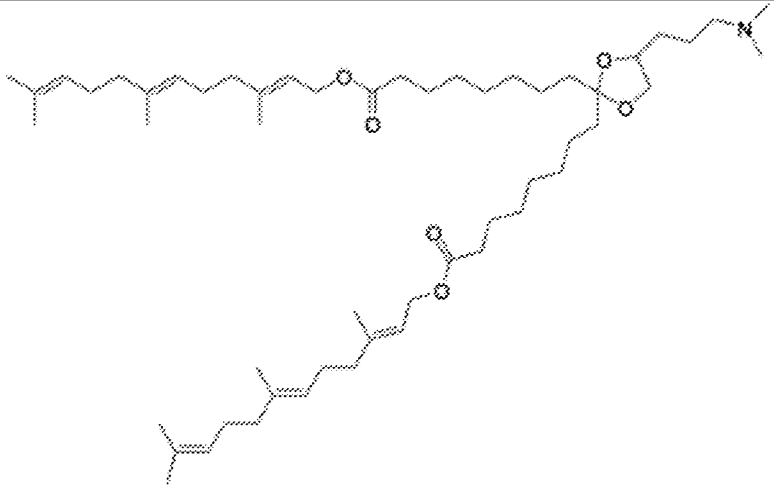

FIG. 1C is a table of additional examples of KCn-X1 compounds that were prepared.

Synthesis of KC3-X2 Ionizable Cationic Lipids

Figure 2A:
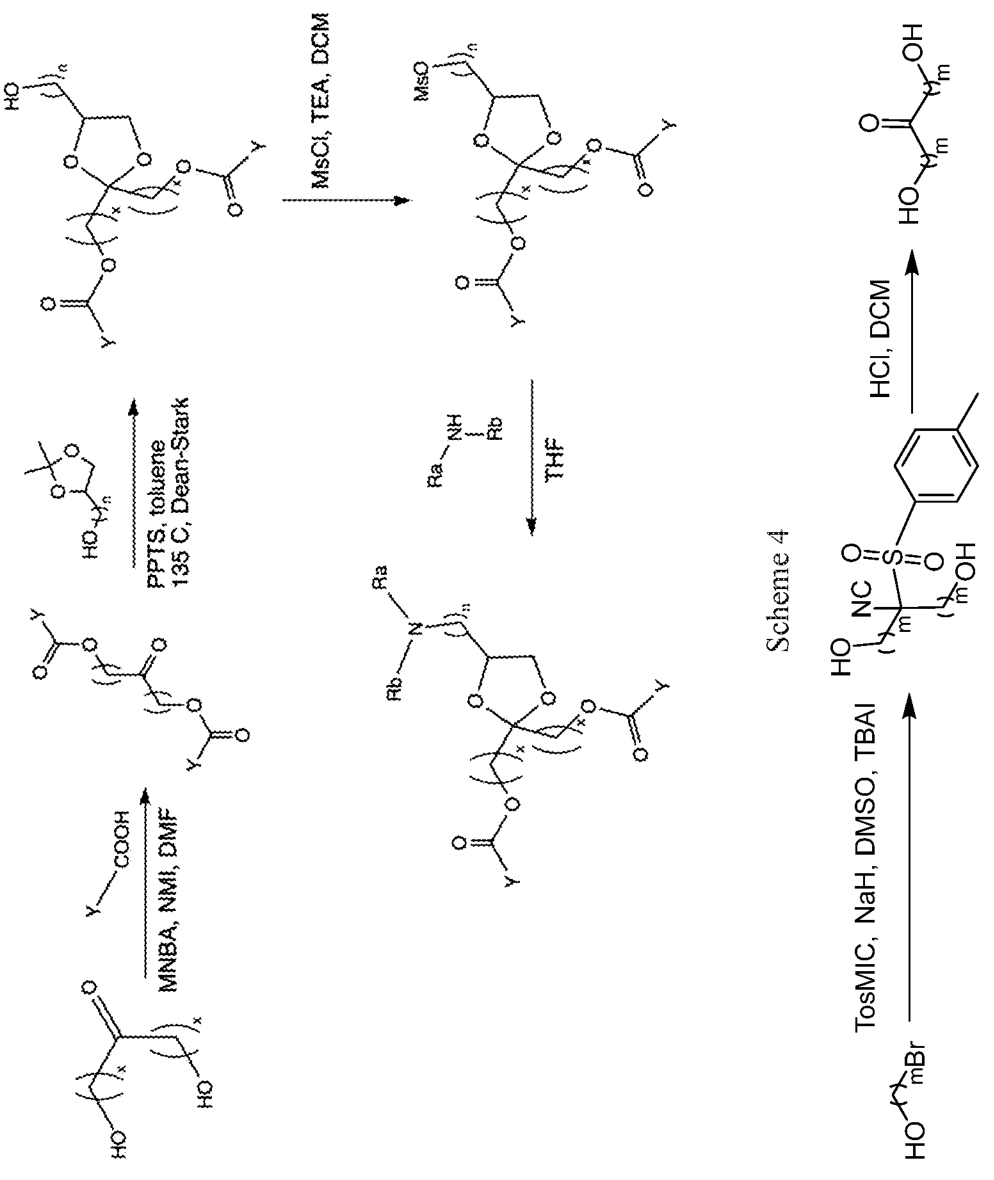
FIG. 2A is a synthetic scheme for preparing certain ionizable cationic lipids.
Figure 2B:
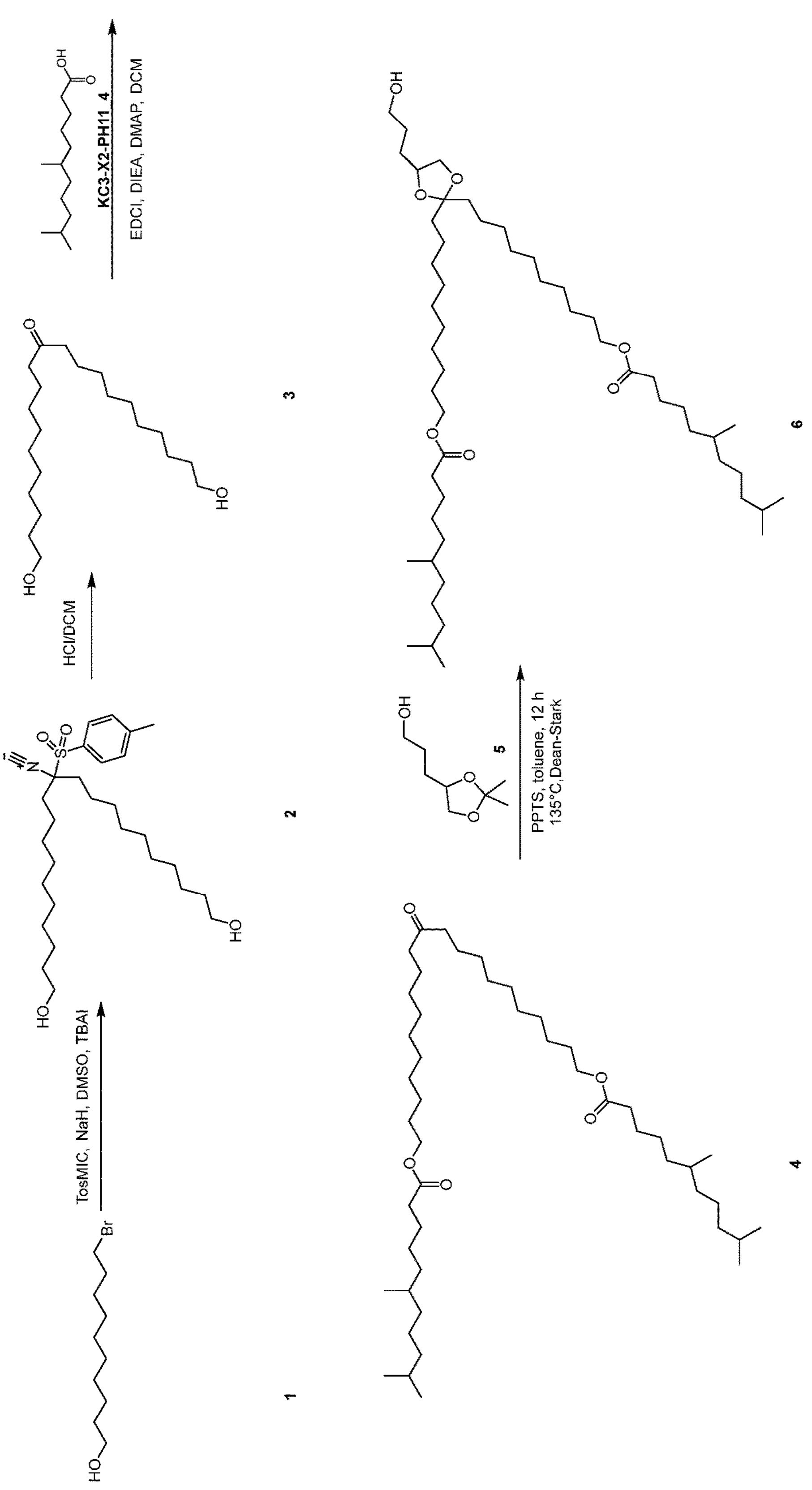
FIG. 2B is a synthetic scheme for preparing an exemplary ionizable cationic lipid designated KC3-X2-PH12.
Figure 2B:
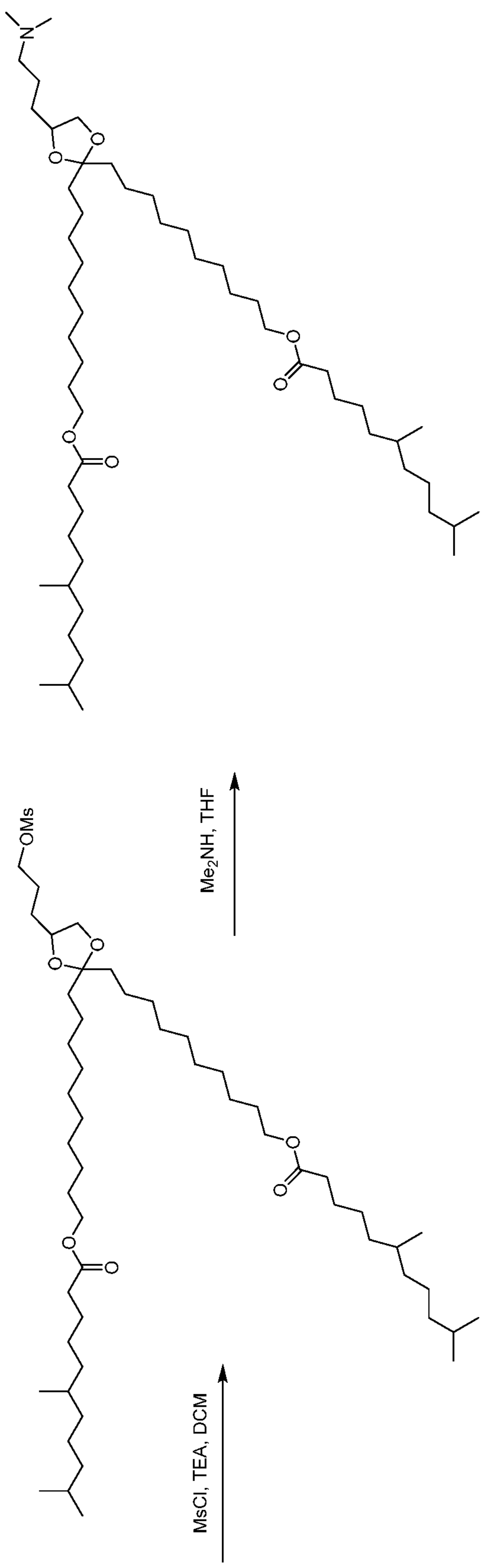

FIG. 2A is a chemical synthesis (Scheme 3 and Scheme 4) for preparing ionizable cationic lipids of Formula (I) wherein -$A_1$- and -$A_2$- are each *—C(O)—O—** wherein * is a covalent bond to —$Y_1$ and —$Y_2$, respectively, and ** is a covalent bond to —$X_1$— and —$X_2$—, respectively, wherein (n) is 2, 3 or 4. (designated "KCn-X2 ICLs"). Scheme 3 is a general synthesis for compounds of Formula (I) wherein $W_1$ and $W_2$ are each *—C(O)—**, * is a covalent bond to $Y_1$ or $Y_2$ and ** is a covalent bond to $X_1$ or $X_2$ (respectively), $X_1$ or $X_2$ are each —$(CH_2)_x$—, and $Y_1$ or $Y_2$ are each identical linear or branched hydrocarbon chains with (y) total carbons (i.e., "KCn-X2" ionizable cationic lipids). A general synthesis for compounds of formula (I) wherein W is —C(O)O— shown in Scheme 3 involves i) esterification of the dihydroxy ketone with a suitable carboxylic acid, ii) acid catalyzed trans ketal formation, iii) Mesylation of the primary alcohol, and finally iv) displacement of the mesyl group using dialkylamine resulting in a tertiary amine. A general synthesis of dihydroxy ketone starting material in Scheme 3 is presented below in Scheme 4. A general synthesis of dihydroxy ketone shown in Scheme 4 involves i) a suitable hydroxy alkyl bromide is treated with toluenesulfonylmethyl isocyanide in the presence of sodium hydride in DMSO, and ii) TosMIC adduct is then converted to a ketone in the presence of HCl.

FIG. 2B is a chemical synthesis for preparing an ionizable cationic lipid of Formula (I) designated KC3-X2-PH12, as described below.

A solution of NaH (5.90 g, 147.51 mmol, 60% purity, 2.4 eq) in DMSO (300 mL) was stirred at 25° C. for 1 hr. Then TBAI (2.27 g, 6.15 mmol, 0.1 eq) and Tosmic (12 g, 61.46 mmol, 1 eq) was added. The mixture was stirred at 25° C. for 15 min. After the addition of compound 1 (30.61 g, 129.07 mmol, 2.1 eq), the mixture was stirred at 25° C. for 1 hr. The reaction mixture was quenched by addition sat-$NH_4Cl$ (aq.200 mL) at 25° C., and then diluted with ice-water (100 mL) and extracted with EtOAc (200 mL*3). The combined organic layers were washed with brine (200 mL*3), dried with anhydrous $Na_2SO_4$, filtered and concentrated in vacuum. The crude product was used directly for the next step without further purification. Compound 2 (32 g, crude) was obtained as a brown oil.

To a solution of compound 2 (32 g, 63.02 mmol, 1 eq) in DCM (210 mL) was added con.HCl (70 mL). The mixture was stirred at 25° C. for 2 hr. The reaction mixture was concentrated under reduced pressure to remove the solvent and then lyophilized. The crude product was triturated with (PE:EtOAc=1:1) at 0° C. for 30 min to give compound 3 (18.9 g, crude) as a yellow solid. 1H NMR (400 MHz, CHLOROFORM-d, EW58397-468-P1A1) δ 3.63 (t, J=6.8 Hz, 4H), 3.38 (t, J=6.8 Hz, 2H), 2.38 (t, J=7.2 Hz, 4H), 1.58-1.52 (m, 8H), 1.36-1.25 (m, 24H).

To a solution of compound 3 (1.6 g, 4.67 mmol, 1 eq) in DCM (20 mL) was added EDCI (3.58 g, 18.68 mmol, 4 eq), DIEA (6.04 g, 46.71 mmol, 8.14 mL, 10 eq), KC3-X2-PH11_4 (2.00 g, 9.34 mmol, 2 eq) and DMAP (1.43 g, 11.68 mmol, 2.5 eq). The mixture was stirred at 40° C. for 16 hr. The reaction mixture was concentrated in vacuum. The residue was purified by column chromatography ($SiO_2$, Petroleum ether/Ethyl acetate=1/0 to 94/6) to give compound 4 (1.8 g, 2.41 mmol, 51% yield) as a yellow oil. $^1$H NMR (400 MHz, CHLOROFORM-d, EW58397-474-P1A1) δ 4.05 (t, J=6.8 Hz, 4H), 2.38 (t, J=7.2 Hz, 4H), 2.30 (t, J=7.4 Hz, 4H), 1.65-1.50 (m, 14H), 1.41-1.21 (m, 38H), 1.17-1.02 (m, 8H), 0.90-0.80 (m, 18H).

A solution of compound 4 (2 g, 2.72 mmol, 1 eq), PPTS (205.08 mg, 816.09 mol, 0.3 eq) and compound 5 (871.64 mg, 5.44 mmol, 2 eq) in Tol. (30 mL) was heated to reflux and the water was removed by Dean-Stark trap. The mixture was stirred at 135° C. for 16 hr. The reaction mixture was quenched by addition sat-$NaHCO_3$(aq. 80 mL) at 25° C., and extracted with EtOAc (30 mL*3). The combined organic layers were washed with brine (20 mL*3), dried with anhydrous $Na_2SO_4$, filtered and concentrated in vacuum. The residue was purified by flash silica gel chromatography (ISCO®; 40 g SepaFlash® Silica Flash Column, Eluent of 0~10% Ethyl acetate/Petroleum ether gradient @60 mL/min) to give compound 6 (850 mg, 832.40 mol, 31% yield) as a yellow oil. $^1$H NMR (400 MHz, CHLOROFORM-d, EW58311-476-P1A1) δ 4.12-4.03 (m, 6H), 3.72-3.64 (m, 2H), 3.52-3.43 (m, 1H), 2.32-2.28 (m, 4H), 1.64-1.56 (m, 18H), 1.35-1.24 (m, 42H), 1.16-1.05 (m, 8H), 0.88-0.83 (m, 18H).

To a solution of compound 6 (840 mg, 1.00 mmol, 1 eq) in DCM (10 mL) was added TEA (507.56 mg, 5.02 mmol, 698.15 μL, 5 eq) and MsCl (270.00 mg, 2.36 mmol, 182.43 μL, 2.35 eq) at 0° C. The mixture was stirred at 0° C. for 1 hr. The reaction mixture was quenched by addition ice-water (30 mL) at 0° C., and extracted with DCM (10 mL*3). The combined organic layers were washed with brine (10 mL*3), dried with anhydrous $Na_2SO_4$, filtered and concentrated in vacuum. The residue was purified by flash silica gel chromatography (ISCO®; 12 g SepaFlash® Silica Flash Column, Eluent of 0~10% Ethylacetate/Petroleum ethergradient @40 mL/min) to give compound 7 (760 mg, 788.70 mol, 79% yield,) as a yellow oil. $^1$H NMR (400 MHz, CHLOROFORM-d, EW58311-477-P1A1) δ 4.33-4.22 (m, 2H), 4.09-4.01 (m, 6H), 3.53-3.42 (m, 1H), 3.02 (s, 3H), 2.30 (t, J=7.6 Hz, 4H), 1.64-1.55 (m, 20H), 1.36-1.23 (m, 40H), 1.16-1.04 (m, 8H), 0.89-0.83 (m, 18H).

A solution of compound 7 (760 mg, 830.21 mol, 1 eq) in $Me_2NH$/THF (2 M, 10 mL) was stirred at 50° C. for 10 hr. The reaction mixture was concentrated under reduced pressure to remove solvent. The residue was purified by flash silica gel chromatography (ISCO®; 12 g SepaFlash® Silica Flash Column, Eluent of 0~8% Ethyl acetate/(Petroleum ether/Dichloromethane=3/1, 0.1% TEA as eluant)@40 mL/min) and followed by reversed-phase HPLC (column: PHS XP Phenyl-Hexyl 150*25 mm*7 um; mobile phase: [$H_2O$ (0.225% FA) -ACN]; gradient: 65%-95% B over 15.0 min) to give AKG-KC3-X2-PH12 (371.1 mg, 422.87 mol, 48% yield, 98.5% purity) as a yellow oil. LCMS (EW58311-481-P1C1): CAD, m/z, M+H=865.0. HRMS (ESI) m/z: $[M+H]^+$ Calcd for $C_{54}H_{106}NO_6^+$ 864.8015, found 864.8032. $^1$H NMR (400 MHz, CHLOROFORM-d, EW58311-481-P1A1) δ 4.13-3.99 (m, 6H), 3.52-3.40 (m, 1H), 2.44-2.21 (m, 12H), 1.67-1.48 (m, 18H), 1.39-1.19 (m, 42H), 1.17-1.04 (m, 8H), 0.92-0.82 (m, 18H).

Figure 2C:
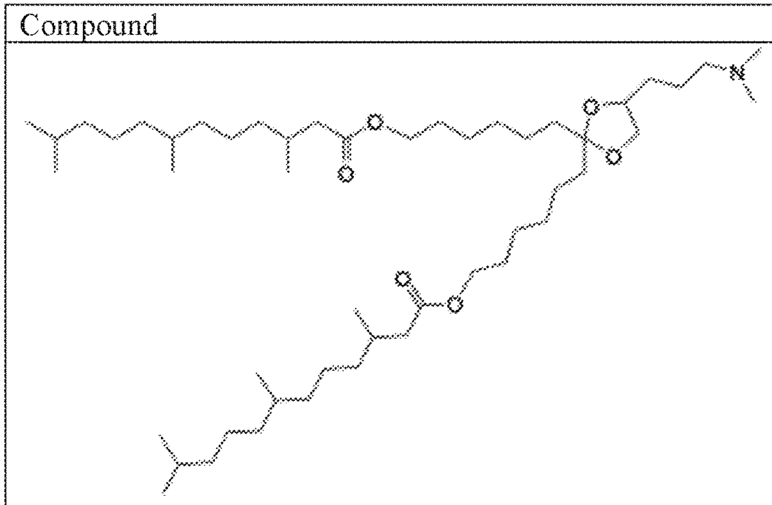
FIG. 2C is a table of ionizable cationic lipids.
Figure 2C:
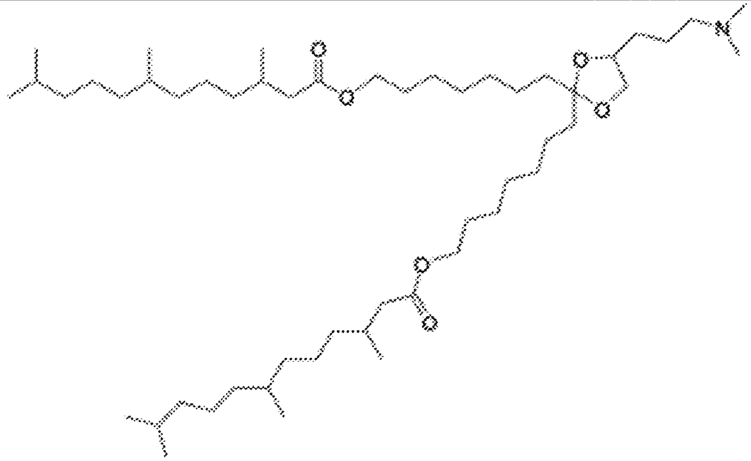
Figure 2C:
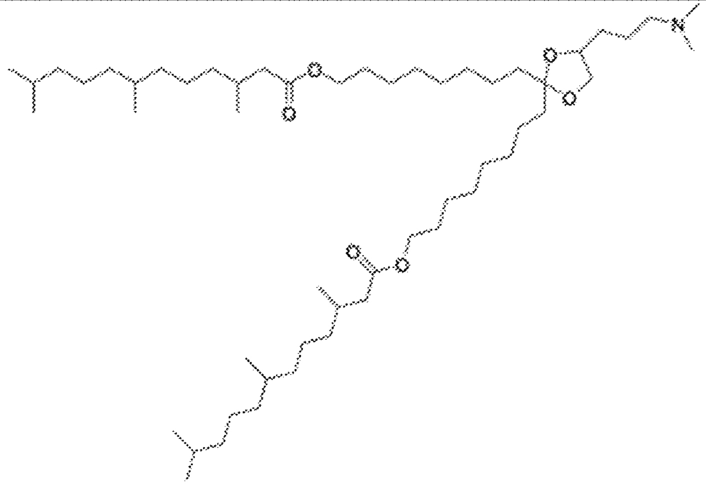
Figure 2C:
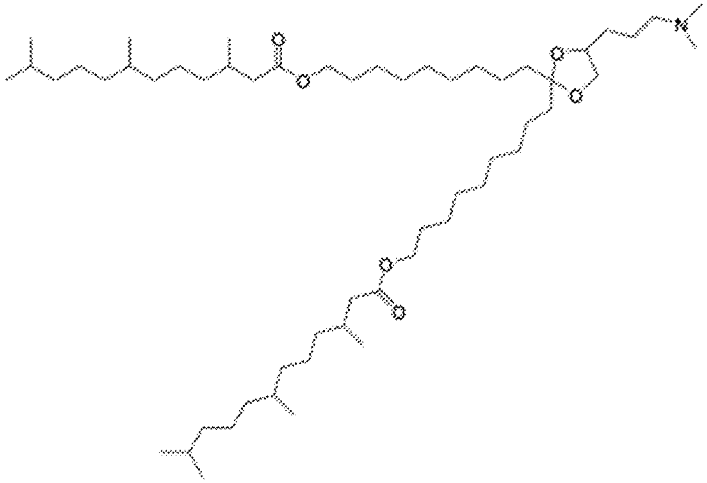
Figure 2C:
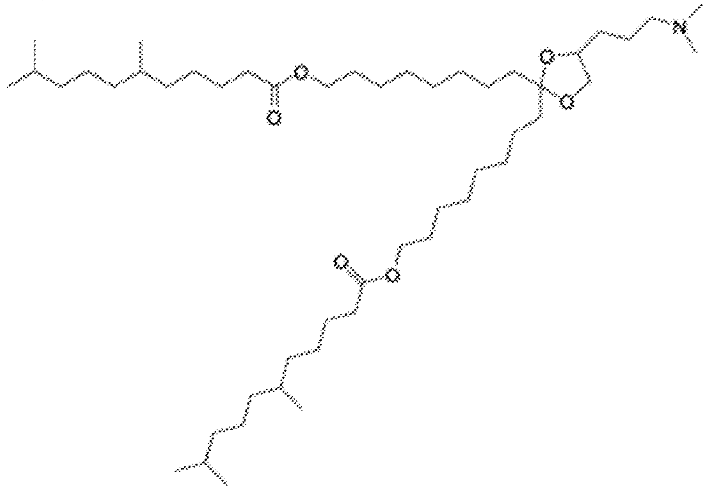
Figure 2C:
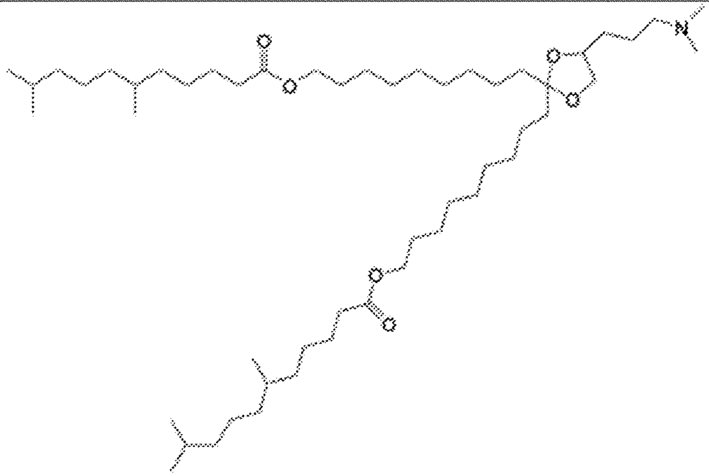
Figure 2C:
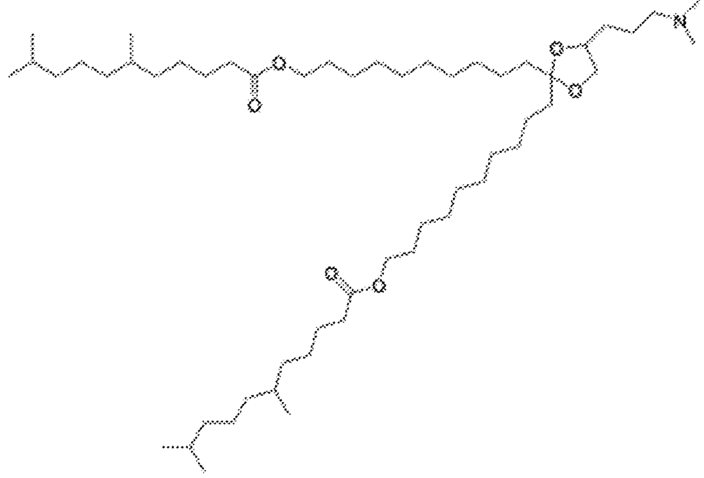
Figure 2C:
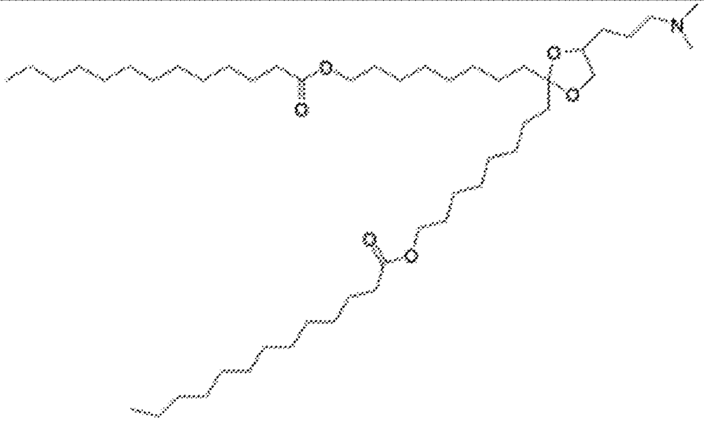
Figure 2C:
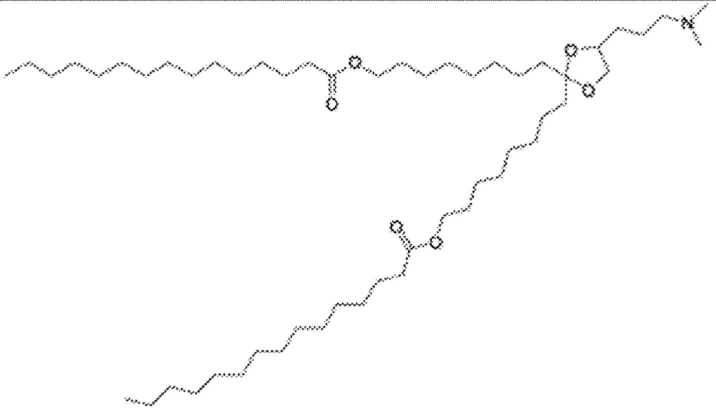
Figure 2C:
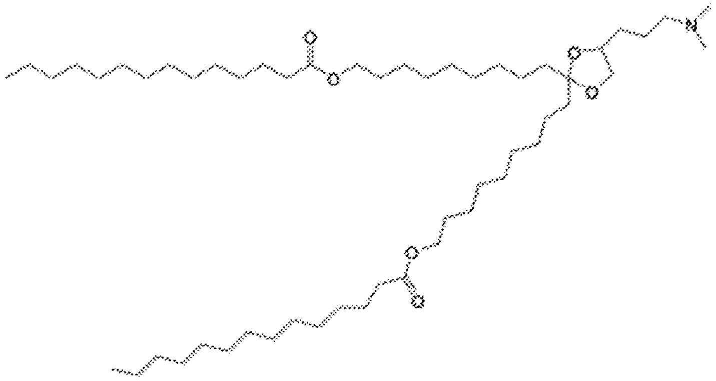
Figure 2C:
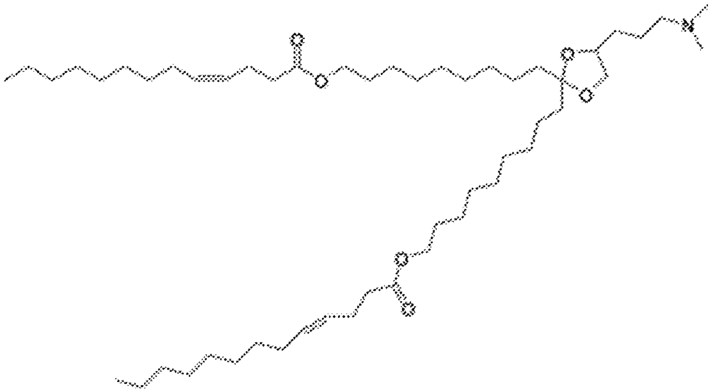

FIG. 2C is a table of additional examples of KCn-X2 compounds that were prepared.

Example 2. LNP Preparation

Lipid nanoparticle (LNP) compositions encapsulating mRNA can be prepared as described in Example 9 (Preparation of lipidic nanoparticles) of Patent Cooperation Treaty Patent Application PCT/US2021/060877 (WO2022/115645), and Example 9 (Preparation of lipidic nanoparticles) of Patent Cooperation Treaty Patent Application PCT/US2023/067517 (WO2023/230587), are incorporated herein by reference in their entirety, modified by using a microfluidics chip from ChipShop (187) to make LNPs at flow rates of 18 mL/min instead of the Nanoprecision Systems microfluidics cassette at 6 ml/min whilst keeping downstream processing and analytical procedures the same as described in the published patents referenced above.

Stock solutions of each lipid are prepared. Ionizable lipids are weighed out in 4 mL glass vials (Thermo B7999-2) and dissolved in ethanol (Sigma-Aldrich 200 proof, RNase free) to a final concentration of 10 mM. Other lipids such as DSPC, DPPC-$NH_4$, DPPS-$NH_4$ and PEG-DMG are weighed out and dissolved in ethanol to a concentration of 1 mM, and cholesterol to concentration of 10 mM.

Lipid mixtures for each individual LNP are prepared by adding the desired volume of each lipid stock solution to a new vial, adding ethanol if needed to achieve a final volume of 1.2 mL.

mRNA solutions are prepared by thawing frozen mRNA (e.g. FFluc-mRNA) vials and diluting mRNA in 6.25 mM sodium acetate (pH 5.0) to a final concentration of 0.033 mg/mL To prepare LNPs, a NanoAssemblr Benchtop microfluidic device (from Precision Nanosystems) is used. 3 mL of mRNA solution is loaded into a 3 mL disposable syringe (BD 309656) and 1 ml of lipid mixture in a 1 ml syringe (BD309659) and placed in the NanoAssemblr heating block for 4 min prior to mixing. LNP formation is achieved by pumping the liquid streams through a disposable microfluidics cassette at 3:1 aqueous:alcohol volume ratio at 6 mL/min mixing speed, or through a ChipShop microfluidics (Jena, Germany) chip (#187) at 18 ml/min. After mixing, 3.6 mL of LNP mixture is collected, while the initial mixed volume of 0.35 mL and last 0.05 mL of mix is discarded. Ethanol is removed by buffer exchange using SpectraPor dialysis tubing (12-14 k MWCO) in PBS (Cytiva, SH30256.01) or by sequential concentration and dilution using Amicon Ultra-4 centrifugal concentrators (10 k MWCO, at 500 g).

LNPs are typically exchanged into PBS, pH 7.4 and then 10 mM Tris, pH 7.4, 10% sucrose, concentrated to 20-50 ug/mL mRNA using an Amicon-Ultra 4 (100,000 MWCO) spin column, sterile filtered (Thermo Nalgene 0.2 μm #720-1320) prior to freezing by immersion in liquid nitrogen for 5 min and long-term storage at −80° C.

Example 3: Characterization of Lipidic Nanoparticles (LNPs) Containing mRNA

A. mRNA Encapsulation Efficiency

Materials: Quant-iT™ RiboGreen™ RNA reagent (1 mL solution in DMSO), 20×TE (25 mL in DEPC-treated water), DNase/RNase-Free Distilled Water (Invitrogen Cat #10977-023, or equivalent), 96-Well Clear-Bottom Microplate MED BINDING (Greiner Bio-One Cat #655096), Detergent (Triton™): Surfact-Amps™ X-100 Cat #28314, RNase/DNase-free 1.5 mL Microcentrifuge tubes (ThermoFisher, Invitrogen Cat #AM12400) or equivalent sterile, nuclease-free tubes. A portion of 1×TE buffer prepared for the experiment was allotted for the dilution of RiboGreen dye. This dye was diluted 200× in 1×TE buffer. As the dye is light sensitive, allow to come to RT protected from light. Ensure the dye has melted (become liquid) as it will remain crystalline in temperatures below RT. Before pipetting the dye vortex mix for one second, three times. Prepare the volume of 1×TE buffer needed in a 15 mL conical tube. Vortex or invert the diluted dye and store protected from light. Standards corresponding to 1500, 1200, 1000, 800, 500, 250, 50, 25 and 0 ng/mL mRNA were prepared in 1×TE buffer from the mRNA used in the preparation of LNPs. The blank contains no mRNA. LNPs are diluted in 1×TE buffer to approximately 2 μg/mL. 100 μL of blank, standards and samples were added to the wells of a 96-well plate in triplicate to which 100 μL of diluted Ribogreen is added and mixed well by pipetting up and down 4-5 times. The plate is covered with foil to protect from light and after 5 min incubation at room temperature. The standards and samples were read using a microplate fluorometer (e.g., SpectraMax M2) using excitation at 485 nm, emission at 530 nm, and instrument default acquisition parameters. A 2% Triton solution is prepared from the 10% stock solution of Surfact-Amps™ X-100 by performing a 1:5 dilution in 1×TE buffer. Invert 5× to mix. Once the pre-Triton readings have been taken and saved, empty prepared Triton (diluted to 2% in 1×TE buffer) into a clean reagent reservoir. A multichannel pipettor was used to add 20 μL of 2% Triton to each plate well and slowly pipette mix 5×. The plate can be read 5 minutes after mixing. The pre-Triton mRNA concentrations are determined by extrapolation to the pre-Triton standard curves and the post-Triton mRNA concentrations are determined by extrapolation to the Triton containing standard using a linear curve fit.

% Encapsulation Efficiency (% E.E) expresses the concentration of encapsulated mRNA as a percent of the total, post-Triton concentration. The formula can be expressed as:

% Encapsulation Efficiency=100−((Pre-Triton concentration/Post-Triton concentration)*100)

B. LNP Particle Size

30 μL of LNP was mixed with 1.5 mL of 0.1 μm filtered PBS in a polystyrene cuvette (Sarstedt, #67.754) and analyzed for particle size using a ZetaSizer Pro (Malvern) The Z-average size and polydispersity index value were obtained by the method of cumulants using ZS Xplorer software, version number 1.4.0.105. Typically, size measurements of LNPs were taken post LNP mixing, post buffer exchange, post sterile filtering and after freezing for 2 min in liquid nitrogen and thawing at 37° C.

C. LNP Zeta Potential

30 μL of LNP is mixed with 1.5 mL 10 mM 2-(N-morpholino)ethanesulfonic acid (MES), 15 mM sodium chloride, pH 5 or 10 mM 4-(2-hydroxyethyl)-1-piperazineethanesulfonic acid (HEPES), 15 mM sodium chloride, pH 7 and injected into a disposable folded capillary cell (Malvern Nanoseries DTS1070) and zeta potential measured on a ZetaSizer Pro at 25° C.

D. LNP Apparent pKa Determination 1.0 L of buffer consisting of 10 mM sodium phosphate, 10 mM ammonium acetate, 10 mM sodium citrate, and 150 mM sodium chloride solution in WFI was prepared. The solution is divided into 50 mL aliquots and the pH of each adjusted with 5M HCl or 10N NaOH to span the pH range of 2-12 in approximately 0.5-unit increments. The actual pH of each aliquot was measured with a pH meter (Thermo Orion 4 Star with a glass combination micro pH electrode (8220BNWP) calibrated with Thermo Orion pH 4.01, 7.00, 10.01 standards).

A 10 mM solution of 6-p-Toluidino-2-naphthalenesulfonic acid (TNS, Abcam ab275049) in 10 mL of DMSO is prepared from which a 1 mM solution in water is prepared. LNPs were diluted to 1 μg/mL mRNA in a well of a 96-well plate in a final volume of 200 μL for each pH prepared above and TNS added to a final concentration of 10 μM after which each well is mixed by pipetting up and down 10 times with a multichannel pipette. The plate was incubated at room temperature for 3 min, then read on a plate reader at Ex.331/Em.445 nm. A plot of pH versus TNS fluorescence signal was prepared in Graph Pad Prism. The pH value at the half maximum value of fluorescence represents the pKa of nanoparticles and is calculated by performing a non-linear regression analysis for a half maximal fluorescence. This value is the pH at which the numbers of ionized (protonated) and deionized groups are equal.

Example 4. In Vitro Assessment of Biodegradability of Ionizable Lipids Using Pancreatin Enzymes An in vitro assay was developed to evaluate the biodegradability of ionizable cationic lipids (ICLs) in the presence of pancreatin enzymes (including trypsin, amylase and lipase). Individual ICL stock solutions were prepared in ethanol at a concentration of 50 mg/mL and stored at −80° C. until use. Bile salts (Millipore, Cat. No. 48305) were dissolved in Dulbecco's phosphate-buffered saline (DPBS; Sigma, Cat. No. 59300C) at 2 mg/mL, and pancreatin (Sigma, Cat. No. P7545) was prepared at 10 mg/mL in the same buffer. The pH of the DPBS was adjusted to 8.0 using 1 M NaOH. All solutions were maintained at 37° C. under continuous mixing. For each reaction, 50 nmol of ICL (from the 50 mg/mL ethanol stock) was added to 2 mL of pancreatin solution. Reactions were performed in duplicate across six time points. The mixture was vortexed for 30 seconds, after which 100 μL aliquots were transferred into separate 2 mL tubes (two replicates per time point). Samples were incubated at 37° C. with shaking. To terminate the reaction, 10 volumes of isopropanol/acetonitrile (IPA/MeCN, 70:30 v/v) were added. The resulting mixture was sonicated for 5 minutes to facilitate phase separation of lipids and enzymes, followed by centrifugation at 14,000×g for 15 minutes. The supernatant was collected and transferred to HPLC vials for analysis. Lipid degradation was quantified using a Thermo Scientific Vanquish Flex UHPLC system equipped with a Charged Aerosol Detector (CAD) and a C18 column (Phenomenex Kinetex 1.7 μm C18 100 Å 150×2.1 mm). Operating conditions for UHPLC are detailed in Table 6. The extent of lipid degradation was expressed as the percentage of the main ICL peak remaining at each time point relative to the peak area at time zero. Quantification was performed using ICL standards prepared in IPA at concentrations ranging from 5 to 40 μg/mL.

TABLE 6

| Chromatographic Conditions | | | |
|---|---|---|---|
| HPLC Instrument | Thermo Scientific Vanquish Flex UHPLC | | |
| HPLC Column | C18 column (Phenomenex Kinetex 1.7 μm C18 100 Å 150 x 2.1 mm) | | |
| HPLC guard column | None | | |
| Column Temperature | 50 °C | | |
| Flow Rate, ml/min | 0.35 | | |
| Injection Volume | 5 μL | | |
| CAD | 10 H | | |
| Run Time | 12 min | | |
| Sample Solvent | 70% IPA/30% MeCN | | |
| Mobile Phase A | 0.1% TFA in water | | |
| Mobile Phase B | 0.05% TFA in MeCN | | |
| Gradient | Time, min | Mobile Phase A % | Mobile Phase B % |
| | −0.5 | 15 | 85 |
| | 0 | 15 | 85 |
| | 0.5 | 15 | 85 |
| | 5 | 5 | 95 |

TABLE 6-continued

| Chromatographic Conditions | | |
|---|---|---|
| 11 | 5 | 95 |
| 11.5 | 15 | 85 |
| 12 | 15 | 85 |

Results are shown in the graphs in FIG. 4A and FIG. 4B showing biodegradability of ionizable cationic lipids (ICLs), measured after 15 minutes (FIG. 4A) and 3 hours (FIG. 41B) in the presence of pancreatin enzymes (including trypsin, amylase and lipase) measured according to the assay of Example 4. FIG. 4A and FIG. 4B are graphs of the biodegradability of ionizable cationic lipids (ICLs) over time in the presence of pancreatin enzymes (including trypsin, amylase and lipase) measured according to the assay of Example 4. The ionizable cationic lipids of Formula (I) that were tested (Table 7 with structures in Table 8) showed significantly greater degradation compared to the ALC-0315, SM-102 or KC3-OA ionizable lipid comparator compounds.

TABLE 7

Results Obtained from Ionizable Lipids Tested in Example 4.

| ICL | t = 15 min. | t = 3 hr |
|---|---|---|
| KC3-OA | 0.98 | 0.94 |
| ALC-0315 | 0.92 | 0.94 |
| SM-102 | 0.89 | 0.53 |
| KC3-X1-PH5 | 0.67 | 0.20 |
| KC3-X1-PH12 | 0.29 | 0.03 |
| KC3-X1-AA | 0.23 | 0.01 |
| KC3-X2-PH12 | 0.08 | 0.02 |

TABLE 8

Chemical structures of Ionizable Lipids Tested in Examples.

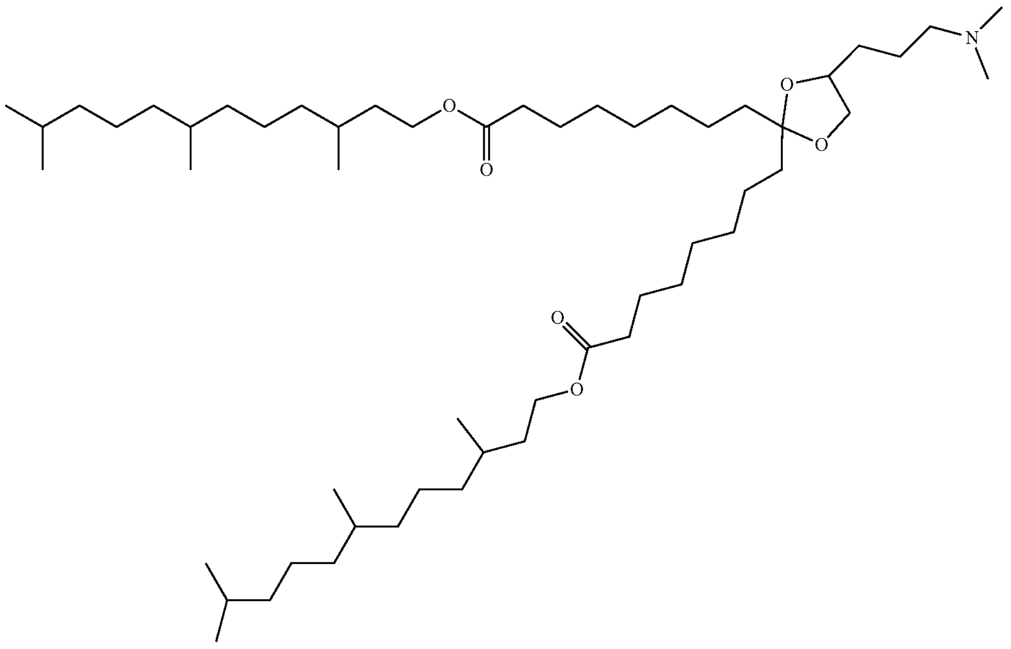 [SMILES: CC(C)CCCC(C)CCCC(C)CCOC(=O)CCCCCCCC1(CCCCCCCC(=O)OCCC(C)CCCC(C)CCCC(C)C)OCC(CCCN(C)C)O1]

KC3-X1-PH5

TABLE 8-continued
Chemical structures of Ionizable Lipids Tested in Examples.
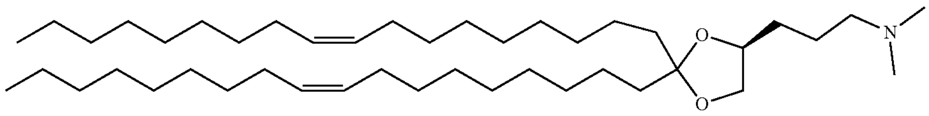 [SMILES: CCCCCCCC/C=C\CCCCCCCCC1(CCCCCCCC/C=C\CCCCCCCC)OC[C@H](CCCN(C)C)O1]
KC3-OA
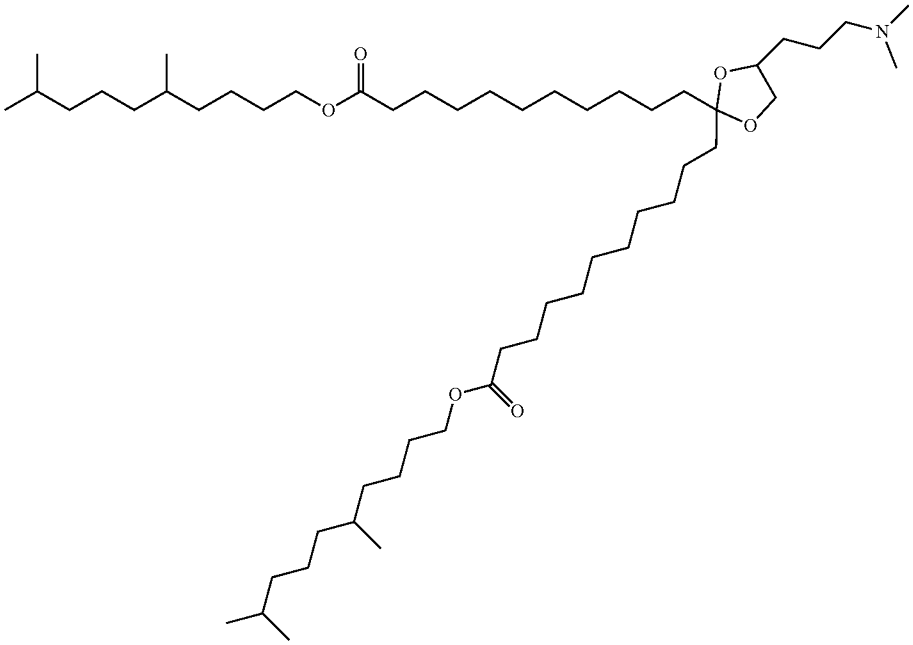 [SMILES: CC(C)CCCC(C)CCCCOC(=O)CCCCCCCCCCC1(CCCCCCCCCCC(=O)OCCCCC(C)CCCC(C)C)OCC(CCCN(C)C)O1]
KC3-X1-PH12
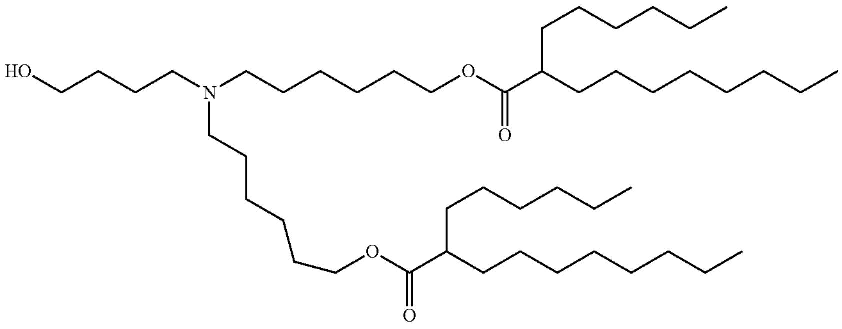 [SMILES: CCCCCCCCC(CCCCCC)C(=O)OCCCCCCN(CCCCO)CCCCCCOC(=O)C(CCCCCC)CCCCCCCC]
ALC-0315

TABLE 8-continued
| Chemical structures of Ionizable Lipids Tested in Examples. |
| --- |
| 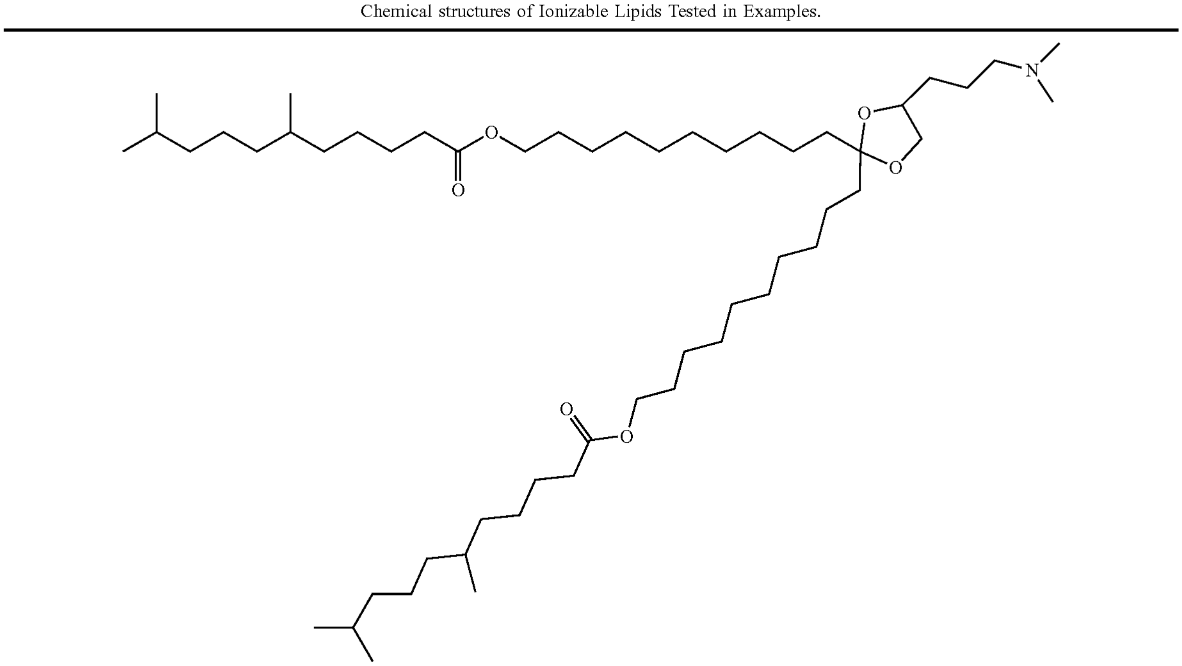 |
| KC3-X2-PH12 |
| 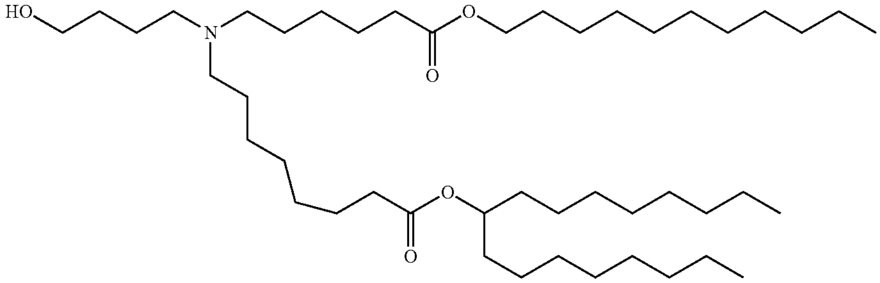 [SMILES: CCCCCCCCCCCOC(=O)CCCCCN(CCCCO)CCCCCCCC(=O)OC(CCCCCCCC)CCCCCCCC] |
| SM-102 |
| 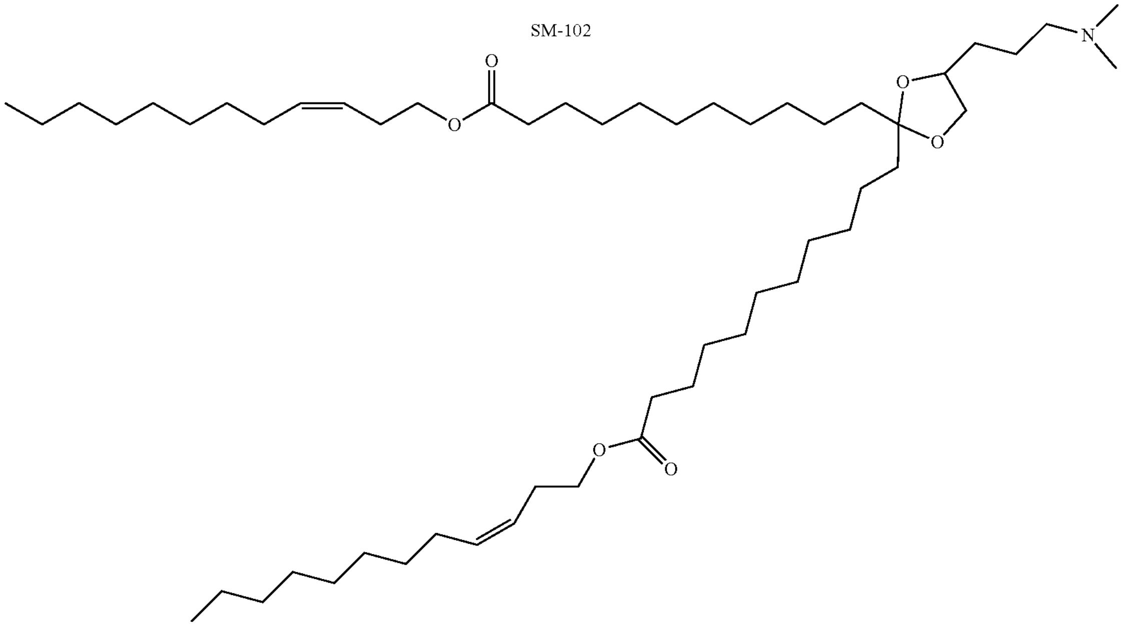 [SMILES: CCCCCCCC/C=C\CCOC(=O)CCCCCCCCCCC1(CCCCCCCCCCC(=O)OCC/C=C\CCCCCCCC)OCC(CCCN(C)C)O1] |
| KC3-X1-AA |

Example 5. Determination of Transfection Efficiency in Murine Dendritic Cells of LNPs Using Firefly Luciferase mRNA Immortalized mouse dendritic cells (MutuDC 1940, Fuertes Marraco et al., Front. Immunol. 2012, 3:331) are cultivated in Gibco™ IMDM medium with GlutaMax™ (Gibco cat. No 31980097), supplemented with 7.5 mg/ml $NaHCO_3$, 10 mM HEPES-Na pH 7, 50 μM beta-mercapto-ethanol, 50 U/ml penicillin, 50 μg/mL streptomycin, and 10% fetal bovine serum, at 37° C., 5% $CO_2$. The cells are rinsed with phosphate-buffered saline (PBS, Cytiva, cat. No SH30526) harvested using 5 mM EDTA in PBS (PBS-EDTA), resuspended in the growth medium, inoculated in the white opaque 96-well cell culture plates (e.g., Costar cat. No 3917) in the wells in columns 3-10 of the plate at 15,000 cells/well in 0.1 ml of the medium and allowed to acclimate overnight. The media are aspirated, replaced with 0.1 ml of the media containing the desired concentration of mRNA LNP (0.1-1 μg/mL mRNA, typically 0.3 μg/mL mRNA—SEQ ID NO: 3 encoding SEQ ID NO: 2), and incubated at 37° C., 5% $CO_2$ for the desired transfection period, typically 24 hours. The mRNA can be an mRNA encoding a firefly luciferase protein sequence such as SEQ ID NO:2. Three to four hours prior to the end of the transfection period, the wells A2 and A11 of the plates are seeded with 0.1 ml of the cell suspension standard containing approximately 1,000,000 viable cells/mL (the viable cell concentration is accurately determined), and wells B2 to G2, and B11 to G11 are seeded with the serial dilutions of the standard at the dilution factor of 1.5 to generate eight cell quantity standards per plate in duplicate. In the wells A1-H1, A12-H12, 0.1 ml of the cell medium is added. At the end of the transfection period, 11 μL of 20 mM aqueous solution of Hoechst 33342 DNA fluorescent dye (Ultrapure grade, cat. No 17533, AAT Bio, USA) is added to each well, carefully mixed by gentle tapping and swirling of the plate by hand, and the plate is incubated at 37° C., 5% $CO_2$ for one hour to allow for the staining of the cellular DNA by added dye.

Luciferase standards are prepared using recombinant firefly luciferase (cat. No. SRE0045, Sigma-Aldrich, USA) reconstituted to 2 mg/ml protein in 1 M Tris-HCl buffer pH 8.5 and stored at −80° C. An interim standard is prepared by diluting the reconstituted luciferase 20-fold (to 0.1 mg/ml) in PBS-EDTA containing 1 mg/ml nuclease- and protease-free bovine serum albumin (PBS-EDTA-BSA). Eight working standards (DA to DH) are prepared by further diluting the interim standard in PBS-EDTA-BSA, first to 1000 ng/mL (DA), and then serially diluting DA down to DH with the dilution factor of three per step. The interim and working standards are prepared fresh.

At the end of one hour incubation, the media from the wells in columns 2-11 of the plate are aspirated, and 0.1 ml of PBS-EDTA is added. The plate is incubated at 37° C., 5% $CO_2$ for 10 min and on the microplate shaker at 700 rpm for 3 min to dislodge the cells. Then the media from the wells A1-H1, A12-H12 are aspirated and 0.1 ml aliquots of the luciferase working standards are added, from the highest (DA) in A1 and A12, to the lowest (DH) in H1 and H12, creating a series of eight luciferase standards per plate in duplicate (plate columns 1 and 12).

The Hoechst 33342 fluorescence of the cell suspensions in the wells is determined using SpectraMax M2 multimode plate reader (Molecular Devices, USA) using excitation at 360 nm, emission at 461 nm, and nine-point well scan option. The plate is auto-mixed for 5 sec prior to measurements. The average fluorescence signal per each well is determined, and the fluorescence readings of the cell standard wells A2-H2, A11-H11 are used to generate the linear standard curve of the average fluorescence vs. cell concentration in the well (0.1 ml). The cell concentration in the 0.1 ml of the cell suspension at the end of transfection is determined from this standard curve for each well in a conventional manner.

The luciferase concentration in the cell suspensions is determined using BrightGlo® Firefly Luciferase assay kit (Promega Corp., USA). To each of the luciferase standard wells, test sample wells, and blank (cells only) wells G2-H2, G11-H11 in the same plate, 0.1 mL of the reconstituted complete Luciferase substrate buffer (prepared according to the manufacturer's recommendations) is added, the contents of the wells are thoroughly mixed, and the luminescence of the mixtures in the wells is determined at 10-15 min after the luciferase substrate addition using SpectraMax M2 multimode plate reader (Molecular Devices, USA) in the luminescence mode under the instrument default settings. The readings of the duplicate standards in the wells A1-H1 and A12-H12, after subtraction of the blank readings of the wells G2-H2 and G11-H11, are used to generate the Luciferase standard curve linearly approximated in double-log coordinates using the minimization of the mean squared relative error. The amount of luciferase formed in each well is calculated from the luminescence readings (with blank readings subtracted) using the luciferase standard curve, normalized to the number of cells per well determined using the Hoechst 33342 method above, and presented in ng of luciferase per 1 million ($10^6$) cells. It was found that for the targeted LNP and the typical assay range of post-transfection cell concentrations of $(99\text{-}1251)\times10^3$ cell/ml in 0.1 ml of the cell harvesting solution ($(9.9\text{-}125.1)\times10^3$ cells/well), observed under the above assay conditions, the Luciferase expression normalized to the final number of the cells in the well was dependent on both initial (plating) cell density and final (post-transfection) cell density, and the dependence was in good agreement with the second-degree polynomial approximation against the logarithm of the post-transfection cell concentration ($R^2$=0.9925). Therefore, for targeted LNPs the assayed luciferase activities in each individual well were corrected to the standard post-transfection cell concentration of $400\times10^3$ cells/ml (cell density $40\times10^3$ cells/well) using the formula: $Luc=Luc(D)*100/(91.6\times\log^2(D)-659.2\times\log(D)+1196.4)$, where D is the measured post-transfection cell concentration in $10^3$ cells/ml, Luc(D) is the measured luciferase expression at the post-transfection cell concentration D.

Example 6. In Vitro Transfection of Ffluc-mRNA LNPs Composed of the Ionizable Lipids Formulated in the Presence and Absence of 5 Mol % DPPS-$NH_4$ A mRNA encoding Ffluc-mRNA was formulated separately into LNPs comprising an ICL/DSPC/Chol/PEG-DMG (52/10/36.5/1.5 mol %) or ICL/DSPC/DPPS-$NH_4$/Chol/PEG-DMG (52/5/5/36.5/1.5 mol %) formulated at an N/P ratio of 5.25. The LNPs were prepared and characterized as described in Example 2 and 3 respectively.

Particle size refers to the Z-Average particle size after freezing and thawing. Zeta refers to zeta potential measurements at either pH 5 or pH 7 in units of mV. mRNA encapsulation efficiency after freezing & thawing is referred to as (E.E,%).

TABLE 9A

Physicochemical properties and characterization of LNPs containing Ffluc mRNA comparing different ICLs in a PS-targeted and non-targeted form.

| ICL | Targeted? | Z-Ave | PDI | % E.E | Zeta pH 5 | Zeta pH 7 |
|---|---|---|---|---|---|---|
| KC3-X1-PH12 | No PS | 84.54 | 0.006 | 95.71 ± 0.27 | 17.41 | 3.66 |
| KC3-X2-PH12 | No PS | 88.77 | 0.036 | 95.78 ± 0.19 | 17.94 | 2.73 |
| KC3-X1-PH5 | No PS | 85.84 | 0.06 | 96.64 ± 0.28 | 20.69 | 4.61 |
| KC3-OA | No PS | 81.68 | 0.077 | 97.20 ± 0.39 | 16.76 | 5.09 |
| KC3-X1-PH12 | 5 mol % PS | 87.15 | 0.065 | 96.78 ± 0.08 | 19.84 | −1.16 |
| KC3-X2-PH12 | 5 mol % PS | 87.65 | 0.017 | 96.69 ± 0.33 | 18.83 | 0.17 |
| KC3-X1-AA | 5 mol % PS | 86.16 | 0.052 | 96.47 ± 0.20 | 19.62 | −1.23 |
| KC3-X1-PH5 | 5 mol % PS | 83.27 | 0.048 | 98.22 ± 0.13 | 19.24 | −2.66 |
| KC3-OA | 5 mol % PS | 82.93 | 0.028 | 97.90 ± 0.09 | 15.77 | −0.89 |

The formulations ranged in size from approximately 82 to 93 nm in diameter The % entrapped mRNA ranged from 94-98% and LNPs exhibited positive surface charge at pH 5 +16-21 and a negative charge at pH 7 −3 to +5 mV.

The activity of the LNPs was evaluated by transfection MutuDC1940 cells in vitro at 0.3 μg/mL mRNA concentration for 24 h as described in Example 5.

TABLE 9B

In vitro activity of LNPs containing Ffluc mRNA comparing different ICLs in a PS-targeted or non-targeted format.

| ICL | Targeted? | Luc (ng/million cells) | T/NT |
|---|---|---|---|
| KC3-X1-PH12 | No PS | 5.03 ± 0.16 | |
| KC3-X2-PH12 | No PS | 8.12 ± 0.55 | |
| KC3-X1-PH5 | No PS | 12.40 ± 1.15 | |
| KC3-OA | No PS | 26.89 ± 4.67 | |
| KC3-X1-PH12 | 5 mol % PS | 334.27 ± 17.96 | 66.5 |
| KC3-X2-PH12 | 5 mol % PS | 447.74 ± 43.72 | 55.2 |
| KC3-X1-PH5 | 5 mol % PS | 199.92 ± 22.25 | 16.1 |
| KC3-OA | 5 mol % PS | 76.19 ± 6.52 | 2.8 |

It was found that the rank order of activity and the activity of the PS-targeted to non-targeted ratio (highest to lowest) was KC3-X2-PH12>KC3-X1-PH12>KC3-X1-PH5>KC3-OA at 0.3 μg/mL.

Example 7. Preparation and Analysis of PS-Containing LNPs Containing KC3-X1-PH12 at Varying Mol % Encapsulating the mRNA FFluc which was Used to Evaluate the Effect of ICL Content on Activity in MutuDC1940 Murine Dendritic Cells In Vitro LNPs were prepared comprising 48, 52, 54, 56, 60 or 64 mol % KC3-X1-PH12 ionizable lipid with the composition KC3-X1-PH12/DSPC/DPPS/Chol/PEG-DMG (x/5/5/(88.5−x)/1.5 mol %) and an N/P ratio of 4.5 encapsulating firefly luciferase mRNA (FFluc) were prepared as described in Example 2 (using a ChipShop 187 chip to mix and prepare the LNPs at a flow rate of 18 ml/min.) where x represents the mol % ionizable lipid. The LNPs were used to evaluate the effect of altering the mol % of KC3-X1-PH12 on in vitro luciferase activity in vitro. The LNPs were characterized using the method of Example 3. Particle size refers to the Z-Average particle size after freezing and thawing. Zeta refers to zeta potential measurements at either pH 5 or pH 7 in units of mV. mRNA encapsulation efficiency is referred to as (E.E,%).

TABLE 10A

Physicochemical properties and characterization of DPPS containing KC3-X1-PH12 LNPs containing FFluc mRNA

| Mol % | Particle Size (nm) | E.E, %, Stdev | Zeta pH 5 | Zeta pH 7 |
|---|---|---|---|---|
| 48 | 101.80 | 87.02 ± 0.76 | 18.68 | −1.84 |
| 52 | 104.20 | 87.42 ± 0.54 | 16.04 | −2.36 |
| 56 | 109.40 | 88.65 ± 0.45 | 15.34 | −3.38 |
| 60 | 111.70 | 88.76 ± 0.52 | 18.70 | −3.34 |
| 64 | 119.30 | 87.06 ± 0.67 | 13.73 | −4.40 |

The formulations ranged in size from approximately 104 to 112 nm in diameter. The % entrapped mRNA ranged from % and LNPs exhibited a surface charge range at pH 5 from approximately +14 to +19 mV and a range from −4 to −2 mV at pH 7.

TABLE 10B

Luciferase expression in MutuDC 1940 cells after exposure to LNPs for 24 h at 0.3 μg/mL total (encapsulated + non-encapsulated) mRNA concentration. A frozen KC3-OA LNP formulation described in Example 11 was used in the luciferase assay as a control.

| Mol % | Luciferase activity (ng/10^6 cells) ± stdev | Luciferase Activity KC3-X1-PH12/KC3OA |
|---|---|---|
| 48 | 421.7 ± 21.8 | 1.07 |
| 52 | 506.5 ± 24.8 | 1.29 |
| 56 | 662.4 ± 44.3 | 1.69 |
| 60 | 592.2 ± 27.8 | 1.51 |
| 64 | 417.8 ± 25.5 | 1.06 |

Example 8. Preparation and Analysis of LNPs Containing KC3X1-PH5,KC3-X1-AA and KC3-X1-PH12 at Different N/P Ratios Encapsulating FFluc mRNA Used to Evaluate Activity In Vitro LNPs were prepared as described in Example 2, comprising of ICL/DSPC/DPPS-$NH_4$/Chol/PEG-DMG (52/5/5/36.5/1.5 mol %) at varying N/P ratios containing the reporter mRNA FFluc and evaluated in vitro for luciferase activity. LNPs were characterized with the methods of Example 3. Particle size refers to the Z-Average particle size after freezing and thawing. Zeta refers to zeta potential measurements at either pH 5 or pH 7 in units of mV. mRNA encapsulation efficiency is referred to as (E.E,%).

TABLE 11A

Physicochemical properties and characterization of KC3-X1-PH5 and KC3-X1-AA LNPs containing FFluc mRNA at different N/P ratios.

| ICL | N/P | Particle Size (nm) | E.E, %, Stdev | Zeta pH 5 | Zeta pH 7 |
|---|---|---|---|---|---|
| KC3-X1-PH5 | 4.0 | 114.60 | 95.63 ± 7.04 | 16.12 | −7.35 |
| KC3-X1-PH5 | 4.25 | 114.60 | 94.76 ± 7.04 | 18.28 | −3.93 |
| KC3-X1-PH5 | 5.0 | 116.10 | 95.76 ± 7.04 | 21.06 | −3.50 |
| KC3-X1-PH5 | 5.5 | 114.40 | 95.42 ± 7.04 | 22.90 | −2.67 |
| KC3-X1-PH5 | 6.0 | 111.90 | 95.00 ± 7.04 | 22.09 | −2.91 |
| KC3-X1-PH5 | 6.5 | 114.50 | 95.61 ± 7.04 | 26.79 | −3.46 |

TABLE 11B

Luciferase expression (ng/million cells ± stdev) in MutuDC 1940 cells after exposure to LNPs for 24 h at 0.1 μg/mL total (encapsulated + non-encapsulated) mRNA concentration.

| ICL | N/P | Luciferase Activity |
|---|---|---|
| KC3-X1-PH5 | 4.0 | 103.7 ± 9.9 |
| KC3-X1-PH5 | 4.25 | 118.9 ± 4.4 |
| KC3-X1-PH5 | 5.0 | 138.9 ± 6.0 |
| KC3-X1-PH5 | 5.5 | 142.8 ± 6.9 |
| KC3-X1-PH5 | 6.0 | 146.6 ± 4.8 |
| KC3-X1-PH5 | 6.5 | 157.8 ± 10.7 |

TABLE 11C

Luciferase expression (ng/million cells ± stdev) in MutuDC 1940 cells after exposure to LNPs for 24 h at 0.3 μg/mL total (encapsulated + non-encapsulated) mRNA concentration.

| ICL | N/P | Luciferase Activity |
|---|---|---|
| KC3-X1-PH5 | 4.0 | 273.3 ± 19.8 |
| KC3-X1-PH5 | 4.25 | 284.4 ± 13.4 |
| KC3-X1-PH5 | 5.0 | 295.3 ± 9.3 |
| KC3-X1-PH5 | 5.5 | 287. ± 12.4 |
| KC3-X1-PH5 | 6.0 | 302.3 ± 13.1 |
| KC3-X1-PH5 | 6.5 | 293.5 ± 11.8 |

LNP formulations prepared with KC3-X1-PH5 and KC3-X1-AA demonstrated peak luciferase activity at an N/P of 6 and 4.25, respectively. All formulations demonstrated greater than 90% encapsulation efficiency and a particle size between 107 and 119 nm, independent of the N/P ratio.

TABLE 12A

Physicochemical properties and characterization of KC3-X1-PH12 LNPs containing FFluc mRNA at different N/P ratios. Some formulations were prepared on more than one occasion.

| N/P | Particle Size (nm) | E.E, %, Stdev | Zeta pH 5 | Zeta pH 7 |
|---|---|---|---|---|
| 1.0 | 129.00 | 16.07 ± 0.48 | −0.08 | −27.50 |
| 2.0 | 151.20 | 56.87 ± 2.77 | 0.29 | −6.67 |
| 3.0 | 109.50 | 76.03 ± 2.39 | 6.80 | −1.54 |
| 3.25 | 110.20 | 82.23 ± 2.17 | 10.95 | −1.50 |
| 3.5 | 109.70 | 89.15 ± 3.14 | 12.50 | −2.95 |
| 3.75 | 111.30 | 93.00 ± 2.93 | 12.99 | −3.60 |
| 4.0 | 107.90 | 92.08 ± 1.99 | 15.52 | −4.01 |
| 4.25 | 107.40 | 92.27 ± 3.66 | 15.22 | −5.62 |
| 4.5 | 107.30 | 92.25 ± 2.68 | 14.96 | −5.37 |
| 4.75 | 110.40 | 92.06 ± 3.88 | 17.68 | −8.92 |
| 5.0 | 108.80 | 92.53 ± 2.02 | 18.66 | −6.93 |
| 4.0 | 108.30 | 89.58 ± 2.13 | 7.347 | −5.356 |
| 4.25 | 104.10 | 88.59 ± 3.19 | 7.788 | −6.262 |
| 4.5 | 105.30 | 89.21 ± 3.33 | 8.238 | −6.534 |
| 4.75 | 110.20 | 89.29 ± 2.45 | 11.34 | −4.663 |
| 5.0 | 105.50 | 88.37 ± 2.67 | 12.34 | −6.036 |
| 5.0 | 114.60 | 89.71 ± 3.51 | 23.56 | −0.36 |
| 5.25 | 113.40 | 91.80 ± 5.23 | 16.56 | −2.33 |
| 5.50 | 108.60 | 89.57 ± 2.81 | 17.31 | −2.29 |
| 5.75 | 109.30 | 90.33 ± 1.74 | 24.24 | −1.67 |
| 6.00 | 110.40 | 91.54 ± 4.31 | 19.47 | −3.63 |

TABLE 12B

Luciferase expression (ng/million cells ± stdev) of KC3-X1-PH12 LNPs in MutuDC 1940 cells after exposure to LNPs for 24 h at 0.3 μg/mL total (encapsulated + non-encapsulated) mRNA concentration.

| N/P | Luc activity | Rel. Luc. Activity |
|---|---|---|
| 1.0 | 0.90 ± 0.13 | 1.00 |
| 2.0 | 1.89 ± 1.33 | 2.10 |
| 3.0 | 139.52 ± 5.09 | 155.02 |
| 3.25 | 252.30 ± 11.47 | 280.33 |
| 3.5 | 357.14 ± 11.79 | 396.82 |
| 3.75 | 439.23 ± 27.62 | 488.03 |
| 4.0 | 435.03 ± 38.70 | 483.37 |
| 4.25 | 441.10 ± 38.06 | 490.11 |
| 4.5 | 469.42 ± 37.90 | 521.58 |
| 4.75 | 400.85 ± 20.80 | 445.39 |
| 5.0 | 400.11 ± 36.32 | 444.57 |
| 4.0 | 536.19 ± 25.21 | 595.77 |
| 4.25 | 494.61 ± 42.91 | 549.57 |
| 4.5 | 471.19 ± 63.12 | 523.54 |
| 4.75 | 476.97 ± 60.50 | 529.97 |
| 5.0 | 498.15 ± 50.44 | 553.50 |
| 5.0 | 457.75 ± 28.64 | 508.61 |
| 5.25 | 429.82 ± 32.22 | 477.58 |
| 5.50 | 390.98 ± 19.98 | 434.42 |
| 5.75 | 379.55 ± 29.30 | 421.72 |
| 6.00 | 372.24 ± 26.92 | 413.60 |

LNP formulations prepared with KC3-X1-PH 12 demonstrated a peak luciferase activity at an N/P of 4.5-5.0 with activity dropping off rapidly below N/P 3.5, which also corresponded to increases in particle size and poly dispersity and a decrease in encapsulation efficiency.

Example 10. Comparing the Immunogenicity of a Quadrivalent mRNA Vaccine in Mice Using KC3-X1-PH12 LNPs and KC3-X2-PH12 LNPs Composed with Different ICL Mol % and N/P Ratios Four mRNAs encoding influenza A subtypes H1 (SEQ ID NO: 13 encoding SEQ ID NO: 12), H3 (SEQ ID NO: 914 encoding SEQ ID NO: 14), influenza B/Victoria (SEQ ID NO: 17 encoding SEQ ID NO: 915) and RSVpreF (SEQ ID NOs: 10 encoding SEQ ID NO: 9) mRNAs were combined at equal weight ratios and encapsulated into LNPs comprising of KC3-X1-PH12/DSPC/DPPS-NH4/Chol/PEG-DMG where the ICL mol % was 52 or 56 mol %, DSPC and DPPS-NH4 were present at 5 mol % each, PEG-DMG was 1.5 mol % and the remainder lipid was cholesterol. Similar LNPs were prepared with 52 or 56 mol % KC3-X2-PH12 and N/P ratios of 4.5 or 5.25. KC3-X1-PH12 was also used at 52 or 56 mol % and an N/P ratio of 5.25 to encapsulate a single influenza subtype H5 mRNA (SEQ ID NO: 15). The LNPs were prepared as in Example 2 and analyzed as in Example 3. An outline of the composition for formulation and a panel of physicochemical characteristics are shown below in Table 14A. Additionally, a portion of the quadrivalent mRNA-LNPs made with 52 mol % KC3-X1-PH12 and 56 mol % KC3-X1-PH12 were lyophilized. The physicochemical characteristics of these mRNA-LNPs after reconstitution are shown below in Table 14B. LNPs were characterized as described in Example 3. Particle size refers to the Z-Average particle size after freezing and at an N/P ratio. Zeta refers to zeta potential measurements at either pH 5 or pH 7 in units of mV. mRNA encapsulation efficiency after freezing & thawing is referred to as (E.E,%), PDI, polydispersity index.

TABLE 14A

The physicochemical details of the KC3-X1-PH12 or KC3-X2-PH12 based LNP formulations.

| Group # | ICL | N/P | mol % | Z-Ave | PDI | % EE ± stdev | Zeta pH 5 | Zeta pH 7 |
|---|---|---|---|---|---|---|---|---|
| 1-4 | KC3-X1-PH12 | 5.25 | 52 | 111.1 | 0.054 | 88.5 ± 0.25 | 16.76 | 0.47 |
| 5-8 | KC3-X1-PH12 | 5.25 | 56 | 116.1 | 0.047 | 88.4 ± 0.29 | 19.70 | 0.12 |
| 9-10 | KC3-X2-PH12 | 4.25 | 52 | 116.8 | 0.056 | 85.3 ± 1.01 | 9.13 | 0.30 |
| 11-12 | KC3-X2-PH12 | 5.25 | 56 | 106.1 | 0.048 | 93.2 ± 0.75 | 15.49 | 0.62 |
| 13-14 | KC3-X2-PH12 | 5.25 | 52 | 97.66 | 0.051 | 94.7 ± 0.29 | 15.20 | −0.61 |
| 15-16 | KC3-X1-PH12 | 5.25 | 52 | 114.1 | 0.044 | 88.2 ± 0.13 | 20.43 | 0.68 |
| 17-18 | KC3-X1-PH12 | 5.25 | 56 | 108.5 | 0.057 | 89.1 ± 0.43 | 13.16 | 0.72 |

The formulations ranged in size from approximately 97 to 117 nm in diameter. The % entrapped mRNA ranged from 85-94% and LNPs exhibited positive surface charge at pH 5 of approximately ~+9 to +20 mV and a charge at pH 7 −1 to +1 mV.

TABLE 14B

Particle size (Z-ave), polydispersity (PDI) and mRNA encapsulation efficiency (%EE) of LNPs that were lyophilized and reconstituted (Post Lyo/R), made with either 52 or 56mol% KC3-X1-PH12. Compare post lyophilization and reconstitution characteristics shown for Groups 3-4 to pre lyophilization characteristics shown for Groups 1-4 in Table 14A. Likewise, compare post lyophilization and reconstitution characteristics shown for Groups 7-8 to pre lyophilization characteristics shown for Groups 5-8 in Table 14A.

| | | | | Post Lyo/R | | |
|---|---|---|---|---|---|---|
| Group # | ICL | N/P | mol % | Z-ave | PDI | %EE |
| 3-4 | KC3-X1-PH12 | 5.25 | 52 | 136.40 | 0.08 | 78.49 ± 1.07 |
| 7-8 | KC3-X1-PH12 | 5.25 | 56 | 140.20 | 0.02 | 75.46 ± 1.60 |

After lyophilization, it was found that the particle size increased by about 25 nm for each, and the % EE was reduced by about 10-12% points.

In Vivo Immunogenicity in Mice.

To measure the ability of these mRNA-LNPs to induce antibodies, BALB/c mice were immunized at a high and 3-fold lower dose in the caudal thigh in a volume of 50 μL. The experimental design and dosing schema is shown in FIG. 6A. Twenty-one days post vaccination, serum was collected and stored at −80° C. until analysis. Mouse IgG endpoint antibody titers against the matching H1, H3, B-Victora, RSVpreF or H5 antigens were determined by standard ELISA. For H1-specific Ab titers, we found for KC3-X1-PH12 that immunogenicity of freeze-dried material was not deleterious for biological activity (FIG. 6B and FIG. 6C). This was true for 52 and 56 mol % ICL with N/P=5.25, indicating that lyophilization may be an option for longer-term storage. Second, antibody titers were comparable between LNPs comprised of KC3-X1-PH12 and KC3-X2-PH12, showing that either orientation of the biodegradable ester bond can be used for PH12 with a KC3 headgroup. Third, we found for KC3-X1-PH12 that either 52 or 56 mol % with N/P=5.25 elicited similar immune responses; the same was true for X2-PH12. For H3-specific Ab titers (FIG. 6D and FIG. 6E), results were similar to H1 titers: lyophilization of the mRNA-LPN was not deleterious to biological activity (H3 titers elicited by lyophilized material trended higher than for non-lyophilized, X1-PH12 and X2-PH12 were comparably immunogenic, and these ICLs can be used with either 52 or 56 mol % without impacting antibody titers.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

All publications, patents and patent applications referenced in this specification are incorporated herein by reference in their entirety for all purposes to the same extent as if each individual publication, patent or patent application were specifically indicated to be so incorporated by reference.

What is claimed is:

1. A lipid nanoparticle (LNP) composition comprising a mRNA nucleic acid encapsulated in lipidic nanoparticles comprising:

a. a KC3-X1-PH12 or a KC3-X2-PH12 ionizable cationic lipid compound at a N/P ratio of 5.25 relative to the mRNA nucleic acid and in a total amount of 52-56 mol % of the total lipid content of the LNP composition:

(KC3-X1-PH12)

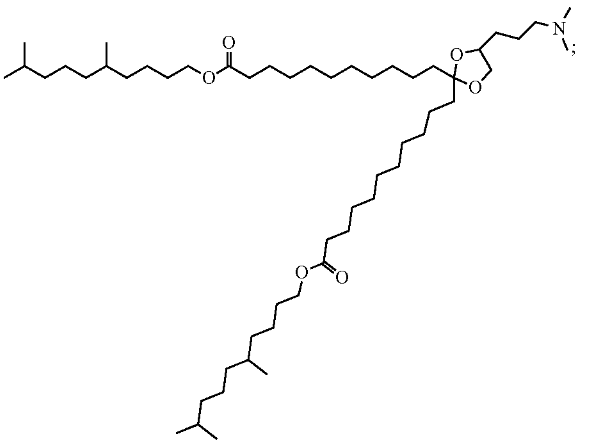

(KC3-X2-PH12)

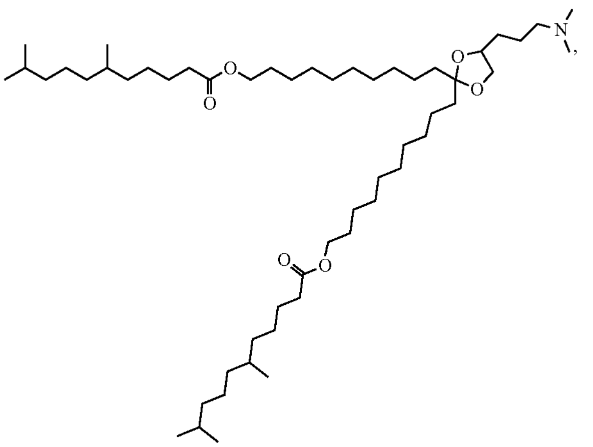

b. dipalmitoylphosphatidyl-L-serine (DPPS) in a total amount of 5 mol % of the total lipid content of the LNP composition;

c. 1,2-distearoyl-sn-glycero-3-phosphocholine (DSPC) in a total amount of 5 mol % of the total lipid content of the LNP composition; and d. PEG(2000)-dimyristoylglycerol (PEG-DMG) in a total amount of 1.50 mol % of the total lipid content of the LNP composition; and e. cholesterol in a total remaining amount of the total lipid content of the LNP composition.

2. The composition of claim 1, wherein the ionizable cationic lipid is KC3-X1-PH12.

3. The composition of claim 2, comprising the KC3-X1-PH12 ionizable cationic lipid compound in a total amount of 52 mol % of the total lipid content of the LNP composition.

4. The composition of claim 2, comprising the KC3-X1-PH12 ionizable cationic lipid compound in a total amount of 56 mol % of the total lipid content of the LNP composition.

5. The composition of claim 1, wherein the ionizable cationic lipid is KC3-X2-PH12.

6. The composition of claim 5, comprising the KC3-X2-PH12 ionizable cationic lipid compound in a total amount of 52 mol % of the total lipid content of the LNP composition.

7. The composition of claim 5, comprising the KC3-X2-PH12 ionizable cationic lipid compound in a total amount of 56 mol % of the total lipid content of the LNP composition.

8. The composition of claim 1, wherein the composition is prepared by a process comprising dissolving a DPPS-$NH_4$ salt in ethanol to obtain a lipid solution and mixing the lipid solution with a second solution comprising the mRNA to obtain the lipid nanoparticles encapsulating the mRNA.

9. The composition of claim 8, wherein the lipid solution further comprises a mixture of DSPC, PEG-DMG, and cholesterol, prior to mixing with the second solution.

10. The composition of claim 9, wherein 94-98% of the mRNA in the composition is entrapped within the lipidic nanoparticles.

11. The composition of claim 1, wherein the composition is frozen and thawed.

12. The composition of claim 1, wherein the lipidic nanoparticles have a Z-Average particle size of 84-140 nm.

13. The composition of claim 12, wherein the lipid nanoparticles have a polydispersity index of 0.006-0.08.

14. The composition of claim 1, wherein the composition is lyophilized.

15. The composition of claim 14, wherein the lyophilized composition is reconstituted.

16. The composition of claim 1, comprising the mRNA nucleic acid encapsulated in lipidic nanoparticles consisting of the ionizable cationic lipid, DPPS, DSPC, PEG-DMG and cholesterol.

17. The composition of claim 1, comprising the mRNA nucleic acid encapsulated in lipidic nanoparticles consisting of 52 mol % of the ionizable cationic lipid, 5 mol % DPPS, 5 mol % DSPC, 1.5 mol % PEG-DMG and 36.5 mol % cholesterol.

18. The composition of claim 17, wherein the ionizable cationic lipid is KC3-X1-PH12.

19. The composition of claim 17, wherein the ionizable cationic lipid is KC3-X2-PH12.

20. The composition of claim 16, wherein the lipidic nanoparticles have a Z-Average particle size of 84-140 nm, and a polydispersity index of 0.006-0.08; and at least 94% of the mRNA in the composition is entrapped within the lipidic nanoparticles.

21. The composition of claim 20, wherein the ionizable cationic lipid is KC3-X1-PH12.

* * * * *

SEQUENCE LISTING

```
Sequence total quantity: 915
SEQ ID NO: 1           moltype =   length =
SEQUENCE: 1
000

SEQ ID NO: 2           moltype = AA  length = 550
FEATURE                Location/Qualifiers
source                 1..550
                       mol_type = protein
                       organism = synthetic construct
SEQUENCE: 2
MEDAKNIKKG PAPFYPLEDG TAGEQLHKAM KRYALVPGTI AFTDAHIEVD ITYAEYFEMS  60
VRLAEAMKRY GLNTNHRIVV CSENSLQFFM PVLGALFIGV AVAPANDIYN ERELLNSMGI  120
SQPTVVFVSK KGLQKILNVQ KKLPIIQKII IMDSKTDYQG FQSMYTFVTS HLPPGFNEYD  180
FVPESFDRDK TIALIMNSSG STGLPKGVAL PHRTACVRFS HARDPIFGNQ IIPDTAILSV  240
VPFHHGFGMF TTLGYLICGF RVVLMYRFEE ELFLRSLQDY KIQSALLVPT LFSFFAKSTL  300
IDKYDLSNLH EIASGGAPLS KEVGEAVAKR FHLPGIRQGY GLTETTSAIL ITPEGDDKPG  360
AVGKVVPFFE AKVVDLDTGK TLGVNQRGEL CVRGPMIMSG YVNNPEATNA LIDKDGWLHS  420
GDIAYWDEDE HFFIVDRLKS LIKYKGYQVA PAELESILLQ HPNIFDAGVA GLPDDDAGEL  480
PAAVVVLEHG KTMTEKEIVD YVASQVTTAK KLRGGVVFVD EVPKGLTGKL DARKIREILI  540
KAKKGGKIAV                                                         550

SEQ ID NO: 3           moltype = RNA  length = 1843
FEATURE                Location/Qualifiers
source                 1..1843
                       mol_type = other RNA
                       organism = synthetic construct
SEQUENCE: 3
acatttgctt ctgacacaac tgtgttcact agcaacctca aacagccacc atggaagatg  60
ccaaaaacat caagaagggt ccggccccat tctacccact ggaagatggt accgcgggcg  120
aacagctgca taaggccatg aagagatacg ccctggtccc tggaaccatc gcgttcaccg  180
acgcccacat tgaagtggac atcacctacg ccgaatactt cgagatgtcc gtgcggctgg  240
ccgaagccat gaagcgctac ggcctgaaca cgaaccatag gatcgtggtc tgctccgaaa  300
acagcctgca gtttttcatg ccggtgctcg gagccctgtt tatcggcgtg gcggtcgcac  360
cagcaaacga catctacaat gagcgggaac tactgaactc gatgggtatt tcccaaccca  420
ctgtggtgtt cgtcagcaaa aagggcctgc aaaagatcct gaacgtgcag aagaagctgc  480
ccatcatcca gaagatcatt attatggaca gcaagacgga ttaccaaggc ttccagtcga  540
tgtacacctt cgtgacctcg catctgccac cgggtttcaa cgaatacgac ttcgtgcccg  600
aatcgtttga ccgcgacaag actattgcct tgatcatgaa cagcagcggt agtactggtt  660
tgcctaaggg ggtggccctg ccacaccgga ccgcctgcgt gagattctcg cacgcgcgcg  720
atcccatatt cggaaatcag atcatccctg acacggctat cctgtccgtg gtcccattcc  780
accacggctt cggcatgttc accactctcg gatacctgat ttgcggattc cgggtggtgc  840
tgatgtaccg cttcgaagag gagctgtttc tccggagcct tcaggactac aaaatccaga  900
gcgccctcct ggtgcccacc ctgttctcct tcttcgctaa gtctaccttg attgacaaat  960
acgacctctc gaacctccac gagatcgcat ccggtggtgc ccattgtcg aaggaagtcg  1020
gagaagcagt ggcgaagcgg ttccacctcc cgggcattcg gcagggttac gggctgactg  1080
aaaccacctc agcgatcctc attactcctg agggggacga caagccgggc gccgtgggaa  1140
aggttgtgcc gttcttcgag gccaaggtcg tcgacctgga taccggaaag accctgggag  1200
tcaaccaaag gggggagctg tgtgtgcgcg gacctatgat tatgtccgga tacgtcaaca  1260
accctgaggc cactaacgcc ctgatcgaca aggacggttg gctgcactcc ggagatatcg  1320
catactggga cgaggacgaa cacttcttca ttgtggatcg gttgaagtcc ctgatcaagt  1380
acaagggcta tcaagtggca ccggccgaac ttgaatcgat ccttctgcaa caccccaaca  1440
tcttcgatgc cggcgtcgcc gggctgcccg acgacgacgc gggagagctg ccggctgcgg  1500
tggtggtgct tgagcacggc aaaaccatga ctgaaaaaga gatcgtggac tacgtggcgt  1560
cccaagtcac caccgcgaag aagctcaggg gcggcgtggt gtttgtggat gaggtgccca  1620
aggggctcac cggaaagttg gacgcccgca agattcgcga gattctgatt aaggccaaga  1680
aggggggaaa gattgccgtg tgataatagg ctcgctttct tgctgtccaa tttctattaa  1740
aggttccttt gttccctaag tccaactact aaactggggg atattatgaa gggccttgag  1800
catctggatt ctgcctaata aaaaacattt attttcattg caa                    1843

SEQ ID NO: 4           moltype = RNA  length = 628
FEATURE                Location/Qualifiers
source                 1..628
                       mol_type = other RNA
                       organism = synthetic construct
SEQUENCE: 4
acatttgctt ctgacacaac tgtgttcact agcaacctca aacagacacc atggtgcatc  60
tgactcctga ggagaagtct gccgttactg ccctgtgggg caaggtgaac gtggatgaag  120
ttggtggtga ggccctgggc aggctgctgg tggtctaccc ttggacccag aggttctttg  180
agtcctttgg ggatctgtcc actcctgatg ctgttatggg caaccctaag gtgaaggctc  240
atggcaagaa agtgctcggt gcctttagtg atggcctggc tcacctggac aacctcaagg  300
gcacctttgc cacactgagt gagctgcact gtgacaagct gcacgtggat cctgagaact  360
tcaggctcct gggcaacgtg ctggtctgtg tgctggccca tcactttggc aaagaattca  420
ccccaccagt gcaggctgcc tatcagaaag tggtggctgg tgtggctaat gccctggccc  480
acaagtatca ctaagctcgc tttcttgctg tccaatttct attaaaggtt cctttgttcc  540
ctaagtccaa ctactaaact gggggatatt atgaagggcc ttgagcatct ggattctgcc  600
taataaaaaa catttatttt cattgcaa                                     628
```

-continued

```
SEQ ID NO: 5            moltype = AA  length = 567
FEATURE                 Location/Qualifiers
source                  1..567
                        mol_type = protein
                        organism = unidentified
SEQUENCE: 5
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCYPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSIYSTAAS  540
SLALAIMMAG LSLWMCSNGS LQCRICI                                     567

SEQ ID NO: 6            moltype = RNA  length = 1894
FEATURE                 Location/Qualifiers
source                  1..1894
                        mol_type = other RNA
                        organism = synthetic construct
SEQUENCE: 6
acatttgctt ctgacacaac tgtgttcact agcaacctca aacagccacc atggagaaca  60
tcgtgctctt gctggcaatc gtgtccctgg tcaagtccga tcagatctgc atcggctacc  120
acgcaaacaa ctccaccgaa caagtggaca ctatcatgga aaagaacgtg acggtcacac  180
acgcccagga cattctggaa aagacccaca atgggaaact gtgtgacctc aacggcgtga  240
agccgctgat cctcaaggat tgctccgtgg ctggatggct cctgggcaac cctatgtgcg  300
atgagttcat tcgggtgccc gagtggtcgt acattgtgga gagggccaac ccggccaatg  360
acctgtgcta ccccggctcg ctgaacgatt acgaagaact caagcacatg ctgtcccgca  420
tcaaccattt cgagaagatc cagatcattc cgaagtccag ctggcctaac cacgaaactt  480
ccctgggagt gtctgctgcc tgcccatacc aaggcgcccc ctcatttttc cggaacgtcg  540
tgtggctcat caagaagaac gatgcgtacc ccactatcaa gatcagctac aacaacacca  600
accgcgagga tctgctgatt ctctggggaa ttcaccattc caacaacgct gaagaacaga  660
ccaacctgta caaaaaccct atcacttaca tctccgtggg tacctccacc ctcaatcagc  720
gcttggcgcc gaagatcgcg accagaagcc aagtcaacgg acagcgggga agaatggact  780
tcttctggac tatactgaag cctgacgatg caatccactt cgaatccaac ggaaacttca  840
tcgcccctga gtatgcctac aagatcgtga agaagggcga cagcaccatc atgaagtcag  900
gagtggagta tggacactgt aacactaagt gccagacccc cgtcggggcc attaacagct  960
ccatgccgtt ccacaacatt cacccctga ctattggaga gtgtccgaaa tacgtgaaga  1020
gtaacaagtt ggtgctggcc actggcctgc gcaactcgcc gcttcgggag aagaggagga  1080
agagaggact gtttggggcg attgcaggat tcattgaggg aggttggcag gggatggtgg  1140
acggttggta cggttaccac cactcgaacg agcagggatc gggctatgcc gccgacaagg  1200
agagcaccca gaaggccatc gacggggtca ccaacaaggt caactccatc attgacaaga  1260
tgaataccca gttcgaagcc gtgggccgcg aattcaacaa cctggaacga cggatcgaga  1320
acctgaacaa gaagatggag gacggcttcc tggacgtgtg gacctacaat gccgaactgc  1380
tcgtgctgat ggagaatgag cggaccctcg acttccatga ctcaaacgtg aagaacctgt  1440
acgacaaagt ccggctgcaa ctgcgggaca atgccaagga actggggaac ggatgctttg  1500
agttctacca taagtgcgat aacgagtgca tggaatcagt gcggaacgga acctacgact  1560
acccacagta ctccgaggaa gcccgcctga agagagaaga aatctccggc gtgaaactcg  1620
aaagcgtggg gacctaccag atcctttcca tctactccac ggctgcgagc tcgttggccc  1680
ttgcgatcat gatggccggc ctttcgctgt ggatgtgctc caacggtagc ctgcagtgcc  1740
gcatttgtat ctgataatag gctcgctttc ttgctgtcca atttctatta aaggttcctt  1800
tgttccctaa gtccaactac taaactgggg gatattatga agggccttga gcatctggat  1860
tctgcctaat aaaaaacatt tattttcatt gcaa                             1894

SEQ ID NO: 7            moltype = AA  length = 584
FEATURE                 Location/Qualifiers
source                  1..584
                        mol_type = protein
                        organism = synthetic construct
SEQUENCE: 7
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCYPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ IGIVAGLAVL  540
AVVVIGAVVA AVMCRRKSSG GKGGSYSQAA CSDSAQGSDV SLTA                  584

SEQ ID NO: 8            moltype = RNA  length = 1945
FEATURE                 Location/Qualifiers
source                  1..1945
                        mol_type = other RNA
                        organism = synthetic construct
SEQUENCE: 8
```

-continued

```
acatttgctt ctgacacaac tgtgttcact agcaacctca aacagccacc atggagaaca  60
tcgtgctctt gctggcaatc gtgtccctgg tcaagtccga tcagatctgc atcggctacc  120
acgcaaacaa ctccaccgaa caagtggaca ctatcatgga aaagaacgtg acggtcacac  180
acgcccagga cattctggaa aagacccaca atgggaaact gtgtgacctc aacggcgtga  240
agccgctgat cctcaaggat tgctccgtgg ctggatggct cctgggcaac cctatgtgcg  300
atgagttcat tcgggtgccc gagtggtcgt acattgtgga gagggccaac ccggccaatg  360
acctgtgcta ccccggctcg ctgaacgatt acgaagaact caagcacatg ctgtcccgca  420
tcaaccattt cgagaagatc cagatcattc cgaagtccag ctggcctaac cacgaaactt  480
ccctgggagt gtctgctgcc tgcccatacc aaggcgcccc ctcatttttc cggaacgtcg  540
tgtggctcat caagaagaac gatgcgtacc ccactatcaa gatcagctac aacaacacca  600
accgcgagga tctgctgatt ctctggggaa ttcaccattc caacaacgct gaagaacaga  660
ccaacctgta caaaaaccct atcacttaca tctccgtggg tacctccacc ctcaatcagc  720
gcttggcgcc gaagatcgcg accagaagcc aagtcaacgg acagcgggga agaatggact  780
tcttctggac tatactgaag cctgacgatg caatccactt cgaatccaac ggaaacttca  840
tcgcccctga gtatgcctac aagatcgtga agaagggcga cagcaccatc atgaagtcag  900
gagtggagta tggacactgt aacactaagt gccagacccc cgtcggggcc attaacagct  960
ccatgccgtt ccacaacatt caccccctga ctattggaga gtgtccgaaa tacgtgaaga  1020
gtaacaagtt ggtgctggcc actggcctgc gcaactcgcc gcttcgggag aagaggagga  1080
agagaggact gtttggggcg attgcaggat tcattgaggg aggttggcag gggatggtgg  1140
acggttggta cggttaccac cactcgaacg agcagggatc gggctatgcc gccgacaagg  1200
agagcaccca gaaggccatc gacggggtca ccaacaaggt caactccatc attgacaaga  1260
tgaataccca gttcgaagcc gtgggccgcg aattcaacaa cctggaacga cggatcgaga  1320
acctgaacaa gaagatggag gacggcttcc tggacgtgtg gacctacaat gccgaactgc  1380
tcgtgctgat ggagaatgag cggaccctcg acttccatga ctcaaacgtg aagaacctgt  1440
acgacaaagt ccggctgcaa ctgcgggaca atgccaagga actggggaac ggatgctttg  1500
agttctacca taagtgcgat aacgagtgca tggaatcagt gcggaacgga acctacgact  1560
acccacagta ctccgaggaa gcccgcctga agagagaaga aatctccggc gtgaaactcg  1620
aaagcgtggg gacctaccag atcgggattg tggccggact ggctgtgttg gccgtggtgg  1680
tcatcggcgc cgtcgtggcg gccgtgatgt gccggcgcaa gtcctccggg ggcaaagggg  1740
gaagctattc ccaagccgcc tgctctgact ccgcccaggg gtcggatgtg tccctgaccg  1800
cctgataata ggctcgcttt cttgctgtcc aatttctatt aaaggttcct ttgttcccta  1860
agtccaacta ctaaactggg ggatattatg aagggccttg agcatctgga ttctgcctaa  1920
taaaaaacat ttattttcat tgcaa                                     1945

SEQ ID NO: 9            moltype = AA  length = 535
FEATURE                 Location/Qualifiers
source                  1..535
                        mol_type = protein
                        organism = synthetic construct
SEQUENCE: 9
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIC SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGKSLYV KGEPIINFYD PLVFPSDEFD ASISQVNEKI NQSLAFIRKS DELLHNVNAG  480
KSTTNIMITT IIIVIIVILL SLIAVGLLLY CKARSTPVTL SKDQLSGINN IAFSN      535

SEQ ID NO: 10           moltype = RNA  length = 1798
FEATURE                 Location/Qualifiers
source                  1..1798
                        mol_type = other RNA
                        organism = synthetic construct
SEQUENCE: 10
acatttgctt ctgacacaac tgtgttcact agcaacctca aacagccacc atggaactcc  60
tcatcctgaa agccaacgcc atcaccacaa ttctcactgc tgtgaccttc tgttttgcct  120
cgggacagaa catcaccgag gagttctacc agtccacatg ctccgctgtg tcgaagggct  180
acctgtcggc gctgaggact ggctggtaca cctccgtgat taccatcgaa ctgtcaaaca  240
tcaaggagaa caagtgcaac ggtactgacg cgaaggtcaa gctgattaag caggaattgg  300
acaagtacaa gaacgccgtg actgagctcc agctgctgat gcagtcaacc cctgcgacgg  360
gaagcgggtc cgcaatctgc tccggagtgg ccgtgtgcaa agtgctgcat ctggagggcg  420
aagtcaacaa gatcaagtcg gccctgctga gcaccaacaa ggccgtggtg tccttgagta  480
acggagtctc cgtcctgacc ttcaaagttc tggacctgaa gaattacatc gataagcagc  540
tcctgcccat cctcaacaag cagagctgct ccatttcgaa catcgaaact gtgatcgagt  600
ttcagcaaaa gaacaaccgg ctgctggaaa tcaccagaga gtttagcgtg aacgcaggag  660
tgactacccc cgtgtctacc tacatgctaa ccaactcaga actgcttagc ttgatcaatg  720
acatgccgat cactaacgat cagaagaagc ttatgtccaa caacgtgcaa atcgtgcgcc  780
agcaatccta ctcgattatg tgcattatca aggaagaggt gctggcctat gtggtgcagc  840
tcccgctgta cggcgtgatt gacactcctt gctggaagct gcacacctcc cccctgtgta  900
ccacgaatac caaggagggg tccaatatct gcctgacccg gaccgaccgc ggatggtact  960
gcgacaacgc cggttcggtg tccttcttcc cacaagccga gacttgcaaa gtccagtcca  1020
atcgcgtgtt ctgcgacact atgaactccc ggaccttgcc gtccgaagtg aacctgtgta  1080
acgtggacat cttcaaccct aaatacgact gcaagattat gacttccaag accgacgtca  1140
gcagctcagt gatcaccagc ctgggcgcca tcgtgtcgtg ttatggaaag accaagtgca  1200
ctgcgtccaa caagaacaga ggcatcatca agaccttcag caacggctgc gattacgtca  1260
gcaacaaggg ggtggatacc gtgtccgtgg gaaacactct ctactgtgtg aacaagcagg  1320
agggaaagtc cctctacgtc aagggcgaac cgatcatcaa cttctacgat cccctggtgt  1380
```

```
tcccatccga cgagttcgac gcctccattt cacaagtcaa cgaaaagatc aaccagtctc  1440
tggcgttcat ccggaagtcg gatgaactcc ttcacaacgt caatgccgga aagtccacta  1500
ctaacatcat gattaccacc atcatcattg tcattattgt gatacttctg agcctcatcg  1560
ccgtgggtct gctgttgtac tgcaaagctc gctccacgcc tgtgaccctg tccaaggatc  1620
agctcagcgg gattaacaac atcgccttct caaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798

SEQ ID NO: 11          moltype =   length =
SEQUENCE: 11
000

SEQ ID NO: 12          moltype = AA  length = 566
FEATURE                Location/Qualifiers
source                 1..566
                       mol_type = protein
                       organism = Alphainfluenzavirus influenzae
SEQUENCE: 12
MKAILVVMLY TFTTANADTL CIGYHANNST DTVDTVLEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGARS FYKNLIWLVK KGKSYPKINQ  180
TYINDKGKEV LVLWGIHHPP TITDQESLYQ NADAYVFVGT SRYSKKFKPE IATRPKVRDQ  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID KITNKVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                      566

SEQ ID NO: 13          moltype = RNA  length = 1891
FEATURE                Location/Qualifiers
source                 1..1891
                       mol_type = other RNA
                       organism = synthetic construct
SEQUENCE: 13
acatttgctt ctgacacaac tgtgttcact agcaacctca aacagccacc atgaaagcca  60
tcctcgtcgt aatgctgtac accttcacta ccgccaatgc cgacaccctg tgcatcggat  120
accatgccaa caactccacc gacaccgtgg acactgtgct ggagaagaac gtgaccgtga  180
cccactcggt gaacttgctg gaagataagc acaacggaaa gctgtgcaag ctcagggggg  240
tcgcacctct gcatctggga cagtgcaaca tcgctggctg gatcctggga aacccggagt  300
gcgagagcct gtccacggcc agaagctgga gctacatcgt ggaaacttcg aattcggata  360
acggcacctg ttatcccggg gatttcatta actacgagga actgcgcgag cagctctcat  420
cggtgtcctc cttcgaacgc ttcgaaatct tccctaaaac ctcatcctgg cctaaccacg  480
acagcgacaa cggcgtgact gcagcctgct cccacgccgg ggcgcggtcg ttctacaaga  540
acctcatctg gctggtcaag aagggaaagt cctatcctaa aatcaaccag acctacatca  600
acgacaaggg aaaggaagtg ttggtgctct ggggggatcca tcatcccccg accatcaccg  660
accaggaaag cctgtaccag aacgccgatg cctacgtgtt tgtcggaacc tcgcgctact  720
caaagaagtt taagccggag attgccaccc ggccgaaagt ccgggaccag gctggacgga  780
tgaactacta ctggaccctg gtggaaccag gggacaagat cacattcgaa gcgaccggaa  840
acctggtggc acctagatac gcgttcacca tggagaagga ggccggttcc ggtatcatca  900
ttagcgacac cccggtgcac gactgcaacg ctacttgcca aactcccgaa ggcgccatca  960
ataccagcct tcccttccaa aacgtgcacc caattaccat cggaaagtgt cccaaatacg  1020
tgcggtccac taagttgagg ttggcgactg ggctgaggaa tgtgcccagc attcagtccc  1080
ggggactgtt cggagccatc gccggtttca tcgagggcgg ctggactgga atggtggacg  1140
gttggtacgg ctaccaccac caaaacgacc agggctcagg ctacgcggct gaccttaagt  1200
ccactcagaa tgcgatcgat aagatcacga acaaggtcaa ctccgtgatt gaaaagatga  1260
acactcagtt taccgccgtc ggaaaggaat tcaaccatct ggagaagcgc attgaaaacc  1320
tgaacaagaa ggtcgatgac ggtttcctcg acgtgtggac ctacaacgcg gagctgcttg  1380
tgctgctcga gaacgagcgg accctggact atcacgatag taacgtgaag aacctgtacg  1440
agaaggtccg ccaccaactg aagaacaacg caaaggaaat cggcaacggc tgtttcgagt  1500
tctaccacaa atgcgataac acttgcatgg aatccgtgaa gaatggcacc tacgactacc  1560
cgaagtactc cgaagaggcc aagctcaacc gagagaagat tgatggagtg aagctggact  1620
ctactagaat ctaccagata cttgccatct actccaccgt ggcctcaagc ctggtgctcg  1680
tggtgtccct gggagccatt tccttctgga tgtgctccaa cgggtcgctc cagtgtcgca  1740
tttgcatttg ataataggct cgctttcttg ctgtccaatt tctattaaag gttcctttgt  1800
tccctaagtc caactactaa actgggggat attatgaagg gccttgagca tctggattct  1860
gcctaataaa aaacatttat tttcattgca a                                1891

SEQ ID NO: 14          moltype = AA  length = 566
FEATURE                Location/Qualifiers
source                 1..566
                       mol_type = protein
                       organism = Alphainfluenzavirus influenzae
SEQUENCE: 14
MKTIIALSNI LCLVFAQKIP GNDNSTATLC LGHHAVPNGT IVKTITNDRI EVTNATELVQ  60
NSSIGEICGS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL TSLNNIYPAQ  180
NVTMPNKEQF DKLYIWGVHH PDTDKNQISL FAQSSGRITV STKRSQQAVI PNIGSRPRIR  240
GIPSRISIYW TIVKPGDILL INSTGNLIAP RGYFKIRSGK SSIMRSDAPI GKCKSECITP  300
```

```
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                       566

SEQ ID NO: 15          moltype = AA  length = 567
FEATURE                Location/Qualifiers
source                 1..567
                       mol_type = protein
                       organism = synthetic construct
SEQUENCE: 15
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH FSNEQGSGYA ADKESTQKAI DGVTNMVNSI IDKMNTQFEA VGMEFNNLER  420
RIENLNKKME DGFIDVWTYN AELLVLMLNE RTLDFHDSNV KNLYDKVRLQ LRDNAKELGN  480
GCFEFYHKCD NECMESVRNG TYDYPQYSEE ARLKREEISG VKLESVGTYQ ILSIYSTAAS  540
SLALAIMMAG LSLWMCSNGS LQCRICI                                      567

SEQ ID NO: 16          moltype = RNA  length = 1894
FEATURE                Location/Qualifiers
source                 1..1894
                       mol_type = other RNA
                       organism = synthetic construct
SEQUENCE: 16
acatttgctt ctgacacaac tgtgttcact agcaacctca aacagccacc atggagaaca  60
tcgtgctctt gctggcaatc gtgtccctgg tcaagtccga tcagatctgc atcggctacc  120
acgcaaacaa ctccaccgaa caagtggaca ctatcatgga aaagaacgtg acggtcacac  180
acgcccagga cattctggaa aagacccaca atgggaaact gtgtgacctc aacggcgtga  240
agccgctgat cctcaaggat tgctccgtgg ctggatggct cctgggcaac cctatgtgcg  300
atgagttcat tcgggtgccc gagtggtcgt acattgtgga gagggccaac ccggccaatg  360
acctgtgctt ccccggctcg ctgaacgatt acgaagaact caagcacatg ctgtcccgca  420
tcaaccattt cgagaagatc cagatcattc cgaagtccag ctggcctaac cacgaaactt  480
ccctgggagt gtctgctgcc tgcccatacc aaggcgcccc ctcattttc cggaacgtcg  540
tgtggctcat caagaagaac gatgcgtacc ccactatcaa gatcagctac aacaacacca  600
accgcgagga tctgctgatt ctctggggaa ttcaccattc caacaacgct gaagaacaga  660
ccaacctgta caaaaaccct atcacttaca tctccgtggg tacctccacc ctcaatcagc  720
gcttggcgcc gaagatcgcg accagaagcc aagtcaacgg acagcgggga agaatggact  780
tcttctggac tatactgaag cctgacgatg caatccactt cgaatccaac ggaaacttca  840
tcgcccctga gtatgcctac aagatcgtga agaagggcga cagcaccatc atgaagtcag  900
gagtggagta tggacactgt aacactaagt gccagacccc cgtcggggcc attaacagct  960
ccatgccgtt ccacaacatt cacccccctga ctattggaga gtgtccgaaa tacgtgaaga  1020
gtaacaagtt ggtgctggcc actggcctgc gcaactcgcc gcttcgggag aagaggagga  1080
agagaggact gtttggggcg attgcaggat tcattgaggg aggttggcag gggatggtgg  1140
acggttggta cggttaccac ttctcgaacg agcagggatc gggctatgcc gccgacaagg  1200
agagcaccca gaaggccatc gacggggtca ccaacatggt caactccatc attgacaaga  1260
tgaataccca gttcgaagcc gtgggcatgg aattcaacaa cctggaacga cggatcgaga  1320
acctgaacaa gaagatggag gacggcttca tcgacgtgtg gacctacaat gccgaactgc  1380
tcgtgctgat gctgaatgag cggaccctcg acttccatga ctcaaacgtg aagaacctgt  1440
acgacaaagt ccggctgcaa ctgcgggaca atgccaagga actggggaac ggatgctttg  1500
agttctacca taagtgcgat aacgagtgca tggaatcagt gcggaacgga acctacgact  1560
acccacagta ctccgaggaa gcccgcctga agagagaaga aatctccggc gtgaaactcg  1620
aaagcgtggg gacctaccag atcctttcca tctactccac ggctgcgagc tcgttggccc  1680
ttgcgatcat gatggccggc ctttcgctgt ggatgtgctc caacggtagc ctgcagtgcc  1740
gcatttgtat ctgataatag gctcgctttc ttgctgtcca atttctatta aaggttcctt  1800
tgttccctaa gtccaactac taaactgggg gatattatga agggccttga gcatctggat  1860
tctgcctaat aaaaaacatt tattttcatt gcaa                              1894

SEQ ID NO: 17          moltype = RNA  length = 1939
FEATURE                Location/Qualifiers
source                 1..1939
                       mol_type = other RNA
                       organism = synthetic construct
SEQUENCE: 17
acatttgctt ctgacacaac tgtgttcact agcaacctca aacagccacc atgaaggcca  60
ttattgtgct cctcatggtc gtgacttcaa acgcggacag gatctgcact gggattacct  120
cctcgaactc cccgcacgtg gtcaaaactg caactcaagg agaagtcaac gtgaccgggg  180
tcataccccct cactacgacc ccgaccaaat cccatttcgc gaaccttaag ggtaccgaga  240
ctcggggaaa actctgcccg aagtgtctga actgtactga cctggatgtg gcgctcgggc  300
gcccaaagtg cacgggaaag attccgtccg cacgcgtcag catcttgcac gaagtcaggc  360
ccgtgacctc cggatgcttt ccaattatgc acgaccggac gaagatccgc cagctcccga  420
acctcttgag gggttatgag cacgtccgcc tctcgactca taacgtcatt aacaccgagg  480
atgcgccggg aggaccctac gaaattggta cctcgggatc atgccttaac atcaccaacg  540
ggaagggatt ctttgccacc atggcctggg cggtgcccaa gaacaagacc gccaccaacc  600
ctcttaccat cgaagtgcca tacatctgca ccgaggaaga ggaccagatc actgtgtggg  660
```

-continued

```
gtttccattc cgacgacgaa actcagatgg cccgcctcta cggggactcc aagccgcaaa  720
agttcacctc gtccgccaat ggagtgacta cccactacgt gtcccaaatt ggagggttcc  780
cgaatcaaac tgaggatggt ggactgcccc agagcggccg gattgtggtg gattacatgg  840
tccagaaaag cggcaagacc ggcaccatca cctaccagcg gggaatcctg ctgcctcaga  900
aggtgtggtg tgcttccggc aagagcaagg tgatcaaggg cagcctgcct ctgatcggcg  960
aagccgactg cctgcacgag aagtacggcg gcctgaacaa gagcaagcct tactacacag  1020
gcgaacatgc caaggccatc ggcaactgcc ccatctgggt gaagaccccc ctgaagctgg  1080
ccaacggaac caagtacaga cctcccgcca agctgctgaa ggaacggggc ttcttcggag  1140
ccatcgccgg cttcctggaa ggaggctggg agggcatgat tgccgggtgg cacggctaca  1200
cctctcatgg agcacacggg gtggccgtgg ctgctgacct gaagtctaca caggaggcca  1260
tcaacaagat caccaagaac ctgaactctt tgtctgagct ggaggtgaaa aacctgcaga  1320
gactgtcagg cgccatggac gaactgcaca atgagatcct ggaactggat gaaaaggtgg  1380
acgacctgag agccgacacc atcagctccc agatcgaact ggctgtgctg ctgagcaacg  1440
agggaatcat caattccgag gacgaacacc tgctggccct ggagcggaag ctgaagaaga  1500
tgctgggccc ttctgccgtg gaaatcggca acggctgctt cgaaaccaag cacaagtgca  1560
accagacctg cctggaccgg attgcagccg gcacctttga cgccggagag ttctccttgc  1620
cgactttcga ctcgctcaac atcactgcgg cctcgcttaa cgacgatggt ctggataacc  1680
acactatcct tttgtattac tccaccgcgg cgtcgtccct cgccgtgacc ctcatgatcg  1740
ctattttcgt ggtgtacatg gtgtcccgcg ataacgtgtc ctgttcaatc tgcctgtgat  1800
aataggctcg ctttcttgct gtccaatttc tattaaaggt tcctttgttc cctaagtcca  1860
actactaaac tgggggatat tatgaagggc cttgagcatc tggattctgc ctaataaaaa  1920
acatttattt tcattgcaa                                              1939

SEQ ID NO: 18          moltype = AA  length = 566
FEATURE                Location/Qualifiers
source                 1..566
                       mol_type = protein
                       organism = unidentified
SEQUENCE: 18
MKAIIALSNI LCLVFAQKIP GNDNSTATLC LGHHAVPNGT IVKTITNDRI EVTNATELVQ  60
NSSIGKICNS PHQILDGGNC TLIDALLGDP QCDGFQNKEW DLFVERSRAN SSCYPYDVPD  120
YASLRSLVAS SGTLEFKDES FNWTGVKQNG TSSACKRGSS NSFFSRLNWL TSLNNIYPAQ  180
NVTMPNKEQF DKLYIWGVHH PDTDKNQFSL FAQSSGRITV STKRSQQAVI PNIGSRPRVR  240
DIPSRISIYW TIVKPGDILL INSTGNLIAP RGYFKIRSGK SSIMRSDAPI GECKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQISGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                      566

SEQ ID NO: 19          moltype =   length =
SEQUENCE: 19
000

SEQ ID NO: 20          moltype =   length =
SEQUENCE: 20
000

SEQ ID NO: 21          moltype =   length =
SEQUENCE: 21
000

SEQ ID NO: 22          moltype =   length =
SEQUENCE: 22
000

SEQ ID NO: 23          moltype =   length =
SEQUENCE: 23
000

SEQ ID NO: 24          moltype =   length =
SEQUENCE: 24
000

SEQ ID NO: 25          moltype =   length =
SEQUENCE: 25
000

SEQ ID NO: 26          moltype =   length =
SEQUENCE: 26
000

SEQ ID NO: 27          moltype =   length =
SEQUENCE: 27
000

SEQ ID NO: 28          moltype =   length =
SEQUENCE: 28
000
```

-continued

```
SEQ ID NO: 29          moltype =   length =
SEQUENCE: 29
000

SEQ ID NO: 30          moltype =   length =
SEQUENCE: 30
000

SEQ ID NO: 31          moltype =   length =
SEQUENCE: 31
000

SEQ ID NO: 32          moltype = AA  length = 17
FEATURE                Location/Qualifiers
source                 1..17
                       mol_type = protein
                       organism = Alphainfluenzavirus influenzae
SEQUENCE: 32
MKAILVVMLY TFTTANA                                                17

SEQ ID NO: 33          moltype = AA  length = 36
FEATURE                Location/Qualifiers
source                 1..36
                       mol_type = protein
                       organism = Alphainfluenzavirus influenzae
SEQUENCE: 33
LAIYSTVASS LVLVVSLGAI SFWMCSNGSL QCRICI                           36

SEQ ID NO: 34          moltype =   length =
SEQUENCE: 34
000

SEQ ID NO: 35          moltype = AA  length = 28
FEATURE                Location/Qualifiers
source                 1..28
                       mol_type = protein
                       organism = Homo sapiens
SEQUENCE: 35
MAAPGSARRP LLLLLLLLLL GLMHCASA                                    28

SEQ ID NO: 36          moltype = AA  length = 35
FEATURE                Location/Qualifiers
source                 1..35
                       mol_type = protein
                       organism = Homo sapiens
SEQUENCE: 36
LIPIAVGGAL AGLVLIVLIA YLVGRKRSHA GYQTI                            35

SEQ ID NO: 37          moltype = AA  length = 469
FEATURE                Location/Qualifiers
source                 1..469
                       mol_type = protein
                       organism = Alphainfluenzavirus influenzae
SEQUENCE: 37
MNPNQKIITI GSVCMTIGTA NLILQIGNII SIWVSHSIQI GNQSQIETCN KSVITYENNT  60
WVNQTFVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NKILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVLS NGANGVKGFS FKYGNGVWIG  360
RTKSISSRKG FEMIWDPNGW TGTDNKFSKK QDIVGINEWS GYSGSFVQHP ELTGLNCIRP  420
CFWVELIRGR PEENTIWTSG SSISFCGVDS DIMGWSWPDG AELPFTIDN             469

SEQ ID NO: 38          moltype = AA  length = 469
FEATURE                Location/Qualifiers
source                 1..469
                       mol_type = protein
                       organism = Alphainfluenzavirus influenzae
SEQUENCE: 38
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDLDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSN DILRTQESEC VCINGTCTVV  240
MTDGNATGKA DTKILFIEEG KIVHTSKLSG SAQHVEECSC YPRYPGVRCV CRDNWKGSNR  300
PIIDINIKDH SIVSRYVCSG LVGDTPRKSD SSSSSHCLNP NNEKGDHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GANLSLMHI             469
```

-continued

```
SEQ ID NO: 39          moltype = AA  length = 466
FEATURE                Location/Qualifiers
source                 1..466
                       mol_type = protein
                       organism = Betainfluenzavirus influenzae
SEQUENCE: 39
MLPSTIQTLT LFLTSGGVLL SLYVSASLSY LLYSDILLKF SQTEITAPTM PLDCANASNV  60
QAVNRSATKG ATLLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANN ILRTQESACN CIGGNCYLMI  240
TDGSASGVSE CRFLKIREGR IIKEIFPTGR VKHTEECTCG FASNKTIECA CRDNRYTAKR  300
PFVKLNVETD TAEIRLMCTD TYLDTPRPND GSITGPCESD GDEGSGGIKG GFVHQRMKSK  360
IGRWYSRTMS KTERMGMGLY VKYGGDPWAD SDALVFSGVM ISMKEPGWYS FGFEIKDKKC  420
DVPCIGIEMV HDGGKETWHS AATAIYCLMG SGQLLWDTIT GVDMAL                466

SEQ ID NO: 40          moltype =   length =
SEQUENCE: 40
000

SEQ ID NO: 41          moltype =   length =
SEQUENCE: 41
000

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype =   length =
SEQUENCE: 50
000

SEQ ID NO: 51          moltype =   length =
SEQUENCE: 51
000

SEQ ID NO: 52          moltype =   length =
SEQUENCE: 52
000

SEQ ID NO: 53          moltype =   length =
SEQUENCE: 53
000

SEQ ID NO: 54          moltype =   length =
SEQUENCE: 54
000

SEQ ID NO: 55          moltype =   length =
SEQUENCE: 55
000
```

-continued

SEQ ID NO: 56 moltype = length =
SEQUENCE: 56
000

SEQ ID NO: 57 moltype = length =
SEQUENCE: 57
000

SEQ ID NO: 58 moltype = length =
SEQUENCE: 58
000

SEQ ID NO: 59 moltype = length =
SEQUENCE: 59
000

SEQ ID NO: 60 moltype = length =
SEQUENCE: 60
000

SEQ ID NO: 61 moltype = length =
SEQUENCE: 61
000

SEQ ID NO: 62 moltype = length =
SEQUENCE: 62
000

SEQ ID NO: 63 moltype = length =
SEQUENCE: 63
000

SEQ ID NO: 64 moltype = length =
SEQUENCE: 64
000

SEQ ID NO: 65 moltype = length =
SEQUENCE: 65
000

SEQ ID NO: 66 moltype = length =
SEQUENCE: 66
000

SEQ ID NO: 67 moltype = length =
SEQUENCE: 67
000

SEQ ID NO: 68 moltype = length =
SEQUENCE: 68
000

SEQ ID NO: 69 moltype = length =
SEQUENCE: 69
000

SEQ ID NO: 70 moltype = length =
SEQUENCE: 70
000

SEQ ID NO: 71 moltype = length =
SEQUENCE: 71
000

SEQ ID NO: 72 moltype = length =
SEQUENCE: 72
000

SEQ ID NO: 73 moltype = length =
SEQUENCE: 73
000

SEQ ID NO: 74 moltype = length =
SEQUENCE: 74
000

SEQ ID NO: 75 moltype = length =
SEQUENCE: 75
000

-continued

SEQ ID NO: 76 moltype = length =
SEQUENCE: 76
000

SEQ ID NO: 77 moltype = length =
SEQUENCE: 77
000

SEQ ID NO: 78 moltype = length =
SEQUENCE: 78
000

SEQ ID NO: 79 moltype = length =
SEQUENCE: 79
000

SEQ ID NO: 80 moltype = length =
SEQUENCE: 80
000

SEQ ID NO: 81 moltype = length =
SEQUENCE: 81
000

SEQ ID NO: 82 moltype = length =
SEQUENCE: 82
000

SEQ ID NO: 83 moltype = length =
SEQUENCE: 83
000

SEQ ID NO: 84 moltype = length =
SEQUENCE: 84
000

SEQ ID NO: 85 moltype = length =
SEQUENCE: 85
000

SEQ ID NO: 86 moltype = length =
SEQUENCE: 86
000

SEQ ID NO: 87 moltype = length =
SEQUENCE: 87
000

SEQ ID NO: 88 moltype = length =
SEQUENCE: 88
000

SEQ ID NO: 89 moltype = length =
SEQUENCE: 89
000

SEQ ID NO: 90 moltype = length =
SEQUENCE: 90
000

SEQ ID NO: 91 moltype = length =
SEQUENCE: 91
000

SEQ ID NO: 92 moltype = length =
SEQUENCE: 92
000

SEQ ID NO: 93 moltype = length =
SEQUENCE: 93
000

SEQ ID NO: 94 moltype = length =
SEQUENCE: 94
000

SEQ ID NO: 95 moltype = length =
SEQUENCE: 95

000

SEQ ID NO: 96 moltype = length =
SEQUENCE: 96
000

SEQ ID NO: 97 moltype = length =
SEQUENCE: 97
000

SEQ ID NO: 98 moltype = length =
SEQUENCE: 98
000

SEQ ID NO: 99 moltype = length =
SEQUENCE: 99
000

SEQ ID NO: 100 moltype = length =
SEQUENCE: 100
000

SEQ ID NO: 101 moltype = length =
SEQUENCE: 101
000

SEQ ID NO: 102 moltype = length =
SEQUENCE: 102
000

SEQ ID NO: 103 moltype = length =
SEQUENCE: 103
000

SEQ ID NO: 104 moltype = length =
SEQUENCE: 104
000

SEQ ID NO: 105 moltype = length =
SEQUENCE: 105
000

SEQ ID NO: 106 moltype = length =
SEQUENCE: 106
000

SEQ ID NO: 107 moltype = length =
SEQUENCE: 107
000

SEQ ID NO: 108 moltype = length =
SEQUENCE: 108
000

SEQ ID NO: 109 moltype = length =
SEQUENCE: 109
000

SEQ ID NO: 110 moltype = length =
SEQUENCE: 110
000

SEQ ID NO: 111 moltype = length =
SEQUENCE: 111
000

SEQ ID NO: 112 moltype = length =
SEQUENCE: 112
000

SEQ ID NO: 113 moltype = length =
SEQUENCE: 113
000

SEQ ID NO: 114 moltype = length =
SEQUENCE: 114
000

SEQ ID NO: 115 moltype = length =

-continued

SEQUENCE: 115
000

SEQ ID NO: 116 moltype = length =
SEQUENCE: 116
000

SEQ ID NO: 117 moltype = length =
SEQUENCE: 117
000

SEQ ID NO: 118 moltype = length =
SEQUENCE: 118
000

SEQ ID NO: 119 moltype = length =
SEQUENCE: 119
000

SEQ ID NO: 120 moltype = length =
SEQUENCE: 120
000

SEQ ID NO: 121 moltype = length =
SEQUENCE: 121
000

SEQ ID NO: 122 moltype = length =
SEQUENCE: 122
000

SEQ ID NO: 123 moltype = length =
SEQUENCE: 123
000

SEQ ID NO: 124 moltype = length =
SEQUENCE: 124
000

SEQ ID NO: 125 moltype = length =
SEQUENCE: 125
000

SEQ ID NO: 126 moltype = length =
SEQUENCE: 126
000

SEQ ID NO: 127 moltype = length =
SEQUENCE: 127
000

SEQ ID NO: 128 moltype = length =
SEQUENCE: 128
000

SEQ ID NO: 129 moltype = length =
SEQUENCE: 129
000

SEQ ID NO: 130 moltype = length =
SEQUENCE: 130
000

SEQ ID NO: 131 moltype = length =
SEQUENCE: 131
000

SEQ ID NO: 132 moltype = length =
SEQUENCE: 132
000

SEQ ID NO: 133 moltype = length =
SEQUENCE: 133
000

SEQ ID NO: 134 moltype = length =
SEQUENCE: 134
000

-continued

SEQ ID NO: 135 moltype = length =
SEQUENCE: 135
000

SEQ ID NO: 136 moltype = length =
SEQUENCE: 136
000

SEQ ID NO: 137 moltype = length =
SEQUENCE: 137
000

SEQ ID NO: 138 moltype = length =
SEQUENCE: 138
000

SEQ ID NO: 139 moltype = length =
SEQUENCE: 139
000

SEQ ID NO: 140 moltype = length =
SEQUENCE: 140
000

SEQ ID NO: 141 moltype = length =
SEQUENCE: 141
000

SEQ ID NO: 142 moltype = length =
SEQUENCE: 142
000

SEQ ID NO: 143 moltype = length =
SEQUENCE: 143
000

SEQ ID NO: 144 moltype = length =
SEQUENCE: 144
000

SEQ ID NO: 145 moltype = length =
SEQUENCE: 145
000

SEQ ID NO: 146 moltype = length =
SEQUENCE: 146
000

SEQ ID NO: 147 moltype = length =
SEQUENCE: 147
000

SEQ ID NO: 148 moltype = length =
SEQUENCE: 148
000

SEQ ID NO: 149 moltype = length =
SEQUENCE: 149
000

SEQ ID NO: 150 moltype = length =
SEQUENCE: 150
000

SEQ ID NO: 151 moltype = length =
SEQUENCE: 151
000

SEQ ID NO: 152 moltype = length =
SEQUENCE: 152
000

SEQ ID NO: 153 moltype = length =
SEQUENCE: 153
000

SEQ ID NO: 154 moltype = length =
SEQUENCE: 154
000

-continued

SEQ ID NO: 155 moltype = length =
SEQUENCE: 155
000

SEQ ID NO: 156 moltype = length =
SEQUENCE: 156
000

SEQ ID NO: 157 moltype = length =
SEQUENCE: 157
000

SEQ ID NO: 158 moltype = length =
SEQUENCE: 158
000

SEQ ID NO: 159 moltype = length =
SEQUENCE: 159
000

SEQ ID NO: 160 moltype = length =
SEQUENCE: 160
000

SEQ ID NO: 161 moltype = length =
SEQUENCE: 161
000

SEQ ID NO: 162 moltype = length =
SEQUENCE: 162
000

SEQ ID NO: 163 moltype = length =
SEQUENCE: 163
000

SEQ ID NO: 164 moltype = length =
SEQUENCE: 164
000

SEQ ID NO: 165 moltype = length =
SEQUENCE: 165
000

SEQ ID NO: 166 moltype = length =
SEQUENCE: 166
000

SEQ ID NO: 167 moltype = length =
SEQUENCE: 167
000

SEQ ID NO: 168 moltype = length =
SEQUENCE: 168
000

SEQ ID NO: 169 moltype = length =
SEQUENCE: 169
000

SEQ ID NO: 170 moltype = length =
SEQUENCE: 170
000

SEQ ID NO: 171 moltype = length =
SEQUENCE: 171
000

SEQ ID NO: 172 moltype = length =
SEQUENCE: 172
000

SEQ ID NO: 173 moltype = length =
SEQUENCE: 173
000

SEQ ID NO: 174 moltype = length =
SEQUENCE: 174

-continued

```
000

SEQ ID NO: 175         moltype =   length =
SEQUENCE: 175
000

SEQ ID NO: 176         moltype =   length =
SEQUENCE: 176
000

SEQ ID NO: 177         moltype =   length =
SEQUENCE: 177
000

SEQ ID NO: 178         moltype =   length =
SEQUENCE: 178
000

SEQ ID NO: 179         moltype =   length =
SEQUENCE: 179
000

SEQ ID NO: 180         moltype =   length =
SEQUENCE: 180
000

SEQ ID NO: 181         moltype =   length =
SEQUENCE: 181
000

SEQ ID NO: 182         moltype =   length =
SEQUENCE: 182
000

SEQ ID NO: 183         moltype =   length =
SEQUENCE: 183
000

SEQ ID NO: 184         moltype =   length =
SEQUENCE: 184
000

SEQ ID NO: 185         moltype =   length =
SEQUENCE: 185
000

SEQ ID NO: 186         moltype =   length =
SEQUENCE: 186
000

SEQ ID NO: 187         moltype =   length =
SEQUENCE: 187
000

SEQ ID NO: 188         moltype =   length =
SEQUENCE: 188
000

SEQ ID NO: 189         moltype =   length =
SEQUENCE: 189
000

SEQ ID NO: 190         moltype =   length =
SEQUENCE: 190
000

SEQ ID NO: 191         moltype =   length =
SEQUENCE: 191
000

SEQ ID NO: 192         moltype =   length =
SEQUENCE: 192
000

SEQ ID NO: 193         moltype =   length =
SEQUENCE: 193
000

SEQ ID NO: 194         moltype =   length =
```

SEQUENCE: 194
000

SEQ ID NO: 195 moltype = length =
SEQUENCE: 195
000

SEQ ID NO: 196 moltype = length =
SEQUENCE: 196
000

SEQ ID NO: 197 moltype = length =
SEQUENCE: 197
000

SEQ ID NO: 198 moltype = length =
SEQUENCE: 198
000

SEQ ID NO: 199 moltype = length =
SEQUENCE: 199
000

SEQ ID NO: 200 moltype = length =
SEQUENCE: 200
000

SEQ ID NO: 201 moltype = length =
SEQUENCE: 201
000

SEQ ID NO: 202 moltype = length =
SEQUENCE: 202
000

SEQ ID NO: 203 moltype = length =
SEQUENCE: 203
000

SEQ ID NO: 204 moltype = length =
SEQUENCE: 204
000

SEQ ID NO: 205 moltype = length =
SEQUENCE: 205
000

SEQ ID NO: 206 moltype = length =
SEQUENCE: 206
000

SEQ ID NO: 207 moltype = length =
SEQUENCE: 207
000

SEQ ID NO: 208 moltype = length =
SEQUENCE: 208
000

SEQ ID NO: 209 moltype = length =
SEQUENCE: 209
000

SEQ ID NO: 210 moltype = length =
SEQUENCE: 210
000

SEQ ID NO: 211 moltype = length =
SEQUENCE: 211
000

SEQ ID NO: 212 moltype = length =
SEQUENCE: 212
000

SEQ ID NO: 213 moltype = length =
SEQUENCE: 213
000

-continued

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223
000

SEQ ID NO: 224 moltype = length =
SEQUENCE: 224
000

SEQ ID NO: 225 moltype = length =
SEQUENCE: 225
000

SEQ ID NO: 226 moltype = length =
SEQUENCE: 226
000

SEQ ID NO: 227 moltype = length =
SEQUENCE: 227
000

SEQ ID NO: 228 moltype = length =
SEQUENCE: 228
000

SEQ ID NO: 229 moltype = length =
SEQUENCE: 229
000

SEQ ID NO: 230 moltype = length =
SEQUENCE: 230
000

SEQ ID NO: 231 moltype = length =
SEQUENCE: 231
000

SEQ ID NO: 232 moltype = length =
SEQUENCE: 232
000

SEQ ID NO: 233 moltype = length =
SEQUENCE: 233
000

-continued

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =
SEQUENCE: 243
000

SEQ ID NO: 244 moltype = length =
SEQUENCE: 244
000

SEQ ID NO: 245 moltype = length =
SEQUENCE: 245
000

SEQ ID NO: 246 moltype = length =
SEQUENCE: 246
000

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252
000

SEQ ID NO: 253 moltype = length =
SEQUENCE: 253

000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =

-continued

SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286
000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

-continued

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =
SEQUENCE: 306
000

SEQ ID NO: 307 moltype = length =
SEQUENCE: 307
000

SEQ ID NO: 308 moltype = length =
SEQUENCE: 308
000

SEQ ID NO: 309 moltype = length =
SEQUENCE: 309
000

SEQ ID NO: 310 moltype = length =
SEQUENCE: 310
000

SEQ ID NO: 311 moltype = length =
SEQUENCE: 311
000

SEQ ID NO: 312 moltype = length =
SEQUENCE: 312
000

-continued

SEQ ID NO: 313 moltype = length =
SEQUENCE: 313
000

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

SEQ ID NO: 320 moltype = length =
SEQUENCE: 320
000

SEQ ID NO: 321 moltype = length =
SEQUENCE: 321
000

SEQ ID NO: 322 moltype = length =
SEQUENCE: 322
000

SEQ ID NO: 323 moltype = length =
SEQUENCE: 323
000

SEQ ID NO: 324 moltype = length =
SEQUENCE: 324
000

SEQ ID NO: 325 moltype = length =
SEQUENCE: 325
000

SEQ ID NO: 326 moltype = length =
SEQUENCE: 326
000

SEQ ID NO: 327 moltype = length =
SEQUENCE: 327
000

SEQ ID NO: 328 moltype = length =
SEQUENCE: 328
000

SEQ ID NO: 329 moltype = length =
SEQUENCE: 329
000

SEQ ID NO: 330 moltype = length =
SEQUENCE: 330
000

SEQ ID NO: 331 moltype = length =
SEQUENCE: 331
000

SEQ ID NO: 332 moltype = length =
SEQUENCE: 332

-continued

000

SEQ ID NO: 333 moltype = length =
SEQUENCE: 333
000

SEQ ID NO: 334 moltype = length =
SEQUENCE: 334
000

SEQ ID NO: 335 moltype = length =
SEQUENCE: 335
000

SEQ ID NO: 336 moltype = length =
SEQUENCE: 336
000

SEQ ID NO: 337 moltype = length =
SEQUENCE: 337
000

SEQ ID NO: 338 moltype = length =
SEQUENCE: 338
000

SEQ ID NO: 339 moltype = length =
SEQUENCE: 339
000

SEQ ID NO: 340 moltype = length =
SEQUENCE: 340
000

SEQ ID NO: 341 moltype = length =
SEQUENCE: 341
000

SEQ ID NO: 342 moltype = length =
SEQUENCE: 342
000

SEQ ID NO: 343 moltype = length =
SEQUENCE: 343
000

SEQ ID NO: 344 moltype = length =
SEQUENCE: 344
000

SEQ ID NO: 345 moltype = length =
SEQUENCE: 345
000

SEQ ID NO: 346 moltype = length =
SEQUENCE: 346
000

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =
SEQUENCE: 351
000

SEQ ID NO: 352 moltype = length =

SEQUENCE: 352
000

SEQ ID NO: 353 moltype = length =
SEQUENCE: 353
000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

-continued

SEQ ID NO: 372 moltype = length =
SEQUENCE: 372
000

SEQ ID NO: 373 moltype = length =
SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =
SEQUENCE: 385
000

SEQ ID NO: 386 moltype = length =
SEQUENCE: 386
000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

SEQ ID NO: 392 moltype = length =
SEQUENCE: 392
000

SEQ ID NO: 393 moltype = length =
SEQUENCE: 393
000

SEQ ID NO: 394 moltype = length =
SEQUENCE: 394
000

SEQ ID NO: 395 moltype = length =
SEQUENCE: 395
000

SEQ ID NO: 396 moltype = length =
SEQUENCE: 396
000

SEQ ID NO: 397 moltype = length =
SEQUENCE: 397
000

SEQ ID NO: 398 moltype = length =
SEQUENCE: 398
000

SEQ ID NO: 399 moltype = length =
SEQUENCE: 399
000

SEQ ID NO: 400 moltype = length =
SEQUENCE: 400
000

SEQ ID NO: 401 moltype = AA length = 1123
FEATURE Location/Qualifiers
source 1..1123
mol_type = protein
organism = synthetic construct
SEQUENCE: 401
MRVTAPRTLI LLLSGALALT ETWAAEMKTD AATLAQEAGN FERISGDLKT QIDQVESTAG 60
SLQGQWRGAA GTAAQAAVVR FQEAANKQKQ ELDEISTNIR QAGVQYSRAD EEQQQALSSQ 120
MGFGPGPGVD FGALPPEINS ARMYAGPGSA SLVAAAQMWD SVASDLFSAA SAFQSVVWGL 180
TVGSWIGSSA GLMVAAASPY VAWMSVTAGQ AELTAAQVRV AAAAYETAYG LTVPPPVIAE 240
NRAELMILIA TNLLGQNTPA IAVNEAEYGE MWAQDAAAMF GYAAATATAT ATLLPFEEAP 300
EMTSAGGLLE QAAAVEEASD TAAANQLMNN VPQALQQLAQ PTQGTTPSSK LGGLWKTVSP 360
HRSPISNMVS MANNHMGPGP GTEQQWNFAG IEAAASAIQG NVTSIHSLLD EGKQSLTKLA 420
AAWGGSGSEA YQGVQQKWDA TATELNNALQ NLARTISEAG QAMASTEGNV TGMFAGPGPG 480
TSRFMTDPHA MRDMAGRFEV HAQTVEDEAR RMWASAQNIS GAGWSGMAEA TSLDTMTQMN 540
QAFRNIVNML HGVRDGLVRD ANNYEQQEQA SQQILSSGPG PGSQIMYNYP AMLGHAGDMA 600
GYAGTLQSLG AEIAVEQAAL QSAWQGDTGI TYQAWQAQWN QAMEDLVRAY HAMSSTHEAN 660
TMAMMARDTA EAAKWGGGPG PGTINYQFGD VDAHGAMIRA QAGSLEAEHQ AIISDVLTAS 720
DFWGGAGSAA CQGFITQLGR NFQVIYEQAN AHGQKVQAAG NNMAQTDSAV GSSWAGPGPG 780
PVGGQSSFYS DWYSPACGKA GCQTYKWETF LTSELPQWLS ANRAVKPTGS AAIGLSMAGS 840
SAMILAAYHP QQFIYAGSLS ALLDPSQGMG GPGPGAQIYQ AVSAQAAAIH GPGPGPSPSM 900
GRDIKVQFQS GPGPGGINTI PIAINEAEYV GPGPGAAFQG AHARFVAAAA GPGPGAGWLA 960
FFRDLVARGL GPGPGASIIR LVGAVLAEQH GPGPGMSFVT TQPEALAAAA GPGPGMHVSF 1020
VMAYPEMLAA GPGPGAYGSF VRTVSLPVGA GPGPGLENDN QLLYNYPGAL GIVAGLAVLA 1080
VVVIGAVVAA VMCRRKSSGG KGGSYSQAAC SDSAQGSDVS LTA 1123

SEQ ID NO: 402 moltype = RNA length = 3562
FEATURE Location/Qualifiers
source 1..3562
mol_type = other RNA
organism = synthetic construct
SEQUENCE: 402
acatttgctt ctgacacaac tgtgttcact agcaacctca aacagccacc atgcgggtca 60
ctgcccccag aaccttgatt ttactactgt cgggagccct cgctctgact gaaacatggg 120
ccgctgagat gaaaaccgac gccgcgaccc tggcccagga agccggaaac ttcgagcgga 180
tttccggaga tcttaagact cagatcgacc aggtcgaatc caccgccgga tcgctccagg 240
gacagtggag aggcgccgcg ggaaccgcgg cccaggccgc cgtcgtgcgg ttccaagagg 300
ccgccaacaa gcagaagcag gaactggacg aaatttccac taacattcgc caagctggcg 360
tgcagtactc gagagccgat gaagaacagc agcaagccct ctcctcacaa atgggtttcg 420
gacctgggcc cggcgtggac ttcggagccc tgccacctga aatcaactcc gcccggatgt 480
acgcaggacc tggatccgcc agcctggtgg cggccgcgca gatgtgggat agcgtggcct 540
ccgacctgtt cagcgcggct tcagctttcc aaagcgtggt ctggggactg actgtgggat 600

-continued

```
cctggatcgg atcaagcgca ggcctcatgg tggccgcggc gtccccttac gtggcctgga  660
tgagcgtgac cgccggccag gcagaactga ccgcagccca agtccgcgtg gccgcagccg  720
cctacgagac tgcctacggt ctgacggtgc cgccgccagt gatcgccgag aacagagcag  780
agctcatgat cctcatcgcg accaacctac tgggccagaa cactccggcg attgccgtga  840
acgaagccga atatggggag atgtgggctc aggacgctgc agccatgttc ggatatgcgg  900
ccgcgactgc taccgccacc gccactctgc tgccgttcga ggaggccccc gaaatgactt  960
ccgcgggagg cctgttggag caagctgccg cggtggagga agctagcgac accgccgcag  1020
ccaaccagct catgaacaac gtgccacagg ccctgcagca gctggcccag cccactcaag  1080
ggaccacccc gagctcaaag ctgggcggtc tgtggaaaac cgtgtccccc caccgctcgc  1140
ccatttccaa catggtgtca atggcgaaca accacatggg tcctggacct ggaacggagc  1200
agcagtggaa cttcgccggg atcgaagccg ccgcctcggc tatccaaggg aatgtcacct  1260
cgatccattc ccttctggac gaaggaaagc agtccctgac caagcttgcg gcagcctggg  1320
gcggaagcgg cagcgaagcc taccagggcg tgcagcaaaa atgggacgca accgccactg  1380
agctgaacaa cgccctccaa aacctggcta gaactatttc cgaggccgga caggctatgg  1440
ccagcaccga gggcaacgtg accgggatgt tcgctggccc tgggccgggc acctcgcggt  1500
tcatgaccga tcctcatgct atgcgggata tggctggacg gttcgaggtg cacgcccaaa  1560
ctgtggagga cgaggcccgc cggatgtggg ccagcgcgca gaacatctcg gggccggct  1620
ggtccggaat ggccgaagcc acctccctcg ataccatgac ccagatgaac caggccttcc  1680
ggaacattgt gaacatgctg catggagtgc gggacggcct ggtccgggac gccaacaatt  1740
acgagcagca ggagcaggcc tctcagcaaa tcctgtccag cgggccgggg cctggatcac  1800
aaatcatgta caactacccg gcaatgctgg gccacgctgg agacatggcc ggctacgccg  1860
gcacgctgca gtcactcggt gccgagatcg ccgtcgagca ggcggcactg cagagcgctt  1920
ggcagggaga cactggcatt acctaccaag cgtggcaggc tcagtggaat caagctatgg  1980
aagatctggt ccgcgcgtac cacgccatgt cctccactca cgaagccaac accatggcta  2040
tgatggccag ggacactgcc gaggcagcca aatggggggg aggaccgggg ccgggaacca  2100
taaactacca gtttggcgac gtcgacgccc acggagccat gatcagggcg caggccgggt  2160
cgctggaagc agaacaccag gccatcatct ccgatgtgct gaccgcctcc gacttttggg  2220
gaggagccgg ttcggctgcc tgccaaggt tcatcacaca attgggaagg aacttccagg  2280
tcatctacga gcaggccaat gcacacggtc aaaaggtcca agcggcggc aacaacatgg  2340
cccagactga ctcggccgtg ggcagcagtt gggccggtcc cggccctggc cctgtcgggg  2400
ggcagtcatc cttctactcc gactggtact cccccgcctg cggaaaggcc ggctgtcaga  2460
cctataagtg ggaaaccttc ctgacctccg aactcccgca gtggctctcg gcgaatcggg  2520
cagtgaagcc caccgggtcg gcggctattg gactgtccat ggccggttcc agcgcgatga  2580
tcctggccgc ctatcacccc cagcaattca tctacgctgg ctccctgtcc gccctgcttg  2640
acccatcgca ggggatgggt ggaccgggcc ctgggcccca gatctaccaa gcagtgtcgg  2700
cccaagccgc agcgatccat ggaccaggac cgggaccgtc cccgagcatg ggccgggata  2760
ttaaggttca gttccagtcc ggacccggcc cgggggtat taacaccatt ccgattgcca  2820
ttaatgaggc agaatacgtc ggccctggtc ccggcgccgc gttccaagga gcccacgcac  2880
gattcgtggc ggcagctgcg ggacccgggc ctggtgccgg ttggctggct tttttccgcg  2940
acctggtggc cagaggactt ggacccggtc cgggcgccag cattatcagg ctggtcgggg  3000
ccgtgctggc ggaacagcat ggacctggcc cgggaatgag cttcgtgacc acccaacctg  3060
aggcgcttgc cgcggcggca ggccctggac ccgggatgca tgtgtctttt gtgatggcct  3120
acccggaaat gctggccgcg ggtccgggcc ccggagccta cggatcattc gtgcgcactg  3180
tgtccctccc cgtgggagcc ggacctggac cggggttgga gaatgataac cagctgctct  3240
acaactatcc gggggccctc ggcatcgtgg cgggcctcgc tgtcctcgcc gtggtggtga  3300
tcggagccgt cgtcgccgct gtgatgtgcc gccgcaagtc cagcggcgga aagggggcca  3360
gctatagcca ggcagcctgt tccgactccg cgcaggggtc ggatgtgtcc ttgaccgcct  3420
gataataggc tcgctttctt gctgtccaat ttctattaaa ggttcctttg ttccctaagt  3480
ccaactacta aactggggga tattatgaag ggccttgagc atctggattc tgcctaataa  3540
aaaacattta ttttcattgc aa                                          3562
```

```
SEQ ID NO: 403          moltype = AA  length = 1109
FEATURE                 Location/Qualifiers
source                  1..1109
                        mol_type = protein
                        organism = synthetic construct
SEQUENCE: 403
MAAPGSARRP LLLLLLLLL GLMHCASAAE MKTDAATLAQ EAGNFERISG DLKTQIDQVE  60
STAGSLQGQW RGAAGTAAQA AVVRFQEAAN KQKQELDEIS TNIRQAGVQY SRADEEQQQA  120
LSSQMGFGPG PGVDFGALPP EINSARMYAG PGSASLVAAA QMWDSVASDL FSAASAFQSV  180
VWGLTVGSWI GSSAGLMVAA ASPYVAWMSV TAGQAELTAA QVRVAAAAYE TAYGLTVPPP  240
VIAENRAELM ILIATNLLGQ NTPAIAVNEA EYGEMWAQDA AAMFGYAAAT ATATATLLPF  300
EEAPEMTSAG GLLEQAAAVE EASDTAAANQ LMNNVPQALQ QLAQPTQGTT PSSKLGGLWK  360
TVSPHRSPIS NMVSMANNHM GPGPGTEQQW NFAGIEAAAS AIQGNVTSIH SLLDEGKQSL  420
TKLAAAWGGS GSEAYQGVQQ KWDATATELN NALQNLARTI SEAGQAMAST EGNVTGMFAG  480
PGPGTSRFMT DPHAMRDMAG RFEVHAQTVE DEARRMWASA QNISGAGWSG MAEATSLDTM  540
TQMNQAFRNI VNMLHGVRDG LVRDANNYEQ QEQASQQILS SGPGPGSQIM YNYPAMLGHA  600
GDMAGYAGTL QSLGAEIAVE QAALQSAWQG DTGITYQAWQ AQWNQAMEDL VRAYHAMSST  660
HEANTMAMMA RDTAEAAKWG GGPGPGTINY QFGDVDAHGA MIRAQAGSLE AEHQAIISDV  720
LTASDFWGGA GSAACQGFIT QLGRNFQVIY EQANAHGQKV QAAGNNMAQT DSAVGSSWAG  780
PGPGPVGGQS SFYSDWYSPA CGKAGCQTYK WETFLTSELP QWLSANRAVK PTGSAAIGLS  840
MAGSSAMILA AYHPQQFIYA GSLSALLDPS QGMGGPGPGA QIYQAVSAQA AAIHGPGPGP  900
SPSMGRDIKV QFQSGPGPGG INTIPIAINE AEYVGPGPGA AFQGAHARFV AAAAGPGPGA  960
GWLAFFRDLV ARGLGPGPGA SIIRLVGAVL AEQHGPGPGM SFVTTQPEAL AAAAGPGPGM  1020
HVSFVMAYPE MLAAGPGPGA YGSFVRTVSL PVGAGPGPGL ENDNQLLYNY PGALLIPIAV  1080
GGALAGLVLI VLIAYLVGRK RSHAGYQTI                                   1109
```

```
SEQ ID NO: 404          moltype = RNA  length = 3520
FEATURE                 Location/Qualifiers
```

-continued

```
source                  1..3520
                        mol_type = other RNA
                        organism = synthetic construct
SEQUENCE: 404
acatttgctt ctgacacaac tgtgttcact agcaacctca aacagccacc atggccgctc  60
ctggatccgc ccgcagaccg ttgttgctcc tgttactact gctcttactt ggactcatgc  120
actgcgcctc cgccgctgag atgaaaaccg acgccgcgac cctggcccag gaagccggaa  180
acttcgagcg gatttccgga gatcttaaga ctcagatcga ccaggtcgaa tccaccgccg  240
gatcgctcca gggacagtgg agaggcgccg cgggaaccgc ggcccaggcc gccgtcgtgc  300
ggttccaaga ggccgccaac aagcagaagc aggaactgga cgaaatttcc actaacattc  360
gccaagctgg cgtgcagtac tcgagagccg atgaagaaca gcagcaagcc ctctcctcac  420
aaatgggttt cggacctggg cccggcgtgg acttcggagc cctgccacct gaaatcaact  480
ccgcccggat gtacgcagga cctggatccg ccagcctggt ggcggccgcg cagatgtggg  540
atagcgtggc ctccgacctg ttcagcgcgg cttcagcttt ccaaagcgtg gtctggggac  600
tgactgtggg atcctggatc ggatcaagcg caggcctcat ggtggccgcg gcgtcccctt  660
acgtggcctg gatgagcgtg accgccggcc aggcagaact gaccgcagcc caagtccgcg  720
tggccgcagc cgcctacgag actgcctacg gtctgacggt gccgccgcca gtgatcgccg  780
agaacagagc agagctcatg atcctcatcg cgaccaacct actgggccag aacactccgg  840
cgattgccgt gaacgaagcc gaatatgggg agatgtgggc tcaggacgct gcagccatgt  900
tcggatatgc ggccgcgact gctaccgcca ccgccactct gctgccgttc gaggaggccc  960
ccgaaatgac ttccgcggga ggcctgttgg agcaagctgc cgcggtggag gaagctagcg  1020
acaccgccgc agccaaccag ctcatgaaca acgtgcccac ggccctgcag cagctggccc  1080
agcccactca agggaccacc ccgagctcaa agctgggcgg tctgtggaaa accgtgtccc  1140
cccaccgctc gcccatttcc aacatggtgt caatggcgaa caaccacatg ggtcctggac  1200
ctggaacgga gcagcagtgg aacttcgccg ggatcgaagc cgccgcctcg gctatccaag  1260
ggaatgtcac ctcgatccat tcccttctgg acgaaggaaa gcagtccctg accaagcttg  1320
cggcagcctg gggcggaagc ggcagcgaag cctaccaggg cgtgcagcaa aaatgggacg  1380
caaccgccac tgagctgaac aacgccctcc aaaacctggc tagaactatt tccgaggccg  1440
gacaggctat ggccagcacc gagggcaacg tgaccgggat gttcgctggc cctgggccgg  1500
gcacctcgcg gttcatgacc gatcctcatg ctatgcggga tatggctgga cggttcgagg  1560
tgcacgccca aactgtggag gacgaggccc gccggatgtg ggccagcgcg cagaacatct  1620
cgggggccgg ctggtccgga atggccgaag ccacctccct cgataccatg acccagatga  1680
accaggcctt ccggaacatt gtgaacatgc tgcatggagt gcgggacggc ctggtccggg  1740
acgccaacaa ttacgagcag caggagcagg cctctcagca aatcctgtcc agcgggccgg  1800
ggcctggatc acaaatcatg tacaactacc cggcaatgct gggccacgct ggagacatgg  1860
ccggctacgc cggcacgctg cagtcactcg gtgccgagat cgccgtcgag caggcggcac  1920
tgcagagcgc ttggcaggga gacactggca ttacctacca agcgtggcag gctcagtgga  1980
atcaagctat ggaagatctg gtccgcgcgt accacgccat gtcctccact cacgaagcca  2040
acaccatggc tatgatggcc agggacactg ccgaggcagc caaatggggg ggaggaccgg  2100
ggccgggaac cataaactac cagtttggcg acgtcgacgc ccacggagcc atgatcaggg  2160
cgcaggccgg gtcgctggaa gcagaacacc aggccatcat ctccgatgtg ctgaccgcct  2220
ccgacttttg gggaggagcc ggttcggctg cctgccaagg gttcatcaca caattgggaa  2280
ggaacttcca ggtcatctac gagcaggcca atgcacacgg tcaaaaggtc caagcggcgg  2340
gcaacaacat ggcccagact gactcggccg tgggcagcag ttgggccggt cccggccctg  2400
gccctgtcgg ggggcagtca tccttctact ccgactggta ctccccgcc tgcggaaagg  2460
ccggctgtca gacctataag tgggaaacct tcctgacctc cgaactcccg cagtggctct  2520
cggcgaatcg ggcagtgaag cccaccgggt cggcggctat tggactgtcc atggccggtt  2580
ccagcgcgat gatcctggcc gcctatcacc cccagcaatt catctacgct ggctccctgt  2640
ccgccctgct tgacccatcg caggggatgg gtggaccggg ccctggggcc cagatctacc  2700
aagcagtgtc ggcccaagcc gcagcgatcc atggaccagg accgggaccg tccccgagca  2760
tgggccggga tattaaggtt cagttccagt ccggacccgg cccggggggt attaacacca  2820
ttccgattgc cattaatgag gcagaatacg tcggccctgg tcccggcgcc gcgttccaag  2880
gagcccacgc acgattcgtg gcggcagctg cgggacccgg gcctggtgcc ggttggctgg  2940
ctttttttccg cgacctggtg gccagaggac ttggacccgg tccgggcgcc agcattatca  3000
ggctggtcgg ggccgtgctg gcggaacagc atggacctgg cccgggaatg agcttcgtga  3060
ccacccaacc tgaggcgctt gccgcggcgg caggccctgg acccgggatg catgtgtctt  3120
ttgtgatggc ctacccggaa atgctggccg cgggtccggg ccccggagcc tacggatcat  3180
tcgtgcgcac tgtgtccctc cccgtgggag ccggacctgg accggggttg gagaatgata  3240
accagctgct ctacaactat ccgggggccc tcctgattcc tatcgccgtg ggcggtgcct  3300
tggccggcct ggtgctgatc gtcctgattg cctatctcgt ggggaggaag agatcgcatg  3360
ccggctacca gaccatctga taataggctc gctttcttgc tgtccaattt ctattaaagg  3420
ttcctttgtt ccctaagtcc aactactaaa ctgggggata ttatgaaggg ccttgagcat  3480
ctggattctg cctaataaaa aacatttatt ttcattgcaa                        3520

SEQ ID NO: 405          moltype = AA  length = 1109
FEATURE                 Location/Qualifiers
source                  1..1109
                        mol_type = protein
                        organism = synthetic construct
SEQUENCE: 405
MRVTAPRTLI LLLSGALALT ETWATAASDN FQLSQGGQGF AIPIGQAMAI AGQIRSGGGS  60
PTVHIGPTAF LGLGVVDNNG NGARVQRVVG SAPAASLGIS TGDVITAVDG APINSATAMA  120
DALNGHHPGD VISVTWQTKS GGTRTGNVTL AEGPPAGPGP GAEMKTDAAT LAQEAGNFER  180
ISGDLKTQID QVESTAGSLQ GQWRGAAGTA AQAAVVRFQE AANKQKQELD EISTNIRQAG  240
VQYSRADEEQ QQALSSQMGF GPGPGVDFGA LPPEINSARM YAGPGSASLV AAAQMWDSVA  300
SDLFSAASAF QSVVWGLTVG SWIGSSAGLM VAAASPYVAW MSVTAGQAEL TAAQVRVAAA  360
AYETAYGLTV PPPVIAENRA ELMILIATNL LGQNTPAIAV NEAEYGEMWA QDAAAMFGYA  420
AATATATATL LPFEEAPEMT SAGGLLEQAA AVEEASDTAA ANQLMNNVPQ ALQQLAQPTQ  480
GTTPSSKLGG LWKTVSPHRS PISNMVSMAN NHMGPGPGTE QQWNFAGIEA AASAIQGNVT  540
```

```
SIHSLLDEGK QSLTKLAAAW GGSGSEAYQG VQQKWDATAT ELNNALQNLA RTISEAGQAM  600
ASTEGNVTGM FAGPGPGTSR FMTDPHAMRD MAGRFEVHAQ TVEDEARRMW ASAQNISGAG  660
WSGMAEATSL DTMTQMNQAF RNIVNMLHGV RDGLVRDANN YEQQEQASQQ ILSSGPGPGS  720
FVMAYPEMLA AAADTLQSIG ATTVASNAAA AAPTTGVVPP AADEVSALTA AHFAAHAAMY  780
QSVSARAAAI HDQFVATLAS SASSYAATEV ANAAAASGPG PGTINYQFGD VDAHGAMIRA  840
QAGSLEAEHQ AIISDVLTAS DFWGGAGSAA CQGFITQLGR NFQVIYEQAN AHGQKVQAAG  900
NNMAQTDSAV GSSWAGPGPG PVGGQSSFYS DWYSPACGKA GCQTYKWETF LTSELPQWLS  960
ANRAVKPTGS AAIGLSMAGS SAMILAAYHP QQFIYAGSLS ALLDPSQGMG GPGPGTVPPP  1020
VVAANRAELA VLAGPGPGMV DPVVVAANRS AFVQLVGIVA GLAVLAVVVI GAVVAAVMCR  1080
RKSSGGKGGS YSQAACSDSA QGSDVSLTA                                  1109

SEQ ID NO: 406          moltype = RNA  length = 3520
FEATURE                 Location/Qualifiers
source                  1..3520
                        mol_type = other RNA
                        organism = synthetic construct
SEQUENCE: 406
acatttgctt ctgacacaac tgtgttcact agcaacctca aacagccacc atgcgcgtga  60
ctgcgcctag gaccctgatt ctgctcctgt cgggtgccct cgctctgacc gaaacctggg  120
ccaccgccgc gagcgacaat tttcagttaa gccagggtgg ccagggattt gccatcccga  180
tcggacaggc catggctatc gcgggccaga tcagatccgg aggcggatcc ccgactgtac  240
acatcggtcc gaccgccttc ttgggactgg gagtggtgga caacaacggg aatggcgcac  300
gggtgcagag ggtcgtgggc tcggcaccag ccgcctctct gggaatcagc accggggacg  360
ttatcaccgc tgtggatggt gcccccatca attccgccac ggcgatggcc gatgccctga  420
acggccatca ccccggggat gtgatatccg tgacctggca gaccaagtcc ggcggtacaa  480
ggaccggcaa cgtcactctg gccgagggtc ctcctgcggg ccctggtcct ggtgctgaga  540
tgaaaaccga cgccgcgacc ctggcccagg aagccggaaa cttcgagcgg atttccggag  600
atcttaagac tcagatcgac caggtcgaat ccaccgccgg atcgctccag ggacagtgga  660
gaggcgccgc gggaaccgcg gcccaggccg ccgtcgtgcg gttccaagag gccgccaaca  720
agcagaagca ggaactggac gaaatttcca ctaacattcg ccaagctggc gtgcagtact  780
cgagagccga tgaagaacag cagcaagccc tctcctcaca aatgggtttc ggacctgggc  840
ccggcgtgga cttcggagcc ctgccacctg aaatcaactc cgcccggatg tacgcaggac  900
ctggatccgc cagcctggtg gcggccgcgc agatgtggga tagcgtggcc tccgacctgt  960
tcagcgcggc ttcagctttc caaagcgtgg tctggggact gactgtggga tcctggatcg  1020
gatcaagcgc aggcctcatg gtggccgcgg cgtcccctta cgtggcctgg atgagcgtga  1080
ccgccggcca ggcagaactg accgcagccc aagtccgcgt ggccgcagcc gcctacgaga  1140
ctgcctacgg tctgacggtg ccgccgccag tgatcgccga gaacagagca gagctcatga  1200
tcctcatcgc gaccaaccta ctgggccaga acactccggc gattgccgtg aacgaagccg  1260
aatatgggga gatgtgggct caggacgctg cagccatgtt cggatatgcg gccgcgactg  1320
ctaccgccac cgccactctg ctgccgttcg aggaggcccc cgaaatgact tccgcgggag  1380
gcctgttgga gcaagctgcc gcggtggagg aagctagcga caccgccgca gccaaccagc  1440
tcatgaacaa cgtgccacag gccctgcagc agctggccca gcccactcaa gggaccaccc  1500
cgagctcaaa gctgggcggt ctgtggaaaa ccgtgtcccc ccaccgctcg cccatttcca  1560
acatggtgtc aatggcgaac aaccacatgg gtcctggacc tggaacggag cagcagtgga  1620
acttcgccgg gatcgaagcc gccgcctcgg ctatccaagg gaatgtcacc tcgatccatt  1680
cccttctgga cgaaggaaag cagtccctga ccaagcttgc ggcagcctgg ggcggaagcg  1740
gcagcgaagc ctaccagggc gtgcagcaaa aatgggacgc aaccgccact gagctgaaca  1800
acgccctcca aaacctggct agaactattt ccgaggccgg acaggctatg gccagcaccg  1860
agggcaacgt gaccgggatg ttcgctggcc ctgggccggg cacctcgcgg ttcatgaccg  1920
atcctcatgc tatgcgggat atggctggac ggttcgaggt gcacgcccaa actgtggagg  1980
acgaggcccg ccggatgtgg gccagcgcgc agaacatctc gggggccggc tggtccggaa  2040
tggccgaagc cacctccctc gataccatga cccagatgaa ccaggccttc cggaacattg  2100
tgaacatgct gcatggagtg cgggacggcc tggtccggga cgccaacaat tacgagcagc  2160
aggagcaggc ctctcagcaa atcctgtcca gcgggccggg gcctggatca ttcgtgatgg  2220
cctaccctga gatgctggca gccgcggccg acaccctgca atccattggc gccactaccg  2280
tggcatcgaa cgcggcagcc gccgcaccga ctaccggcgt ggtgccgccc gccgctgatg  2340
aagtgtccgc ccttactgcc gcccacttcg ccgcccacgc cgcgatgtac cagtccgtgt  2400
ccgcgcgcgc cgccgctatc cacgatcagt tcgtcgccac actggccagc tcagcctcct  2460
catacgccgc tactgaagtg gcaaacgcag ccgctgcatc cggcccggga cccggaacga  2520
tcaactacca gtttggcgac gtggacgcgc acggggcgat gatcagggct caagcggggt  2580
ccctcgaggc cgaacaccaa gcgattatct cggatgtcct caccgcgtcc gacttctggg  2640
gtggagccgg aagcgccgcc tgccaaggtt tcatcaccca actgggtcgc aactttcaag  2700
tcatctacga acaggccaac gcccacggac agaaggtcca agccgccgga aacaacatgg  2760
cacagaccga ctccgcggtc ggatcgagct gggccggacc cgggccaggt cccgtgggcg  2820
gacagagctc gttctattct gactggtact cacccgcatg tggaaaggcc gggtgccaga  2880
cctacaaatg ggaaaccttc ttgacttccg agctgcctca gtggttgtcc gccaatcggg  2940
ccgtgaagcc gaccggctcg gcggccatcg gcctctccat ggccggctcg tccgcgatga  3000
ttcttgccgc ctaccacccg cagcagttca tctacgccgg gtccctctcg gcactgctgg  3060
accccagtca gggaatgggc ggacccggac cgggaactgt cccgccccccg gtggtggctg  3120
ctaaccgcgc cgaacttgcc gtgctggccg gtccagggcc gggaatggtg gacccagtgg  3180
tggtggcagc gaacagatcc gcattcgtgc aactggtcgg cattgtggcc ggactggccg  3240
tgttggccgt cgtcgtgatc ggcgctgtgg tcgccgccgt gatgtgccga agaaagtcca  3300
gcggtggaaa ggggggatcc tactcacaag cagcctgcag cgactcagcg caggggtcgg  3360
acgtgtcact gacagcatga taataggctc gctttcttgc tgtccaattt ctattaaagg  3420
ttcctttgtt ccctaagtcc aactactaaa ctgggggata ttatgaaggg ccttgagcat  3480
ctggattctg cctaataaaa aacatttatt ttcattgcaa                      3520

SEQ ID NO: 407          moltype = AA  length = 1095
FEATURE                 Location/Qualifiers
```

```
source                  1..1095
                        mol_type = protein
                        organism = synthetic construct
SEQUENCE: 407
MAAPGSARRP LLLLLLLLLL GLMHCASATA ASDNFQLSQG GQGFAIPIGQ AMAIAGQIRS  60
GGGSPTVHIG PTAFLGLGVV DNNGNGARVQ RVVGSAPAAS LGISTGDVIT AVDGAPINSA  120
TAMADALNGH HPGDVISVTW QTKSGGTRTG NVTLAEGPPA GPGPGAEMKT DAATLAQEAG  180
NFERISGDLK TQIDQVESTA GSLQGQWRGA AGTAAQAAVV RFQEAANKQK QELDEISTNI  240
RQAGVQYSRA DEEQQQALSS QMGFGPGPGV DFGALPPEIN SARMYAGPGS ASLVAAAQMW  300
DSVASDLFSA ASAFQSVVWG LTVGSWIGSS AGLMVAAASP YVAWMSVTAG QAELTAAQVR  360
VAAAAYETAY GLTVPPPVIA ENRAELMILI ATNLLGQNTP AIAVNEAEYG EMWAQDAAAM  420
FGYAAATATA TATLLPFEEA PEMTSAGGLL EQAAAVEEAS DTAAANQLMN NVPQALQQLA  480
QPTQGTTPSS KLGGLWKTVS PHRSPISNMV SMANNHMGPG PGTEQQWNFA GIEAAASAIQ  540
GNVTSIHSLL DEGKQSLTKL AAAWGGSGSE AYQGVQQKWD ATATELNNAL QNLARTISEA  600
GQAMASTEGN VTGMFAGPGP GTSRFMTDPH AMRDMAGRFE VHAQTVEDEA RRMWASAQNI  660
SGAGWSGMAE ATSLDTMTQM NQAFRNIVNM LHGVRDGLVR DANNYEQQEQ ASQQILSSGP  720
GPGSFVMAYP EMLAAAADTL QSIGATTVAS NAAAAAPTTG VVPPAADEVS ALTAAHFAAH  780
AAMYQSVSAR AAIHDQFVA TLASSASSYA ATEVANAAAA SGPGPGTINY QFGDVDAHGA  840
MIRAQAGSLE AEHQAIISDV LTASDFWGGA GSAACQGFIT QLGRNFQVIY EQANAHGQKV  900
QAAGNNMAQT DSAVGSSWAG PGPGPVGGQS SFYSDWYSPA CGKAGCQTYK WETFLTSELP  960
QWLSANRAVK PTGSAAIGLS MAGSSAMILA AYHPQQFIYA GSLSALLDPS QGMGGPGPGT  1020
VPPPVVAANR AELAVLAGPG PGMVDPVVVA ANRSAFVQLV LIPIAVGGAL AGLVLIVLIA  1080
YLVGRKRSHA GYQTI                                                 1095

SEQ ID NO: 408          moltype = RNA  length = 3478
FEATURE                 Location/Qualifiers
source                  1..3478
                        mol_type = other RNA
                        organism = synthetic construct
SEQUENCE: 408
acatttgctt ctgacacaac tgtgttcact agcaacctca aacagccacc atggcggctc  60
cgggaagcgc acgacgcccg ctgctgctct tgttgctgct cctcctgctg ggtctgatgc  120
actgcgcctc ggccaccgcc gcgagcgaca attttcagtt aagccagggt ggccagggat  180
ttgccatccc gatcggacag gccatggcta tcgcgggcca gatcagatcc ggaggcggat  240
ccccgactgt acacatcggt ccgaccgcct tcttgggact gggagtggtg gacaacaacg  300
ggaatggcgc acgggtgcag agggtcgtgg gctcggcacc agccgcctct ctgggaatca  360
gcaccgggga cgttatcacc gctgtggatg gtgcccccat caattccgcc acggcgatgg  420
ccgatgccct gaacggccat caccccgggg atgtgatatc cgtgacctgg cagaccaagt  480
ccggcggtac aaggaccggc aacgtcactc tggccgaggg tcctcctgcg ggccctggtc  540
ctggtgctga gatgaaaacc gacgccgcga ccctggccca ggaagccgga aacttcgagc  600
ggatttccgg agatcttaag actcagatcg accaggtcga atccaccgcc ggatcgctcc  660
agggacagtg gagaggcgcc gcgggaaccg cggcccaggc cgccgtcgtg cggttccaag  720
aggccgccaa caagcagaag caggaactgg acgaaatttc cactaacatt cgccaagctg  780
gcgtgcagta ctcgagagcc gatgaagaac agcagcaagc cctctcctca caaatgggtt  840
tcggacctgg gcccggcgtg gacttcggag ccctgccacc tgaaatcaac tccgcccgga  900
tgtacgcagg acctggatcc gccagcctgg tggcagccgc gcagatgtgg gatagcgtgg  960
cctccgacct gttcagcgcg gcttcagctt tccaaagcgt ggtctgggga ctgactgtgg  1020
gatcctggat cggatcaagc gcaggcctca tggtggccgc ggcgtcccct tacgtggcct  1080
ggatgagcgt gaccgccggc caggcagaac tgaccgcagc ccaagtccgc gtggccgcag  1140
ccgcctacga gactgcctac ggtctgacgg tgccgccgcc agtgatcgcc gagaacagag  1200
cagagctcat gatcctcatc gcgaccaacc tactgggcca gaacactccg gcgattgccg  1260
tgaacgaagc cgaatatggg gagatgtggg ctcaggacgc tgcagccatg ttcggatatg  1320
cagccgcgac tgctaccgcc accgccactc tgctgccgtt cgaggaggcc cccgaaatga  1380
cttccgcggg aggcctgttg gagcaagctg ccgcggtgga ggaagctagc gacaccgccg  1440
cagccaacca gctcatgaac aacgtgccac aggccctgca gcagctggcc cagcccactc  1500
aagggaccac cccgagctca aagctgggcg gtctgtggaa aaccgtgtcc ccccaccgct  1560
cgcccatttc caacatggtg tcaatggcga acaaccacat gggtcctgga cctggaacgg  1620
agcagcagtg gaacttcgcc gggatcgaag ccgccgcctc ggctatccaa gggaatgtca  1680
cctcgatcca ttcccttctg gacgaaggaa agcagtccct gaccaagctt gcggcagcct  1740
ggggcggaag cggcagcgaa gcctaccagg gcgtgcagca aaaatgggac gcaaccgcca  1800
ctgagctgaa caacgccctc caaaacctgg ctagaactat ttccgaggcc ggacaggcta  1860
tggccagcac cgagggcaac gtgaccggga tgttcgctgg ccctgggccg ggcacctcgc  1920
ggttcatgac cgatcctcat gctatgcggg atatggctgg acggttcgag gtgcacgccc  1980
aaactgtgga ggacgaggcc cgccggatgt gggccagcgc gcagaacatc tcgggggccg  2040
gctggtccgg aatggccgaa gccacctccc tcgataccat gacccagatg aaccaggcct  2100
tccggaacat tgtgaacatg ctgcatggag tgcgggacgg cctggtccgg gacgccaaca  2160
attacgagca gcaggagcag gcctctcagc aaatcctgtc cagcgggccg gggcctggat  2220
cattcgtgat ggcctaccct gagatgctgg cagccgcggc cgacaccctg caatccattg  2280
gcgccactac cgtggcatcg aacgcggcag ccgccgcacc gactaccggc gtggtgccgc  2340
ccgccgctga tgaagtgtcc gcccttactg ccgcccactt cgccgcccac gccgcgatgt  2400
accagtccgt gtccgcgcgc gccgccgcta tccacgatca gttcgtcgcc acactggcca  2460
gctcagcctc ctcatacgcc gctactgaag tggcaaacgc agccgctgca tccggcccgg  2520
gacccggaac gatcaactac cagtttggcg acgtggacgc gcacggggcg atgatcaggg  2580
ctcaagcggg gtccctcgag gccgaacacc aagcgattat ctcggatgtc ctcaccgcgt  2640
ccgacttctg gggtggagcc ggaagcgccg cctgccaagg tttcatcacc caactgggtc  2700
gcaactttca agtcatctac gaacaggcca acgcccacgg acagaaggtc caagccgccg  2760
gaaacaacat ggcacagacc gactccgcgg tcggatcgag ctgggccgga cccgggccag  2820
gtcccgtggg cggacagagc tcgttctatt ctgactggta ctcacccgca tgtggaaagg  2880
ccgggtgcca gacctacaaa tgggaaacct tcttgacttc cgagctgcct cagtggttgt  2940
```

-continued

```
ccgccaatcg ggccgtgaag ccgaccggct cggcggccat cggcctctcc atggccggct  3000
cgtccgcgat gattcttgcc gcctaccacc cgcagcagtt catctacgcc gggtccctct  3060
cggcactgct ggaccccagt cagggaatgg gcggacccgg accgggaact gtcccgcccc  3120
cggtggtggc tgctaaccgc gccgaacttg ccgtgctggc cggtccaggg ccgggaatgg  3180
tggacccagt ggtggtggca gcgaacagat ccgcattcgt gcaactggtc ctgattccta  3240
ttgcggtcgg cggggctctc gccgggctcg tgctcattgt cctgattgcc tacctggtcg  3300
gacgcaagag gtcccatgcg ggctaccaga ccatctgata ataggctcgc tttcttgctg  3360
tccaatttct attaaaggtt cctttgttcc ctaagtccaa ctactaaact gggggatatt  3420
atgaagggcc ttgagcatct ggattctgcc taataaaaaa catttatttt cattgcaa    3478

SEQ ID NO: 409         moltype = AA  length = 1179
FEATURE                Location/Qualifiers
source                 1..1179
                       mol_type = protein
                       organism = synthetic construct
SEQUENCE: 409
MAVMAPRTLL LLLLGALALT QTWAGSTAAS DNFQLSQGGQ GFAIPIGQAM AIAGQIRSGG  60
GSPTVHIGPT AFLGLGVVDN NGNGARVQRV VGSAPAASLG ISTGDVITAV DGAPINSATA  120
MADALNGHHP GDVISVTWQT KSGGTRTGNV TLAEGPPAGG SGGGGSGGAE MKTDAATLAQ  180
EAGNFERISG DLKTQIDQVE STAGSLQGQW RGAAGTAAQA AVVRFQEAAN KQKQELDEIS  240
TNIRQAGVQY SRADEEQQQA LSSQMGFGGS GGGGSGGVDF GALPPEINSA RMYAGPGSAS  300
LVAAAQMWDS VASDLFSAAS AFQSVVWGLT VGSWIGSSAG LMVAAAASPYV AWMSVTAGQA  360
ELTAAQVRVA AAAYETAYGL TVPPPVIAEN RAELMILIAT NLLGQNTPAI AVNEAEYGEM  420
WAQDAAAMFG YAAATATATA TLLPFEEAPE MTSAGGLLEQ AAAVEEASDT AAANQLMNNV  480
PQALQQLAQP TQGTTPSSKL GGLWKTVSPH RSPISNMVSM ANNHMGGSGG GGSGGTEQQW  540
NFAGIEAAAS AIQGNVTSIH SLLDEGKQSL TKLAAAWGGS GSEAYQGVQQ KWDATATELN  600
NALQNLARTI SEAGQAMAST EGNVTGMFAG GSGGGGSGGT SRFMTDPHAM RDMAGRFEVH  660
AQTVEDEARR MWASAQNISG AGWSGMAEAT SLDTMTQMNQ AFRNIVNMLH GVRDGLVRDA  720
NNYEQQEQAS QQILSSGGSG GGGSGGSFVM AYPEMLAAAA DTLQSIGATT VASNAAAAAP  780
TTGVVPPAAD EVSALTAAHF AAHAAMYQSV SARAAAIHDQ FVATLASSAS SYAATEVANA  840
AAASGGSGGG GSGGTINYQF GDVDAHGAMI RAQAGSLEAE HQAIISDVLT ASDFWGGAGS  900
AACQGFITQL GRNFQVIYEQ ANAHGQKVQA AGNNMAQTDS AVGSSWAGGS GGGGSGGPVG  960
GQSSFYSDWY SPACGKAGCQ TYKWETFLTS ELPQWLSANR AVKPTGSAAI GLSMAGSSAM  1020
ILAAYHPQQF IYAGSLSALL DPSQGMGGGS GGGGSGGFAA TVPPPVVAAN RAELAVLAAT  1080
NGGSGGGGSG GRAAMVDPVV VAANRSAFVQ LVLSNEPSSQ STVPIVGIVA GLAVLAVVVI  1140
GAVVAAVMCR RKSSGGKGGS YSQAACSDSA QGSDVSLTA                         1179

SEQ ID NO: 410         moltype = RNA  length = 3730
FEATURE                Location/Qualifiers
source                 1..3730
                       mol_type = other RNA
                       organism = synthetic construct
SEQUENCE: 410
acatttgctt ctgacacaac tgtgttcact agcaacctca aacagccacc atggccgtga  60
tggcccccag aactctcttg ctgcttctgt tgggagctct ggcgctgacc cagacctggg  120
ctggatcgac cgctgcctcc gacaacttcc aactgtcaca aggaggacaa gggtttgcca  180
tcccgatcgg ccaagccatg gccatcgccg gacaaattcg gagcggggga ggaagcccca  240
ctgtgcacat tggtccgacc gccttcctcg ggctgggcgt ggtggacaac aacggcaacg  300
gcgccagggt gcagagggtc gtgggatccg caccggccgc ctctctcgga atttcgaccg  360
gcgacgtgat taccgccgtg gacggggcgc cgattaactc cgccacggca atggccgacg  420
cgctcaacgg tcaccacccg ggagatgtca tctccgtgac ctggcagacc aagagcggag  480
gcactcgcac cggaaacgtc actctcgccg agggcccacc cgccggaggt tctggaggag  540
gcggctccgg tggcgcggag atgaaaaccg atgcggccac cctggcacag gaggctggaa  600
acttcgaaag aatcagcggc gacctcaaga ctcagatcga ccaggtcgaa tcgactgccg  660
gaagcctcca gggccagtgg aggggagccg ctggaactgc ggcgcaggcg gccgtggtca  720
gattccagga ggccgccaac aagcagaagc aggaactgga tgaaatttcc actaacatca  780
gacaggctgg ggtgcaatac tcccgcgcgg acgaagaaca gcagcaggcc ctgtccagcc  840
aaatgggatt cggtggcagc gggggtggcg gctcaggggg agtggatttc ggggctctgc  900
cacctgagat caactctgcc cggatgtacg cggggccggg cagcgcatcc cttgtggccg  960
ccgcccagat gtgggatagc gtggcttccg acctcttctc cgccgcatcc gcctttcaat  1020
ccgtggtctg gggctgact gtgggctcgt ggatcggatc atctgctggc ctcatggtgg  1080
ccgcggcatc ccccatacgtg gcctggatga gtgtgaccgc tggccaggct gaattgaccg  1140
ccgcacaagt ccgcgtcgct gccgccgcat acgaaaccgc ctacgggctg accgttccgc  1200
cccccgtgat tgccgaaaat agggccgaac tcatgatcct catcgcgact aatctgctgg  1260
gtcagaacac cccggctatc gccgtgaatg aggccgaata cggcgaaatg tgggcccagg  1320
acgccgctgc catgttcggc tacgccgccg ccactgcgac cgcgaccgcc actctgctgc  1380
ctttcgaaga ggcccctgag atgacctccg cgggtggcct gctagaacaa gcggcagctg  1440
tggaagaagc ctcggatacc gccgccgcta accagctgat gaacaacgtg ccccaggcgc  1500
tgcagcagct cgcccagccg actcagggaa ccaccccgag ctcaaagctt ggtggcctgt  1560
ggaaaaccgt atcgcctcat cgctcaccaa tcagcaacat ggtcagcatg gcgaacaacc  1620
acatgggtgg ctcaggcggc gggggctccg gaggcaccga gcagcagtgg aacttcgccg  1680
gaatcgaggc cgcagcgagc gcaatccagg gcaatgtcac ctccattcac tccctgctgg  1740
atgagggcaa acagtccctg actaagcttg ccgcagcgtg gggaggttcc ggctccgaag  1800
cctaccaggg cgtgcagcag aaatgggacg ctactgctac cgaactgaac aacgccctgc  1860
agaatcttgc tcggaccatt agcgaagccg gacaagcgat ggcctccacc gagggaaacg  1920
tgaccgggat gtttgccggg gggtccggag gaggaggctc aggaggaacc agccgcttca  1980
tgactgaccc tcatgccatg cgggacatgg ccggacgctt cgaagtgcat gcgcagactg  2040
tggaggacga agcccggcgg atgtgggcat cggcccagaa catctccgga gcgggatggt  2100
ccggaatggc cgaggccacc tccctcgaca ccatgacgca gatgaaccag gcctttcgca  2160
```

-continued

```
atatcgtgaa catgctgcac ggcgtgcgcg acggcctcgt gcgggacgcc aacaactacg  2220
agcaacagga gcaggcgtca cagcagattc tgtcctcggg cggttcggga ggcggtggat  2280
cggggggtc attcgtgatg gcttaccccg agatgttggc tgctgcggct gacacccttc  2340
agagcatcgg agccactacc gtcgcctcga acgccgcggc agccgcccct accaccgggg  2400
tggtgcctcc agccgccgac gaagtctccg ccctgactgc cgcgcacttc gccgcccacg  2460
cagccatgta ccagtcggtg tcggcccggg cggcagctat ccacgatcag ttcgtggcca  2520
cgttagcatc cagcgcgtca agctatgccg ccacggaagt ggccaacgca gctgcagcct  2580
ctggaggaag cgggggcgga ggaagtggcg gcactatcaa ctaccaattc ggagatgtgg  2640
acgcgcacgg cgccatgatc cgcgcccaag cgggatccct tgaagcggag catcaggcca  2700
ttatctccga cgtcttgacc gcctccgact tttggggtgg agccgggagc gccgcgtgcc  2760
agggattcat cacccaactg ggcggaatt tccaggtcat ctacgaacag gctaacgccc  2820
acggtcaaaa ggttcaggct gccggcaaca acatggccca gaccgactcc gccgtggggt  2880
cctcctgggc cggaggctcc ggcggtggcg gatcaggagg ccctgtggga ggacagtcct  2940
ccttctattc cgattggtac tcccccgcct gcggaaaggc cggatgtcag acgtataagt  3000
gggagacatt cctgacctcc gagctgcccc agtggctctc ggccaaccgg gctgtgaagc  3060
cgactggatc cgccgcaatt gggctgtcca tggcgggctc gtcggcgatg atcctggccg  3120
cttaccaccc acaacagttc atctacgccg gatccttgtc ggcactgctg gacccgagcc  3180
aggggatggg cggtggttcc gggggcgggg gatccggagg tttcgccgcg accgtgccac  3240
ctccggtcgt ggcagccaac cgcgccgaac tggccgtcct ggcggctacc aacgggggat  3300
cgggtggagg ggggtcggga ggcagagccg ccatggtcga ccctgtggtg gtcgccgcca  3360
atagatcagc cttcgtgcaa ctcgtgctgt cgaacgagcc ctccagccaa tccaccgtgc  3420
cgatcgtcgg aattgtggcc ggcctggctg tgctggcagt ggtggtcatt ggagccgtgg  3480
tggctgccgt gatgtgcaga agaaagagca gcggaggaaa gggaggatcc tactcacaag  3540
ccgcgtgctc cgatagcgcc cagggttcgg atgtgtcact caccgcctga taataggctc  3600
gctttcttgc tgtccaattt ctattaaagg ttcctttgtt ccctaagtcc aactactaaa  3660
ctgggggata ttatgaaggg ccttgagcat ctggattctg cctaataaaa aacatttatt  3720
ttcattgcaa                                                         3730

SEQ ID NO: 411          moltype = AA  length = 1189
FEATURE                 Location/Qualifiers
source                  1..1189
                        mol_type = protein
                        organism = synthetic construct
SEQUENCE: 411
MAVMAPRTLL LLLLGALALT QTWAGSTAAS DNFQLSQGGQ GFAIPIGQAM AIAGQIRSGG  60
GSPTVHIGPT AFLGLGVVDN NGNGARVQRV VGSAPAASLG ISTGDVITAV DGAPINSATA  120
MADALNGHHP GDVISVTWQT KSGGTRTGNV TLAEGPPAGG SGGGGSGGVD FGALPPEINS  180
ARMYAGPGSA SLVAAAQMWD SVASDLFSAA SAFQSVVWGL TVGSWIGSSA GLMVAAASPY  240
VAWMSVTAGQ AELTAAQVRV AAAAYETAYG LTVPPPVIAE NRAELMILIA TNLLGQNTPA  300
IAVNEAEYGE MWAQDAAAMF GYAAATATAT ATLLPFEEAP EMTSAGGLLE QAAAVEEASD  360
TAAANQLMNN VPQALQQLAQ PTQGTTPSSK LGGLWKTVSP HRSPISNMVS MANNHMGGSG  420
GGGSGGAEMK TDAATLAQEA GNFERISGDL KTQIDQVEST AGSLQGQWRG AAGTAAQAAV  480
VRFQEAANKQ KQELDEISTN IRQAGVQYSR ADEEQQQALS SQMGFGGGGS GGGGSTEQQW  540
NFAGIEAAAS AIQGNVTSIH SLLDEGKQSL TKLAAAWGGS GSEAYQGVQQ KWDATATELN  600
NALQNLARTI SEAGQAMAST EGNVTGMFAG GSGGGGSGGS FVMAYPEMLA AAADTLQSIG  660
ATTVASNAAA AAPTTGVVPP AADEVSALTA AHFAAHAAMY QSVSARAAAI HDQFVATLAS  720
SASSYAATEV ANAAAASGGS GGGGSGGTSR FMTDPHAMRD MAGRFEVHAQ TVEDEARRMW  780
ASAQNISGAG WSGMAEATSL DTMTQMNQAF RNIVNMLHGV RDGLVRDANN YEQQEQASQQ  840
ILSSGGGGSG GGGSTINYQF GDVDAHGAMI RAQAGSLEAE HQAIISDVLT ASDFWGGAGS  900
AACQGFITQL GRNFQVIYEQ ANAHGQKVQA AGNNMAQTDS AVGSSWAGGS GGGGSGGPVG  960
GQSSFYSDWY SPACGKAGCQ TYKWETFLTS ELPQWLSANR AVKPTGSAAI GLSMAGSSAM  1020
ILAAYHPQQF IYAGSLSALL DPSQGMGGGS GGGGSGGFAA TVPPPVVAAN RAELAVLAAT  1080
NGGSGGGGSG GRAAMVDPVV VAANRSAFVQ LVLSNGGSGG GGSGGEPSSQ STVPIVGIVA  1140
GLAVLAVVVI GAVVAAVMCR RKSSGGKGGS YSQAACSDSA QGSDVSLTA              1189

SEQ ID NO: 412          moltype = RNA  length = 3760
FEATURE                 Location/Qualifiers
source                  1..3760
                        mol_type = other RNA
                        organism = synthetic construct
SEQUENCE: 412
acatttgctt ctgacacaac tgtgttcact agcaacctca aacagccacc atggccgtga  60
tggcccccag aactctcttg ctgcttctgt tgggagctct ggcgctgacc cagacctggg  120
ctggatcgac cgctgcctcc gacaacttcc aactgtcaca aggaggacaa gggtttgcca  180
tcccgatcgg ccaagccatg gccatcgccg gacaaattcg gagcggggga ggaagcccca  240
ctgtgcacat tggtccgacc gccttcctcg ggctgggcgt ggtggacaac aacggcaacg  300
gcgccagggt gcagagggtc gtgggatccg caccggccgc ctctctcgga atttcgaccg  360
gcgacgtgat taccgccgtg gacggggcgc cgattaactc cgccacggca atggccgacg  420
cgctcaacgg tcaccacccg ggagatgtca tctccgtgac ctggcagacc aagagcggag  480
gcactcgcac cggaaacgtc actctcgccg agggcccacc cgccggtggc agcgggggtg  540
gcggctcagg gggagtggat ttcggggctc tgccacctga gatcaactct gcccggatgt  600
acgcggggcc gggcagcgca tcccttgtgg ccgccgccca gatgtgggat agcgtggctt  660
ccgacctctt ctccgccgca tccgcctttc aatccgtggt ctgggggctg actgtgggct  720
cgtggatcgg atcatctgct ggcctcatgg tggccgcggc atccccatac gtggcctgga  780
tgagtgtgac cgctggccag gctgaattga ccgccgcaca agtccgcgtc gctgccgccg  840
catacgaaac cgcctacggg ctgaccgttc cgccccccgt gattgccgaa aatagggccg  900
aactcatgat cctcatcgcg actaatctgc tgggtcagaa caccccggct atcgccgtga  960
atgaggccga atacggcgaa atgtgggccc aggacgccgc tgccatgttc ggctacgccg  1020
ccgccactgc gaccgcgacc gccactctgc tgcctttcga agaggcccct gagatgacct  1080
```

-continued

```
ccgcgggtgg cctgctagaa caagcggcag ctgtggaaga agcctcggat accgccgccg  1140
ctaaccagct gatgaacaac gtgccccagg cgctgcagca gctcgcccag ccgactcagg  1200
gaaccacccc gagctcaaag cttggtggcc tgtggaaaac cgtatcgcct catcgctcac  1260
caatcagcaa catggtcagc atggcgaaca accacatggg tggctcaggc ggcgggggct  1320
ccggaggcgc cgaaatgaag actgacgcag ccactctggc ccaggaggct gggaacttcg  1380
aacgcatctc aggagatctc aagacccaga tcgatcaggt ggaatccact gccggcagcc  1440
tccaaggcca gtggcgagga gccgccggta ctgccgctca ggccgcagtg gtgcgcttcc  1500
aggaggccgc caacaagcag aagcaggaac tggacgagat tagcaccaat atccgccaag  1560
ccggagtgca atatagccgg gccgacgagg aacagcaaca agccctctcc tcccaaatgg  1620
ggttcggcgg aggaggaagc ggaggcggcg gcagcaccga gcagcagtgg aacttcgccg  1680
gaatcgaggc cgcagcgagc gcaatccagg gcaatgtcac ctccattcac tccctgctgg  1740
atgagggcaa acagtccctg actaagcttg ccgcagcgtg gggaggttcc ggctccgaag  1800
cctaccaggg cgtgcagcag aaatgggacg ctactgctac cgaactgaac aacgccctgc  1860
agaatcttgc tcggaccatt agcgaagccg gacaagcgat ggcctccacc gagggaaacg  1920
tgaccgggat gtttgccgga ggatcgggcg ggggcggctc cggagggtcc tttgtcatgg  1980
catacccaga gatgctggcc gccgccgcgg ataccctgca gtcgattgga gccactaccg  2040
tggcctcaaa cgccgcagcg gctgccccca ccactggagt ggtgccccca gcagccgacg  2100
aagtctccgc cttaactgcc gcccactttg ccgcccatgc ggcgatgtac cagtccgtgt  2160
cagcccgcgc cgccgcaatc cacgatcagt tcgtcgcaac actggcgtcc agcgcgtcgt  2220
cgtacgccgc caccgaggtg gccaacgcgg cggcggcctc aggggggtcc ggaggaggag  2280
gctcaggagg aaccagccgc ttcatgactg accctcatgc catgcgggac atggccggac  2340
gcttcgaagt gcatgcgcag actgtggagg acgaagcccg gcggatgtgg gcatcggccc  2400
agaacatctc cggagcggga tggtccggaa tggccgaggc cacctccctc gacaccatga  2460
cgcagatgaa ccaggccttt cgcaatatcg tgaacatgct gcacggcgtg cgcgacggcc  2520
tcgtgcggga cgccaacaac tacgagcaac aggagcaggc gtcacagcag attctgtcct  2580
cgggcggtgg aggaagcggg ggcggaggaa gtactatcaa ctaccaattc ggagatgtgg  2640
acgcgcacgg cgccatgatc cgcgcccaag cgggatccct tgaagcggag catcaggcca  2700
ttatctccga cgtcttgacc gcctccgact tttggggtgg agccgggagc gccgcgtgcc  2760
agggattcat cacccaactg ggcggaattt tccaggtcat ctacgaacag gctaacgccc  2820
acggtcaaaa ggttcaggct gccggcaaca acatggccca gaccgactcc gccgtggggt  2880
cctcctgggc cggaggctcc ggcggtggcg gatcaggagg ccctgtggga ggacagtcct  2940
ccttctattc cgattggtac tccccgcct gcggaaaggc cggatgtcag acgtataagt  3000
gggagacatt cctgacctcc gagctgcccc agtggctctc ggccaaccgg gctgtgaagc  3060
cgactggatc cgccgcaatt gggctgtcca tggcgggctc gtcggcgatg atcctggccg  3120
cttaccaccc acaacagttc atctacgccg gatccttgtc ggcactgctg gacccgagcc  3180
aggggatggg cggtggttcc gggggcgggg gatccggagg tttcgccgcg accgtgccac  3240
ctccggtcgt ggcagccaac cgcgccgaac tggccgtcct ggcggctacc aacgggggat  3300
cgggtggagg ggggtcggga ggcagagccg ccatggtcga ccctgtggtg gtcgccgcca  3360
atagatcagc cttcgtgcaa ctcgtgctgt cgaacggggg atccggaggg gggggttccg  3420
gcggcgagcc ctccagccaa tccaccgtgc cgatcgtcgg aattgtggcc ggcctggctg  3480
tgctggcagt ggtggtcatt ggagccgtgg tggctgccgt gatgtgcaga agaaagagca  3540
gcggaggaaa gggaggatcc tactcacaag ccgcgtgctc cgatagcgcc cagggttcgg  3600
atgtgtcact caccgcctga taataggctc gctttcttgc tgtccaattt ctattaaagg  3660
ttcctttgtt ccctaagtcc aactactaaa ctgggggata ttatgaaggg ccttgagcat  3720
ctggattctg cctaataaaa aacatttatt ttcattgcaa                        3760
```

```
SEQ ID NO: 413          moltype = AA  length = 1252
FEATURE                 Location/Qualifiers
source                  1..1252
                        mol_type = protein
                        organism = synthetic construct
SEQUENCE: 413
MAVMAPRTLL LLLLGALALT QTWAGSTAAS DNFQLSQGGQ GFAIPIGQAM AIAGQIRSGG  60
GSPTVHIGPT AFLGLGVVDN NGNGARVQRV VGSAPAASLG ISTGDVITAV DGAPINSATA  120
MADALNGHHP GDVISVTWQT KSGGTRTGNV TLAEGPPAGG SGGGGSGGAE MKTDAATLAQ  180
EAGNFERISG DLKTQIDQVE STAGSLQGQW RGAGGSGGGG SGGTSRFMTD PHAMRDMAGR  240
FEVHAQTVED EARRMWASAQ NISGAGWSGG GSGGGGSGGT EQQWNFAGIE AAASAIQGNV  300
TSIHSLLDEG KQSLTKLAAA WGGSGSGGSG GGGSGGTINY QFGDVDAHGA MIRAQAGSLE  360
AEHQAIISDV LTASDFWGGA GSGGSGGGGS GGVDFGALPP EINSARMYAG PGSASLVAAA  420
QMWDSVASDL FSAASAFQSV VWGLTVGSWI GSSAGLMVAA ASPYVAWMSV TAGQAELTAA  480
QVRVAAAAYE TAYGLTVPPP VIAENRAELM ILIATNLLGQ NTPAIAVNEA EYGEMWAQDA  540
AAMFGYAAAT ATATATLLPF EEAPEMTSAG GLLEQAAAVE EASDTAAANQ LMNNVPQALQ  600
QLAQPTQGTT PSSKLGGLWK TVSPHRSPIS NMVSMANNHM GGSGGGGSGG SFVMAYPEML  660
AAAADTLQSI GATTVASNAA AAPTTGVVP PAADEVSALT AAHFAAHAAM YQSVSARAAA  720
IHDQFVATLA SSASSYAATE VANAAAASGG SGGGGSGGGQ WRGAAGTAAQ AAVVRFQEAA  780
NKQKQELDEI STNIRQAGVQ YSRADEEQQQ ALSSQMGFGG SGGGGSGGSG AGWSGMAEAT  840
SLDTMTQMNQ AFRNIVNMLH GVRDGLVRDA NNYEQQEQAS QQILSSGGSG GGGSGGGGSG  900
SEAYQGVQQK WDATATELNN ALQNLARTIS EAGQAMASTE GNVTGMFAGG SGGGGSGGGG  960
AGSAACQGFI TQLGRNFQVI YEQANAHGQK VQAAGNNMAQ TDSAVGSSWA GGSGGGGSGG  1020
PVGGQSSFYS DWYSPACGKA GCQTYKWETF LTSELPQWLS ANRAVKPTGS AAIGLSMAGS  1080
SAMILAAYHP QQFIYAGSLS ALLDPSQGMG GGSGGGGSGG FAATVPPPVV AANRAELAVL  1140
AATNGGSGGG GSGGRAAMVD PVVVAANRSA FVQLVLSNGG SGGGGSGGEP SSQSTVPIVG  1200
IVAGLAVLAV VVIGAVVAAV MCRRKSSGGK GGSYSQAACS DSAQGSDVSL TA          1252
```

```
SEQ ID NO: 414          moltype = RNA  length = 3949
FEATURE                 Location/Qualifiers
source                  1..3949
                        mol_type = other RNA
                        organism = synthetic construct
```

-continued

SEQUENCE: 414
acatttgctt ctgacacaac tgtgttcact agcaacctca aacagccacc atggccgtga 60
tggcccccag aactctcttg ctgcttctgt tgggagctct ggcgctgacc cagacctggg 120
ctggatcgac cgctgcctcc gacaacttcc aactgtcaca aggaggacaa gggtttgcca 180
tcccgatcgg ccaagccatg gccatcgccg gacaaattcg gagcggggga ggaagcccca 240
ctgtgcacat tggtccgacc gccttcctcg ggctgggcgt ggtggacaac aacggcaacg 300
gcgccagggt gcagagggtc gtgggatccg caccggccgc ctctctcgga atttcgaccg 360
gcgacgtgat taccgccgtg gacggggcgc cgattaactc cgccacggca atggccgacg 420
cgctcaacgg tcaccacccg ggagatgtca tctccgtgac ctggcagacc aagagcggag 480
gcactcgcac cggaaacgtc actctcgccg agggcccacc cgccggaggt tctggaggag 540
gcggctccgg tggcgcggag atgaaaaccg atgcggccac cctggcacag gaggctggaa 600
acttcgaaag aatcagcggc gacctcaaga ctcagatcga ccaggtcgaa tcgactgccg 660
gaagcctcca gggccagtgg aggggagccg gtggatccgg aggaggggga tccggcggaa 720
ccagccgctt catgaccgat cctcacgcta tgcgcgacat ggcgggtcgc ttcgaagtgc 780
atgcccagac tgtcgaggac gaggcccggc gaatgtgggc cagcgcgcag aacatcagcg 840
gcgccggttg gtcaggaggc gggtccgggg ggggaggttc tggcggtacc gagcagcaat 900
ggaacttcgc gggtattgaa gccgcggcat ccgcgatcca gggcaacgtg acctccattc 960
acagcctgtt agacgaagga aagcagagcc tgaccaagtt ggccgccgcc tgggggggggt 1020
cagggtccgg aggttccgga ggcggtggct cgggcggcac catcaattac cagttcgggg 1080
acgtggacgc acacggagcc atgatccggg cccaggcggg ctccctggaa gcggagcatc 1140
aggccatcat tagcgatgtg ctcacggcta gcgatttctg ggggggagcc ggaagcggtg 1200
gcagcggggg tggcggctca gggggagtgg atttcggggc tctgccacct gagatcaact 1260
ctgcccggat gtacgcgggg ccgggcagcg catcccttgt ggccgccgcc cagatgtggg 1320
atagcgtggc ttccgacctc ttctccgccg catccgcctt tcaatccgtg gtctgggggc 1380
tgactgtggg ctcgtggatc ggatcatctg ctggcctcat ggtggccgcg gcatccccat 1440
acgtggcctg gatgagtgtg accgctggcc aggctgaatt gaccgccgca caagtccgcg 1500
tcgctgccgc cgcatacgaa accgcctacg ggctgaccgt tccgcccccc gtgattgccg 1560
aaaataggc cgaactcatg atcctcatcg cgactaatct gctgggtcag aacaccccgg 1620
ctatcgccgt gaatgaggcc gaatacggcg aaatgtgggc ccaggacgcc gctgccatgt 1680
tcggctacgc cgccgccact gcgaccgcga ccgccactct gctgcctttc gaagaggccc 1740
ctgagatgac ctccgcgggt ggcctgctag aacaagcggc agctgtggaa gaagcctcgg 1800
ataccgccgc cgctaaccag ctgatgaaca acgtgcccca ggcgctgcag cagctcgccc 1860
agccgactca gggaaccacc ccgagctcaa agcttggtgg cctgtggaaa accgtatcgc 1920
ctcatcgctc accaatcagc aacatggtca gcatggcgaa caaccacatg ggtggctcag 1980
gcggcggggg ctccggaggc agctttgtga tggcctaccc cgaaatgctc gcagccgcag 2040
cggatacctt gcagtcaatt ggcgccacca ccgtggcctc caacgccgct gccgccgccc 2100
cgactacggg ggtggtcccg cccgccgcag atgaagtgtc cgctcttacc gcagcgcact 2160
ttgccgccca tgctgccatg taccagtccg tgtcggctag agctgccgcg atccacgacc 2220
agttcgtggc taccctggcc agctcggcat cgagctacgc cgccaccgag gtggctaacg 2280
ccgccgccgc cagcgggggg tccggaggag gaggctcagg aggaggccaa tggcggggtg 2340
ccgccggaac cgccgcccaa gcggctgtcg tgcgcttcca ggaggccgcc aacaagcaga 2400
agcaggaact cgacgaaata tcaaccaaca tccggcaagc tggggtgcag tacagcagag 2460
ccgatgagga acagcaacag gcgctctcct cgcaaatggg cttcggaggc tcaggagggg 2520
gcggatcggg tggctccgga gcgggatggt ccggaatggc cgaggccacc tccctcgaca 2580
ccatgacgca gatgaaccag gcctttcgca atatcgtgaa catgctgcac ggcgtgcgcg 2640
acggcctcgt gcgggacgcc aacaactacg agcaacagga gcaggcgtca cagcagattc 2700
tgtcctcggg cggttcggga ggcggtggat cggggggggg aggatccgga tcagaagcct 2760
atcaaggtgt gcagcagaag tgggacgcca ccgcgaccga acttaataac gccttgcaga 2820
acttggcccg gacgatatcc gaagccggcc aagccatggc ctccacggaa ggcaatgtga 2880
ctggcatgtt cgcgggagga agcgggggcg gaggaagtgg cggcggtgga gccgggagcg 2940
ccgcgtgcca gggattcatc acccaactgg ggcggaattt ccaggtcatc tacgaacagg 3000
ctaacgccca cggtcaaaag gttcaggctg ccggcaacaa catggcccag accgactccg 3060
ccgtggggtc ctcctgggcc ggaggctccg gcggtggcgg atcaggaggc cctgtgggag 3120
gacagtcctc cttctattcc gattggtact cccccgcctg cggaaaggcc ggatgtcaga 3180
cgtataagtg ggagacattc ctgacctccg agctgcccca gtggctctcg gccaaccggg 3240
ctgtgaagcc gactggatcc gccgcaattg ggctgtccat ggcgggctcg tcggcgatga 3300
tcctggccgc ttaccaccca caacagttca tctacgccgg atccttgtcg gcactgctgg 3360
acccgagcca ggggatgggc ggtggttccg ggggcggggg atccggaggt ttcgccgcga 3420
ccgtgccacc tccggtcgtg gcagccaacc gcgccgaact ggccgtcctg gcggctacca 3480
acgggggatc gggtggaggg gggtcgggag gcagagccgc catggtcgac cctgtggtgg 3540
tcgccgccaa tagatcagcc ttcgtgcaac tcgtgctgtc gaacgggggc tccggcggtg 3600
gtggctcggg cggggagccc tccagccaat ccaccgtgcc gatcgtcgga attgtggccg 3660
gcctggctgt gctggcagtg gtggtcattg gagccgtggt ggctgccgtg atgtgcagaa 3720
gaaagagcag cggaggaaag ggaggatcct actcacaagc cgcgtgctcc gatagcgccc 3780
agggttcgga tgtgtcactc accgcctgat aataggctcg ctttcttgct gtccaatttc 3840
tattaaaggt tcctttgttc cctaagtcca actactaaac tggggggatat tatgaagggc 3900
cttgagcatc tggattctgc ctaataaaaa acatttattt tcattgcaa 3949

SEQ ID NO: 415 moltype = AA length = 1162
FEATURE Location/Qualifiers
source 1..1162
mol_type = protein
organism = synthetic construct SEQUENCE: 415
MAAPGSARRP LLLLLLLLLL GLMHCASATA ASDNFQLSQG GQGFAIPIGQ AMAIAGQIRS 60
GGGSPTVHIG PTAFLGLGVV DNNGNGARVQ RVVGSAPAAS LGISTGDVIT AVDGAPINSA 120
TAMADALNGH HPGDVISVTW QTKSGGTRTG NVTLAEGPPA GGSGGGGSGG AEMKTDAATL 180
AQEAGNFERI SGDLKTQIDQ VESTAGSLQG QWRGAAGTAA QAAVVRFQEA ANKQKQELDE 240
ISTNIRQAGV QYSRADEEQQ QALSSQMGFG GSGGGGSGGV DFGALPPEIN SARMYAGPGS 300

```
ASLVAAAQMW DSVASDLFSA ASAFQSVVWG LTVGSWIGSS AGLMVAAASP YVAWMSVTAG  360
QAELTAAQVR VAAAAYETAY GLTVPPPVIA ENRAELMILI ATNLLGQNTP AIAVNEAEYG  420
EMWAQDAAAM FGYAAATATA TATLLPFEEA PEMTSAGGLL EQAAAVEEAS DTAAANQLMN  480
NVPQALQQLA QPTQGTTPSS KLGGLWKTVS PHRSPISNMV SMANNHMGGS GGGGSGGTEQ  540
QWNFAGIEAA ASAIQGNVTS IHSLLDEGKQ SLTKLAAAWG GSGSEAYQGV QQKWDATATE  600
LNNALQNLAR TISEAGQAMA STEGNVTGMF AGGSGGGGSG GTSRFMTDPH AMRDMAGRFE  660
VHAQTVEDEA RRMWASAQNI SGAGWSGMAE ATSLDTMTQM NQAFRNIVNM LHGVRDGLVR  720
DANNYEQQEQ ASQQILSSGG SGGGGSGGSF VMAYPEMLAA AADTLQSIGA TTVASNAAAA  780
APTTGVVPPA ADEVSALTAA HFAAHAAMYQ SVSARAAAIH DQFVATLASS ASSYAATEVA  840
NAAAASGGSG GGGSGGTINY QFGDVDAHGA MIRAQAGSLE AEHQAIISDV LTASDFWGGA  900
GSAACQGFIT QLGRNFQVIY EQANAHGQKV QAAGNNMAQT DSAVGSSWAG GSGGGGSGGP  960
VGGQSSFYSD WYSPACGKAG CQTYKWETFL TSELPQWLSA NRAVKPTGSA AIGLSMAGSS  1020
AMILAAYHPQ QFIYAGSLSA LLDPSQGMGG GSGGGGSGGF AATVPPPVVA ANRAELAVLA  1080
ATNGGSGGGG SGGRAAMVDP VVVAANRSAF VQLVLSNGGS GGGGSGGLIP IAVGGALAGL  1140
VLIVLIAYLV GRKRSHAGYQ TI                                           1162

SEQ ID NO: 416          moltype = RNA  length = 3679
FEATURE                 Location/Qualifiers
source                  1..3679
                        mol_type = other RNA
                        organism = synthetic construct
SEQUENCE: 416
acatttgctt ctgacacaac tgtgttcact agcaacctca aacagccacc atggccgccc  60
ctggcagcgc cagaagacct ctgctgctgc tgctgctgct gctgctgctg ggcctgatgc  120
actgcgcctc agccaccgcc gcttctgaca acttccagct gagccagggc ggccagggat  180
tcgccatccc tattggtcag gccatggcca tcgccggcca gatcagaagt ggaggtggct  240
ctccaaccgt gcacatcggc cccactgcct tcctgggcct aggagtggtg gataacaacg  300
gcaatggcgc cagagtgcaa agagtggtgg gttcagctcc tgccgccagc ctggggatca  360
gcaccggcga cgtgatcacc gcagtggacg gcgctcctat caactccgcc acagccatgg  420
ccgatgccct gaacggccac caccctggag atgtcatctc tgtgacctgg cagacaaaga  480
gcggcggcac cagaacagga aacgtgaccc tggccgaggg gcctcctgcc ggcggctccg  540
gaggcggtgg atctggaggc gccgagatga agaccgacgc cgctacactg gcgcaggagg  600
ccggcaactt cgagagaatc tcaggggatc tgaagaccca gatcgaccag gtggaaagca  660
ccgcaggatc tcttcagggc cagtggcggg gcgccgctgg cacagccgcc caggctgctg  720
tggtgcggtt ccaggaggcc gccaacaagc agaaacagga gctggatgag atcagcacca  780
acattcgcca ggccggcgtg caatacagca gagccgacga agaacagcag caggctctgt  840
ctagccagat gggatttggc ggttctggtg gtggcggatc aggtggcgtc gacttcggcg  900
ccctccccc cgaaatcaac agcgccagaa tgtacgccgg acctggcagc gccagcctgg  960
tggcagcagc ccaaatgtgg gatagcgtgg cttctgacct gttctccgcc gctagcgctt  1020
ttcagtccgt ggtgtggggc ctgaccgtgg gcagctggat cggcagcagc gctggactga  1080
tggtggcagc tgccagcccc tacgtggcct ggatgagcgt gacagctgga caggctgaac  1140
tgacagccgc ccaagtgcgg gtggctgccg ccgcctatga gacagcttac ggcctgacag  1200
tgcccccccc agtgattgcc gaaaaccggg ccgagctgat gatcctgatc gccaccaatc  1260
tgctgggcca gaacacccct gccatcgccg tgaacgaggc ggaatacggc gagatgtggg  1320
cccaggacgc cgccgccatg ttcggctacg cagccgctac cgccaccgcc acagccaccc  1380
tgctgccttt cgaggaagct ccagagatga ccagcgctgg cggcctattg gagcaggccg  1440
ccgcagttga ggaagcttct gatacagccg ccgcgaacca gctgatgaac aacgtgccac  1500
aggccctgca gcagctggct caacctaccc agggcaccac acctagctcc aagctgggcg  1560
gtctgtggaa gaccgtgagc cctcatagat ctcccatcag caatatggtc tctatggcca  1620
acaaccacat gggcggctcc ggtggaggcg ggagcggcgg cacagagcag caatggaact  1680
tcgccggcat cgaggcagcc gcttctgcca tccagggcaa tgtgaccagc atccattctc  1740
tgttggacga gggcaaacag agcctgacca agctggccgc cgcctgggga ggcagcggct  1800
ctgaggccta ccagggcgtt caacaaaaat gggacgccac tgccaccgaa ctgaacaacg  1860
ccctgcagaa tttagcccgg acaatcagcg aggccggcca ggctatggcc tctactgaag  1920
gcaacgtgac cggcatgttc gccggcggca gcggaggcgg cggtagtgga ggcaccagca  1980
gattcatgac ggatccccac gccatgcggg atatggccgg cagattcgag gtgcatgctc  2040
agaccgtcga ggacgaggcc aggcggatgt gggctagcgc ccagaacatc agcggcgccg  2100
gctggagcgg aatggccgaa gctacaagcc tggacaccat gacgcaaatg aaccaggcct  2160
ttagaaacat cgtgaatatg ctgcacggcg tgcgcgacgg gctggtgcgg gacgctaaca  2220
actacgagca gcaggagcag gccagccagc agatcctgtc ttctggcggc agcggtggag  2280
gaggctctgg cggctcattt gtaatggcgt atcctgaaat gctggcagcc gccgcggata  2340
ccctccagag catcggcgcc accaccgtgg ccagcaacgc cgccgctgcc gcccccacca  2400
caggtgtggt gccacctgct gccgacgagg tgagcgccct gaccgccgcc cacttcgccg  2460
ctcacgccgc gatgtaccag agcgtgtccg ctagagccgc tgcaatccac gaccagttcg  2520
tggctaccct ggccagcagc gcctcgagct acgccgcaac tgaggtcgcc aacgccgctg  2580
ctgccagcgg cggaagcggc ggtggtggaa gcggcggaac aatcaactac cagtttggcg  2640
acgtggacgc ccacggagct atgatcagag cccaggccgg cagcctggaa gccgaacacc  2700
aggccatcat ttcagacgtg ctgacagctt ctgatttctg gggtggggcc ggctctgctg  2760
cctgccaggg ctttatcaca cagctgggca gaaatttcca agtcatctac gagcaggcga  2820
atgcccacgg ccagaaggtg caggccgcgg ggaacaacat ggcccagaca gactcggctg  2880
tcggatcttc ttgggccggg ggcagcggtg gcggcggatc tggcgggcct gtgggcggac  2940
agtctagctt ctacagtgac tggtactccc ctgcatgcgg caaggctggc tgtcagacct  3000
acaagtggga aaccttcctg accagcgagc tccctcagtg gctgagcgcc aatagagcag  3060
ttaagcctac cggctctgcc gccatcggcc tgagcatggc cgggagtagc gccatgatcc  3120
tggccgccta ccaccccag cagttcatct atgccggaag cctgagcgcc ctgctggacc  3180
ctagccaggg gatgggagga ggttcaggtg gaggtggatc tggcggcttc gccgcgaccg  3240
tgcctccacc tgtggtcgcc gccaatagag ctgaactggc cgtgctggcc gcgacaaacg  3300
gggggttctgg aggtggcggg tctggcggca gagccgctat ggtggacccc gtggtggtgg  3360
ccgccaaccg gagcgccttc gtgcagctgg tgctgagcaa cggcggcagc ggcggtggcg  3420
```

-continued

```
gatcaggcgg cctgatcccc atcgccgttg gcggtgccct ggctggcctg gtcctgatcg  3480
tgctgatcgc ctacctggtg gggagaaagc ggagccacgc cggttaccag accatctgat  3540
aataggctcg ctttcttgct gtccaatttc tattaaaggt tcctttgttc cctaagtcca  3600
actactaaac tgggggatat tatgaagggc cttgagcatc tggattctgc ctaataaaaa  3660
acatttattt tcattgcaa                                              3679

SEQ ID NO: 417          moltype = AA  length = 1162
FEATURE                 Location/Qualifiers
source                  1..1162
                        mol_type = protein
                        organism = synthetic construct
SEQUENCE: 417
MAAPGSARRP LLLLLLLLLL GLMHCASATA ASDNFQLSQG GQGFAIPIGQ AMAIAGQIRS  60
GGGSPTVHIG PTAFLGLGVV DNNGNGARVQ RVVGSAPAAS LGISTGDVIT AVDGAPINSA  120
TAMADALNGH HPGDVISVTW QTKSGGTRTG NVTLAEGPPA GGSGGGGSGG VDFGALPPEI  180
NSARMYAGPG SASLVAAAQM WDSVASDLFS AASAFQSVVW GLTVGSWIGS SAGLMVAAAS  240
PYVAWMSVTA GQAELTAAQV RVAAAAYETA YGLTVPPPVI AENRAELMIL IATNLLGQNT  300
PAIAVNEAEY GEMWAQDAAA MFGYAAATAT ATATLLPFEE APEMTSAGGL LEQAAAVEEA  360
SDTAAANQLM NNVPQALQQL AQPTQGTTPS SKLGGLWKTV SPHRSPISNM VSMANNHMGG  420
SGGGGSGGAE MKTDAATLAQ EAGNFERISG DLKTQIDQVE STAGSLQGQW RGAAGTAAQA  480
AVVRFQEAAN KQKQELDEIS TNIRQAGVQY SRADEEQQQA LSSQMGFGGG GSGGGGSTEQ  540
QWNFAGIEAA ASAIQGNVTS IHSLLDEGKQ SLTKLAAAWG GSGSEAYQGV QQKWDATATE  600
LNNALQNLAR TISEAGQAMA STEGNVTGMF AGGSGGGGSG GSFVMAYPEM LAAAADTLQS  660
IGATTVASNA AAAAPTTGVV PPAADEVSAL TAAHFAAHAA MYQSVSARAA AIHDQFVATL  720
ASSASSYAAT EVANAAAASG GSGGGGSGGT SRFMTDPHAM RDMAGRFEVH AQTVEDEARR  780
MWASAQNISG AGWSGMAEAT SLDTMTQMNQ AFRNIVNMLH GVRDGLVRDA NNYEQQEQAS  840
QQILSSGGGG SGGGGSTINY QFGDVDAHGA MIRAQAGSLE AEHQAIISDV LTASDFWGGA  900
GSAACQGFIT QLGRNFQVIY EQANAHGQKV QAAGNNMAQT DSAVGSSWAG GSGGGGSGGP  960
VGGQSSFYSD WYSPACGKAG CQTYKWETFL TSELPQWLSA NRAVKPTGSA AIGLSMAGSS  1020
AMILAAYHPQ QFIYAGSLSA LLDPSQGMGG GSGGGGSGGF AATVPPPVVA ANRAELAVLA  1080
ATNGGSGGGG SGGRAAMVDP VVVAANRSAF VQLVLSNGGS GGGGSGGLIP IAVGGALAGL  1140
VLIVLIAYLV GRKRSHAGYQ TI                                          1162

SEQ ID NO: 418          moltype = RNA  length = 3679
FEATURE                 Location/Qualifiers
source                  1..3679
                        mol_type = other RNA
                        organism = synthetic construct
SEQUENCE: 418
acatttgctt ctgacacaac tgtgttcact agcaacctca aacagccacc atggccgccc  60
ctggcagcgc cagaagaccc ctgttactgt tgctgctgtt attgctgctg ggactgatgc  120
actgcgccag cgctaccgct gcgtctgata acttccagct gagccagggt gggcagggct  180
ttgctattcc catcgggcag gccatggcca tcgccggcca gatccgcagc ggaggtggct  240
ctccaaccgt gcacatcggc cctacagctt tcctgggcct gggagtggtg gacaacaacg  300
gcaacggcgc aagggtgcaa agagtggtgg gctcagcccc tgctgcctcc ctgggcatca  360
gcaccggcga cgtgatcacc gccgtggacg gcgcccctat caacagcgcc acagccatgg  420
ccgacgccct caacggccac catcctggag atgtgatcag cgtgacctgg cagacaaaga  480
gcggcggcac cagaaccggc aatgtgaccc tggccgaagg ccctcctgcc ggaggctctg  540
gaggcggtgg atctggcgga gttgatttcg gcgccctgcc ccccgaaatt aacagcgcca  600
gaatgtacgc cggccccggc tccgctagcc tggttgcagc cgctcagatg tgggatagcg  660
tggccagcga cctgttcagc gcggcctctg ccttccaaag cgtggtgtgg ggcctgacag  720
tggggagctg gatcggctcc agcgccggac tgatggtggc tgccgcaagc ccttacgtgg  780
cctggatgag cgtcacagcc gggcaggccg agctgaccgc cgctcaggtt cgggtggccg  840
ctgccgccta tgaaaccgcc tacggattaa cagtgccacc tcctgtcatc gccgagaacc  900
gggctgagct gatgatcctg atcgccacca atctgctggg ccagaatacc cctgctatcg  960
ccgtgaacga ggccgaatac ggcgagatgt gggcccagga cgcagccgct atgttcggct  1020
acgccgccgc caccgccacc gctaccgcta ccctgctccc cttcgaagaa gcccctgaga  1080
tgacatctgc cggcggcctg cttgagcagg ccgccgccgt ggaggaagcc tccgacaccg  1140
ccgcagctaa ccagctgatg aacaacgtgc cccaggctct gcagcagctg gcccaaccta  1200
cccagggcac cacccctagc agcaagctgg gaggactgtg gaagaccgtc tcccctcaca  1260
gaagccctat ctctaacatg gtctccatgg ctaacaacca catgggcggc agcggtggtg  1320
gcggatcagg cggagccgaa atgaaaaccg acgccgccac cctggcccaa gaggcgggca  1380
acttcgagcg gatcagcggg gacctgaaga cccagattga ccaggtggag agcaccgccg  1440
gctccctgca aggccaatgg agaggcgccg ccggtacggc tgcccaggcc gctgtggtta  1500
gatttcagga ggctgctaac aagcagaagc aggagctgga cgagatcagc accaacatcc  1560
ggcaggcagg cgtgcagtac agtagagccg acgaggaaca gcagcaagct ctgagcagcc  1620
agatgggctt cggtggaggc gggagcggag gcggcggtag tacagagcag cagtggaact  1680
ttgccggaat cgaggcggca gccagtgcca tccagggcaa cgtgacatca attcacagcc  1740
tgctggacga gggcaaacag agcctgacca agctggccgc agcctgggga ggctctggct  1800
ctgaagctta ccagggcgtt cagcaaaagt gggacgcaac agccaccgaa ctgaacaacg  1860
ccctgcagaa cctggcccgg accataagcg aggccggaca ggcaatggcc agcaccgagg  1920
gcaatgtgac cggaatgttc gccggcggca gcggtggagg aggctctgga ggtagttttg  1980
tgatggctta cccagaaatg ctggccgctg ccgccgacac cctgcagtct atcggcgcaa  2040
caaccgtggc ctctaatgcc gccgccgccg cccctaccac aggcgtggtg ccgcctgccg  2100
ctgacgaggt gtcagctctg accgcggcgc atttcgcggc ccacgccgcc atgtaccaga  2160
gcgtgtctgc cagagccgcc gccatccacg accagttcgt ggccaccctg gccagcagcg  2220
ccagtagcta cgctgccaca gaagtggcta acgcagccgc cgccagcggt ggttccggcg  2280
gtggtggaag cggcggaacc tccagattca tgaccgatcc ccacgccatg agagacatgg  2340
ccggtagatt cgaggtgcac gcccagaccg ttgaagatga agcccggaga atgtgggcta  2400
```

```
gcgcccaaaa tatctccggc gccggatggt ctggcatggc tgaggccaca agcttggata  2460
cgatgaccca gatgaaccag gcctttagaa acatcgtgaa catgctccac ggcgttagag  2520
acggcctggt gcgggacgcc aacaattacg agcagcagga acaggcctct cagcagatcc  2580
tgagctctgg tggcggcgga tctggcggag gaggttcaac aatcaactac cagtttggcg  2640
atgtggatgc ccacggagcc atgatcagag cccaggctgg ctctcttgaa gccgagcacc  2700
aggccatcat cagcgatgtg ctgactgcaa gcgacttctg gggcggtgcc ggctccgctg  2760
cttgtcaggg cttcatcaca cagctgggaa gaaacttcca ggtgatctac gagcaggcca  2820
atgcgcatgg ccaaaaagtg caggcagccg gaaacaacat ggcccagacc gacagcgctg  2880
tgggaagcag ctgggccggc ggcagcggtg gaggtggatc tggcggtcca gtgggcggcc  2940
agagcagctt ctacagcgac tggtacagcc ctgcgtgcgg caaggccggc tgccagacct  3000
acaaatggga gacattcctg acatctgagc tgcctcagtg gctgagcgcc aatcgggccg  3060
tgaagcccac cggcagtgcc gccatcggac tgagcatggc tggctcctcc gccatgattc  3120
tggctgccta ccacccccag cagttcatct atgccgggag cctgagcgcc ctgctggacc  3180
ccagccaggg aatgggtggc gggtctggcg gtggcggatc aggcggcttc gccgccaccg  3240
tgcctccacc tgtggtcgcc gccaacagag ccgagctggc tgtgctggcc gctacaaacg  3300
ggggcagcgg aggcggaggt agtggcggca gagccgccat ggtggaccct gtggtggtgg  3360
ccgccaaccg gagcgctttt gtgcagctgg tgctgagcaa tggcggctct ggtggtggag  3420
ggtcaggcgg gctgatccct atcgccgtgg gcggtgccct ggccggccta gtgctgatcg  3480
tgctgatcgc ctacctggtg ggcagaaagc ggagccacgc cggctaccag acaatctgat  3540
aataggctcg ctttcttgct gtccaatttc tattaaaggt tcctttgttc cctaagtcca  3600
actactaaac tgggggatat tatgaagggc cttgagcatc tggattctgc ctaataaaaa  3660
acatttattt tcattgcaa                                              3679
```

```
SEQ ID NO: 419          moltype = AA  length = 1225
FEATURE                 Location/Qualifiers
source                  1..1225
                        mol_type = protein
                        organism = synthetic construct
SEQUENCE: 419
MAAPGSARRP LLLLLLLLLL GLMHCASATA ASDNFQLSQG GQGFAIPIGQ AMAIAGQIRS  60
GGGSPTVHIG PTAFLGLGVV DNNGNGARVQ RVVGSAPAAS LGISTGDVIT AVDGAPINSA  120
TAMADALNGH HPGDVISVTW QTKSGGTRTG NVTLAEGPPA GGSGGGGSGG AEMKTDAATL  180
AQEAGNFERI SGDLKTQIDQ VESTAGSLQG QWRGAGGSGG GGSGGTSRFM TDPHAMRDMA  240
GRFEVHAQTV EDEARRMWAS AQNISGAGWS GGGSGGGGSG GTEQQWNFAG IEAAASAIQG  300
NVTSIHSLLD EGKQSLTKLA AAWGGSGSGG SGGGGSGGTI NYQFGDVDAH GAMIRAQAGS  360
LEAEHQAIIS DVLTASDFWG GAGSGGSGGG GSGGVDFGAL PPEINSARMY AGPGSASLVA  420
AAQMWDSVAS DLFSAASAFQ SVVWGLTVGS WIGSSAGLMV AAASPYVAWM SVTAGQAELT  480
AAQVRVAAAA YETAYGLTVP PPVIAENRAE LMILIATNLL GQNTPAIAVN EAEYGEMWAQ  540
DAAAMFGYAA ATATATATLL PFEEAPEMTS AGGLLEQAAA VEEASDTAAA NQLMNNVPQA  600
LQQLAQPTQG TTPSSKLGGL WKTVSPHRSP ISNMVSMANN HMGGSGGGGS GGSFVMAYPE  660
MLAAAADTLQ SIGATTVASN AAAAAPTTGV VPPAADEVSA LTAAHFAAHA AMYQSVSARA  720
AAIHDQFVAT LASSASSYAA TEVANAAAAS GGSGGGGSGG GQWRGAAGTA AQAAVVRFQE  780
AANKQKQELD EISTNIRQAG VQYSRADEEQ QQALSSQMGF GGSGGGGSGG SGAGWSGMAE  840
ATSLDTMTQM NQAFRNIVNM LHGVRDGLVR DANNYEQQEQ ASQQILSSGG SGGGGSGGGG  900
SGSEAYQGVQ QKWDATATEL NNALQNLART ISEAGQAMAS TEGNVTGMFA GGSGGGGSGG  960
GGAGSAACQG FITQLGRNFQ VIYEQANAHG QKVQAAGNNM AQTDSAVGSS WAGGSGGGGS  1020
GGPVGGQSSF YSDWYSPACG KAGCQTYKWE TFLTSELPQW LSANRAVKPT GSAAIGLSMA  1080
GSSAMILAAY HPQQFIYAGS LSALLDPSQG MGGGSGGGGS GGFAATVPPP VVAANRAELA  1140
VLAATNGGSG GGGSGGRAAM VDPVVVAANR SAFVQLVLSN GGSGGGGSGG LIPIAVGGAL  1200
AGLVLIVLIA YLVGRKRSHA GYQTI                                       1225
```

```
SEQ ID NO: 420          moltype = RNA  length = 3868
FEATURE                 Location/Qualifiers
source                  1..3868
                        mol_type = other RNA
                        organism = synthetic construct
SEQUENCE: 420
acatttgctt ctgacacaac tgtgttcact agcaacctca aacagccacc atggccgcac  60
ctggctcagc ccgcagacct ctgctgctgc tgctattgct gctgctcctg ggactgatgc  120
actgcgcctc tgccaccgcc gcttccgaca acttccagct gagccagggc ggccaaggct  180
tcgccatccc catcggccag gctatggcaa tcgcgggaca aatcagaagc ggaggtggct  240
ctcccactgt gcacatcggc cctaccgcat tcctgggcct gggcgtggtg gacaacaacg  300
gcaacggcgc ccgggtgcag agagtggtgg gctcagctcc cgccgccagc ctgggcataa  360
gcaccgggga tgtgataaca gccgtggatg gcgcccctat caacagcgct actgccatgg  420
ccgatgccct gaacggccac caccccggcg acgtgatcag cgtgacctgg cagactaaga  480
gcggcggcac aagaacaggc aatgtgaccc tggccgaagg ccctcctgcc ggcggctctg  540
gaggcggtgg atctggcggc gccgaaatga agacagacgc cgccaccctg gcccaggagg  600
ccggaaattt cgaaagaatc agcggcgatc tgaagaccca gatcgaccag gtcgagagca  660
cagcgggaag cctgcagggc cagtggagag gcgccggcgg ctccggtggt ggcggatcag  720
gcggcacaag ccgattcatg accgatccgc acgccatgcg ggacatggcc gggaggttcg  780
aggtgcacgc ccagaccgtg gaagatgaag cccggcggat gtgggctagc gctcagaaca  840
tcagcggggc cggatggagc ggaggcggga gcggaggcgg cggtagtgga ggcaccgagc  900
agcaatggaa cttcgctgga atcgaggccg ccgccagcgc tattcagggc aacgtgacca  960
gcatccactc tctgctggac gagggcaaac agtccctgac caaactggcc gccgcctggg  1020
gcggcagcgg ctctggcgga agcggtggag gaggctctgg cggaaccata aactaccagt  1080
tcggcgacgt ggatgctcac ggcgccatga tccgggccca ggccggaagc ctggaagccg  1140
aacaccaggc catcatcagc gacgtgctga ccgcatctga cttctggggc ggcgcgggct  1200
ccggaggttc cggcggtggt ggaagcggag gcgtggactt cggcgctctc ccccctgaga  1260
tcaacagcgc cagaatgtac gccggaccag gctcagcctc cctggtagcg gcggctcaga  1320
```

```
tgtgggacag cgtggctagc gacctgttca gcgccgccag cgccttccag agcgtggtct  1380
ggggactgac cgtgggcagc tggatcggaa gcagcgccgg cctgatggtg gccgccgcca  1440
gcccctacgt ggcctggatg agcgttaccg ccggtcaagc cgagctgaca gccgctcagg  1500
tgcgcgtggc cgccgctgcc tacgagacag cctatggcct gaccgtgccc ccccccgtga  1560
ttgctgaaaa ccgggccgag ctgatgatcc tcatcgccac caacctgctt ggccagaaca  1620
cccctgccat cgccgtgaac gaggccgaat acggcgagat gtgggctcag gacgccgccg  1680
ccatgttcgg ctacgccgcc gccacagcta ccgccaccgc tacactatta ccattcgaag  1740
aggcccctga aatgacctcc gccggcggcc tgctggaaca agccgcggcc gtggaagagg  1800
ccagcgatac cgctgccgcc aaccagctga tgaacaatgt gccacaggcc ctgcagcagc  1860
tggctcaacc tacccagggc accacaccta gcagcaagct gggaggcctg tggaagaccg  1920
tgtccccaca cagaagcccc atcagcaaca tggtctccat ggctaacaac cacatgggcg  1980
gaagcggtgg cggcggatct ggcggcagtt ttgtgatggc ttatcctgag atgctggccg  2040
ctgctgccga caccctgcag agtatcggtg ccaccaccgt ggccagcaac gcagccgcgg  2100
ctgcccctac aaccggcgtg gtgcctcccg ctgccgacga ggtgtctgcc ctgacggccg  2160
cccatttcgc cgctcatgcc gctatgtacc agagcgtgtc cgccagagcc gccgccattc  2220
atgaccagtt cgtagcgaca ctggcctctt ctgcctcctc atatgccgcc acagaggtgg  2280
ccaacgccgc tgccgcatcc gggggcagcg gcggaggagg ttcaggcggc ggacagtggc  2340
ggggcgctgc tggcaccgcc gcccaggcgg cagtggtgag atttcaggag gctgccaaca  2400
agcagaaaca ggagctggac gagatctcca ccaatatcag acaggccggc gttcagtaca  2460
gccgggctga cgaggaacag cagcaggccc tgtcaagcca gatgggattt ggcggtagcg  2520
gtggaggtgg atctggcggc agcggagccg gatggtccgg catggccgag gccacctctc  2580
tggatacaat gacccaaatg aaccaagcat tccggaacat cgtgaacatg ctgcacggcg  2640
ttagagacgg ccttgtgcgg gacgccaaca actacgagca gcaggagcag gcaagccagc  2700
agatcctatc tagcggtggc agcggaggtg gcgggtctgg cggtggcgga tcaggctctg  2760
aagcctacca gggagtccag cagaaatggg acgccacagc tacggaactg aacaatgccc  2820
tgcaaaatct ggctagaacc atcagcgagg cgggacaggc tatggccagc accgaaggca  2880
atgtcacagg catgttcgcc ggcggctctg gaggcggagg tagtgggggc ggcggcgctg  2940
gctcggccgc ttgccagggg ttcatcaccc agctgggcag aaacttccag gtgatctacg  3000
agcaggccaa cgctcacggc cagaaggtgc aggcggccgg aaacaacatg gcccagaccg  3060
acagcgccgt ggggtcaagc tgggccggcg gaagcggtgg tggagggtca ggcggccctg  3120
tgggcggaca gtctagcttc tacagcgact ggtacagccc tgcctgcggg aaggccggtt  3180
gtcagacata caagtgggag acattcctga ccagcgagct gcctcagtgg ctgtctgcga  3240
atagagccgt gaagcctacc gggagcgcag ccatcggcct gagtatggcc ggctcgtctg  3300
ccatgatcct ggccgcttac caccctcagc aatttatcta cgcaggatct ctgagcgccc  3360
tgctggaccc ttctcaaggc atgggcggtg gaagcggagg aggcggttct ggaggctttg  3420
ccgccaccgt gccacctcct gtggttgccg ctaaccggcc cgaactggct gtgctggctg  3480
cgacgaacgg cggatctggc ggcggcggta gcggaggcag agccgcaatg gtggaccccg  3540
tggtcgtggc cgcaaataga agcgcctttg tgcagctggt gctgtctaat ggcgggagcg  3600
gcgggggcgg tagcggcggc ctgatcccta ttgccgtcgg cggcgcactg gccggcctgg  3660
tgctgatcgt gctgatcgcc tacctggttg gcagaaagag aagtcacgcc ggttatcaaa  3720
caatctgata ataggctcgc tttcttgctg tccaatttct attaaaggtt cctttgttcc  3780
ctaagtccaa ctactaaact gggggatatt atgaagggcc ttgagcatct ggattctgcc  3840
taataaaaaa catttatttt cattgcaa                                    3868
```

```
SEQ ID NO: 421         moltype = AA  length = 1185
FEATURE                Location/Qualifiers
source                 1..1185
                       mol_type = protein
                       organism = synthetic construct
SEQUENCE: 421
MAVMAPRTLL LLLLGALALT QTWAGSSRAF IIDPTISAID GLYDLLGIGI PNQGGILYSS  60
LEYFEKALEE LAAAFPGDGW LGSAADKYAG KNRNHVNFFQ ELADLDRQLI SLIHDQANAV  120
QTTRDILEGA KKGLEFVRPV AVDLTYIPVV GHALSAAFQA PFCAGAMAVV GGALAYLVVK  180
TLINATQLLK LLAKLAELVA AAIADIISDV ADIIKGTLGE VWEFITNALN GLKELWDKLT  240
GWVTGLFSRG WSNLESFFAG VPGLTGATSG LSQVTGLFGA AGLSASSGLA HADSLASSAS  300
LPALAGIGGG SGFGGLPSLA QVHAASTRQA LRPRADGPVG AAAEQVGGQS QLVSAQGSQG  360
MGGPVGMGGM HPSSGASKGT TTKKYSEGAA AGTEDAERAP VEADAGGGQK VLVRNVVGGS  420
GGGGSGGITD RLPAKAPLLE LDGGSGGGGS GGAITINMVN PTGFIRYEDV EQEAMTSDVT  480
VGPAPGQYQL SHLRLLEEAA IHVIREVAAE FERPVLLFSG GKDSIVMLHL ALKAFRPGRL  540
PFPVMHVDTG HNFDEVIATR DELVAAAGVR LVVASVQDDI DAGRVVETIP SRNPIQTVTL  600
LRAIRENQFD AAFGGARRDE EKARAKERVF SFRDEFGQWD PKAQRPELWN LYNGRHHKGE  660
HIRVFPLSNW TEFDIWSYIG AEQVRLPSIY FAHRRKVFQR DGMLLAVHRH MQPRADEPVF  720
EATVRFRTVG DVTCTGCVES SASTVAEVIA ETAVARLTER GATRADDRIS EAGMEDRKRQ  780
GYFGGSGGGG SGGKRVEIEV DDDLIQKVIR GGSGGGGSGG APPALSQDRF ADFPALPLDP  840
SAMVAQVGPQ VVNINTKLGY NNAVGAGTGI VIDPNGVVLT NNHVIAGATD INAFSVGSGQ  900
TYGVDVVGYD RTQDVAVLQL RGAGGLPSAA IGGGVAVGEP VVAMGNSGGQ GGTPRAVPGR  960
VVALGQTVQA SDSLTGAEET LNGLIQFDAA IQPGDSGGPV VNGLGQVVGM NGGSGGGGSG  1020
GALAWMCDRA VDLLLLGGSG GGGSGGAIHV MTTVLATLPA DGGSGGGGSG GTTRVMATRR  1080
NVLDRQGGSG GGGSGGVARV LRPGGHFLYT DGGSGGGGSG GEPSSQSTVP IVGIVAGLAV  1140
LAVVVIGAVV AAVMCRRKSS GGKGGSYSQA ACSDSAQGSD VSLTA                 1185
```

```
SEQ ID NO: 422         moltype = RNA  length = 3748
FEATURE                Location/Qualifiers
source                 1..3748
                       mol_type = other RNA
                       organism = synthetic construct
SEQUENCE: 422
acatttgctt ctgacacaac tgtgttcact agcaacctca aacagccacc atggctgtga  60
tggccccgcg caccctcctg ctgctcctgc tgggagcgct cgcattgacc cagacttggg  120
```

-continued

```
ccgggtcatc ccgcgccttc attattgacc ctaccatttc cgccattgac ggtctgtacg  180
atctgctggg aatcggcatc ccaaaccaag gagggatcct ctactcctcg ttggaatact  240
tcgagaaggc actcgaggaa cttgccgccg cattcccggg cgatggatgg ctgggaagcg  300
ctgctgacaa atacgcgggg aagaaccgga accatgtcaa cttcttccaa gagctcgccg  360
acctggaccg gcagctcata tccctgattc acgaccaggc caatgctgtg cagaccactc  420
gggatatcct ggagggagct aagaagggat tggaattcgt gcggcctgtg gctgtggacc  480
tgacctacat tccggtggtc ggccacgcgc tgtccgcggc gttccaggcg cctttctgtg  540
ccggagctat ggccgtggtc ggtggagctc tcgcctacct cgtggtcaaa accctgatca  600
atgccaccca gctgctgaag ctgctggcta agctcgcgga gttggtcgcc gccgcgattg  660
ccgatatcat tagcgacgtg gcagacatca tcaagggcac cctcggagaa gtctgggaat  720
tcatcaccaa cgccctgaac ggtctgaagg aactgtggga taagctgact ggatgggtca  780
ccggactgtt cagccgcgga tggtccaacc tggagagctt cttcgccgga gtgcccggac  840
tcaccggtgc cacctccggg ctttcccaag ttaccggact cttcggggcc gccggcctgt  900
cggcctcatc cggcctggca cacgccgata gcctggcatc ctcggcatcg ctccccgcgc  960
tcgcgggcat cgggggtggc agcggatttg gcggactgcc ctcgctggca caagtgcacg  1020
ccgccagcac tcggcaggcg ctgcgcccga gagccgacgg ccccgtggga gccgctgcgg  1080
aacaagtcgg tggccagtct caacttgtgt ccgcgcaggg aagccagggg atgggtggcc  1140
ctgtgggaat gggcggaatg catccaagct ccggggcctc gaagggcact accaccaaga  1200
agtactccga gggcgctgcg gccggcactg aagatgctga acgggccccg gtggaggccg  1260
atgccggtgg cgggcaaaag gtgctcgtac ggaatgtcgt gggaggttct ggtggcgggg  1320
gctccggtgg aatcaccgac cggctcccgg ccaaggctcc cctgctggag cttgatggtg  1380
gatccggggg aggcggttcc ggcggtgcca tcaccatcaa catggtcaac cccactggct  1440
ttatccgcta tgaggatgtg gaacaggagg ccatgacctc agacgtgacc gtgggacccg  1500
cccccggcca gtaccagctg tcccacctcc gcctgctcga ggccgaagcg attcacgtga  1560
tcagggaagt ggcggccgaa tttgagcgcc cggtgctgct gttcagcggt ggaaaggata  1620
gcattgtgat gttgcatttg gccctcaagg ccttccgacc tggtcggctc ccgttccctg  1680
tgatgcatgt ggataccgga cacaacttcg acgaggtcat cgcaacgcgc gacgagttgg  1740
tggcagccgc cggcgtgcgc ctggtagtgg ccagcgtgca agacgacatc gacgccggca  1800
gagtggtgga aaccatcccc tcccgcaacc ctattcagac cgtgaccctg ctgagagcca  1860
ttagggaaaa ccagttcgac gctgccttcg gaggcgcccg gcgggatgag gagaaagcgc  1920
gcgcgaagga aagagtgttc tcctttcggg acgagtttgg acagtgggac cctaaggcgc  1980
aacggcccga gttgtggaac ctgtacaacg gacggcacca taagggggag cacatccggg  2040
tctttcctct gtccaactgg acagagttcg atatttggag ctacattgga gccgaacaag  2100
tccggctgcc gtccatctac ttcgcacacc ggagaaaagt gttccagcgc gacggcatgc  2160
tcctcgcggt gcacaggcat atgcagccca gggcagacga gccggtgttt gaagccaccg  2220
tcagattccg cacagtgggc gacgtgactt gcaccggctg cgtggaatcc tccgcgtcca  2280
ccgtggccga agtgatcgct gagactgcgg tcgccagatt gaccgagcgg ggtgccacaa  2340
gagccgatga ccgcattagc gaagcgggga tggaggatcg gaagagacaa ggatactttg  2400
gaggctcagg gggtggaggc tcgggcggaa agcgcgtcga gatcgaagtc gacgatgatc  2460
tgatccaaaa ggtcatccgg ggtggaagcg gcggaggggg aagcgggggc gcgccgcccg  2520
cgttaagtca ggaccggttc gccgacttcc cggccctgcc cctggaccct tcggcgatgg  2580
tggcccaagt tggcccccaa gtggtgaaca ttaacactaa gctgggatac aacaacgctg  2640
tgggcgcggg cactggaatc gtcatcgacc ctaacggcgt ggtgctaacc aacaaccatg  2700
tgatagccgg ggccaccgat atcaacgcct tcagcgtggg gtccggacag acttacggag  2760
tggacgtcgt gggttacgac aggacccagg acgtggccgt gctgcaactg aggggagccg  2820
gaggactgcc cagcgccgcg atcggaggag gggtggccgt gggtgaaccg gtggtggcca  2880
tgggaaattc cggcggacag ggaggcaccc cgagggcggt gcccggccgc gtggtcgctc  2940
tcggtcaaac cgtgcaggcc tccgacagcc tgactggcgc cgaggaaact ctgaacggcc  3000
tgatccagtt cgatgcggcc atccagccgg gagactcggg gggacctgtg gtcaacggac  3060
tgggacaggt cgtgggcatg aacggcggct cgggaggggg tggctccggg ggcgccctgg  3120
cctggatgtg cgacagagct gtggatttgc tccttctggg gggatcgggt ggtggcggat  3180
ctggagggggc catccacgtg atgacgactg tcctggccac cctgccggcc gatggcggct  3240
ccggcggagg aggttcgggc ggaactacta gagtgatggc cacacgacgg aacgtgctgg  3300
accgccaggg gggatccggc ggcgggggca gcggaggagt ggcccgcgtc cttagacctg  3360
gaggacactt cctgtatacc gacggaggat ccggaggagg aggatcaggc ggagaaccga  3420
gttcccagtc aaccgtgccc atcgtcggga tcgtggcagg actcgccgtg ttggcagtcg  3480
tcgtcattgg cgccgtggtg gccgccgtga tgtgccgccg gaagtcctca gggggggaagg  3540
gaggctcgta cagccaggcc gcctgttccg actcggccca ggggtccgac gtgtccctta  3600
ctgcatgata ataggctcgc tttcttgctg tccaatttct attaaaggtt cctttgttcc  3660
ctaagtccaa ctactaaact gggggatatt atgaagggcc ttgagcatct ggattctgcc  3720
taataaaaaa catttatttt cattgcaa                                     3748
```

```
SEQ ID NO: 423          moltype = AA  length = 1158
FEATURE                 Location/Qualifiers
source                  1..1158
                        mol_type = protein
                        organism = synthetic construct
SEQUENCE: 423
MAAPGSARRP LLLLLLLLLL GLMHCASASR AFIIDPTISA IDGLYDLLGI GIPNQGGILY  60
SSLEYFEKAL EELAAAFPGD GWLGSAADKY AGKNRNHVNF FQELADLDRQ LISLIHDQAN  120
AVQTTRDILE GAKKGLEFVR PVAVDLTYIP VVGHALSAAF QAPFCAGAMA VVGGALAYLV  180
VKTLINATQL LKLLAKLAEL VAAAIADIIS DVADIIKGTL GEVWEFITNA LNGLKELWDK  240
LTGWVTGLFS RGWSNLESFF AGVPGLTGAT SGLSQVTGLF GAAGLSASSG LAHADSLASS  300
ASLPALAGIG GGSGFGGLPS LAQVHAASTR QALRPRADGP VGAAAEQVGG QSQLVSAQGS  360
QGMGGPVGMG GMHPSSGASK GTTTKKYSEG AAAGTEDAER APVEADAGGG QKVLVRNVVG  420
GSGGGGSGGI TDRLPAKAPL LELDGGSGGG GSGGAITINM VNPTGFIRYE DVEQEAMTSD  480
VTVGPAPGQY QLSHLRLLEA EAIHVIREVA AEFERPVLLF SGGKDSIVML HLALKAFRPG  540
RLPFPVMHVD TGHNFDEVIA TRDELVAAAG VRLVVASVQD DIDAGRVVET IPSRNPIQTV  600
TLLRAIRENQ FDAAFGGARR DEEKARAKER VFSFRDEFGQ WDPKAQRPEL WNLYNGRHHK  660
```

-continued

```
GEHIRVFPLS NWTEFDIWSY IGAEQVRLPS IYFAHRRKVF QRDGMLLAVH RHMQPRADEP  720
VFEATVRFRT VGDVTCTGCV ESSASTVAEV IAETAVARLT ERGATRADDR ISEAGMEDRK  780
RQGYFGGSGG GGSGGKRVEI EVDDDLIQKV IRGGSGGGGS GGAPPALSQD RFADFPALPL  840
DPSAMVAQVG PQVVNINTKL GYNNAVGAGT GIVIDPNGVV LTNNHVIAGA TDINAFSVGS  900
GQTYGVDVVG YDRTQDVAVL QLRGAGGLPS AAIGGGVAVG EPVVAMGNSG GQGGTPRAVP  960
GRVVALGQTV QASDSLTGAE ETLNGLIQFD AAIQPGDSGG PVVNGLGQVV GMNGGSGGGG  1020
SGGALAWMCD RAVDLLLLGG SGGGGSGGAI HVMTTVLATL PADGGSGGGG SGGTTRVMAT  1080
RRNVLDRQGG SGGGGSGGVA RVLRPGGHFL YTDGGSGGGG SGGLIPIAVG GALAGLVLIV  1140
LIAYLVGRKR SHAGYQTI                                                1158

SEQ ID NO: 424         moltype = RNA  length = 3667
FEATURE                Location/Qualifiers
source                 1..3667
                       mol_type = other RNA
                       organism = synthetic construct
SEQUENCE: 424
acatttgctt ctgacacaac tgtgttcact agcaacctca aacagccacc atggccgctc  60
ctggcagcgc tcggcggcca ctgctgctgc tactcctcct gctgctgctg ggactgatgc  120
actgcgcgag cgcctccaga gcatttatca tcgatcctac catttctgcc atcgacgggc  180
tgtacgatct gctgggcatc ggcatcccta accagggcgg catcctgtat agctctctgg  240
agtactttga gaaggctctg gaggaactgg ctgccgcgtt tcctggcgat ggatggctgg  300
gcagcgccgc cgacaaatac gccggaaaaa acagaaacca cgttaacttc ttccaggagc  360
tggccgacct cgacagacag ctcatctccc tgatacatga tcaggccaac gccgtccaga  420
ccacccggga catcctggaa ggcgccaaaa agggcctgga gttcgtgcgg cccgtggccg  480
tggatctgac ttacatcccc gtggtggggc acgctctgag cgccgccttc caagcccctt  540
tctgcgccgg tgctatggcc gtcgtaggcg gcgccctggc ttatctggtg gttaagaccc  600
tgatcaacgc cacacagctg ctgaagttac ttgccaagct ggccgagctg gtcgctgctg  660
ccatcgctga tataatcagc gatgtggcgg acatcatcaa gggcaccctg ggcgaggtgt  720
gggagttcat caccaacgcc ctgaacggcc tgaaggagct gtgggataag ctgacagggt  780
gggtcacagg acttttcagc agaggctggt ccaatctgga aagcttcttc gctggggtgc  840
ctggcctaac cggcgccaca agcggcctga gtcaggtgac aggactgttc ggagccgctg  900
gcctgtctgc ttctagcggc ctggctcacg ccgacagtct ggcctctagc gccagcctgc  960
ctgccctggc cggcatcgga ggtggctctg gcttcggcgg cctgccaagc ctggcacagg  1020
tgcacgccgc cagcacacgg caagccctca gacctagagc cgatggccct gtgggcgccg  1080
ccgccgaaca ggtcggaggc cagagccagc tggtgtccgc ccaaggtagc cagggcatgg  1140
gaggacctgt aggcatgggc ggcatgcatc ctagcagcgg cgcctcaaag ggcaccacca  1200
caaagaagta cagcgagggc gcagccgccg gaactgagga cgcagaacgg gcccctgtcg  1260
aagccgacgc cggcggcggc caaaaagtgc tggttcggaa cgtggtgggg ggatctggag  1320
gcggtggatc tggcggcatc accgacagac tgcctgccaa ggcccctctg ctggaactgg  1380
acggcggcag cggtggtggc ggatcaggag gcgctatcac aatcaacatg gtcaatccca  1440
ccggttttat cagatacgag gacgtggaac aggaggccat gacaagcgac gtgaccgtgg  1500
gccccgctcc aggacagtac cagctgagcc acctgcggct gcttgaggcc gaagccatcc  1560
acgtgattag agaagtggcc gccgaatttg agagacccgt gcttctgttc tccggaggca  1620
aggacagcat cgtgatgctg cacctggcat tgaaagcctt tcggcctggc agactgcctt  1680
ttcctgtgat gcacgtggac accggccaca acttcgacga ggtgatcgcc accagagacg  1740
aactggtggc ggcagccgga gtgaggctgg tggtggccag cgtgcaggat gatatcgatg  1800
ccggcagagt ggtggaaacc attcccagca gaaaccccat ccaaacagtg accttactgc  1860
gggccatcag agagaaccag ttcgacgcgg ccttcggcgg cgcccggaga gatgaggaaa  1920
aggcccgggc caaagagaga gtgttttctt tcagagacga gttcggccag tgggatccca  1980
aggcccagcg gcctgagctg tggaacctgt acaacggaag acaccacaag ggagaacaca  2040
tccgggtgtt ccctctgagc aactggaccg agttcgatat ttggagctac ataggcgccg  2100
agcaggtgcg tctgcccagc atctacttcg cccatagaag aaaggtgttc caaagagatg  2160
gcatgctgct ggccgtgcac cggcacatgc agcctagagc cgatgaacct gtgttcgagg  2220
ccaccgtgcg cttccggaca gtgggcgacg tcacctgcac cggctgtgtg gagtcttctg  2280
cctctaccgt cgcagaagtg atcgccgaga cagccgtggc cagactgacc gagagaggcg  2340
ctacccgggc cgacgatcgg atctctgagg ccggcatgga agatagaaag agacagggct  2400
acttcggagg atccggtgga ggcgggagcg gcggcaagcg ggtcgagatc gaggtggacg  2460
atgacctgat ccagaaggtg attagaggag gcagcggagg cggcggtagt ggcggggctc  2520
cacctgccct gtcccaggac cgcttcgccg acttcccagc cctccctctg gaccctagcg  2580
ccatggtggc ccaggtgggc cctcaggtgg tgaacatcaa taccaagctg ggctacaaca  2640
acgctgtggg ggccggcaca ggcatcgtga tcgaccccaa tggagtggtg ctgacaaaca  2700
atcacgtgat cgccggcgcc accgatatca acgccttcag cgtgggcagc ggccagacat  2760
acggcgtgga cgtggttgga tacgacagaa cacaggacgt ggccgtgctg cagctgagag  2820
gcgcgggcgg actaccaagc gccgccatcg gcggaggtgt ggccgtgggc gagcctgtgg  2880
tggccatggg caacagcggc ggtcagggcg gcacacctcg ggctgtgccc ggcagagtgg  2940
tggctttggg ccagaccgtg caggctagcg acagcctgac cggggccgag gaaaccctga  3000
acggcctgat ccagttcgac gctgctatcc agcccggcga cagcgggggg cccgtggtga  3060
acggccttgg gcaggttgtg ggcatgaacg gcggaagcgg tggaggaggc tctggcggcg  3120
ccctggcctg gatgtgcgac agagctgttg atctgctgct gctgggcggc agcggcggtg  3180
gtggaagcgg tggtgcgatc cacgtgatga ccacagtgtt ggccacactg ccggcagacg  3240
gcggttccgg tggcggcgga tctggcggca ccaccagggt gatggccacg cgcagaaatg  3300
tgctggaccg tcaaggcggc tctggcggag gaggttcagg cggcgtggcc cgggtcctga  3360
gacctggcgg acacttcctg tacaccgatg gcggatctgg tggaggtgga tctggcggcc  3420
tgattcctat cgccgtgggg ggcgccctag caggcctggt cctgatcgtg ctgatcgcct  3480
acctggtggg cagaaagcgc agccacgccg gctatcagac catctgataa taggctcgct  3540
ttcttgctgt ccaatttcta ttaaaggttc ctttgttccc taagtccaac tactaaactg  3600
ggggatatta tgaagggcct tgagcatctg gattctgcct aataaaaaac atttattttc  3660
attgcaa                                                            3667
```

```
SEQ ID NO: 425          moltype = AA  length = 1185
FEATURE                 Location/Qualifiers
source                  1..1185
                        mol_type = protein
                        organism = synthetic construct
SEQUENCE: 425
MAVMAPRTLL LLLSGALALT QTWAGSSRAF IIDPTISAID GLYDLLGIGI PNQGGILYSS  60
LEYFEKALEE LAAAFPGDGW LGSAADKYAG KNRNHVNFFQ ELADLDRQLI SLIHDQANAV  120
QTTRDILEGA KKGLEFVRPV AVDLTYIPVV GHALSAAFQA PFCAGAMAVV GGALAYLVVK  180
TLINATQLLK LLAKLAELVA AAIADIISDV ADIIKGTLGE VWEFITNALN GLKELWDKLT  240
GWVTGLFSRG WSNLESFFAG VPGLTGATSG LSQVTGLFGA AGLSASSGLA HADSLASSAS  300
LPALAGIGGG SGFGGLPSLA QVHAASTRQA LRPRADGPVG AAAEQVGGQS QLVSAQGSQG  360
MGGPVGMGGM HPSSGASKGT TTKKYSEGAA AGTEDAERAP VEADAGGGQK VLVRNVVGGS  420
GGGGSGGITD RLPAKAPLLE LDGGSGGGGS GGAITINMVN PTGFIRYEDV EQEAMTSDVT  480
VGPAPGQYQL SHLRLLEAEA IHVIREVAAE FERPVLLFSG GKDSIVMLHL ALKAFRPGRL  540
PFPVMHVDTG HNFDEVIATR DELVAAAGVR LVVASVQDDI DAGRVVETIP SRNPIQTVTL  600
LRAIRENQFD AAFGGARRDE EKARAKERVF SFRDEFGQWD PKAQRPELWN LYNGRHHKGE  660
HIRVFPLSNW TEFDIWSYIG AEQVRLPSIY FAHRRKVFQR DGMLLAVHRH MQPRADEPVF  720
EATVRFRTVG DVTCTGCVES SASTVAEVIA ETAVARLTER GATRADDRIS EAGMEDRKRQ  780
GYFGGSGGGG SGGKRVEIEV DDDLIQKVIR GGSGGGGSGG APPALSQDRF ADFPALPLDP  840
SAMVAQVGPQ VVNINTKLGY NNAVGAGTGI VIDPNGVVLT NNHVIAGATD INAFSVGSGQ  900
TYGVDVVGYD RTQDVAVLQL RGAGGLPSAA IGGGVAVGEP VVAMGNSGGQ GGTPRAVPGR  960
VVALGQTVQA SDSLTGAEET LNGLIQFDAA IQPGDSGGPV VNGLGQVVGM NGGSGGGGSG  1020
GALAWMCDRA VDLLLLGGSG GGGSGGAIHV MTTVLATLPA DGGSGGGGSG GTTRVMATRR  1080
NVLDRQGGSG GGGSGGVARV LRPGGHFLYT DGGSGGGGSG GEPSSQSTVP IVGIVAGLAV  1140
LAVVVIGAVV AAVMCRRKSS GGKGGSYSQA ACSDSAQGSD VSLTA                  1185

SEQ ID NO: 426          moltype = RNA  length = 3748
FEATURE                 Location/Qualifiers
source                  1..3748
                        mol_type = other RNA
                        organism = synthetic construct
SEQUENCE: 426
acatttgctt ctgacacaac tgtgttcact agcaacctca aacagccacc atggctgtga  60
tggccccgcg caccctcctg ctgctcctgt cgggagcgct cgcattgacc cagacttggg  120
ccgggtcatc ccgcgccttc attattgacc ctaccatttc cgccattgac ggtctgtacg  180
atctgctggg aatcggcatc ccaaaccaag gagggatcct ctactcctcg ttggaatact  240
tcgagaaggc actcgaggaa cttgccgccg cattcccggg cgatggatgg ctgggaagcg  300
ctgctgacaa atacgcgggg aagaaccgga accatgtcaa cttcttccaa gagctcgccg  360
acctggaccg gcagctcata tccctgattc acgaccaggc caatgctgtg cagaccactc  420
gggatatcct ggagggagct aagaagggat tggaattcgt gcggcctgtg gctgtggacc  480
tgacctacat tccggtggtc ggccacgcgc tgtccgcggc gttccaggcg cctttctgtg  540
ccggagctat ggccgtggtc ggtggagctc tcgcctacct cgtggtcaaa accctgatca  600
atgccaccca gctgctgaag ctgctggcta agctcgcgga gttggtcgcc gccgcgattg  660
ccgatatcat tagcgacgtg gcagacatca tcaagggcac cctcggagaa gtctgggaat  720
tcatcaccaa cgccctgaac ggtctgaagg aactgtggga taagctgact ggatgggtca  780
ccggactgtt cagccgcgga tggtccaacc tggagagctt cttcgccgga gtgcccggac  840
tcaccggtgc cacctccggg ctttcccaag ttaccggact cttcggggcc gccggcctgt  900
cggcctcatc cggcctggca cacgccgata gcctggcatc ctcggcatcg ctccccgcgc  960
tcgcgggcat cgggggtggc agcggatttg gcggactgcc ctcgctggca caagtgcacg  1020
ccgccagcac tcggcaggcg ctgcgcccga gagccgacgg ccccgtggga gccgctgcgg  1080
aacaagtcgg tggccagtct caacttgtgt ccgcgcaggg aagccagggg atgggtggcc  1140
ctgtgggaat gggcggaatg catccaagct ccggggcctc gaagggcact accaccaaga  1200
agtactccga gggcgctgcg gccggcactg aagatgctga acgggccccg gtggaggccg  1260
atgccggtgg cgggcaaaag gtgctcgtac ggaatgtcgt gggaggttct ggtggcgggg  1320
gctccggtgg aatcaccgac cggctcccgg ccaaggctcc cctgctggag cttgatggtg  1380
gatccggggg aggcggttcc ggcggtgcca tcaccatcaa catggtcaac cccactggct  1440
ttatccgcta tgaggatgtg gaacaggagg ccatgacctc agacgtgacc gtgggacccg  1500
cccccggcca gtaccagctg tcccacctcc gcctgctcga ggccgaagcg attcacgtga  1560
tcagggaagt ggcggccgaa tttgagcgcc cggtgctgct gttcagcggt ggaaaggata  1620
gcattgtgat gttgcatttg gccctcaagg ccttccgacc tggtcggctc ccgttccctg  1680
tgatgcatgt ggataccgga cacaacttcg acgaggtcat cgcaacgcgc gacgagttgg  1740
tggcagccgc cggcgtgcgc ctggtagtgg ccagcgtgca agacgacatc gacgccggca  1800
gagtggtgga aaccatcccc tcccgcaacc ctattcagac cgtgaccctg ctgagagcca  1860
ttagggaaaa ccagttcgac gctgccttcg gaggcgcccg gcgggatgag gagaaagcgc  1920
gcgcgaagga aagagtgttc tcctttcggg acgagtttgg acagtgggac cctaaggcgc  1980
aacggcccga gttgtggaac ctgtacaacg gacggcacca taagggggag cacatccggg  2040
tctttcctct gtccaactgg acagagttcg atatttggag ctacattgga gccgaacaag  2100
tccggctgcc gtccatctac ttcgcacacc ggagaaaagt gttccagcgc gacggcatgc  2160
tcctcgcggt gcacaggcat atgcagccca gggcagacga gccggtgttt gaagccaccg  2220
tcagattccg cacagtgggc gacgtgactt gcaccggctg cgtggaatcc tccgcgtcca  2280
ccgtggccga agtgatcgct gagactgcgg tcgccagatt gaccgagcgg ggtgccacaa  2340
gagccgatga ccgcattagc gaagcgggga tggaggatcg gaagagacaa ggatactttg  2400
gaggctcagg gggtggaggc tcgggcggaa agcgcgtcga gatcgaagtc gacgatgatc  2460
tgatccaaaa ggtcatccgg ggtggaagcg gcggaggggg aagcgggggc gcgccgcccg  2520
cgttaagtca ggaccggttc gccgacttcc cggccctgcc cctggaccct tcggcgatgg  2580
tggcccaagt tggcccccaa gtggtgaaca ttaacactaa gctgggatac aacaacgctg  2640
tgggcgcggg cactggaatc gtcatcgacc ctaacggcgt ggtgctaacc aacaaccatg  2700
tgatagccgg ggccaccgat atcaacgcct tcagcgtggg gtccggacag acttacggag  2760
```

-continued

```
tggacgtcgt gggttacgac aggacccagg acgtggccgt gctgcaactg aggggagccg  2820
gaggactgcc cagcgccgcg atcggaggag gggtggccgt gggtgaaccg gtggtggcca  2880
tgggaaattc cggcggacag ggaggcaccc cgagggcggt gcccggccgc gtggtcgctc  2940
tcggtcaaac cgtgcaggcc tccgacagcc tgactggcgc cgaggaaact ctgaacggcc  3000
tgatccagtt cgatgcggcc atccagccgg gagactcggg gggacctgtg gtcaacggac  3060
tgggacaggt cgtgggcatg aacggcggct cgggaggggg tggctccggg ggcgccctgg  3120
cctggatgtg cgacagagct gtggatttgc tccttctggg gggatcgggt ggtggcggat  3180
ctggaggggc catccacgtg atgacgactg tcctggccac cctgccggcc gatggcggct  3240
ccggcggagg aggttcgggc ggaactacta gagtgatggc cacacgacgg aacgtgctgg  3300
accgccaggg gggatccggc ggcgggggca gcggaggagt ggcccgcgtc cttagacctg  3360
gaggacactt cctgtatacc gacggaggat ccggaggagg aggatcaggc ggagaaccga  3420
gttcccagtc aaccgtgccc atcgtcggga tcgtggcagg actcgccgtg ttggcagtcg  3480
tcgtcattgg cgccgtggtg gccgccgtga tgtgccgccg gaagtcctca ggggggaagg  3540
gaggctcgta cagccaggcc gcctgttccg actcggccca ggggtccgac gtgtccctta  3600
ctgcatgata ataggctcgc tttcttgctg tccaatttct attaaaggtt cctttgttcc  3660
ctaagtccaa ctactaaact gggggatatt atgaagggcc ttgagcatct ggattctgcc  3720
taataaaaaa catttatttt cattgcaa                                     3748

SEQ ID NO: 427         moltype = AA  length = 1195
FEATURE                Location/Qualifiers
source                 1..1195
                       mol_type = protein
                       organism = synthetic construct
SEQUENCE: 427
MAVMAPRTLL LLLLGALALT QTWAGSSRAF IIDPTISAID GLYDLLGIGI PNQGGILYSS  60
LEYFEKALEE LAAAFPGDGW LGSAADKYAG KNRNHVNFFQ ELADLDRQLI SLIHDQANAV  120
QTTRDILEGA KKGLEFVRPV AVDLTYIPVV GHALSAAFQA PFCAGAMAVV GGALAYLVVK  180
TLINATQLLK LLAKLAELVA AAIADIISDV ADIIKGTLGE VWEFITNALN GLKELWDKLT  240
GWVTGLFSRG WSNLESFFAG VPGLTGATSG LSQVTGLFGA AGLSASSGLA HADSLASSAS  300
LPALAGIGGG SGFGGLPSLA QVHAASTRQA LRPRADGPVG AAAEQVGGQS QLVSAQGSQG  360
MGGPVGMGGM HPSSGASKGT TTKKYSEGAA AGTEDAERAP VEADAGGGQK VLVRNVVGGS  420
GGGGSGGITD RLPAKAPLLE LDGGSGGGGS GGAITINMVN PTGFIRYEDV EQEAMTSDVT  480
VGPAPGQYQL SHLRLLEAEA IHVIREVAAE FERPVLLFSG GKDSIVMLHL ALKAFRPGRL  540
PFPVMHVDTG HNFDEVIATR DELVAAAGVR LVVASVQDDI DAGRVVETIP SRNPIQTVTL  600
LRAIRENQFD AAFGGARRDE EKARAKERVF SFRDEFGQWD PKAQRPELWN LYNGRHHKGE  660
HIRVFPLSNW TEFDIWSYIG AEQVRLPSIY FAHRRKVFQR DGMLLAVHRH MQPRADEPVF  720
EATVRFRTVG DVTCTGCVES SASTVAEVIA ETAVARLTER GATRADDRIS EAGMEDRKRQ  780
GYFGGSGGGG SGGKRVEIEV DDDLIQKVIR GGSGGGGSGG APPALSQDRF ADFPALPLDP  840
SAMVAQVGPQ VVNINTKLGY NNAVGAGTGI VIDPNGVVLT NNHVIAGATD INAFSVGSGQ  900
TYGVDVVGYD RTQDVAVLQL RGAGGLPSAA IGGGVAVGEP VVAMGNSGGQ GGTPRAVPGR  960
VVALGQTVQA SDSLTGAEET LNGLIQFDAA IQPGDSGGPV VNGLGQVVGM NGGSGGGGSG  1020
GALAWMCDRA VDLLLLGGSG GGGSGGAIHV MTTVLATLPA DGGSGGGGSG GTTRVMATRR  1080
NVLDRQGGSG GGGSGGVARV LRPGGHFLYT DGGSGGGGSG GENLRMKLPK PEPSSQSTVP  1140
IVGIVAGLAV LAVVVIGAVV AAVMCRRKSS GGKGGSYSQA ACSDSAQGSD VSLTA        1195

SEQ ID NO: 428         moltype = RNA  length = 3778
FEATURE                Location/Qualifiers
source                 1..3778
                       mol_type = other RNA
                       organism = synthetic construct
SEQUENCE: 428
acatttgctt ctgacacaac tgtgttcact agcaacctca aacagccacc atggctgtga  60
tggccccgcg caccctcctg ctgctcctgc tgggagcgct cgcattgacc cagacttggg  120
ccgggtcatc ccgcgccttc attattgacc ctaccatttc cgccattgac ggtctgtacg  180
atctgctggg aatcggcatc ccaaaccaag gagggatcct ctactcctcg ttggaatact  240
tcgagaaggc actcgaggaa cttgccgccg cattcccggg cgatggatgg ctgggaagcg  300
ctgctgacaa atacgcgggg aagaaccgga accatgtcaa cttcttccaa gagctcgccg  360
acctggaccg gcagctcata tccctgattc acgaccaggc caatgctgtg cagaccactc  420
gggatatcct ggagggagct aagaagggat tggaattcgt gcggcctgtg gctgtggacc  480
tgacctacat tccggtggtc ggccacgcgc tgtccgcggc gttccaggcg cctttctgtg  540
ccggagctat ggccgtggtc ggtggagctc tcgcctacct cgtggtcaaa accctgatca  600
atgccaccca gctgctgaag ctgctggcta agctcgcgga gttggtcgcc gccgcgattg  660
ccgatatcat tagcgacgtg gcagacatca tcaagggcac cctcggagaa gtctgggaat  720
tcatcaccaa cgccctgaac ggtctgaagg aactgtggga taagctgact ggatgggtca  780
ccggactgtt cagccgcgga tggtccaacc tggagagctt cttcgccgga gtgcccggac  840
tcaccggtgc cacctccggg ctttcccaag ttaccggact cttcggggcc gccggcctgt  900
cggcctcatc cgggctggca cacgccgata gcctggcatc ctcggcatcg ctccccgcgc  960
tcgcgggcat cgggggtggc agcggatttg gcggactgcc ctcgctggca caagtgcacg  1020
ccgccagcac tcggcaggcg ctgcgcccga gagccgacgg ccccgtggga gccgctgcgg  1080
aacaagtcgg tggccagtct caacttgtgt ccgcgcaggg aagccagggg atgggtggcc  1140
ctgtgggaat gggcggaatg catccaagct ccggggcctc gaagggcact accaccaaga  1200
agtactccga gggcgctgcg gccggcactg aagatgctga acgggccccg gtggaggccg  1260
atgccggtgg cgggcaaaag gtgctcgtac ggaatgtcgt gggaggttct ggtggcgggg  1320
gctccggtgg aatcaccgac cggctcccgg ccaaggctcc cctgctggag cttgatggtg  1380
gatccggggg aggcggttcc ggcggtgcca tcaccatcaa catggtcaac cccactggct  1440
ttatccgcta tgaggatgtg gaacaggagg ccatgacctc agacgtgacc gtgggacccg  1500
cccccggcca gtaccagctg tcccacctcc gcctgctcga ggccgaagcg attcacgtga  1560
tcagggaagt ggcggccgaa tttgagcgcc cggtgctgct gttcagcggt ggaaaggata  1620
gcattgtgat gttgcatttg gccctcaagg ccttccgacc tggtcggctc ccgttccctg  1680
```

```
tgatgcatgt ggataccgga cacaacttcg acgaggtcat cgcaacgcgc gacgagttgg  1740
tggcagccgc cggcgtgcgc ctggtagtgg ccagcgtgca agacgacatc gacgccggca  1800
gagtggtgga aaccatcccc tcccgcaacc ctattcagac cgtgaccctg ctgagagcca  1860
ttagggaaaa ccagttcgac gctgccttcg gaggcgcccg gcgggatgag gagaaagcgc  1920
gcgcgaagga aagagtgttc tcctttcggg acgagtttgg acagtgggac cctaaggcgc  1980
aacggcccga gttgtggaac ctgtacaacg gacggcacca taagggggag cacatccggg  2040
tctttcctct gtccaactgg acagagttcg atatttggag ctacattgga gccgaacaag  2100
tccggctgcc gtccatctac ttcgcacacc ggagaaaagt gttccagcgc gacggcatgc  2160
tcctcgcggt gcacaggcat atgcagccca gggcagacga gccggtgttt gaagccaccg  2220
tcagattccg cacagtgggc gacgtgactt gcaccggctg cgtggaatcc tccgcgtcca  2280
ccgtggccga agtgatcgct gagactgcgg tcgccagatt gaccgagcgg ggtgccacaa  2340
gagccgatga ccgcattagc gaagcgggga tggaggatcg gaagagacaa ggatactttg  2400
gaggctcagg gggtggaggc tcgggcggaa agcgcgtcga gatcgaagtc gacgatgatc  2460
tgatccaaaa ggtcatccgg ggtggaagcg gcggaggggg aagcgggggc gcgccgcccg  2520
cgttaagtca ggaccggttc gccgacttcc cggccctgcc cctggaccct tcggcgatgg  2580
tggcccaagt tggcccccaa gtggtgaaca ttaacactaa gctgggatac aacaacgctg  2640
tgggcgcggg cactggaatc gtcatcgacc ctaacggcgt ggtgctaacc aacaaccatg  2700
tgatagccgg ggccaccgat atcaacgcct tcagcgtggg gtccggacag acttacggag  2760
tggacgtcgt gggttacgac aggacccagg acgtggccgt gctgcaactg aggggagccg  2820
gaggactgcc cagcgccgcg atcggaggag gggtggccgt gggtgaaccg gtggtggcca  2880
tgggaaattc cggcggacag ggaggcaccc cgagggcggt gcccggccgc gtggtcgctc  2940
tcggtcaaac cgtgcaggcc tccgacagcc tgactggcgc cgaggaaact ctgaacggcc  3000
tgatccagtt cgatgcggcc atccagccgg gagactcggg gggacctgtg gtcaacggac  3060
tgggacaggt cgtgggcatg aacggcggct cgggaggggg tggctccggg ggcgccctgg  3120
cctggatgtg cgacagagct gtggatttgc tccttctggg gggatcgggt ggtggcggat  3180
ctggaggggc catccacgtg atgacgactg tcctggccac cctgccggcc gatggcggct  3240
ccggcggagg aggttcgggc ggaactacta gagtgatggc cacacgacgg aacgtgctgg  3300
accgccaggg gggatccggc ggcgggggca gcggaggagt ggcccgcgtc cttagacctg  3360
gaggacactt cctgtatacc gacggaggat ccggaggagg aggatcaggc ggagagaact  3420
tgagaatgaa gctgcccaag cccgaaccga gttcccagtc aaccgtgccc atcgtcggga  3480
tcgtggcagg actcgccgtg ttggcagtcg tcgtcattgg cgccgtggtg gccgccgtga  3540
tgtgccgccg gaagtcctca ggggggaagg gaggctcgta cagccaggcc gcctgttccg  3600
actcggccca ggggtccgac gtgtccctta ctgcatgata ataggctcgc tttcttgctg  3660
tccaatttct attaaaggtt cctttgttcc ctaagtccaa ctactaaact gggggatatt  3720
atgaagggcc ttgagcatct ggattctgcc taataaaaaa catttatttt cattgcaa    3778
```

```
SEQ ID NO: 429          moltype = AA  length = 1006
FEATURE                 Location/Qualifiers
source                  1..1006
                        mol_type = protein
                        organism = synthetic construct
SEQUENCE: 429
MAAPGSARRP LLLLLLLLLL GLMHCASASR AFIIDPTISA IDGLYDLLGI GIPNQGGILY  60
SSLEYFEKAL EELAAAFPGD GWLGSAADKY AGKNRNHVNF FQELADLDRQ LISLIHDQAN  120
AVQTTRDILE GAKKGLEFVR PVAVDLTYIP VVGHALSAAF QAPFCAGAMA VVGGALAYLV  180
VKTLINATQL LKLLAKLAEL VAAAIADIIS DVADIIKGTL GEVWEFITNA LNGLKELWDK  240
LTGWVTGLFS RGWSNLESFF AGVPGLTGAT SGLSQVTGLF GAAGLSASSG LAHADSLASS  300
ASLPALAGIG GGSGFGGLPS LAQVHAASTR QALRPRADGP VGAAAEQVGG QSQLVSAQGS  360
QGMGGPVGMG GMHPSSGASK GTTTKKYSEG AAAGTEDAER APVEADAGGG QKVLVRNVVG  420
GSGGGGSGGA ITINMVNPTG FIRYEDVEQE AMTSDVTVGP APGQYQLSHL RLLEAEAIHV  480
IREVAAEFER PVLLFSGGKD SIVMLHLALK AFRPGRLPFP VMHVDTGHNF DEVIATRDEL  540
VAAAGVRLVV ASVQDDIDAG RVVETIPSRN PIQTVTLLRA IRENQFDAAF GGARRDEEKA  600
RAKERVFSFR DEFGQWDPKA QRPELWNLYN GRHHKGEHIR VFPLSNWTEF DIWSYIGAEQ  660
VRLPSIYFAH RRKVFQRDGM LLAVHRHMQP RADEPVFEAT VRFRTVGDVT CTGCVESSAS  720
TVAEVIAETA VARLTERGAT RADDRISEAG MEDRKRQGYF GGSGGGGSGG APPALSQDRF  780
ADFPALPLDP SAMVAQVGPQ VVNINTKLGY NNAVGAGTGI VIDPNGVVLT NNHVIAGATD  840
INAFSVGSGQ TYGVDVVGYD RTQDVAVLQL RGAGGLPSAA IGGGVAVGEP VVAMGNSGGQ  900
GGTPRAVPGR VVALGQTVQA SDSLTGAEET LNGLIQFDAA IQPGDSGGPV VNGLGQVVGM  960
NGGSGGGGSG GLIPIAVGGA LAGLVLIVLI AYLVGRKRSH AGYQTI                 1006
```

```
SEQ ID NO: 430          moltype = RNA  length = 3211
FEATURE                 Location/Qualifiers
source                  1..3211
                        mol_type = other RNA
                        organism = synthetic construct
SEQUENCE: 430
acatttgctt ctgacacaac tgtgttcact agcaacctca aacagccacc atggccgccc  60
ctggatcagc caggcgcccc cttctgctgc tgctcctcct gctgcttctg ggtctgatgc  120
attgcgccag cgccagccgc gccttcatta ttgaccctac catttccgcc attgacggtc  180
tgtacgatct gctgggaatc ggcatcccaa accaaggagg gatcctctac tcctcgttgg  240
aatacttcga gaaggcactc gaggaacttg ccgccgcatt cccgggcgat ggatggctgg  300
gaagcgctgc tgacaaatac gcggggaaga accggaacca tgtcaacttc ttccaagagc  360
tcgccgacct ggaccggcag ctcatatccc tgattcacga ccaggccaat gctgtgcaga  420
ccactcggga tatcctggag ggagctaaga agggattgga attcgtgcgg cctgtggctg  480
tggacctgac ctacattccg gtggtcggcc acgcgctgtc cgcggcgttc caggcgcctt  540
tctgtgccgg agctatggcc gtggtcggtg gagctctcgc ctacctcgtg gtcaaaaccc  600
tgatcaatgc cacccagctg ctgaagctgc tggctaagct cgcggagttg gtcgccgccg  660
cgattgccga tatcattagc gacgtggcag acatcatcaa gggcaccctc ggagaagtct  720
gggaattcat caccaacgcc ctgaacggtc tgaaggaact gtgggataag ctgactggat  780
```

-continued

```
gggtcaccgg actgttcagc cgcggatggt ccaacctgga gagcttcttc gccggagtgc  840
ccggactcac cggtgccacc tccgggcttt cccaagttac cggactcttc ggggccgccg  900
gcctgtcggc ctcatccggg ctggcacacg ccgatagcct ggcatcctcg gcatcgctcc  960
ccgcgctcgc gggcatcggg ggtggcagcg gatttggcgg actgccctcg ctggcacaag  1020
tgcacgccgc cagcactcgg caggcgctgc gcccgagagc cgacggcccc gtgggagccg  1080
ctgcggaaca agtcggtggc cagtctcaac ttgtgtccgc gcagggaagc caggggatgg  1140
gtggccctgt gggaatgggc ggaatgcatc caagctccgg ggcctcgaag ggcactacca  1200
ccaagaagta ctccgagggc gctgcggccg gcactgaaga tgctgaacgg gccccggtgg  1260
aggccgatgc cggtggcggg caaaaggtgc tcgtacggaa tgtcgtgggt ggatccgggg  1320
gaggcggttc cggcggtgcc atcaccatca acatggtcaa ccccactggc tttatccgct  1380
atgaggatgt ggaacaggag gccatgacct cagacgtgac cgtgggaccc gcccccggcc  1440
agtaccagct gtcccacctc cgcctgctcg aggccgaagc gattcacgtg atcagggaag  1500
tggcggccga atttgagcgc ccggtgctgc tgttcagcgg tggaaaggat agcattgtga  1560
tgttgcattt ggccctcaag gccttccgac ctggtcggct cccgttccct gtgatgcatg  1620
tggataccgg acacaacttc gacgaggtca tcgcaacgcg cgacgagttg gtggcagccg  1680
ccggcgtgcg cctggtagtg gccagcgtgc aagacgacat cgacgccggc agagtggtgg  1740
aaaccatccc ctcccgcaac cctattcaga ccgtgaccct gctgagagcc attagggaaa  1800
accagttcga cgctgccttc ggaggcgccc ggcgggatga ggagaaagcg cgcgcgaagg  1860
aaagagtgtt ctcctttcgg gacgagtttg gacagtggga ccctaaggcg caacggcccg  1920
agttgtggaa cctgtacaac ggacggcacc ataaggggga gcacatccgg gtctttcctc  1980
tgtccaactg gacagagttc gatatttgga gctacattgg agccgaacaa gtccggctgc  2040
cgtccatcta cttcgcacac cggagaaaag tgttccagcg cgacggcatg ctcctcgcgg  2100
tgcacaggca tatgcagccc agggcagacg agccggtgtt tgaagccacc gtcagattcc  2160
gcacagtggg cgacgtgact tgcaccggct gcgtggaatc ctccgcgtcc accgtggccg  2220
aagtgatcgc tgagactgcg gtcgccagat tgaccgagcg gggtgccaca agagccgatg  2280
accgcattag cgaagcgggg atggaggatc ggaagagaca aggatacttt ggtggaagcg  2340
gcggaggggg aagcgggggc gcgccgcccg cgttaagtca ggaccggttc gccgacttcc  2400
cggccctgcc cctggaccct tcggcgatgg tggcccaagt tggcccccaa gtggtgaaca  2460
ttaacactaa gctgggatac aacaacgctg tgggcgcggg cactggaatc gtcatcgacc  2520
ctaacggcgt ggtgctaacc aacaaccatg tgatagccgg ggccaccgat atcaacgcct  2580
tcagcgtggg gtccggacag acttacggag tggacgtcgt gggttacgac aggacccagg  2640
acgtggccgt gctgcaactg aggggagccg gaggactgcc cagcgccgcg atcggaggag  2700
gggtggccgt gggtgaaccg gtggtggcca tgggaaattc cggcggacag ggaggcaccc  2760
cgagggcggt gcccggccgc gtggtcgctc tcggtcaaac cgtgcaggcc tccgacagcc  2820
tgactggcgc cgaggaaact ctgaacggcc tgatccagtt cgatgcggcc atccagccgg  2880
gagactcggg gggacctgtg gtcaacggac tgggacaggt cgtgggcatg aacggcggct  2940
cgggaggggg tggctccggt ggcctgattc caatcgccgt cgggggagca ctggccggac  3000
tggtgctcat tgtgctgatc gcttacctcg tgggaagaaa gcgctcccac gccggatacc  3060
agaccatctg ataataggct cgctttcttg ctgtccaatt tctattaaag gttcctttgt  3120
tccctaagtc caactactaa actgggggat attatgaagg gccttgagca tctggattct  3180
gcctaataaa aaacatttat tttcattgca a                                3211
```

```
SEQ ID NO: 431         moltype = AA  length = 844
FEATURE                Location/Qualifiers
source                 1..844
                       mol_type = protein
                       organism = synthetic construct
SEQUENCE: 431
MAAPGSARRP LLLLLLLLLL GLMHCASADF GALPPEINSA RMYAGAGAGP MMAAGAAWNG  60
LAAELGTTAA SYESVITRLT TESWMGPASM AMVAAAQPYL AWLTYTAEAA AHAGSQAMAS  120
AAAYEAAYAM TVPPEVVAAN RALLAALVAT NVLGINTPAI MATEALYAEM WAQDALAMYG  180
YAAASGAAGM LQPLSPPSQT TNPGGLAAQS AAVGSAAATA AVNQVSVADL ISSLPNAVSG  240
LASPVTSVLD STGLSGIIAD IDALLATPFV ANIINSAVNT AAWYVNAAIP TAIFLANALN  300
SGAPVAIAEG AIEAAEGAAS AAAAGLADSV TPAGLGASLG EATLVGRLSV PAAWSTAAPA  360
TTAGATALEG SGWTVAAEEA GPVTGMMPGM ASAAKGTGAY AGPRYGFKPT VMPKQVVVGG  420
SGGGGSGGDF ALLPPEVNSA RMYTGPGAGS LLAAAGGWDS LAAELATTAE AYGSVLSGLA  480
ALHWRGPAAE SMAVTAAPYI GWLYTTAEKT QQTAIQARAA ALAFEQAYAM TLPPPVVAAN  540
RIQLLALIAT NFFGQNTAAI AATEAQYAEM WAQDAAAMYG YATASAAAAL LTPFSPPRQT  600
TNPAGLTAQA AAVSQATDPL SLLIETVTQA LQALTIPSFI PEDFTFLDAI FAGYATVGVT  660
QDVESFVAGT IGAESNLGLL NVGDENPAEV TPGDFGIGEL VSATSPGGGV SASGAGGAAS  720
VGNTVLASVG RANSIGQLSV PPSWAAPSTR PVSALSPAGL TTLPGTDVAE HGMPGVPGVP  780
VAAGRASGVL PRYGVRLTVM AHPPAAGGSL IPIAVGGALA GLVLIVLIAY LVGRKRSHAG  840
YQTI                                                              844
```

```
SEQ ID NO: 432         moltype = RNA  length = 2725
FEATURE                Location/Qualifiers
source                 1..2725
                       mol_type = other RNA
                       organism = synthetic construct
SEQUENCE: 432
acatttgctt ctgacacaac tgtgttcact agcaacctca aacagccacc atggccgcac  60
ctggatccgc aagacgccct ttactccttc tcctgcttct gctgctgctg ggcctcatgc  120
attgcgcctc cgccgatttc ggagccctgc cacctgaaat caactcggcc aggatgtacg  180
ccggagctgg agctggcccg atgatggccg caggagctgc ttggaacggt ctggcagcgg  240
aactcggcac tactgccgcc tcctacgaga gcgtgatcac tcgccttacc accgaaagct  300
ggatgggacc ggcgtccatg gccatggtcg cggctgctca accctacctg gcgtggctta  360
cctacaccgc tgaagcggca gcccatgctg gatcccaagc aatggcgtcc gcagctgcat  420
acgaggcagc ctacgccatg actgtgccac cggaggtcgt ggcagccaat cgagccctcc  480
ttgccgcttt ggtggccacg aacgtgctgg gcatcaacac tcccgcaatt atggctaccg  540
```

-continued

```
aggcgctcta cgcggagatg tgggcccagg acgctctggc tatgtacggc tacgctgccg  600
catcgggagc agccggcatg ctacaacctc tgtcacctcc aagccaaacc accaatcccg  660
gaggccttgc tgcccaatca gctgccgtgg gatctgcggc agccactgct gcggtcaatc  720
aagtctccgt ggccgatctc atttcctccc tgcccaacgc cgtgtcgggc ttggcatcgc  780
ccgtgacttc ggtcctggac agcaccggtc tgtccggcat tatcgccgac atcgatgccc  840
tgcttgcgac ccccttcgtc gccaatatca tcaactccgc cgtgaacacc gccgcttggt  900
acgtgaacgc ggccatccca accgccattt tcctggcgaa cgctctcaac tcgggagctc  960
ctgtcgccat cgccgaaggc gccattgaag cagcggaagg agccgcgtca gcagctgcag  1020
ccggattggc ggatagcgtg actccagccg gacttggggc ttccttgggg gaagccactc  1080
tggtcggtcg gcttagcgtg ccagccgcat ggtccactgc cgcaccagca accaccgcgg  1140
gagctactgc cttggaaggg tccggttgga cggtcgccgc agaggaagcc ggacccgtga  1200
ctgggatgat gcccggaatg gcttccgcgg ccaagggaac tggagcctat gccgggccta  1260
gatatggctt caagcctacc gtcatgccta aacaggtcgt cgtgggaggg agtgggggtg  1320
gaggatcggg aggagacttc gcgctgcttc cgcctgaagt gaacagcgcc cggatgtaca  1380
ccggacctgg agcaggatcc ctgttggccg ctgcaggagg ttgggactcg ttggctgcgg  1440
aactggccac caccgctgag gcctacgggt ccgtgctctc cggcttggcg gcactgcact  1500
ggaggggacc agctgccgaa tccatggccg tgactgccgc tccgtacatt ggctggctgt  1560
acaccaccgc cgaaaagacc cagcagaccg ccattcaagc acgggcagca gctcttgcct  1620
ttgagcaggc gtacgcgatg actctccctc cgcctgtggt cgctgccaac cgcatccagc  1680
tgctggccct gatcgcgacc aacttcttcg gccagaacac agccgccatc gctgccaccg  1740
aagcacagta cgccgaaatg tgggcgcagg atgctgccgc gatgtacgga tacgccaccg  1800
catcagccgc tgcggcattg ctgacaccgt tctcccctcc gcgccaaacg accaacccag  1860
cgggtctgac tgcacaggca gccgctgtgt cccaagccac tgatccgctc tccctgctga  1920
tcgaaactgt gactcaagcc ctgcaagccc tgaccatccc ttccttcatc cctgaggact  1980
tcaccttcct cgacgccatc ttcgctggct acgcgaccgt gggagtgacc caggacgtgg  2040
aaagctttgt ggccggaacc atcggagcag agtccaacct gggactgctg aacgtcgggg  2100
atgagaaccc cgcggaagtg acccccggcg atttcggcat tggggagctg gtgtccgcta  2160
cctcacccgg tggaggggtg tcggcatccg gtgctggagg agctgccagc gtgggcaata  2220
ctgtgctcgc ctcagtcgga cgcgccaaca gcattggcca gctgagcgtg cctccgtcat  2280
gggccgcacc ctcaactcgc cctgtgtcag ccctgagccc tgctgggctg accaccctcc  2340
cgggaacaga cgtggctgag cacggcatgc cgggagtccc aggagtgcca gttgcagccg  2400
ggagagctag cggggtgctc cctagatacg gagtccggct caccgtgatg gcccatccac  2460
cggcagcagg aggctcgctg atcccgatag cagtgggagg agcgcttgcg ggcttggtgt  2520
tgattgtcct catcgcctac ctcgtgggaa gaaagcggtc acacgccgga taccagacca  2580
tttgataata ggctcgcttt cttgctgtcc aatttctatt aaaggttcct ttgttcccta  2640
agtccaacta ctaaactggg ggatattatg aagggccttg agcatctgga ttctgcctaa  2700
taaaaaacat ttattttcat tgcaa                                      2725

SEQ ID NO: 433         moltype = AA  length = 19
FEATURE                Location/Qualifiers
source                 1..19
                       mol_type = protein
                       organism = Homo sapiens
SEQUENCE: 433
MGFLPKLLLL ASFFPAGQA                                              19

SEQ ID NO: 434         moltype = AA  length = 31
FEATURE                Location/Qualifiers
source                 1..31
                       mol_type = protein
                       organism = Homo sapiens
SEQUENCE: 434
LLWVLGLLVG LLLLLLGLGA CYTWRRRRVC K                                31

SEQ ID NO: 435         moltype =   length =
SEQUENCE: 435
000

SEQ ID NO: 436         moltype =   length =
SEQUENCE: 436
000

SEQ ID NO: 437         moltype = AA  length = 725
FEATURE                Location/Qualifiers
source                 1..725
                       mol_type = protein
                       organism = Mycobacterium tuberculosis
SEQUENCE: 437
MHHTAASDNF QLSQGGQGFA IPIGQAMAIA GQIRSGGGSP TVHIGPTAFL GLGVVDNNGN  60
GARVQRVVGS APAASLGIST GDVITAVDGA PINSATAMAD ALNGHHPGDV ISVTWQTKSG  120
GTRTGNVTLA EGPPAEFMVD FGALPPEINS ARMYAGPGSA SLVAAAQMWD SVASDLFSAA  180
SAFQSVVWGL TVGSWIGSSA GLMVAAASPY VAWMSVTAGQ AELTAAQVRV AAAAYETAYG  240
LTVPPPVIAE NRAELMILIA TNLLGQNTPA IAVNEAEYGE MWAQDAAAMF GYAAATATAT  300
ATLLPFEEAP EMTSAGGLLE QAAAVEEASD TAAANQLMNN VPQALQQLAQ PTQGTTPSSK  360
LGGLWKTVSP HRSPISNMVS MANNHMSMTN SGVSMTNTLS SMLKGFAPAA AAQAVQTAAQ  420
NGVRAMSSLG SSLGSSGLGG GVAANLGRAA SVGSLSVPQA WAAANQAVTP AARALPLTSL  480
TSAAERGPGQ MLGGLPVGQM GARAGGGLSG VLRVPPRPYV MPHSPAAGDI APPALSQDRF  540
ADFPALPLDP SAMVAQVGPQ VVNINTKLGY NNAVGAGTGI VIDPNGVVLT NNHVIAGATD  600
INAFSVGSGQ TYGVDVVGYD RTQDVAVLQL RGAGGLPSAA IGGGVAVGEP VVAMGNSGGQ  660
```

-continued

```
GGTPRAVPGR VVALGQTVQA SDSLTGAEET LNGLIQFDAA IQPGDAGGPV VNGLGQVVGM  720
NTAAS                                                              725

SEQ ID NO: 438          moltype = AA  length = 775
FEATURE                 Location/Qualifiers
source                  1..775
                        mol_type = protein
                        organism = synthetic construct
SEQUENCE: 438
MGFLPKLLLL ASFFPAGQAM TAASDNFQLS QGGQGFAIPI GQAMAIAGQI RSGGGSPTVH  60
IGPTAFLGLG VVDNNGNGAR VQRVVGSAPA ASLGISTGDV ITAVDGAPIN SATAMADALN  120
GHHPGDVISV TWQTKSGGTR TGNVTLAEGP PAEFMVDFGA LPPEINSARM YAGPGSASLV  180
AAAQMWDSVA SDLFSAASAF QSVVWGLTVG SWIGSSAGLM VAAASPYVAW MSVTAGQAEL  240
TAAQVRVAAA AYETAYGLTV PPPVIAENRA ELMILIATNL LGQNTPAIAV NEAEYGEMWA  300
QDAAAMFGYA AATATATATL LPFEEAPEMT SAGGLLEQAA AVEEASDTAA ANQLMNNVPQ  360
ALQQLAQPTQ GTTPSSKLGG LWKTVSPHRS PISNMVSMAN NHMSMTNSGV SMTNTLSSML  420
KGFAPAAAAQ AVQTAAQNGV RAMSSLGSSL GSSGLGGGVA ANLGRAASVG SLSVPQAWAA  480
ANQAVTPAAR ALPLTSLTSA AERGPGQMLG GLPVGQMGAR AGGGLSGVLR VPPRPYVMPH  540
SPAAGDIAPP ALSQDRFADF PALPLDPSAM VAQVGPQVVN INTKLGYNNA VGAGTGIVID  600
PNGVVLTNNH VIAGATDINA FSVGSGQTYG VDVVGYDRTQ DVAVLQLRGA GGLPSAAIGG  660
GVAVGEPVVA MGNSGGQGGT PRAVPGRVVA LGQTVQASDS LTGAEETLNG LIQFDAAIQP  720
GDAGGPVVNG LGQVVGMNTA ASGSLLWVLG LLVGLLLLLL GLGACYTWRR RRVCK        775

SEQ ID NO: 439          moltype = RNA  length = 2518
FEATURE                 Location/Qualifiers
source                  1..2518
                        mol_type = other RNA
                        organism = synthetic construct
SEQUENCE: 439
acatttgctt ctgacacaac tgtgttcact agcaacctca aacagccacc atgggctttt  60
tgccgaagct gttactgctg gcctcattct ttccggccgg tcaagcgatg acggcggcca  120
gcgacaactt tcagttgtct cagggcggtc aaggctttgc catacccatc ggtcaagcta  180
tggccattgc gggccagatt cgttcgggcg gcggcagtcc gactgtgcat atcggtccga  240
ctgcgttttt aggtctgggt gtggtcgaca acaacggaaa tggtgcacgc gtccaacgcg  300
ttgtgggctc agcaccagcg gcgtcactgg gaatcagcac gggtgacgta attactgcag  360
tggacggtgc gccgattaac tctgccacgg ccatggcgga tgctctgaac ggtcaccacc  420
cgggggatgt tatttccgtc acttggcaaa ccaaatctgg tgggacccgt acgggcaacg  480
ttaccctggc ggaagggccg ccggcagagt tcatggttga tttcggtgcc cttccgcccg  540
agatcaactc ggcccgtatg tatgctggcc ccggctctgc tagtctggtg gctgcggcgc  600
aaatgtggga tagtgtagcc tctgaccttt tcagtgcggc tagcgcgttc cagtcggtcg  660
tgtggggtct tactgttggc tcgtggattg gctcatcagc gggtctgatg gtggcggctg  720
ctagcccata tgtcgcgtgg atgtccgtga cggccgggca ggctgaactt accgctgccc  780
aggtaagagt tgctgcagcc gcgtacgaaa cagcgtatgg cctgacggtt cccccgcccg  840
tgatcgcgga aaaccgcgcc gaactgatga ttctcatcgc gactaacctc ctcggccaga  900
acaccccggc aattgcggtg aacgaggcgg aatatggtga aatgtgggcg caggacgcag  960
ccgccatgtt cggctacgca gcggcaacag cgacagcaac agcaaccctg ctgcctttcg  1020
aagaagcgcc tgaaatgacc agtgccggcg gcctgttgga acaggcagca gccgtggagg  1080
aagcgtccga tactgctgcc gccaatcagc tgatgaacaa tgtgcctcag gcgctgcagc  1140
aactggccca gcctacccag ggcaccaccc cgagcagcaa actcggcggg ctgtggaaaa  1200
ccgtctcccc gcaccgcagc ccgatttcta atatggtgtc catggccaat aatcatatga  1260
gcatgaccaa tagcggcgtc agcatgacca acactctgag cagcatgctg aaaggctttg  1320
ccccggcggc tgccgcgcag gccgtccaga ccgccgcgca aaatggtgtg cgcgctatgt  1380
cgtccctggg aagttcactc ggttcttccg gtctgggggg tggtgtggca gccaacttag  1440
gtcgtgccgc gagcgttggc agcttatcgg taccacaggc atgggcagca gcgaaccagg  1500
ctgtaacgcc agcagcacgc gcgttgccgc taacctcgct aacctccgcg gcagagcgtg  1560
ggccgggcca gatgcttgga ggacttccag ttgggcaaat gggggcacgt gcaggtggtg  1620
ggctttcagg agtattgcgg gtacctcctc gtccctatgt gatgccacat tccccggctg  1680
ctggtgatat cgcaccacca gcgctatctc aagatcggtt tgcagatttt ccggcgctgc  1740
cgctggaccc tagcgccatg gtagcgcagg tgggcccgca ggttgtcaat ataaatacca  1800
agttaggtta taataacgcg gtcggcgctg gcacgggcat tgtcatcgat ccgaatggtg  1860
tggttctgac caacaatcat gtgatcgcgg gcgcgaccga tattaacgcc tttagtgtgg  1920
ggagtggaca gacgtacggc gtggatgtcg ttggctacga ccgaacacag gatgttgccg  1980
tgctgcagct ccgtggtgcc ggtgggttac cgtcggcggc gattggtgga ggcgtagccg  2040
tcggtgaacc agttgtagca atgggcaatt cgggcggaca agggggggaca cctcgagcag  2100
taccgggaag ggtggtggcc ctgggccaaa ccgttcaagc cagcgatagt ttgacgggag  2160
cagaggaaac gttaaatggt ctgattcagt ttgatgcggc catccaaccg ggcgatgctg  2220
gcggtccggt tgttaatggc ctgggccagg ttgtgggtat gaacacggcg gcttctggta  2280
gcctcctgtg ggtgctgggc ctgttggtcg gtctgttgtt gttactgtta ggcctggggg  2340
cgtgttacac ctggcgtcgc cgccgcgtct gcaaatgata ataggctcgc tttcttgctg  2400
tccaatttct attaaaggtt cctttgttcc ctaagtccaa ctactaaact gggggatatt  2460
atgaagggcc ttgagcatct ggattctgcc taataaaaaa catttatttt cattgcaa    2518

SEQ ID NO: 440          moltype = AA  length = 778
FEATURE                 Location/Qualifiers
source                  1..778
                        mol_type = protein
                        organism = synthetic construct
SEQUENCE: 440
MKAILVVMLY TFTTANAMTA ASDNFQLSQG GQGFAIPIGQ AMAIAGQIRS GGGSPTVHIG  60
```

```
PTAFLGLGVV DNNGNGARVQ RVVGSAPAAS LGISTGDVIT AVDGAPINSA TAMADALNGH  120
HPGDVISVTW QTKSGGTRTG NVTLAEGPPA EFMVDFGALP PEINSARMYA GPGSASLVAA  180
AQMWDSVASD LFSAASAFQS VVWGLTVGSW IGSSAGLMVA AASPYVAWMS VTAGQAELTA  240
AQVRVAAAAY ETAYGLTVPP PVIAENRAEL MILIATNLLG QNTPAIAVNE AEYGEMWAQD  300
AAAMFGYAAA TATATATLLP FEEAPEMTSA GGLLEQAAAV EEASDTAAAN QLMNNVPQAL  360
QQLAQPTQGT TPSSKLGGLW KTVSPHRSPI SNMVSMANNH MSMTNSGVSM TNTLSSMLKG  420
FAPAAAAQAV QTAAQNGVRA MSSLGSSLGS SGLGGGVAAN LGRAASVGSL SVPQAWAAAN  480
QAVTPAARAL PLTSLTSAAE RGPGQMLGGL PVGQMGARAG GGLSGVLRVP PRPYVMPHSP  540
AAGDIAPPAL SQDRFADFPA LPLDPSAMVA QVGPQVVNIN TKLGYNNAVG AGTGIVIDPN  600
GVVLTNNHVI AGATDINAFS VGSGQTYGVD VVGYDRTQDV AVLQLRGAGG LPSAAIGGGV  660
AVGEPVVAMG NSGGQGGTPR AVPGRVVALG QTVQASDSLT GAEETLNGLI QFDAAIQPGD  720
AGGPVVNGLG QVVGMNTAAS GSLAIYSTVA SSLVLVVSLG AISFWMCSNG SLQCRICI    778

SEQ ID NO: 441          moltype = RNA  length = 2527
FEATURE                 Location/Qualifiers
source                  1..2527
                        mol_type = other RNA
                        organism = synthetic construct
SEQUENCE: 441
acatttgctt ctgacacaac tgtgttcact agcaacctca aacagccacc atgaaagcca  60
ttttggtcgt gatgctgtac accttcacca ctgccaacgc gatgaccgct gcctcggata  120
acttccagtt atcacagggg ggccaaggct tcgcaatccc gataggtcag gcgatggcaa  180
tcgccggaca aattcgttct gggggtggtt cgcctaccgt gcacatcggc ccccaccgcct  240
ttctgggttt aggtgtggtg gataacaatg gcaacggcgc gagggtgcag cgcgtggtcg  300
gaagcgcccc tgccgccagt ctcggtattt ccacgggcga cgtcatcacg gctgtcgatg  360
gtgcaccgat caattcagcc acggccatgg ccgacgcatt aaacgggcat cacccgggtg  420
acgtgatttc ggtcacttgg cagacgaaat ccggtggcac ccgtacgggc aacgtcaccc  480
tggctgaagg ccctcccgcc gaatttatgg ttgacttcgg cgcactgccg ccagaaatca  540
atagtgctcg gatgtatgct ggcccgggga gcgcgtctct tgtggcggca gcccaaatgt  600
gggatagtgt cgcctcggat ctctttttctg cggcgagcgc gtttcaatcg gttgtgtggg  660
ggcttacggt agggtcgtgg attggctcct ccgctggcct gatggttgcc gcagcgagtc  720
cgtatgtggc gtggatgtca gtaactgcag gacaggcgga acttacggca gcacaggtac  780
gcgtagcagc tgcagcgtac gaaacggcgt acggcctgac cgtcccaccg ccagtgatcg  840
cggaaaatcg cgccgagtta atgatcctga ttgccactaa cctcttgggc cagaacaccc  900
ccgctatcgc ggtaaacgag gccgaatacg gtgaaatgtg ggcgcaggat gcggcagcga  960
tgttcggtta tgcggcggct acggcgactg ctacagcaac cctgttaccg tttgaggagg  1020
cacctgagat gaccagcgca ggtggcctgc tggaacaagc cgctgcggtt gaagaagcct  1080
cagacaccgc cgctgcgaat cagctgatga ataatgttcc gcaagcgctg cagcagctgg  1140
cgcagccgac ccagggtaca acgccgagct ccaaactggg cggtctgtgg aagaccgtgt  1200
cacctcatcg tagcccgatt tctaatatgg tgagcatggc caataatcat atgagcatga  1260
ccaattcggg cgtctctatg acgaacacac tcagctccat gctcaaaggt tttgctccgg  1320
ccgctgcagc tcaggcggtt cagaccgcgg cgcagaatgg cgttcgtgcg atgagctccc  1380
tagggtcaag cttgggaagc tctggtttgg gtggcggtgt agctgcgaac ttgggtcgtg  1440
ccgcgtcagt gggctcattg tcggtaccgc aggcttgggc agctgcgaat caagcggtaa  1500
ctcccgccgc acgtgccctg cctcttacat ctctgacaag tgctgccgaa cgcggtccgg  1560
gtcaaatgct tggaggctta cctgtgggtc agatgggcgc aagagcgggt ggtgggctga  1620
gtggcgtctt gcgtgtgccg ccacgcccat atgttatgcc ccatagtcca gcggccggag  1680
atattgcccc gccagcgttg tcccaagatc gctttgcgga ttttccggct ctgcctctgg  1740
atccgtccgc catggttgcg caggttggcc cgcaggtggt gaacattaac accaagctgg  1800
gctataacaa tgcggtcggc gctggcaccg gcatcgttat tgatccgaat ggcgtcgtcc  1860
tgaccaacaa ccacgtgatt gcgggcgcca ccgatatcaa tgcattctcg gtcggtagcg  1920
gtcagactta tggcgtggac gtggttggtt atgaccgcac acaggatgtg gccgtactgc  1980
agctgcgcgg ggcgggcggt ctgccatccg cagcaattgg aggtggcgtt gcagtaggag  2040
aacccgttgt ggcaatgggg aacagcggcg gacaaggtgg gactccacgg gcggttccgg  2100
ggcgagttgt agcgctagga cagacagtgc aggcaagcga cagtcttacg ggggcagaag  2160
agaccctgaa tggcctgatc caatttgatg cggcgataca accgggcgat gccggcggac  2220
cggtggtgaa cggtctgggc caagttgtcg gtatgaacac cgcggcctct ggtagcctcg  2280
caatttacag tacggttgcc agcagtttag tgctggtcgt ttctttaggt gcgatttctt  2340
tctggatgtg ctcgaacggc agcctgcaat gtcgtatttg catttgataa taggctcgct  2400
ttcttgctgt ccaatttcta ttaaaggttc ctttgttccc taagtccaac tactaaactg  2460
gggggatatta tgaagggcct tgagcatctg gattctgcct aataaaaaac atttattttc  2520
attgcaa                                                           2527

SEQ ID NO: 442          moltype = AA  length = 776
FEATURE                 Location/Qualifiers
source                  1..776
                        mol_type = protein
                        organism = synthetic construct
SEQUENCE: 442
MKAILVVMLY TFTTANAMTA ASDNFQLSQG GQGFAIPIGQ AMAIAGQIRS GGGSPTVHIG  60
PTAFLGLGVV DNNGNGARVQ RVVGSAPAAS LGISTGDVIT AVDGAPINSA TAMADALNGH  120
HPGDVISVTW QTKSGGTRTG NVTLAEGPPA EFMVDFGALP PEINSARMYA GPGSASLVAA  180
AQMWDSVASD LFSAASAFQS VVWGLTVGSW IGSSAGLMVA AASPYVAWMS VTAGQAELTA  240
AQVRVAAAAY ETAYGLTVPP PVIAENRAEL MILIATNLLG QNTPAIAVNE AEYGEMWAQD  300
AAAMFGYAAA TATATATLLP FEEAPEMTSA GGLLEQAAAV EEASDTAAAN QLMNNVPQAL  360
QQLAQPTQGT TPSSKLGGLW KTVSPHRSPI SNMVSMANNH MSMTNSGVSM TNTLSSMLKG  420
FAPAAAAQAV QTAAQNGVRA MSSLGSSLGS SGLGGGVAAN LGRAASVGSL SVPQAWAAAN  480
QAVTPAARAL PLTSLTSAAE RGPGQMLGGL PVGQMGARAG GGLSGVLRVP PRPYVMPHSP  540
AAGDIAPPAL SQDRFADFPA LPLDPSAMVA QVGPQVVNIN TKLGYNNAVG AGTGIVIDPN  600
```

-continued

```
GVVLTNNHVI AGATDINAFS VGSGQTYGVD VVGYDRTQDV AVLQLRGAGG LPSAAIGGGV  660
AVGEPVVAMG NSGGQGGTPR AVPGRVVALG QTVQASDSLT GAEETLNGLI QFDAAIQPGD  720
AGGPVVNGLG QVVGMNTAAS GSLIPIAVGG ALAGLVLIVL IAYLVGRKRS HGYQTI      776

SEQ ID NO: 443          moltype = RNA  length = 1388
FEATURE                 Location/Qualifiers
source                  1..1388
                        mol_type = genomic RNA
                        organism = Mycobacterium tuberculosis
SEQUENCE: 443
acatttgctt ctgacacaac tgtgttcact agcaacctca aacagccacc atgaaggcca  60
ttttagttgt catgttatat acgttcacca cggcgaacgc gatgacggcc gccagcgata  120
atttccaact aagccagggc ggccaaggct ttgcaattcc catcggacag gcgatggcca  180
tcgctggcca aattcgtagt ggcggcggaa gcccgacggt gcatatcggc ccgactgctt  240
ttcttggcct gggcgtcgta gataataacg gtaacggggc ccgagtacag cgcgtggtag  300
gttcggcgcc agcggcatca ctgggtatat cgacggggga cgttatcaca gctgtggatg  360
gggcgccaat taacagcgca accgcgatgg ccgatgccct gaatggccat catccggggg  420
atgtgattag tgtcacgtgg caaaccaagt caggtggcac ccgcaccggc aacgttaccc  480
tggccgaggg tccgcctgcg gagtttatgg tggatttcgg cgcactgccg ccggaaatca  540
actctgcgcg tatgtatgct ggtccgggca gcgcctcact ggtcgcggcg gctcaaatgt  600
gggactcagt ggctagtgat ctcttctcag cagcgtcggc cttccaatcg gtggtttggg  660
gcttgactgt gggtagttgg atcggcagtt ccgctggtct catggtggcc gccgcgtcgc  720
cgtatgtggc ttggatgagt gtgacagcag gtcaggccga acttactgcc gctcaggtaa  780
gagtcgccgc ggctgcgtat gaaactgcct atggcctgac cgttccgccg ccggtcattg  840
ccgaaaatcg cgctgaactc atgattctca ttgccacgaa tctgctgggt caaaatacgc  900
ctgccatcgc agtgaatgaa gccgagtacg gcgagatgtg ggcccaggat gcggcggcaa  960
tgttcggtta cgctgcagca acggcgactg caaccgccac ccttttgccg tttgaagaag  1020
cgcctgaaat gacgtcggca ggcggcctgt tggaacaggc ggctgccgtc gaagaggcca  1080
gcgataccgc ggcagccaac cagttaatga ataacgtccc tcaagccctg cagcagctgg  1140
cccagcctac tcagggtacc actccgagct ctaaattagg tggcctctgg aaaacggtga  1200
gcccccaccg ctccccgatt agtaacatgg tctccatggc gaacaaccat atgagcatga  1260
cgaattcggg tgtcagcatg acaaacaccc tgtcgtccat gctgaaaggc tttgcgccgg  1320
cggctgcggc gcaggcggtt caaaccgcag ctcagaacgg agtgcgtgca atgtcttctc  1380
tgggctcc                                                          1388

SEQ ID NO: 444          moltype = AA  length = 338
FEATURE                 Location/Qualifiers
source                  1..338
                        mol_type = protein
                        organism = Mycobacterium tuberculosis
SEQUENCE: 444
MQLVDRVRGA VTGMSRRLVV GAVGAALVSG LVGAVGGTAT AGAFSRPGLP VEYLQVPSPS  60
MGRDIKVQFQ SGGANSPALY LLDGLRAQDD FSGWDINTPA FEWYDQSGLS VVMPVGGQSS  120
FYSDWYQPAC GKAGCQTYKW ETFLTSELPG WLQANRHVKP TGSAVVGLSM AASSALTLAI  180
YHPQQFVYAG AMSGLLDPSQ AMGPTLIGLA MGDAGGYKAS DMWGPKEDPA WQRNDPLLNV  240
GKLIANNTRV WVYCGNGKPS DLGGNNLPAK FLEGFVRTSN IKFQDAYNAG GGHNGVFDFP  300
DSGTHSWEYW GAQLNAMKPD LQRALGATPN TGPAPQGA                          338

SEQ ID NO: 445          moltype = AA  length = 347
FEATURE                 Location/Qualifiers
source                  1..347
                        mol_type = protein
                        organism = synthetic construct
SEQUENCE: 445
MGFLPKLLLL ASFFPAGQAF SRPGLPVEYL QVPSPSMGRD IKVQFQSGGA NSPALYLLDG  60
LRAQDDFSGW DINTPAFEWY DQSGLSVVMP VGGQSSFYSD WYQPACGKAG CQTYKWETFL  120
TSELPGWLQA NRHVKPTGSA VVGLSMAASS ALTLAIYHPQ QFVYAGAMSG LLDPSQAMGP  180
TLIGLAMGDA GGYKASDMWG PKEDPAWQRN DPLLNVGKLI ANNTRVWVYC GNGKPSDLGG  240
NNLPAKFLEG FVRTSNIKFQ DAYNAGGGHN GVFDFPDSGT HSWEYWGAQL NAMKPDLQRA  300
LGATPNTGPA PQGAGSLLWV LGLLVGLLLL LLGLGACYTW RRRRVCK                347

SEQ ID NO: 446          moltype = RNA  length = 1234
FEATURE                 Location/Qualifiers
source                  1..1234
                        mol_type = other RNA
                        organism = synthetic construct
SEQUENCE: 446
acatttgctt ctgacacaac tgtgttcact agcaacctca aacagccacc atgggctttc  60
tcccgaaact gctgttactg gcaagctttt tcccagccgg ccaggcgttc tcccgcccgg  120
gattgcctgt agaatatctg caagtaccga gcccgtctat gggtcgggac atcaaagtgc  180
agtttcaaag tggtggcgcc aatagccccg cgctgtacct gcttgatggg ctgcgtgcgc  240
aagacgattt tagcggctgg gacattaata cgccggcgtt tgaatggtat gatcagtcgg  300
ggctgtcggt tgtgatgcct gtgggcgggc agtctagctt ttatagcgat tggtatcaac  360
cagcctgtgg aaaagccggc tgccagacct acaaatggga aacctttctg actagtgagc  420
tgccgggatg gctgcaggct aaccgtcatg tcaaaccaac cggcagtgcg gtggtcggtt  480
tatcgatggc tgcatctagc gcgctgacgc tggccattta tcacccgcag cagttcgtat  540
acgcaggcgc gatgtccggt ttgttagatc cctcacaggc tatgggtcca accctcattg  600
gtctggccat gggtgatgct ggcggctata aagcctcaga tatgtggggt ccgaaagagg  660
acccggcttg gcaacgtaac gaccctttgt tgaacgttgg gaagttaatc gcgaacaaca  720
```

```
cgcgagtttg ggtttactgt ggcaatggca aaccatcgga tctggggggt aataacctgc  780
cggccaagtt tttggaaggt tttgtgcgta catccaacat caaattccag gatgcctaca  840
acgcgggcgg cggccataat ggtgttttcg acttcccgga tagtggtact cactcatggg  900
aatactgggg cgcacaactt aatgcaatga agccggatct tcagcgcgca ctgggtgcaa  960
cacctaatac cggaccggcg ccccagggcg cgggctctct gctatgggtc ttaggtttac  1020
tggtcggtct acttctcctg ctgctcgggt tgggagcgtg ctatacctgg agacgccgcc  1080
gcgtgtgcaa atgataatag gctcgctttc ttgctgtcca atttctatta aaggttcctt  1140
tgttccctaa gtccaactac taaactgggg gatattatga agggccttga gcatctggat  1200
tctgcctaat aaaaaacatt tattttcatt gcaa                              1234

SEQ ID NO: 447         moltype = AA  length = 350
FEATURE                Location/Qualifiers
source                 1..350
                       mol_type = protein
                       organism = synthetic construct
SEQUENCE: 447
MKAILVVMLY TFTTANAFSR PGLPVEYLQV PSPSMGRDIK VQFQSGGANS PALYLLDGLR  60
AQDDFSGWDI NTPAFEWYDQ SGLSVVMPVG GQSSFYSDWY QPACGKAGCQ TYKWETFLTS  120
ELPGWLQANR HVKPTGSAVV GLSMAASSAL TLAIYHPQQF VYAGAMSGLL DPSQAMGPTL  180
IGLAMGDAGG YKASDMWGPK EDPAWQRNDP LLNVGKLIAN NTRVWVYCGN GKPSDLGGNN  240
LPAKFLEGFV RTSNIKFQDA YNAGGGHNGV FDFPDSGTHS WEYWGAQLNA MKPDLQRALG  300
ATPNTGPAPQ GAGSLAIYST VASSLVLVVS LGAISFWMCS NGSLQCRICI             350

SEQ ID NO: 448         moltype = RNA  length = 1243
FEATURE                Location/Qualifiers
source                 1..1243
                       mol_type = other RNA
                       organism = synthetic construct
SEQUENCE: 448
acatttgctt ctgacacaac tgtgttcact agcaacctca aacagccacc atgaaagcca  60
ttctggtggt gatgttatat acctttacca ccgctaacgc tttctcacgc cctgggttgc  120
cggtagaata cctgcaagtg cccagtccgt cgatgggacg ggacattaag gttcaatttc  180
aatctggagg tgcgaattcg cccgcgctgt acttactgga tggcctgcgt gcccaggatg  240
attttagcgg ttgggatatt aataccccgg cctttgagtg gtatgaccag agtggcctgt  300
cggttgtgat gcctgtcggc ggccagtcca gcttttattc cgactggtac cagccggcat  360
gtggcaaagc tggctgccaa acttataaat gggaaacttt tctcacgagt gaactgccag  420
gctggctaca agcgaaccgc cacgttaaac cgacggggag tgccgtagtc ggcttgagta  480
tggctgcgag ctctgcgctg actctcgcga tctatcatcc acagcagttt gtttatgcgg  540
gtgctatgag cggacttctg gatcccagcc aggccatggg accgacgtta atcgggcttg  600
ccatgggcga tgccgggggt tacaaagcaa gcgatatgtg ggtcctaaa gaggatccgg  660
cgtggcagcg aaacgatccg ctgctcaatg ttgggaagct gatcgcgaat aatacccgtg  720
tctgggtcta ttgcggtaac ggcaaaccat cggacctagg tggtaataac ctgccggcca  780
agttcctgga aggttttgta cgcaccagca atataaaatt ccaggacgcg tacaacgcag  840
gcggtggcca taatggcgtg ttcgacttcc cggattcagg cacgcactct tgggaatact  900
ggggcgccca gttgaacgct atgaaaccgg atctgcaacg tgcgttaggt gcaacaccta  960
acacagggcc ggcgccacag ggtgcaggta gcctggcaat ttattcaacc gtggcgtctt  1020
cactggtgct tgtggtctcc ctgggtgcaa tctccttctg gatgtgttcc aacggcagct  1080
tgcagtgccg catttgtatc tgataatagg ctcgctttct tgctgtccaa tttctattaa  1140
aggttccttt gttccctaag tccaactact aaactggggg atattatgaa gggccttgag  1200
catctggatt ctgcctaata aaaaacattt attttcattg caa                    1243

SEQ ID NO: 449         moltype = AA  length = 374
FEATURE                Location/Qualifiers
source                 1..374
                       mol_type = protein
                       organism = Mycobacterium tuberculosis
SEQUENCE: 449
VKIRLHTLLA VLTAAPLLLA AAGCGSKPPS GSPETGAGAG TVATTPASSP VTLAETGSTL  60
LYPLFNLWGP AFHERYPNVT ITAQGTGSGA GIAQAAAGTV NIGASDAYLS EGDMAAHKGL  120
MNIALAISAQ QVNYNLPGVS EHLKLNGKVL AAMYQGTIKT WDDPQIAALN PGVNLPGTAV  180
VPLHRSDGSG DTFLFTQYLS KQDPEGWGKS PGFGTTVDFP AVPGALGENG NGGMVTGCAE  240
TPGCVAYIGI SFLDQASQRG LGEAQLGNSS GNFLLPDAQS IQAAAAGFAS KTPANQAISM  300
IDGPAPDGYP IINYEYAIVN NRQKDAATAQ TLQAFLHWAI TDGNKASFLD QVHFQPLPPA  360
VVKLSDALIA TISS                                                    374

SEQ ID NO: 450         moltype = AA  length = 159
FEATURE                Location/Qualifiers
source                 1..159
                       mol_type = protein
                       organism = Mycobacterium tuberculosis
SEQUENCE: 450
VKRGLTVAVA GAAILVAGLS GCSSNKSTTG SGETTTAAGT TASPGAASGP KVVIDGKDQN  60
VTGSVVCTTA AGNVNIAIGG AATGIAAVLT DGNPPEVKSV GLGNVNGVTL GYTSGTGQGN  120
ASATKDGSHY KITGTATGVD MANPMSPVNK SFEIEVTCS                         159

SEQ ID NO: 451         moltype = AA  length = 554
FEATURE                Location/Qualifiers
source                 1..554
                       mol_type = protein
```

```
                         organism = synthetic construct
SEQUENCE: 451
MKAILVVMLY TFTTANACGS KPPSGSPETG AGAGTVATTP ASSPVTLAET GSTLLYPLFN  60
LWGPAFHERY PNVTITAQGT GSGAGIAQAA AGTVNIGASD AYLSEGDMAA HKGLMNIALA  120
ISAQQVNYNL PGVSEHLKLN GKVLAAMYQG TIKTWDDPQI AALNPGVNLP GTAVVPLHRS  180
DGSGDTFLFT QYLSKQDPEG WGKSPGFGTT VDFPAVPGAL GENGNGGMVT GCAETPGCVA  240
YIGISFLDQA SQRGLGEAQL GNSSGNFLLP DAQSIQAAAA GFASKTPANQ AISMIDGPAP  300
DGYPIINYEY AIVNNRQKDA ATAQTLQAFL HWAITDGNKA SFLDQVHFQP LPPAVVKLSD  360
ALIATISSGG SGGGGSGGCS SNKSTTGSGE TTTAAGTTAS PGAASGPKVV IDGKDQNVTG  420
SVVCTTAAGN VNIAIGGAAT GIAAVLTDGN PPEVKSVGLG NVNGVTLGYT SGTGQGNASA  480
TKDGSHYKIT GTATGVDMAN PMSPVNKSFE IEVTCSGSLA IYSTVASSLV LVVSLGAISF  540
WMCSNGSLQC RICI                                                    554

SEQ ID NO: 452          moltype = RNA  length = 1855
FEATURE                 Location/Qualifiers
source                  1..1855
                        mol_type = other RNA
                        organism = synthetic construct
SEQUENCE: 452
acatttgctt ctgacacaac tgtgttcact agcaacctca aacagccacc atgaaggcga  60
ttttggtcgt tatgctttat accttcacca ccgcgaacgc ttgcgggtca aaaccgccaa  120
gcggcagccc ggaaactgga gctggggcag gaactgtagc aacaacacca gcatcatccc  180
ccgtgacgct tgcggagacg ggatcaaccc tgttgtatcc gctctttaac ctgtggggcc  240
cagcctttca cgagcgctat cccaatgtta ccattacggc tcaggggact ggatctggtg  300
caggcatcgc acaggcggca gcaggcacag ttaatatagg cgcgagcgat gcatatctct  360
cggaaggcga tatggctgcg cataagggcc tgatgaacat tgctttagcg attagcgcgc  420
agcaggtcaa ttacaacctg ccgggtgtca gcgaacatct gaagctgaat ggcaaagtcc  480
tcgccgccat gtaccaaggt accatcaaaa cctgggatga tccccaaatc gcggccctga  540
accctggcgt taacctgcca ggtaccgcgg tggtgccttt gcatcgttcg gacggctcgg  600
gtgacacttt tctgttcacg cagtacttat ctaaacaaga tccggaaggt tgggggaaat  660
caccgggctt cggtactacg gtggactttc ctgcagtacc gggtgctctg ggggaaaacg  720
gaaatggtgg gatggtgacc gggtgtgcgg aaacaccggg ttgtgtggcc tatattggta  780
tttcgtttct ggatcaggct agccagcgtg gcttaggcga agcgcaatta ggtaattcca  840
gcggcaactt tttactaccg gacgcacaga gcatccaagc agccgccgcg gggtttgcgt  900
caaaaacccc ggccaatcag gcaattagca tgattgatgg cccggcgcca gacggctacc  960
ccatcatcaa ctatgaatat gcgattgtta ataatcggca gaaagacgcg gcgaccgcgc  1020
agacccttca ggcgtttctc cactgggcga tcaccgatgg caacaaggcc tcgttcctgg  1080
atcaagtgca ttttcaaccg ctaccgccgg ccgtagtaaa actgtcggat gcgctgatcg  1140
ccaccatcag tagtggtggc agtggtggtg gaggtagtgg cggatgctca agcaacaaaa  1200
gtacaacggg atctggcgag acgactaccg cagcgggcac aacggcttcc cctggtgcgg  1260
caagtggccc taaagttgtg atcgacggca aggatcaaaa tgtgacgggg tctgtcgttt  1320
gtaccacggc cgccggtaac gtcaacatcg ccattggggg tgcagccact ggcatagcgg  1380
ccgtcctgac cgatggcaat ccgccagaag tgaaatcggt tggcttgggc aatgttaacg  1440
gcgtaacgct tggctacacg tccggtaccg gtcagggcaa cgcttccgct actaaagacg  1500
ggtctcacta taaaatcacc ggcaccgcta ccggtgtcga tatggccaat ccgatgtctc  1560
cggttaacaa atccttcgag attgaagtga cgtgcagcgg ttctctggct atttacagta  1620
ccgtagccag ctctctggtg ttggtggtgt cgctgggtgc cattagcttc tggatgtgca  1680
gcaatggttc cctgcagtgt cgcatttgca tttgataata ggctcgcttt cttgctgtcc  1740
aatttctatt aaaggttcct ttgttcccta agtccaacta ctaaactggg ggatattatg  1800
aagggccttg agcatctgga ttctgcctaa taaaaaacat ttattttcat tgcaa       1855

SEQ ID NO: 453          moltype =   length =
SEQUENCE: 453
000

SEQ ID NO: 454          moltype =   length =
SEQUENCE: 454
000

SEQ ID NO: 455          moltype =   length =
SEQUENCE: 455
000

SEQ ID NO: 456          moltype =   length =
SEQUENCE: 456
000

SEQ ID NO: 457          moltype =   length =
SEQUENCE: 457
000

SEQ ID NO: 458          moltype =   length =
SEQUENCE: 458
000

SEQ ID NO: 459          moltype =   length =
SEQUENCE: 459
000
```

-continued

SEQ ID NO: 460 moltype = length =
SEQUENCE: 460
000

SEQ ID NO: 461 moltype = length =
SEQUENCE: 461
000

SEQ ID NO: 462 moltype = length =
SEQUENCE: 462
000

SEQ ID NO: 463 moltype = length =
SEQUENCE: 463
000

SEQ ID NO: 464 moltype = length =
SEQUENCE: 464
000

SEQ ID NO: 465 moltype = length =
SEQUENCE: 465
000

SEQ ID NO: 466 moltype = length =
SEQUENCE: 466
000

SEQ ID NO: 467 moltype = length =
SEQUENCE: 467
000

SEQ ID NO: 468 moltype = length =
SEQUENCE: 468
000

SEQ ID NO: 469 moltype = length =
SEQUENCE: 469
000

SEQ ID NO: 470 moltype = length =
SEQUENCE: 470
000

SEQ ID NO: 471 moltype = length =
SEQUENCE: 471
000

SEQ ID NO: 472 moltype = length =
SEQUENCE: 472
000

SEQ ID NO: 473 moltype = length =
SEQUENCE: 473
000

SEQ ID NO: 474 moltype = length =
SEQUENCE: 474
000

SEQ ID NO: 475 moltype = length =
SEQUENCE: 475
000

SEQ ID NO: 476 moltype = length =
SEQUENCE: 476
000

SEQ ID NO: 477 moltype = length =
SEQUENCE: 477
000

SEQ ID NO: 478 moltype = length =
SEQUENCE: 478
000

SEQ ID NO: 479 moltype = length =
SEQUENCE: 479
000

-continued

SEQ ID NO: 480 moltype = length =
SEQUENCE: 480
000

SEQ ID NO: 481 moltype = length =
SEQUENCE: 481
000

SEQ ID NO: 482 moltype = length =
SEQUENCE: 482
000

SEQ ID NO: 483 moltype = length =
SEQUENCE: 483
000

SEQ ID NO: 484 moltype = length =
SEQUENCE: 484
000

SEQ ID NO: 485 moltype = length =
SEQUENCE: 485
000

SEQ ID NO: 486 moltype = length =
SEQUENCE: 486
000

SEQ ID NO: 487 moltype = length =
SEQUENCE: 487
000

SEQ ID NO: 488 moltype = length =
SEQUENCE: 488
000

SEQ ID NO: 489 moltype = length =
SEQUENCE: 489
000

SEQ ID NO: 490 moltype = length =
SEQUENCE: 490
000

SEQ ID NO: 491 moltype = length =
SEQUENCE: 491
000

SEQ ID NO: 492 moltype = length =
SEQUENCE: 492
000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499

```
000

SEQ ID NO: 500         moltype =   length =
SEQUENCE: 500
000

SEQ ID NO: 501         moltype = RNA  length = 50
FEATURE                Location/Qualifiers
source                 1..50
                       mol_type = other RNA
                       organism = synthetic construct
SEQUENCE: 501
acatttgctt ctgacacaac tgtgttcact agcaacctca aacagccacc             50

SEQ ID NO: 502         moltype = RNA  length = 134
FEATURE                Location/Qualifiers
source                 1..134
                       mol_type = other RNA
                       organism = synthetic construct
SEQUENCE: 502
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gcaa                                                    134

SEQ ID NO: 503         moltype =   length =
SEQUENCE: 503
000

SEQ ID NO: 504         moltype =   length =
SEQUENCE: 504
000

SEQ ID NO: 505         moltype = RNA  length = 1796
FEATURE                Location/Qualifiers
source                 1..1796
                       mol_type = other RNA
                       organism = synthetic construct
SEQUENCE: 505
acatttgctt ctgacacaac tgtgttcact agcaacctca aacagccacc atggaactgc  60
tgatcctgaa ggccaacgcc atcaccacta ttctgaccgc cgtgaccttt tgcttcgcct  120
ccggccagaa catcacagag gaattctacc agagcacctg ttctgccgtc agcaagggct  180
acctgtctgc cctgagaaca ggctggtaca cctctgtgat caccatagag ctgagtaaca  240
tcaaagagaa caagtgtaat ggaaccgatg caaaggtgaa actgattaaa caggagctgg  300
acaagtacaa gaacgccgtc accgagctgc agctactgat gcagagcacc cccgccaccg  360
gctcaggcag cgccatctgc agcggcgtcg ccgtgtgcaa ggtgctgcac ctggaaggcg  420
aagtgaacaa aatcaagtct gctctgctgt ccacaaacaa ggctgttgtg agcctgagca  480
atggcgtgag cgtgctgaca ttcaaggtgc tagatctgaa aaactacatc gataagcaac  540
tgctgcctat cctgaacaag cagagctgca gcatcagcaa catcgagaca gtgatcgaat  600
ttcagcagaa aaacaaccgg ctgctggaaa tcacaagaga gttcagcgtg aacgccggag  660
tgaccacccc tgtgtctacc tacatgctga caaatagcga gctgctgagc ctgatcaacg  720
acatgcctat taccaacgac cagaagaagc tgatgagcaa caacgtgcag atcgtgcggc  780
agcaatcata ctctatcatg tgcatcatca aggaagaagt gctggcttac gtggtgcaac  840
tgcctctgta cggcgtaatc gacacaccat gctggaagct gcacaccagc cctctgtgca  900
caaccaacac caaggaaggc tccaacatct gtctgaccag gacagataga ggctggtatt  960
gtgacaacgc cggcagcgtg agcttcttcc cccaggccga gacatgcaaa gtgcagagca  1020
atagagtgtt ttgcgacacc atgaacagca gaaccctgcc atctgaggtg aacctgtgta  1080
acgtggacat cttcaacccc aagtacgact gcaagatcat gaccagcaaa acagatgtga  1140
gttctagcgt catcaccagc ctgggtgcca tcgtatcttg ctacggcaaa accaagtgca  1200
ccgccagcaa taagaatcgg ggaatcatca agacattcag caacggctgc gactacgttt  1260
ctaataaggg agtggatacc gtgtctgtgg gaaataccct gtactgtgtg aacaagcagg  1320
agggcaagag cctgtatgtg aagggcgagc ctatcatcaa cttctacgat cctctggtgt  1380
tccctagcga cgagttcgac gctagcatca gccaggtgaa tgagaagatc aaccagtccc  1440
tcgccttcat cagaaagtcc gacgagctgc tccacaacgt gaacgctggc aagagcacaa  1500
caaacatcat gatcaccaca attatcatcg tgatcatcgt gatcctgctg agcctgatcg  1560
ccgtgggcct gctgctgtac tgcaaggcca gaagcacccc cgtgaccctg tccaaggacc  1620
agctgagcgg catcaacaac atcgccttta gcaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgc      1796

SEQ ID NO: 506         moltype = RNA  length = 1798
FEATURE                Location/Qualifiers
source                 1..1798
                       mol_type = other RNA
                       organism = synthetic construct
SEQUENCE: 506
acatttgctt ctgacacaac tgtgttcact agcaacctca aacagccacc atggagctgc  60
tgatcctgaa ggccaacgcc atcaccacca ttctgacagc cgtcaccttc tgctttgcct  120
ctggtcagaa catcaccgag gagttctacc agagcacctg cagcgccgtg agcaaggggt  180
acttgtccgc cctgcggacc ggctggtaca ccagcgtcat taccattgag ctctccaaca  240
```

```
tcaaggagaa caagtgcaat ggtactgacg ccaaggtgaa gctgatcaag caggagctgg  300
acaagtacaa gaatgccgtc acggagctgc agctgctcat gcagagcaca cccgccaccg  360
ggtccggcag cgccatctgc agcggcgtgg ccgtctgcaa ggtgctgcac ctggagggcg  420
aggtgaacaa gatcaagtct gctctgctga gcaccaacaa ggcagtggtg agcctgtcaa  480
atggggtgag cgtgttgacc ttcaaggtgc tcgacctgaa gaattacatt gacaagcagc  540
tgctgccaat tctgaacaag cagagttgca gcatctcgaa catcgagacc gtgatcgagt  600
tccagcagaa gaacaatcgg ctgctggaga tcaccaggga gttctccgtg aacgccgggg  660
tgaccacccc cgtgagcaca tacatgctga ccaatagcga gctgctgtct ctgatcaacg  720
acatgcccat caccaacgac cagaagaagc tgatgagcaa caacgtgcag atcgtgagac  780
agcagagcta cagcattatg tgcatcatca aggaggaggt cctggcttac gtggtgcagc  840
tgccgctgta cggcgtgatc gataccccct gttggaagct gcacactagt ccactgtgca  900
caaccaacac caaggagggc agcaacatct gcctgacgag gacggaccgg ggctggtatt  960
gcgacaatgc cggctccgtg tccttcttcc ctcaggcaga gacctgcaag gtgcagtcca  1020
accgggtgtt ctgtgacacc atgaacagcc ggacgctgcc ctccgaggtg aacctgtgca  1080
atgtggacat cttcaatccc aagtacgatt gcaagatcat gaccagcaag accgatgtgt  1140
cctccagcgt gatcacctcg ctgggggcca tcgtgtcttg ctacggcaag accaagtgta  1200
cagcttccaa caagaacagg ggtatcatca agacgttcag caacggctgc gactacgtga  1260
gcaacaaggg ggtggacacc gtgagcgtgg ggaacaccct gtactgcgtg aacaagcagg  1320
aggggaagag cctgtacgtg aagggggagc ccatcatcaa cttttacgac cccctggtct  1380
tcccctccga cgagttcgac gccagtatca gccaggtgaa tgagaagatc aatcagagcc  1440
tggctttcat cagaaagtct gatgagctgc tgcacaatgt gaacgccggg aagagcacca  1500
ccaacatcat gatcacgacc atcatcatcg tgatcatcgt gatcctgctc agcctgatcg  1560
ctgtgggtct gctgctgtac tgcaaggccc gcagtacacc agtgaccctc agcaaggatc  1620
agctgagcgg gatcaacaac atcgccttct ccaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798
```

```
SEQ ID NO: 507          moltype = RNA  length = 1798
FEATURE                 Location/Qualifiers
source                  1..1798
                        mol_type = other RNA
                        organism = synthetic construct
SEQUENCE: 507
acatttgctt ctgacacaac tgtgttcact agcaacctca aacagccacc atggagttgc  60
tgatcctgaa ggctaatgcc atcaccacga ttctgacggc cgtgacattt tgcttcgcct  120
ccgggcagaa catcacggag gagttctatc agtctacttg ttctgcagtc agcaaggggt  180
acttgtccgc cctgcggacc ggctggtaca ctagcgtcat taccattgag ctctccaaca  240
tcaaggagaa caagtgcaat ggtactgacg ctaaggtgaa gctgatcaag caggagctgg  300
acaagtacaa gaacgccgtg accgagctgc agctgctgat gcagagcact cccgccaccg  360
ggagtggctc tgccatctgc agcggggtcg cggtgtgcaa ggtcctgcac cttgagggtg  420
aggtcaacaa gatcaagtct gctctgctga gcaccaacaa ggcggtggtc agcctgagca  480
acggggtctc tgtcctcacc ttcaaggtgc tggacctgaa gaactacatc gataagcagc  540
tgctgccaat tctgaacaag cagagttgca gcatcagcaa tatcgagacg gtgatcgagt  600
tccagcagaa gaacaatcgg ctgctggaga tcacccggga gttcagcgtg aacgccgggg  660
tgacaacccc ggtgtccacc tacatgctga ccaactccga gcttctgtct ctgatcaatg  720
atatgcctat caccaatgat cagaagaagc tgatgtccaa caatgtgcag atcgtgcgcc  780
agcagtccta ctccataatg tgcatcatta aggaggaggt gctggcgtac gtggtgcagc  840
ttccactgta cggggtgatc gacaccccgt gctggaagct gcacacctct cctttgtgta  900
ccaccaacac aaaggagggg tccaacatct gcctgacgag gacggaccgg ggctggtatt  960
gcgacaatgc cggctccgtg tccttcttcc ctcaggcaga gacctgcaag gtgcagagta  1020
accgggtgtt ctgtgacacc atgaacagcc ggactctgcc ctcggaggtc aatctgtgca  1080
atgtggacat cttcaacccc aagtatgact gcaagatcat gacaagtaag actgatgtga  1140
gctcctccgt gatcaccagc ctgggggcga tcgtgtcttg ctacggcaag acaaagtgca  1200
cggcctccaa caagaatcgt gggatcatta agaccttcag taatggttgt gattatgtgt  1260
ccaacaaggg ggtggacact gtcagcgttg gcaacacgct gtactgcgtg aacaagcagg  1320
agggcaagtc gctctacgtg aagggcgagc cgattattaa cttctacgat cccctggtgt  1380
tccctagcga cgagttcgac gctagcatca gccaggtgaa cgagaagatt aatcagtcgc  1440
tcgccttcat cagtaagagc gacgagctcc tgcacaatgt caacgctggc aagtccacca  1500
ccaacatcat gatcacaacc attatcattg tgatcattgt gatcctgctc agcctgatcg  1560
ctgtgggtct gctgctgtac tgcaaggccc gcagtacacc agtgaccctc agcaaggatc  1620
agctgagcgg gatcaacaat atcgcgttca gcaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798
```

```
SEQ ID NO: 508          moltype = RNA  length = 1798
FEATURE                 Location/Qualifiers
source                  1..1798
                        mol_type = other RNA
                        organism = synthetic construct
SEQUENCE: 508
acatttgctt ctgacacaac tgtgttcact agcaacctca aacagccacc atggagttgc  60
tgatcctgaa ggcgaatgct attaccacca tcctgacagc tgtgaccttc tgttttgcct  120
ccgggcagaa catcacggag gagttctatc agtctacttg ttctgcagtc agcaaggggt  180
acctgtccgc gttgcgcacg ggtggtaca cctccgtgat cacgattgag ctctctaaca  240
tcaaggagaa taagtgtaac ggcactgacg ccaaggtcaa gctgatcaag caggagctgg  300
acaagtataa gaacgctgtg accgagttac agcttcttat gcagtccact cctgctacag  360
gcagcggctc cgctatctgt agcggagtcg ctgtctgtaa ggtcttgcac ctggagggcg  420
aggtgaacaa gatcaagtcc gccttgctct ccaccaacaa ggccgtggtc agcttgtcca  480
atggcgtcag tgtccttaca tttaaggtcc ttgatctcaa gaattacatt gataagcagc  540
```

```
tgctgcctat tctgaataag cagagctgct ctatcagtaa tattgagacg gtgatcgagt  600
tccagcagaa gaacaatcgg ctgctggaga tcaccagaga gttcagcgtg aacgcggggg  660
tgaccacccc ggtcagcacc tacatgctga ccaactctga gctgttgtcg ctcatcaacg  720
acatgccgat caccaatgat cagaagaagt tgatgagcaa caacgttcag atcgtgcgcc  780
agcagtccta ctccataatg tgcatcatta aggaggaggt gctggcgtac gtggtgcagc  840
ttccactgta cggggtgatc gacaccccgt gctggaagct gcacacctct cctttgtgta  900
ccaccaacac aaaggagggg tccaacatct gcctgacgag gacggaccgg ggctggtatt  960
gcgacaatgc cggctccgtg tccttcttcc ctcaggcaga gacctgcaag gtgcagagta  1020
accgggtgtt ctgtgacacc atgaacagcc ggactctgcc ctcggaggtc aacctgtgca  1080
acgtggacat cttcaacccc aagtatgact gcaagatcat gacaagtaag actgatgtga  1140
gctcctccgt gatcacgtca ctgggggcga tcgtgtcttg ctacggcaag accaagtgca  1200
ccgccagcaa taagaacagg gggatcatta agacatttag taatggttgt gattatgtgt  1260
ccaacaaggg ggtggacact gtcagcgttg gcaacacgct gtactgcgtg aacaagcagg  1320
agggcaagtc gctctacgtg aagggcgagc cgattattaa cttctatgac ccgctggtgt  1380
tcccgtcgga cgagttcgac gcgagcatca gccaggtcaa cgagaagatt aatcagtcgc  1440
tcgcctttat acgtaagagc gacgaactcc tgcacaatgt caacgctggc aagtccacca  1500
ccaacatcat gatcacaacc attattatcg tgatcatagt gatcctcctg tctcttattg  1560
cggtgggcct cttgctgtac tgcaaggcac ggtcgacccc agtgacgctg agcaaggacc  1620
agctgtcagg aattaataac atcgccttca gcaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798
```

```
SEQ ID NO: 509          moltype = AA  length = 321
FEATURE                 Location/Qualifiers
source                  1..321
                        mol_type = protein
                        organism = Human respiratory syncytial virus A
SEQUENCE: 509
MSKTKDQRTA KTLERTWDTL NHLLFISSCL YKLNLKSIAQ ITLSILAMII STSLIIAAII  60
FIASANHKVT PTTAIIQDAT NQIKNTTPTH LTQNPQLGIS LSNLSGTTSQ STTILASTTP  120
SAESTPQSTT VKIINTTTTQ ILPSKPTTKQ RQNKPQNKPN NDFHFEVFNF VPCSICSNNP  180
TCWAICKRIP NKKPGKKTTT KPTKKPTLKT TKKDPKPQTT KPKGVLTTKP TGKPTINTTK  240
TNSRTTLLTS NTKGNPEHTS QKETIHSTTS EGYPSPSQVY TTSDQEETLH STTSEGYPSP  300
SQVYTTSEYL SQSLSSSNTT K                                          321

SEQ ID NO: 510          moltype = AA  length = 48
FEATURE                 Location/Qualifiers
source                  1..48
                        mol_type = protein
                        organism = Human respiratory syncytial virus A
SEQUENCE: 510
RQNKPQNKPN NDFHFEVFNF VPCSICSNNP TCWAICKRIP NKKPGKKT             48

SEQ ID NO: 511          moltype = AA  length = 310
FEATURE                 Location/Qualifiers
source                  1..310
                        mol_type = protein
                        organism = Human respiratory syncytial virus B
SEQUENCE: 511
MSKNKNQRTA RTLEKTWDTL NHLIVISSCL YKLNLKSIAQ IALSVLAMII STSLIIAAII  60
FIISANHKVT LTTATVQTIK NHTEKNITTY LTQVSPERVS PSKQPTATPP IHTNSATISP  120
NTKSETHHTT TQTKGTISTP TQNNKPSTKP RPKNPPKKDD YHFEVFNFVP CSICGNNQLC  180
KSICKTIPSN KPKKKPTTKP TNKPPTKTTN KRDPKTLAKT PKKETTINPT KKPTPKTTER  240
DTSTPQSTVL DITTSKHTER DTSTSQSIAL DTTTSKHTTQ QQSLYSTIPE NTPNSTQTPT  300
ASEPSTSNSI                                                       310

SEQ ID NO: 512          moltype = AA  length = 43
FEATURE                 Location/Qualifiers
source                  1..43
                        mol_type = protein
                        organism = Human respiratory syncytial virus B
SEQUENCE: 512
KNPPKKDDYH FEVFNFVPCS ICGNNQLCKS ICKTIPSNKP KKK                  43

SEQ ID NO: 513          moltype = AA  length = 612
FEATURE                 Location/Qualifiers
source                  1..612
                        mol_type = protein
                        organism = synthetic construct
SEQUENCE: 513
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIC SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGKSLYV KGEPIINFYD PLVFPSDEFD ASISQVNEKI NQSLAFIRKS DELLSAIGGY  480
IPEAPRDGQA YVRKDGEWVL LSTFLGSGGG SGGRQNKPQN KPNNDFHFEV FNFVPCSICS  540
```

```
NNPTCWAICK RIPNKKPGKK TGSGGGSGGK NPPKKDDYHF EVFNFVPCSI CGNNQLCKSI  600
CKTIPSNKPK KK                                                      612

SEQ ID NO: 514          moltype = RNA  length = 2029
FEATURE                 Location/Qualifiers
source                  1..2029
                        mol_type = other RNA
                        organism = synthetic construct
SEQUENCE: 514
acatttgctt ctgacacaac tgtgttcact agcaacctca aacagccacc atggaactcc  60
tcatcctgaa agccaacgcc atcaccacaa ttctcactgc tgtgaccttc tgttttgcct  120
cgggacagaa catcaccgag gagttctacc agtccacatg ctccgctgtg tcgaagggct  180
acctgtcggc gctgaggact ggctggtaca cctccgtgat taccatcgaa ctgtcaaaca  240
tcaaggagaa caagtgcaac ggtactgacg cgaaggtcaa gctgattaag caggaattgg  300
acaagtacaa gaacgccgtg actgagctcc agctgctgat gcagtcaacc cctgcgacgg  360
gaagcgggtc cgcaatctgc tccggagtgg ccgtgtgcaa agtgctgcat ctggagggcg  420
aagtcaacaa gatcaagtcg gccctgctga gcaccaacaa ggccgtggtg tccttgagta  480
acggagtctc cgtcctgacc ttcaaagttc tggacctgaa gaattacatc gataagcagc  540
tcctgcccat cctcaacaag cagagctgct ccatttcgaa catcgaaact gtgatcgagt  600
ttcagcaaaa gaacaaccgg ctgctggaaa tcaccagaga gtttagcgtg aacgcaggag  660
tgactacccc cgtgtctacc tacatgctaa ccaactcaga actgcttagc ttgatcaatg  720
acatgccgat cactaacgat cagaagaagc ttatgtccaa caacgtgcaa atcgtgcgcc  780
agcaatccta ctcgattatg tgcattatca aggaagaggt gctggcctat gtggtgcagc  840
tcccgctgta cggcgtgatt gacactcctt gctggaagct gcacacctcc cccctgtgta  900
ccacgaatac caaggagggg tccaatatct gcctgacccg gaccgaccgc ggatggtact  960
gcgacaacgc cggttcggtg tccttcttcc cacaagccga gacttgcaaa gtccagtcca  1020
atcgcgtgtt ctgcgacact atgaactccc ggaccttgcc gtccgaagtg aacctgtgta  1080
acgtggacat cttcaaccct aaatacgact gcaagattat gacttccaag accgacgtca  1140
gcagctcagt gatcaccagc ctgggcgcca tcgtgtcgtg ttatggaaag accaagtgca  1200
ctgcgtccaa caagaacaga ggcatcatca agaccttcag caacggctgc gattacgtca  1260
gcaacaaggg ggtggatacc gtgtccgtgg gaaacactct ctactgtgtg aacaagcagg  1320
agggaaagtc cctctacgtc aagggcgaac cgatcatcaa cttctacgat cccctggtgt  1380
tcccatccga cgagttcgac gcctccattt cacaagtcaa cgaaaagatc aaccagtctc  1440
tggcgttcat ccggaagtcg gatgaactcc tttccgccat tggtggatac attcctgagg  1500
ctcctcgcga tggccaggcc tacgtcagga aagacggaga atgggtgctg ctttcaacct  1560
tcctgggatc cgggggtggc tcaggcggca gacaaaacaa gccccagaac aagccgaaca  1620
acgacttcca ctttgaagtg ttcaatttcg taccgtgctc gatttgttcc aacaacccca  1680
cttgctgggc aatctgcaag cggatcccaa acaagaagcc tggaaagaaa accgggagcg  1740
gcggaggttc cggagggaag aacccgccta agaaggacga ctaccacttc gaggtgttca  1800
acttcgtccc gtgttcgatc tgcggcaaca atcagctgtg caagtcaatt tgcaagacca  1860
tcccctccaa caagcccaag aagaagtgat aataggctcg ctttcttgct gtccaatttc  1920
tattaaaggt tcctttgttc cctaagtcca actactaaac tgggggatat tatgaagggc  1980
cttgagcatc tggattctgc ctaataaaaa acatttattt tcattgcaa             2029

SEQ ID NO: 515          moltype = AA  length = 165
FEATURE                 Location/Qualifiers
source                  1..165
                        mol_type = protein
                        organism = synthetic construct
SEQUENCE: 515
MSKTKDQRTA KTLERTWDTL NHLLFISSCL YKLNLKSIAQ ITLSILALII STSLIIAAII  60
FIAGGSRQNK PQNKPNNDFH FEVFNFVPCS ICSNNPTCWA ICKRIPNKKP GKKTGSGGGS  120
GGKNPPKKDD YHFEVFNFVP CSICGNNQLC KSICKTIPSN KPKKK                 165

SEQ ID NO: 516          moltype = RNA  length = 688
FEATURE                 Location/Qualifiers
source                  1..688
                        mol_type = other RNA
                        organism = synthetic construct
SEQUENCE: 516
acatttgctt ctgacacaac tgtgttcact agcaacctca aacagccacc atgagcaaga  60
ccaaggacca gcggaccgcc aaaaccctcg aaaggacttg ggataccctt aatcatctgc  120
tgttcatttc ctcgtgctta tacaagctga acctgaagtc cattgcacaa attaccctgt  180
caattctggc cctcatcatc tccacctccc tgatcattgc cgctatcatc ttcatcgcgg  240
gcggtagcag acaaaacaag ccccagaaca agccgaacaa cgacttccac tttgaagtgt  300
tcaatttcgt accgtgctcg atttgttcca acaaccccac ttgctgggca atctgcaagc  360
ggatcccaaa caagaagcct ggaaagaaaa ccgggagcgg cggaggttcc ggagggaaga  420
acccgcctaa gaaggacgac taccacttcg aggtgttcaa cttcgtcccg tgttcgatct  480
gcggcaacaa tcagctgtgc aagtcaattt gcaagaccat cccctccaac aagcccaaga  540
agaagtgata ataggctcgc tttcttgctg tccaatttct attaaaggtt cctttgttcc  600
ctaagtccaa ctactaaact gggggatatt atgaagggcc ttgagcatct ggattctgcc  660
taataaaaaa catttatttt cattgcaa                                    688

SEQ ID NO: 517          moltype =   length =
SEQUENCE: 517
000

SEQ ID NO: 518          moltype =   length =
SEQUENCE: 518
```

000

SEQ ID NO: 519 moltype = length =
SEQUENCE: 519
000

SEQ ID NO: 520 moltype = length =
SEQUENCE: 520
000

SEQ ID NO: 521 moltype = length =
SEQUENCE: 521
000

SEQ ID NO: 522 moltype = length =
SEQUENCE: 522
000

SEQ ID NO: 523 moltype = length =
SEQUENCE: 523
000

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =

SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

SEQ ID NO: 543 moltype = length =
SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =
SEQUENCE: 550
000

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = length =
SEQUENCE: 561
000

SEQ ID NO: 562 moltype = length =
SEQUENCE: 562
000

SEQ ID NO: 563 moltype = length =
SEQUENCE: 563
000

SEQ ID NO: 564 moltype = length =
SEQUENCE: 564
000

SEQ ID NO: 565 moltype = length =
SEQUENCE: 565
000

SEQ ID NO: 566 moltype = length =
SEQUENCE: 566
000

SEQ ID NO: 567 moltype = length =
SEQUENCE: 567
000

SEQ ID NO: 568 moltype = length =
SEQUENCE: 568
000

SEQ ID NO: 569 moltype = length =
SEQUENCE: 569
000

SEQ ID NO: 570 moltype = length =
SEQUENCE: 570
000

SEQ ID NO: 571 moltype = length =
SEQUENCE: 571
000

SEQ ID NO: 572 moltype = length =
SEQUENCE: 572
000

SEQ ID NO: 573 moltype = length =
SEQUENCE: 573
000

SEQ ID NO: 574 moltype = length =
SEQUENCE: 574
000

SEQ ID NO: 575 moltype = length =
SEQUENCE: 575
000

SEQ ID NO: 576 moltype = length =
SEQUENCE: 576
000

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582
000

SEQ ID NO: 583 moltype = length =
SEQUENCE: 583
000

SEQ ID NO: 584 moltype = length =
SEQUENCE: 584
000

SEQ ID NO: 585 moltype = length =
SEQUENCE: 585
000

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590
000

SEQ ID NO: 591 moltype = length =
SEQUENCE: 591
000

SEQ ID NO: 592 moltype = length =
SEQUENCE: 592
000

SEQ ID NO: 593 moltype = length =
SEQUENCE: 593
000

SEQ ID NO: 594 moltype = length =
SEQUENCE: 594
000

SEQ ID NO: 595 moltype = length =
SEQUENCE: 595
000

SEQ ID NO: 596 moltype = length =
SEQUENCE: 596
000

SEQ ID NO: 597 moltype = length =
SEQUENCE: 597

000

SEQ ID NO: 598 moltype = length =
SEQUENCE: 598
000

SEQ ID NO: 599 moltype = length =
SEQUENCE: 599
000

SEQ ID NO: 600 moltype = length =
SEQUENCE: 600
000

SEQ ID NO: 601 moltype = length =
SEQUENCE: 601
000

SEQ ID NO: 602 moltype = length =
SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605
000

SEQ ID NO: 606 moltype = length =
SEQUENCE: 606
000

SEQ ID NO: 607 moltype = length =
SEQUENCE: 607
000

SEQ ID NO: 608 moltype = length =
SEQUENCE: 608
000

SEQ ID NO: 609 moltype = length =
SEQUENCE: 609
000

SEQ ID NO: 610 moltype = length =
SEQUENCE: 610
000

SEQ ID NO: 611 moltype = length =
SEQUENCE: 611
000

SEQ ID NO: 612 moltype = length =
SEQUENCE: 612
000

SEQ ID NO: 613 moltype = length =
SEQUENCE: 613
000

SEQ ID NO: 614 moltype = length =
SEQUENCE: 614
000

SEQ ID NO: 615 moltype = length =
SEQUENCE: 615
000

SEQ ID NO: 616 moltype = length =
SEQUENCE: 616
000

SEQ ID NO: 617 moltype = length =

SEQUENCE: 617
000

SEQ ID NO: 618 moltype = length =
SEQUENCE: 618
000

SEQ ID NO: 619 moltype = length =
SEQUENCE: 619
000

SEQ ID NO: 620 moltype = length =
SEQUENCE: 620
000

SEQ ID NO: 621 moltype = length =
SEQUENCE: 621
000

SEQ ID NO: 622 moltype = length =
SEQUENCE: 622
000

SEQ ID NO: 623 moltype = length =
SEQUENCE: 623
000

SEQ ID NO: 624 moltype = length =
SEQUENCE: 624
000

SEQ ID NO: 625 moltype = length =
SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =
SEQUENCE: 629
000

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

SEQ ID NO: 636 moltype = length =
SEQUENCE: 636
000

-continued

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =
SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

SEQ ID NO: 660 moltype = length =
SEQUENCE: 660
000

SEQ ID NO: 661 moltype = length =
SEQUENCE: 661
000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676

000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =
SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684
000

SEQ ID NO: 685 moltype = length =
SEQUENCE: 685
000

SEQ ID NO: 686 moltype = length =
SEQUENCE: 686
000

SEQ ID NO: 687 moltype = length =
SEQUENCE: 687
000

SEQ ID NO: 688 moltype = length =
SEQUENCE: 688
000

SEQ ID NO: 689 moltype = length =
SEQUENCE: 689
000

SEQ ID NO: 690 moltype = length =
SEQUENCE: 690
000

SEQ ID NO: 691 moltype = length =
SEQUENCE: 691
000

SEQ ID NO: 692 moltype = length =
SEQUENCE: 692
000

SEQ ID NO: 693 moltype = length =
SEQUENCE: 693
000

SEQ ID NO: 694 moltype = length =
SEQUENCE: 694
000

SEQ ID NO: 695 moltype = length =
SEQUENCE: 695
000

SEQ ID NO: 696 moltype = length =

SEQUENCE: 696
000

SEQ ID NO: 697 moltype = length =
SEQUENCE: 697
000

SEQ ID NO: 698 moltype = length =
SEQUENCE: 698
000

SEQ ID NO: 699 moltype = length =
SEQUENCE: 699
000

SEQ ID NO: 700 moltype = length =
SEQUENCE: 700
000

SEQ ID NO: 701 moltype = length =
SEQUENCE: 701
000

SEQ ID NO: 702 moltype = length =
SEQUENCE: 702
000

SEQ ID NO: 703 moltype = length =
SEQUENCE: 703
000

SEQ ID NO: 704 moltype = length =
SEQUENCE: 704
000

SEQ ID NO: 705 moltype = length =
SEQUENCE: 705
000

SEQ ID NO: 706 moltype = length =
SEQUENCE: 706
000

SEQ ID NO: 707 moltype = length =
SEQUENCE: 707
000

SEQ ID NO: 708 moltype = length =
SEQUENCE: 708
000

SEQ ID NO: 709 moltype = length =
SEQUENCE: 709
000

SEQ ID NO: 710 moltype = length =
SEQUENCE: 710
000

SEQ ID NO: 711 moltype = length =
SEQUENCE: 711
000

SEQ ID NO: 712 moltype = length =
SEQUENCE: 712
000

SEQ ID NO: 713 moltype = length =
SEQUENCE: 713
000

SEQ ID NO: 714 moltype = length =
SEQUENCE: 714
000

SEQ ID NO: 715 moltype = length =
SEQUENCE: 715
000

-continued

SEQ ID NO: 716 moltype = length =
SEQUENCE: 716
000

SEQ ID NO: 717 moltype = length =
SEQUENCE: 717
000

SEQ ID NO: 718 moltype = length =
SEQUENCE: 718
000

SEQ ID NO: 719 moltype = length =
SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740
000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748
000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754
000

SEQ ID NO: 755 moltype = length =
SEQUENCE: 755

000

SEQ ID NO: 756 moltype = length =
SEQUENCE: 756
000

SEQ ID NO: 757 moltype = length =
SEQUENCE: 757
000

SEQ ID NO: 758 moltype = length =
SEQUENCE: 758
000

SEQ ID NO: 759 moltype = length =
SEQUENCE: 759
000

SEQ ID NO: 760 moltype = length =
SEQUENCE: 760
000

SEQ ID NO: 761 moltype = length =
SEQUENCE: 761
000

SEQ ID NO: 762 moltype = length =
SEQUENCE: 762
000

SEQ ID NO: 763 moltype = length =
SEQUENCE: 763
000

SEQ ID NO: 764 moltype = length =
SEQUENCE: 764
000

SEQ ID NO: 765 moltype = length =
SEQUENCE: 765
000

SEQ ID NO: 766 moltype = length =
SEQUENCE: 766
000

SEQ ID NO: 767 moltype = length =
SEQUENCE: 767
000

SEQ ID NO: 768 moltype = length =
SEQUENCE: 768
000

SEQ ID NO: 769 moltype = length =
SEQUENCE: 769
000

SEQ ID NO: 770 moltype = length =
SEQUENCE: 770
000

SEQ ID NO: 771 moltype = length =
SEQUENCE: 771
000

SEQ ID NO: 772 moltype = length =
SEQUENCE: 772
000

SEQ ID NO: 773 moltype = length =
SEQUENCE: 773
000

SEQ ID NO: 774 moltype = length =
SEQUENCE: 774
000

SEQ ID NO: 775 moltype = length =

SEQUENCE: 775
000

SEQ ID NO: 776 moltype = length =
SEQUENCE: 776
000

SEQ ID NO: 777 moltype = length =
SEQUENCE: 777
000

SEQ ID NO: 778 moltype = length =
SEQUENCE: 778
000

SEQ ID NO: 779 moltype = length =
SEQUENCE: 779
000

SEQ ID NO: 780 moltype = length =
SEQUENCE: 780
000

SEQ ID NO: 781 moltype = length =
SEQUENCE: 781
000

SEQ ID NO: 782 moltype = length =
SEQUENCE: 782
000

SEQ ID NO: 783 moltype = length =
SEQUENCE: 783
000

SEQ ID NO: 784 moltype = length =
SEQUENCE: 784
000

SEQ ID NO: 785 moltype = length =
SEQUENCE: 785
000

SEQ ID NO: 786 moltype = length =
SEQUENCE: 786
000

SEQ ID NO: 787 moltype = length =
SEQUENCE: 787
000

SEQ ID NO: 788 moltype = length =
SEQUENCE: 788
000

SEQ ID NO: 789 moltype = length =
SEQUENCE: 789
000

SEQ ID NO: 790 moltype = length =
SEQUENCE: 790
000

SEQ ID NO: 791 moltype = length =
SEQUENCE: 791
000

SEQ ID NO: 792 moltype = length =
SEQUENCE: 792
000

SEQ ID NO: 793 moltype = length =
SEQUENCE: 793
000

SEQ ID NO: 794 moltype = length =
SEQUENCE: 794
000

SEQ ID NO: 795 moltype = length =
SEQUENCE: 795
000

SEQ ID NO: 796 moltype = length =
SEQUENCE: 796
000

SEQ ID NO: 797 moltype = length =
SEQUENCE: 797
000

SEQ ID NO: 798 moltype = length =
SEQUENCE: 798
000

SEQ ID NO: 799 moltype = length =
SEQUENCE: 799
000

SEQ ID NO: 800 moltype = length =
SEQUENCE: 800
000

SEQ ID NO: 801 moltype = AA length = 1010
FEATURE Location/Qualifiers
source 1..1010
mol_type = protein
organism = synthetic construct
SEQUENCE: 801
MAAPGSARRP LLLLLLLLLL GLMHCASASA SKEIKSFLWT QSLRRELSGY CSNIKLQVVK 60
DAQALLHGLD FSEVSNVQRL MRKERRDDND LKRLRDLNQA VNNLVELKST QQKSILRVGT 120
LTSDDLLILA ADLEKLKSKV IRTERPLSAG VYMGNLSSQQ LDQRRALLNM IGMSGGNQGA 180
RAGRDGVVRV WDVKNAELLN NQFGTMPSLT LACLTKQGQV DLNDAVQALT DLGLIYTAKY 240
PNTSDLDRLT QSHPILNMID TKKSSLNISG YNFSLGAAVK AGACMLDGGN MLETIKVSPQ 300
TMDGILKSIL KVKKALGMFI SDTPGERNPY ENILYKICLS GDGWPYIASR TSITGRAWEN 360
TVVDLESDGK PQKADSNNSS KSLQSAGFTA GLTYSQLMTL KDAMLQLDPN AKTWMDIEGR 420
PEDPVEIALY QPSSGCYIHF FREPTDLKQF KQDAKYSHGI DVTDLFATQP GLTSAVIDAL 480
PRNMVITCQG SDDIRKLLES QGRKDIKLID IALSKTDSRK YENAVWDQYK DLCHMHTGVV 540
VEKKKRGGKE EITPHCALMD CIMFDAAVSG GLNTSVLRAV LPRDMVFRTS TPRVVLGPGP 600
GTSLYKGVYE LQTLELNMET LNMTMPLSCT KNNSHHYIMV GNETGLELTL TNTSIINHKF 660
CNLSDAHKKN LYDHALMSII STFHLSIPNF NQYEAMSCDF NGGKISVQYN LSHSYAGDAA 720
NHCGTVANGV LQTFMRMAWG GSYIALDSGR GNWDCIMTSY QYLIIQNTTW EDHCQFSRPS 780
PIGYLGLLSQ RTRDIYISRR LLGTFTWTLS DSEGKDTPGG YCLTRWMLIE AELKCFGNTA 840
VAKCNEKHDE EFCDMLRLFD FNKQAIQRLK AEAQMSIQLI NKAVNALIND QLIMKNHLRD 900
IMGIPYCNYS KYWYLNHTTT GRTSLPKCWL VSNGSYLNET HFSDDIEQQA DNMITEMLQK 960
EYMERQGKTP LGLVDLIPIA VGGALAGLVL IVLIAYLVGR KRSHAGYQTI 1010

SEQ ID NO: 802 moltype = RNA length = 3223
FEATURE Location/Qualifiers
source 1..3223
mol_type = other RNA
organism = synthetic construct
SEQUENCE: 802
acatttgctt ctgacacaac tgtgttcact agcaacctca aacagccacc atggccgccc 60
ccgggagcgc taggcgccct cttctgctct tgctgttgct gctgcttctg ggctgatgc 120
attgcgcatc agcaagcgcc tccaaggaga tcaagtcgtt cctgtggacc cagtccctcc 180
ggcgggagct gtcgggctac tgctcgaaca tcaagctcca agtcgtgaaa gacgcgcagg 240
ccctgctgca cggactggat ttctcggaag tctccaacgt ccaaagattg atgcggaaag 300
aaaggaggga cgacaatgat ctgaagaggc tccgcgacct caaccaggcg gttaacaacc 360
tggtggaact gaagtcgacc cagcaaaaga gcattctgcg cgtgggcacc ctcacctccg 420
acgaccttct gatcctggcc gccgatctgg agaagttgaa gtccaaggtc atccgcaccg 480
aacggccgct gtccgccggg gtgtacatgg gaaacctgtc aagccagcag ctggatcagc 540
gcagagcact tcttaacatg atcggaatgt ccggtggaaa tcagggtgcc agagcaggcc 600
gggacggagt cgtgcgggtc tgggacgtga agaacgcgga gctgctgaac aaccagttcg 660
gcaccatgcc gtcactgacc ctggcctgtc tcacaaagca gggccaagtg gacctgaatg 720
acgcagtgca ggcccttacg gacctgggcc tgatctacac cgctaagtac ccgaatacca 780
gcgacctgga tagactgact cagtcgcatc caattctgaa tatgatcgac accaagaagt 840
cctcgctgaa catttccggt tataacttct ccttgggagc ggccgtgaag gccggagcgt 900
gcatgctgga cggcgggaac atgctggaaa ccatcaaagt gtccccgcaa accatggacg 960
gaatcctcaa gtccatcctg aaagtcaaga aggccctggg aatgttcatt tctgacaccc 1020
cgggagagag gaacccatac gagaatatcc tgtacaagat ttgtctgagc ggggacggct 1080
ggccgtacat tgcgagccgg actagcatca ccggtagagc ctgggagaac accgtggtcg 1140
accttgaatc cgatggaaag ccacagaagg cagactccaa caactcttcc aagtccctgc 1200
aaagcgccgg attcaccgcg ggactcacct actcccaact catgaccctg aaggatgcaa 1260
tgctccagct cgacccaaac gctaagactt ggatggacat cgaaggccgg cccgaagatc 1320
ccgtggaaat tgccctctac caaccctcaa gcggttgcta catccacttc ttccgcgaac 1380
cgactgacct gaaacagttt aagcaggacg caaagtactc ccacggtatc gatgtgaccg 1440
acctctttgc tacccaacct ggcctgacct ccgccgtgat cgatgccctg ccccgcaaca 1500

-continued

```
tggtcatcac ttgtcaaggc agtgatgata tcaggaagct gctcgagagc cagggtagaa  1560
aggatatcaa gctgatcgac atcgcgctga gcaagactga cagccgcaaa tacgaaaacg  1620
ctgtgtggga ccagtacaag gacttgtgcc acatgcacac aggggtggtg gtcgaaaaga  1680
agaagcgggg aggaaaggag gagatcaccc cacattgcgc cctgatggac tgcattatgt  1740
tcgacgcggc cgtgtcagga ggactcaaca cttccgtgct ccgggccgtg ctgccccggg  1800
acatggtgtt cagaacttcc actcctcgcg tggtgctggg cccgggacct ggaacctcac  1860
tgtacaaggg ggtgtacgaa ctgcagaccc tggaattgaa catggaaact ctgaacatga  1920
ccatgcctct ctcctgtacc aagaacaatt cccaccacta cattatggtc ggaaacgaaa  1980
ctgggctcga gctgaccctc accaacacct ccataatcaa ccacaagttc tgcaaccttt  2040
ctgatgccca caagaagaac ctatacgacc atgccctgat gtccattatc tccaccttcc  2100
acctctcaat ccccaacttc aatcaatacg aagcgatgtc ctgtgatttc aacggcggaa  2160
agatctcggt gcagtacaac ctctcgcatt catacgccgg agatgccgcc aaccactgcg  2220
gtactgtggc caacggggtg ctccagacct ttatgaggat ggcgtgggga ggatcctaca  2280
tcgccttgga ctccggacgc ggcaactggg actgcatcat gaccagctac cagtacctga  2340
ttattcagaa caccacctgg gaggaccact gccagttctc gcgcccttcg ccgattgggt  2400
accttggcct cctgtcgcaa agaaccagag acatctacat cagccgccgg ttactgggaa  2460
cttttacttg gaccctttcg gattccgagg gaaaggacac gcccggcggt tactgcctga  2520
cgcggtggat gctgattgaa gctgaactca agtgtttcgg caacaccgcc gtggccaagt  2580
gcaacgagaa gcacgacgaa gagttctgcg atatgctgcg actgttcgat ttcaacaagc  2640
aggctattca gcggctgaag gccgaggccc agatgagcat tcagctgatc aacaaggccg  2700
tgaacgccct gattaacgat cagctcatta tgaagaacca tctgcgggac atcatgggca  2760
tcccttactg caactactcc aagtattggt acctgaacca cactaccact ggccgcacca  2820
gcctccccgaa gtgctggctc gtgtccaacg gatcctatct gaacgaaacc cacttttccg  2880
acgacattga gcagcaggcc gacaacatga tcaccgagat gttgcagaag gagtacatgg  2940
agcgccaggg gaaaactccc ctgggactgg tggaccttat ccctattgct gtgggcggtg  3000
ccttggctgg cctggtactg atcgtgctga tcgcgtatct cgtgggccgg aaacggtcac  3060
acgccgggta ccagactatc tgataatagg ctcgctttct tgctgtccaa tttctattaa  3120
aggttccttt gttccctaag tccaactact aaactggggg atattatgaa gggccttgag  3180
catctggatt ctgcctaata aaaaacattt attttcattg caa                   3223

SEQ ID NO: 803          moltype = AA  length = 1024
FEATURE                 Location/Qualifiers
source                  1..1024
                        mol_type = protein
                        organism = synthetic construct
SEQUENCE: 803
MRVTAPRTLI LLLSGALALT ETWASASKEI KSFLWTQSLR RELSGYCSNI KLQVVKDAQA  60
LLHGLDFSEV SNVQRLMRKE RRDDNDLKRL RDLNQAVNNL VELKSTQQKS ILRVGTLTSD  120
DLLILAADLE KLKSKVIRTE RPLSAGVYMG NLSSQQLDQR RALLNMIGMS GGNQGARAGR  180
DGVVRVWDVK NAELLNNQFG TMPSLTLACL TKQGQVDLND AVQALTDLGL IYTAKYPNTS  240
DLDRLTQSHP ILNMIDTKKS SLNISGYNFS LGAAVKAGAC MLDGGNMLET IKVSPQTMDG  300
ILKSILKVKK ALGMFISDTP GERNPYENIL YKICLSGDGW PYIASRTSIT GRAWENTVVD  360
LESDGKPQKA DSNNSSKSLQ SAGFTAGLTY SQLMTLKDAM LQLDPNAKTW MDIEGRPEDP  420
VEIALYQPSS GCYIHFFREP TDLKQFKQDA KYSHGIDVTD LFATQPGLTS AVIDALPRNM  480
VITCQGSDDI RKLLESQGRK DIKLIDIALS KTDSRKYENA VWDQYKDLCH MHTGVVVEKK  540
KRGGKEEITP HCALMDCIMF DAAVSGGLNT SVLRAVLPRD MVFRTSTPRV VLGPGPGTSL  600
YKGVYELQTL ELNMETLNMT MPLSCTKNNS HHYIMVGNET GLELTLTNTS IINHKFCNLS  660
DAHKKNLYDH ALMSIISTFH LSIPNFNQYE AMSCDFNGGK ISVQYNLSHS YAGDAANHCG  720
TVANGVLQTF MRMAWGGSYI ALDSGRGNWD CIMTSYQYLI IQNTTWEDHC QFSRPSPIGY  780
LGLLSQRTRD IYISRRLLGT FTWTLSDSEG KDTPGGYCLT RWMLIEAELK CFGNTAVAKC  840
NEKHDEEFCD MLRLFDFNKQ AIQRLKAEAQ MSIQLINKAV NALINDQLIM KNHLRDIMGI  900
PYCNYSKYWY LNHTTTGRTS LPKCWLVSNG SYLNETHFSD DIEQQADNMI TEMLQKEYME  960
RQGKTPLGLV DGIVAGLAVL AVVVIGAVVA AVMCRRKSSG GKGGSYSQAA CSDSAQGSDV  1020
SLTA                                                              1024

SEQ ID NO: 804          moltype = RNA  length = 3265
FEATURE                 Location/Qualifiers
source                  1..3265
                        mol_type = other RNA
                        organism = synthetic construct
SEQUENCE: 804
acatttgctt ctgacacaac tgtgttcact agcaacctca aacagccacc atgcgggtca  60
ctgcgccgag aaccctcatt cttctcctat ccggggcgct ggctctcacc gaaacctggg  120
caagcgcctc caaggagatc aagtcgttcc tgtggaccca gtccctccgg cgggagctgt  180
cgggctactg ctcgaacatc aagctccaag tcgtgaaaga cgcgcaggcc ctgctgcacg  240
gactggattt ctcggaagtc tccaacgtcc aaagattgat gcggaaagaa aggagggacg  300
acaatgatct gaagaggctc cgcgacctca accaggcggt taacaacctg gtggaactga  360
agtcgaccca gcaaaagagc attctgcgcg tgggcaccct cacctccgac gaccttctga  420
tcctggccgc cgatctggag aagttgaagt ccaaggtcat ccgcaccgaa cggccgctgt  480
ccgccggggt gtacatggga aacctgtcaa gccagcagct ggatcagcgc agagcacttc  540
ttaacatgat cggaatgtcc ggtggaaatc agggtgccag agcaggccgg gacggagtcg  600
tgcgggtctg ggacgtgaag aacgcggagc tgctgaacaa ccagttcggc accatgccgt  660
cactgaccct ggcctgtctc acaaagcagg gccaagtgga cctgaatgac gcagtgcagg  720
cccttacgga cctgggcctg atctacaccg ctaagtaccc gaataccagc gacctggata  780
gactgactca gtcgcatcca attctgaata tgatcgacac caagaagtcc tcgctgaaca  840
tttccggtta taacttctcc ttgggagcgg ccgtgaaggc cggagcgtgc atgctggacg  900
gcgggaacat gctggaaacc atcaaagtgt ccccgcaaac catggacgga atcctcaagt  960
ccatcctgaa agtcaagaag gccctgggaa tgttcatttc tgacaccccg ggagagagga  1020
acccatacga gaatatcctg tacaagattt gtctgagcgg ggacggctgg ccgtacattg  1080
```

-continued

```
cgagccggac tagcatcacc ggtagagcct gggagaacac cgtggtcgac cttgaatccg  1140
atggaaagcc acagaaggca gactccaaca actcttccaa gtccctgcaa agcgccggat  1200
tcaccgcggg actcacctac tcccaactca tgaccctgaa ggatgcaatg ctccagctcg  1260
acccaaacgc taagacttgg atggacatcg aaggccggcc cgaagatccc gtggaaattg  1320
ccctctacca accctcaagc ggttgctaca tccacttctt ccgcgaaccg actgacctga  1380
aacagtttaa gcaggacgca aagtactccc acggtatcga tgtgaccgac ctctttgcta  1440
cccaacctgg cctgacctcc gccgtgatcg atgccctgcc ccgcaacatg gtcatcactt  1500
gtcaaggcag tgatgatatc aggaagctgc tcgagagcca gggtagaaag gatatcaagc  1560
tgatcgacat cgcgctgagc aagactgaca gccgcaaata cgaaaacgct gtgtgggacc  1620
agtacaagga cttgtgccac atgcacacag gggtggtggt cgaaaagaag aagcggggag  1680
gaaaggagga gatcacccca cattgcgccc tgatggactg cattatgttc gacgcggccg  1740
tgtcaggagg actcaacact tccgtgctcc gggccgtgct gccccgggac atggtgttca  1800
gaacttccac tcctcgcgtg gtgctgggcc cgggacctgg aacctcactg tacaaggggg  1860
tgtacgaact gcagaccctg gaattgaaca tggaaactct gaacatgacc atgcctctct  1920
cctgtaccaa gaacaattcc caccactaca ttatggtcgg aaacgaaact gggctcgagc  1980
tgaccctcac caacacctcc ataatcaacc acaagttctg caacctttct gatgcccaca  2040
agaagaacct atacgaccat gccctgatgt ccattatctc caccttccac ctctcaatcc  2100
ccaacttcaa tcaatacgaa gcgatgtcct gtgatttcaa cggcggaaag atctcggtgc  2160
agtacaacct ctcgcattca tacgccggag atgccgccaa ccactgcggt actgtggcca  2220
acggggtgct ccagaccttt atgaggatgg cgtggggagg atcctacatc gccttggact  2280
ccggacgcgg caactgggac tgcatcatga ccagctacca gtacctgatt attcagaaca  2340
ccacctggga ggaccactgc cagttctcgc gcccttcgcc gattgggtac cttggcctcc  2400
tgtcgcaaag aaccagagac atctacatca gccgccggtt actgggaact tttacttgga  2460
ccctttcgga ttccgaggga aaggacacgc ccggcggtta ctgcctgacg cggtggatgc  2520
tgattgaagc tgaactcaag tgtttcggca acaccgccgt ggccaagtgc aacgagaagc  2580
acgacgaaga gttctgcgat atgctgcgac tgttcgattt caacaagcag gctattcagc  2640
ggctgaaggc cgaggcccag atgagcattc agctgatcaa caaggccgtg aacgccctga  2700
ttaacgatca gctcattatg aagaaccatc tgcgggacat catgggcatc ccttactgca  2760
actactccaa gtattggtac ctgaaccaca ctaccactgg ccgcaccagc ctcccgaagt  2820
gctggctcgt gtccaacgga tcctatctga acgaaaccca cttttccgac gacattgagc  2880
agcaggccga caacatgatc accgagatgt tgcagaagga gtacatggag cgccagggga  2940
aaactcccct gggactggtg gacgggattg tggctgggtt ggcggtcctg gcggtggtgg  3000
tgatcggtgc cgtggtggca gccgtgatgt gcaggagaaa gtcgtccggc gggaagggag  3060
ggtcctacag ccaagcggcc tgttctgact ccgcccaggg ctccgacgtg tcactgacag  3120
cctgataata ggctcgcttt cttgctgtcc aatttctatt aaaggttcct ttgttcccta  3180
agtccaacta ctaaactggg ggatattatg aagggccttg agcatctgga ttctgcctaa  3240
taaaaaacat ttattttcat tgcaa                                         3265
```

SEQ ID NO: 805 moltype = length =
SEQUENCE: 805
000

SEQ ID NO: 806 moltype = length =
SEQUENCE: 806
000

SEQ ID NO: 807 moltype = length =
SEQUENCE: 807
000

SEQ ID NO: 808 moltype = length =
SEQUENCE: 808
000

SEQ ID NO: 809 moltype = length =
SEQUENCE: 809
000

SEQ ID NO: 810 moltype = length =
SEQUENCE: 810
000

SEQ ID NO: 811 moltype = length =
SEQUENCE: 811
000

SEQ ID NO: 812 moltype = length =
SEQUENCE: 812
000

SEQ ID NO: 813 moltype = length =
SEQUENCE: 813
000

SEQ ID NO: 814 moltype = length =
SEQUENCE: 814
000

SEQ ID NO: 815 moltype = length =

SEQUENCE: 815
000

SEQ ID NO: 816 moltype = length =
SEQUENCE: 816
000

SEQ ID NO: 817 moltype = length =
SEQUENCE: 817
000

SEQ ID NO: 818 moltype = length =
SEQUENCE: 818
000

SEQ ID NO: 819 moltype = length =
SEQUENCE: 819
000

SEQ ID NO: 820 moltype = length =
SEQUENCE: 820
000

SEQ ID NO: 821 moltype = length =
SEQUENCE: 821
000

SEQ ID NO: 822 moltype = length =
SEQUENCE: 822
000

SEQ ID NO: 823 moltype = length =
SEQUENCE: 823
000

SEQ ID NO: 824 moltype = length =
SEQUENCE: 824
000

SEQ ID NO: 825 moltype = length =
SEQUENCE: 825
000

SEQ ID NO: 826 moltype = length =
SEQUENCE: 826
000

SEQ ID NO: 827 moltype = length =
SEQUENCE: 827
000

SEQ ID NO: 828 moltype = length =
SEQUENCE: 828
000

SEQ ID NO: 829 moltype = length =
SEQUENCE: 829
000

SEQ ID NO: 830 moltype = length =
SEQUENCE: 830
000

SEQ ID NO: 831 moltype = length =
SEQUENCE: 831
000

SEQ ID NO: 832 moltype = length =
SEQUENCE: 832
000

SEQ ID NO: 833 moltype = length =
SEQUENCE: 833
000

SEQ ID NO: 834 moltype = length =
SEQUENCE: 834
000

-continued

SEQ ID NO: 835 moltype = length =
SEQUENCE: 835
000

SEQ ID NO: 836 moltype = length =
SEQUENCE: 836
000

SEQ ID NO: 837 moltype = length =
SEQUENCE: 837
000

SEQ ID NO: 838 moltype = length =
SEQUENCE: 838
000

SEQ ID NO: 839 moltype = length =
SEQUENCE: 839
000

SEQ ID NO: 840 moltype = length =
SEQUENCE: 840
000

SEQ ID NO: 841 moltype = length =
SEQUENCE: 841
000

SEQ ID NO: 842 moltype = length =
SEQUENCE: 842
000

SEQ ID NO: 843 moltype = length =
SEQUENCE: 843
000

SEQ ID NO: 844 moltype = length =
SEQUENCE: 844
000

SEQ ID NO: 845 moltype = length =
SEQUENCE: 845
000

SEQ ID NO: 846 moltype = length =
SEQUENCE: 846
000

SEQ ID NO: 847 moltype = length =
SEQUENCE: 847
000

SEQ ID NO: 848 moltype = length =
SEQUENCE: 848
000

SEQ ID NO: 849 moltype = length =
SEQUENCE: 849
000

SEQ ID NO: 850 moltype = length =
SEQUENCE: 850
000

SEQ ID NO: 851 moltype = length =
SEQUENCE: 851
000

SEQ ID NO: 852 moltype = length =
SEQUENCE: 852
000

SEQ ID NO: 853 moltype = length =
SEQUENCE: 853
000

SEQ ID NO: 854 moltype = length =
SEQUENCE: 854
000

SEQ ID NO: 855 moltype = length =
SEQUENCE: 855
000

SEQ ID NO: 856 moltype = length =
SEQUENCE: 856
000

SEQ ID NO: 857 moltype = length =
SEQUENCE: 857
000

SEQ ID NO: 858 moltype = length =
SEQUENCE: 858
000

SEQ ID NO: 859 moltype = length =
SEQUENCE: 859
000

SEQ ID NO: 860 moltype = length =
SEQUENCE: 860
000

SEQ ID NO: 861 moltype = length =
SEQUENCE: 861
000

SEQ ID NO: 862 moltype = length =
SEQUENCE: 862
000

SEQ ID NO: 863 moltype = length =
SEQUENCE: 863
000

SEQ ID NO: 864 moltype = length =
SEQUENCE: 864
000

SEQ ID NO: 865 moltype = length =
SEQUENCE: 865
000

SEQ ID NO: 866 moltype = length =
SEQUENCE: 866
000

SEQ ID NO: 867 moltype = length =
SEQUENCE: 867
000

SEQ ID NO: 868 moltype = length =
SEQUENCE: 868
000

SEQ ID NO: 869 moltype = length =
SEQUENCE: 869
000

SEQ ID NO: 870 moltype = length =
SEQUENCE: 870
000

SEQ ID NO: 871 moltype = length =
SEQUENCE: 871
000

SEQ ID NO: 872 moltype = length =
SEQUENCE: 872
000

SEQ ID NO: 873 moltype = length =
SEQUENCE: 873
000

SEQ ID NO: 874 moltype = length =
SEQUENCE: 874

000

SEQ ID NO: 875 moltype = length =
SEQUENCE: 875
000

SEQ ID NO: 876 moltype = length =
SEQUENCE: 876
000

SEQ ID NO: 877 moltype = length =
SEQUENCE: 877
000

SEQ ID NO: 878 moltype = length =
SEQUENCE: 878
000

SEQ ID NO: 879 moltype = length =
SEQUENCE: 879
000

SEQ ID NO: 880 moltype = length =
SEQUENCE: 880
000

SEQ ID NO: 881 moltype = length =
SEQUENCE: 881
000

SEQ ID NO: 882 moltype = length =
SEQUENCE: 882
000

SEQ ID NO: 883 moltype = length =
SEQUENCE: 883
000

SEQ ID NO: 884 moltype = length =
SEQUENCE: 884
000

SEQ ID NO: 885 moltype = length =
SEQUENCE: 885
000

SEQ ID NO: 886 moltype = length =
SEQUENCE: 886
000

SEQ ID NO: 887 moltype = length =
SEQUENCE: 887
000

SEQ ID NO: 888 moltype = length =
SEQUENCE: 888
000

SEQ ID NO: 889 moltype = length =
SEQUENCE: 889
000

SEQ ID NO: 890 moltype = length =
SEQUENCE: 890
000

SEQ ID NO: 891 moltype = length =
SEQUENCE: 891
000

SEQ ID NO: 892 moltype = length =
SEQUENCE: 892
000

SEQ ID NO: 893 moltype = length =
SEQUENCE: 893
000

SEQ ID NO: 894 moltype = length =

```
SEQUENCE: 894
000

SEQ ID NO: 895         moltype =   length =
SEQUENCE: 895
000

SEQ ID NO: 896         moltype =   length =
SEQUENCE: 896
000

SEQ ID NO: 897         moltype =   length =
SEQUENCE: 897
000

SEQ ID NO: 898         moltype =   length =
SEQUENCE: 898
000

SEQ ID NO: 899         moltype =   length =
SEQUENCE: 899
000

SEQ ID NO: 900         moltype =   length =
SEQUENCE: 900
000

SEQ ID NO: 901         moltype = RNA  length = 1798
FEATURE                Location/Qualifiers
source                 1..1798
                       mol_type = other RNA
                       organism = synthetic construct
SEQUENCE: 901
acatttgctt ctgacacaac tgtgttcact agcaacctca aacagccacc atggaactgc  60
tgatcctgaa ggccaacgcc atcaccacta ttctgaccgc cgtgaccttt tgcttcgcct  120
ccggccagaa catcacagag gaattctacc agagcacctg ttctgccgtc agcaagggct  180
acctgtctgc cctgagaaca ggctggtaca cctctgtgat caccatagag ctgagtaaca  240
tcaaagagaa caagtgtaat ggaaccgatg caaaggtgaa actgattaaa caggagctgg  300
acaagtacaa gaacgccgtc accgagctgc agctactgat gcagagcacc cccgccaccg  360
gctcaggcag cgccatctgc agcggcgtcg ccgtgtgcaa ggtgctgcac ctggaaggcg  420
aagtgaacaa aatcaagtct gctctgctgt ccacaaacaa ggctgttgtg agcctgagca  480
atggcgtgag cgtgctgaca ttcaaggtgc tagatctgaa aaactacatc gataagcaac  540
tgctgcctat cctgaacaag cagagctgca gcatcagcaa catcgagaca gtgatcgaat  600
ttcagcagaa aaacaaccgg ctgctggaaa tcacaagaga gttcagcgtg aacgccggag  660
tgaccacccc tgtgtctacc tacatgctga caaatagcga gctgctgagc ctgatcaacg  720
acatgcctat taccaacgac cagaagaagc tgatgagcaa caacgtgcag atcgtgcggc  780
agcaatcata ctctatcatg tgcatcatca aggaagaagt gctggcttac gtggtgcaac  840
tgcctctgta cggcgtaatc gacacaccat gctggaagct gcacaccagc cctctgtgca  900
caaccaacac caaggaaggc tccaacatct gtctgaccag gacagataga ggctggtatt  960
gtgacaacgc cggcagcgtg agcttcttcc cccaggccga gacatgcaaa gtgcagagca  1020
atagagtgtt ttgcgacacc atgaacagca gaaccctgcc atctgaggtg aacctgtgta  1080
acgtggacat cttcaacccc aagtacgact gcaagatcat gaccagcaaa acagatgtga  1140
gttctagcgt catcaccagc ctgggtgcca tcgtatcttg ctacggcaaa accaagtgca  1200
ccgccagcaa taagaatcgg ggaatcatca agacattcag caacggctgc gactacgttt  1260
ctaataaggg agtggatacc gtgtctgtgg gaaataccct gtactgtgtg aacaagcagg  1320
agggcaagag cctgtatgtg aagggcgagc ctatcatcaa cttctacgat cctctggtgt  1380
tccctagcga cgagttcgac gctagcatca gccaggtgaa tgagaagatc aaccagtccc  1440
tcgccttcat cagaaagtcc gacgagctgc tccacaacgt gaacgctggc aagagcacaa  1500
caaacatcat gatcaccaca attatcatcg tgatcatcgt gatcctgctg agcctgatcg  1560
ccgtgggcct gctgctgtac tgcaaggcca gaagcacccc cgtgaccctg tccaaggacc  1620
agctgagcgg catcaacaac atcgccttta gcaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798

SEQ ID NO: 902         moltype = RNA  length = 1798
FEATURE                Location/Qualifiers
source                 1..1798
                       mol_type = other RNA
                       organism = synthetic construct
SEQUENCE: 902
acatttgctt ctgacacaac tgtgttcact agcaacctca aacagccacc atggagctgc  60
tgatcctgaa ggccaacgcc atcaccacca ttctgacagc cgtcaccttc tgctttgcct  120
ctggtcagaa catcaccgag gagttctacc agagcacctg cagcgccgtg agcaaggggt  180
acttgtccgc cctgcggacc ggctggtaca ccagcgtcat taccattgag ctctccaaca  240
tcaaggagaa caagtgcaat ggtactgacg ccaaggtgaa gctgatcaag caggagctgg  300
acaagtacaa gaatgccgtc acggagctgc agctgctcat gcagagcaca cccgccaccg  360
ggtccggcag cgccatctgc agcggcgtgg ccgtctgcaa ggtgctgcac ctggagggcg  420
aggtgaacaa gatcaagtct gctctgctga gcaccaacaa ggcagtggtg agcctgtcaa  480
atggggtgag cgtgttgacc ttcaaggtgc tcgacctgaa gaattacatt gacaagcagc  540
```

-continued

```
tgctgccaat tctgaacaag cagagttgca gcatctcgaa catcgagacc gtgatcgagt  600
tccagcagaa gaacaatcgg ctgctggaga tcaccaggga gttctccgtg aacgccgggg  660
tgaccacccc cgtgagcaca tacatgctga ccaatagcga gctgctgtct ctgatcaacg  720
acatgcccat caccaacgac cagaagaagc tgatgagcaa caacgtgcag atcgtgagac  780
agcagagcta cagcattatg tgcatcatca aggaggaggt cctggcttac gtggtgcagc  840
tgccgctgta cggcgtgatc gataccccctt gttggaagct gcacactagt ccactgtgca  900
caaccaacac caaggagggc agcaacatct gcctgacgag gacggaccgg ggctggtatt  960
gcgacaatgc cggctccgtg tccttcttcc ctcaggcaga gacctgcaag gtgcagtcca  1020
accgggtgtt ctgtgacacc atgaacagcc ggacgctgcc ctccgaggtg aacctgtgca  1080
atgtggacat cttcaatccc aagtacgatt gcaagatcat gaccagcaag accgatgtgt  1140
cctccagcgt gatcacctcg ctgggggcca tcgtgtcttg ctacggcaag accaagtgta  1200
cagcttccaa caagaacagg ggtatcatca agacgttcag caacggctgc gactacgtga  1260
gcaacaaggg ggtggacacc gtgagcgtgg ggaacaccct gtactgcgtg aacaagcagg  1320
aggggaagag cctgtacgtg aagggggagc ccatcatcaa cttttacgac cccctggtct  1380
tcccctccga cgagttcgac gccagtatca gccaggtgaa tgagaagatc aatcagagcc  1440
tggctttcat cagaaagtct gatgagctgc tgcacaatgt gaacgccggg aagagcacca  1500
ccaacatcat gatcacgacc atcatcatcg tgatcatcgt gatcctgctc agcctgatcg  1560
ctgtgggtct gctgctgtac tgcaaggccc gcagtacacc agtgaccctc agcaaggatc  1620
agctgagcgg gatcaacaac atcgccttct ccaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798
```

```
SEQ ID NO: 903          moltype = RNA  length = 1798
FEATURE                 Location/Qualifiers
source                  1..1798
                        mol_type = other RNA
                        organism = synthetic construct
SEQUENCE: 903
acatttgctt ctgacacaac tgtgttcact agcaacctca aacagccacc atggagttgc  60
tgatcctgaa ggctaatgcc atcaccacga ttctgacggc cgtgacattt tgcttcgcct  120
ccgggcagaa catcacggag gagttctatc agtctacttg ttctgcagtc agcaaggggt  180
acttgtccgc cctgcggacc ggctggtaca ctagcgtcat taccattgag ctctccaaca  240
tcaaggagaa caagtgcaat ggtactgacg ctaaggtgaa gctgatcaag caggagctgg  300
acaagtacaa gaacgccgtg accgagctgc agctgctgat gcagagcact cccgccaccg  360
ggagtggctc tgccatctgc agcggggtcg cggtgtgcaa ggtcctgcac cttgagggtg  420
aggtcaacaa gatcaagtct gctctgctga gcaccaacaa ggcggtggtc agcctgagca  480
acggggtctc tgtcctcacc ttcaaggtgc tggacctgaa gaactacatc gataagcagc  540
tgctgccaat tctgaacaag cagagttgca gcatcagcaa tatcgagacg gtgatcgagt  600
tccagcagaa gaacaatcgg ctgctggaga tcacccggga gttcagcgtg aacgccgggg  660
tgacaacccc ggtgtccacc tacatgctga ccaactccga gcttctgtct ctgatcaatg  720
atatgcctat caccaatgat cagaagaagc tgatgtccaa caatgtgcag atcgtgcgcc  780
agcagtccta ctccataatg tgcatcatta aggaggaggt gctggcgtac gtggtgcagc  840
ttccactgta cggggtgatc gacaccccgt gctggaagct gcacacctct cctttgtgta  900
ccaccaacac aaaggagggg tccaacatct gcctgacgag gacggaccgg ggctggtatt  960
gcgacaatgc cggctccgtg tccttcttcc ctcaggcaga gacctgcaag gtgcagagta  1020
accgggtgtt ctgtgacacc atgaacagcc ggactctgcc ctcggaggtc aatctgtgca  1080
atgtggacat cttcaacccc aagtatgact gcaagatcat gacaagtaag actgatgtga  1140
gctcctccgt gatcaccagc ctgggggcga tcgtgtcttg ctacggcaag acaaagtgca  1200
cggcctccaa caagaatcgt gggatcatta agaccttcag taatggttgt gattatgtgt  1260
ccaacaaggg ggtggacact gtcagcgttg gcaacacgct gtactgcgtg aacaagcagg  1320
agggcaagtc gctctacgtg aagggcgagc cgattattaa cttctacgat cccctggtgt  1380
tccctagcga cgagttcgac gctagcatca gccaggtgaa cgagaagatt aatcagtcgc  1440
tcgccttcat cagtaagagc gacgagctcc tgcacaatgt caacgctggc aagtccacca  1500
ccaacatcat gatcacaacc attatcatcg tgatcattgt gatcctgctc agcctgatcg  1560
ctgtgggtct gctgctgtac tgcaaggccc gcagtacacc agtgaccctc agcaaggatc  1620
agctgagcgg gatcaacaat atcgcgttca gcaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798
```

```
SEQ ID NO: 904          moltype = RNA  length = 1798
FEATURE                 Location/Qualifiers
source                  1..1798
                        mol_type = other RNA
                        organism = synthetic construct
SEQUENCE: 904
acatttgctt ctgacacaac tgtgttcact agcaacctca aacagccacc atggagttgc  60
tgatcctgaa ggcgaatgct attaccacca tcctgacagc tgtgaccttc tgttttgcct  120
ccgggcagaa catcacggag gagttctatc agtctacttg ttctgcagtc agcaaggggt  180
acctgtccgc gttgcgcacg gggtggtaca cctccgtgat cacgattgag ctctctaaca  240
tcaaggagaa taagtgtaac ggcactgacg ccaaggtcaa gctgatcaag caggagctgg  300
acaagtataa gaacgctgtg accgagttac agcttcttat gcagtccact cctgctacag  360
gcagcggctc cgctatctgt agcggagtcg ctgtctgtaa ggtcttgcac ctggagggcg  420
aggtgaacaa gatcaagtcc gccttgctct ccaccaacaa ggccgtggtc agcttgtcca  480
atggcgtcag tgtccttaca tttaaggtcc ttgatctcaa gaattacatt gataagcagc  540
tgctgcctat tctgaataag cagagctgct ctatcagtaa tattgagacg gtgatcgagt  600
tccagcagaa gaacaatcgg ctgctggaga tcaccagaga gttcagcgtg aacgcggggg  660
tgaccacccc ggtcagcacc tacatgctga ccaactctga gctgttgtcg ctcatcaacg  720
acatgccgat caccaatgat cagaagaagt tgatgagcaa caacgttcag atcgtgcgcc  780
agcagtccta ctccataatg tgcatcatta aggaggaggt gctggcgtac gtggtgcagc  840
```

-continued

```
ttccactgta cggggtgatc gacaccccgt gctggaagct gcacacctct cctttgtgta  900
ccaccaacac aaaggagggg tccaacatct gcctgacgag gacggaccgg ggctggtatt  960
gcgacaatgc cggctccgtg tccttcttcc ctcaggcaga gacctgcaag gtgcagagta  1020
accgggtgtt ctgtgacacc atgaacagcc ggactctgcc ctcggaggtc aacctgtgca  1080
acgtggacat cttcaacccc aagtatgact gcaagatcat gacaagtaag actgatgtga  1140
gctcctccgt gatcacgtca ctgggggcga tcgtgtcttg ctacggcaag accaagtgca  1200
ccgccagcaa taagaacagg gggatcatta agacatttag taatggttgt gattatgtgt  1260
ccaacaaggg ggtggacact gtcagcgttg gcaacacgct gtactgcgtg aacaagcagg  1320
agggcaagtc gctctacgtg aagggcgagc cgattattaa cttctatgac ccgctggtgt  1380
tcccgtcgga cgagttcgac gcgagcatca gccaggtcaa cgagaagatt aatcagtcgc  1440
tcgcctttat acgtaagagc gacgaactcc tgcacaatgt caacgctggc aagtccacca  1500
ccaacatcat gatcacaacc attattatcg tgatcatagt gatcctcctg tctcttattg  1560
cggtgggcct cttgctgtac tgcaaggcac ggtcgacccc agtgacgctg agcaaggacc  1620
agctgtcagg aattaataac atcgccttca gcaactgata ataggctcgc tttcttgctg  1680
tccaatttct attaaaggtt cctttgttcc ctaagtccaa ctactaaact gggggatatt  1740
atgaagggcc ttgagcatct ggattctgcc taataaaaaa catttatttt cattgcaa    1798
```

```
SEQ ID NO: 905          moltype = AA  length = 566
FEATURE                 Location/Qualifiers
source                  1..566
                        mol_type = protein
                        organism = Alphainfluenzavirus influenzae
SEQUENCE: 905
MKAILVVMLY TFTTANADTL CIGYHANNST DTVDTVLEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGARS FYKNLIWLVK KGKSYPKINQ  180
TYINDKGKEV LVLWGIHHPP TITDQESLYQ NADAYVFVGT SRYSKKFKPE IAARPKVRDR  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID KITNKVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                      566

SEQ ID NO: 906          moltype = AA  length = 566
FEATURE                 Location/Qualifiers
source                  1..566
                        mol_type = protein
                        organism = Alphainfluenzavirus influenzae
SEQUENCE: 906
MKAIIALSNI LCLVFAQKIP GNDNSTATLC LGHHAVPNGT IVKTITNDRI EVTNATELVQ  60
NSSIGKICNS PHQILDGGNC TLIDALLGDP QCDGFQNKEW DLFVERSRAN SSCYPYDVPD  120
YASLRSLVAS SGTLEFKDES FNWTGVKQNG TSSACKRGSS NSFFSRLNWL TSLNNIYPAQ  180
NVTMPNKEQF DKLYIWGVHH PDTDKNQFSL FAQSSGRITV STKRSQQAVI PNIGSRPRVR  240
DIPSRISIYW TIVKPGDILL INSTGNLIAP RGYFKIRSGK SSIMRSDAPI GECKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQISGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                      566

SEQ ID NO: 907          moltype = AA  length = 566
FEATURE                 Location/Qualifiers
source                  1..566
                        mol_type = protein
                        organism = Alphainfluenzavirus influenzae
SEQUENCE: 907
MKAIIALSNI LCLVFAQKIP GNDNSTATLC LGHHAVPNGT IVKTITNDRI EVTNATELVQ  60
NSSIGKICNS PHQILDGGNC TLIDALLGDP QCDGFQNKEW DLFVERSRAN SSCYPYDVPD  120
YASLRSLVAS SGTLEFKDES FNWTGVKQNG TSSACKRGSS NSFFSRLNWL TSLNNIYPAQ  180
NVTMPNKEQF DKLYIWGVHH PATDKNQFSL FAQSSGRITV STKRSQQAVI PNIGSRPRVR  240
DIPSRISIYW TIVKPGDILL INSTGNLIAP RGYFKIRSGK SSIMRSDAPI GECKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQISGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                      566

SEQ ID NO: 908          moltype =   length =
SEQUENCE: 908
000

SEQ ID NO: 909          moltype =   length =
SEQUENCE: 909
000

SEQ ID NO: 910          moltype =   length =
SEQUENCE: 910
000
```

-continued

```
SEQ ID NO: 911         moltype = AA  length = 188
FEATURE                Location/Qualifiers
source                 1..188
                       mol_type = protein
                       organism = unidentified
SEQUENCE: 911
MFFKCNQVFT LVFLLLLYFN NIVYTHVDDI KNTSQKKITY DKYNKNKENM NNEKNDNKDN  60
KDNIYNDNIN NDNINNDNIN NEDEYKFLSM KHYKDSLSNK LNNENDHMNY LIRKRKDNTQ  120
GSQHFNENIE NNENVENNEN IENNENNENI ENIENNENNE NNENIENNEN NENNENSSIM  180
NSESYNNI                                                           188

SEQ ID NO: 912         moltype = AA  length = 320
FEATURE                Location/Qualifiers
source                 1..320
                       mol_type = protein
                       organism = synthetic construct
SEQUENCE: 912
KNVNFLQYHF KELSNYNIAN SIDILQEKEG HLDFVIIPHY TFLDYYKHLS YNSIYHKSST  60
YGKCIAVDAF IKKINETYDK VKSKCNDIKN DLIATIKKLE HPYDINNKNM NRTFKKMMDE  120
YNTKKKKLIK CIKNHENDFN KICMDMKNYG TNLFEQLSCY NNNFCNTNGI RYHYDEYIHK  180
LILSVKSKNL NKDLSDMTNI LQQSELLLTN LNKKMGSYIY IDTIKFIHKE MKHIFNRIEY  240
HTKIINDKTK IIQDKIKLNI WRTFQKDELL KRILDMSNEY SLFITSDHLR QMLYNTFYSK  300
EKHLNNIFHH LIYVLQMKFN                                              320

SEQ ID NO: 913         moltype =   length =
SEQUENCE: 913
000

SEQ ID NO: 914         moltype = RNA  length = 1891
FEATURE                Location/Qualifiers
source                 1..1891
                       mol_type = other RNA
                       organism = synthetic construct
SEQUENCE: 914
acatttgctt ctgacacaac tgtgttcact agcaacctca aacagccacc atgaaaacta  60
tcatcgccct ctccaacata ctctgcttgg tgttcgcaca aaagatccct ggaaacgaca  120
atagcaccgc aaccctgtgt ctcggacatc acgcggtgcc gaacgggacc attgtcaaga  180
ccattaccaa tgatcgcatc gaagtgacaa acgccaccga gctggtgcag aactcgtcca  240
tcggagagat ctgcggcagc ccgcatcaga tcctggacgg cggcaactgc actctgatcg  300
atgccctcct gggtgatcct cagtgtgacg gcttccaaaa caaggagtgg gatctgttcg  360
tggagcggag ccgggccaac agcaactgtt accectacga tgtgcctgac tacgcctcac  420
ttcggtccct ggtcgcatcc tccgggacgc tggaattcaa aaacgagtcg ttcaactgga  480
cgggagtgaa acagaacggc acctccagtg cttgcatccg gggctcctcc tcatcctttt  540
tctcgcgact gaactggctt acctcgctga acaatatcta cccggcgcag aacgtcacca  600
tgcccaacaa ggagcaattt gacaagctct acatttgggg ggtgcaccac cccgacactg  660
acaagaacca gatctccctg tttgcccaaa gctcaggtcg cattactgtg tccaccaaga  720
ggtcccagca ggccgtgatc cccaaacattg gaagcagacc gagaatccgc ggcatcccat  780
cccggatctc aatctactgg actattgtga agccggggga catcctgctg atcaactcca  840
ccggaaacct gattgccccg cgcggctatt tcaagattcg cagcggaaag tcgtccatta  900
tgagatcgga cgcgcctatc gggaagtgca agagcgaatg tatcaccccc aacggatcca  960
tccccaatga caagccgttc cagaacgtga accgcatcac ttacggagct tgccctcgct  1020
acgtgaagca gtcaaccctc aaactggcca ccggcatgcg gaacgtgccc gaaaagcaga  1080
ccagaggaat tttcggggcc atcgcgggtt tcattgaaaa tggatgggag ggaatggtgg  1140
acggttggta cggattcagg caccaaaact ccgagggtcg gggccaggcc gccgacctga  1200
agtccaccca ggccgcgatt gaccagatca acggaaagct gaacaggctg attggaaaga  1260
ccaacgaaaa gttccaccaa atcgagaagg aattctcgga ggtcgaaggg agagtccagg  1320
acctcgagaa atacgtggag gacactaaga ttgatctgtg gtcttacaac gccgaactgt  1380
tggtggccct ggaaaaccag cacaccatcg atctgactga tagcgagatg aacaagctgt  1440
tcgaaaagac taagaagcag ttgcgcgaga acgccgagga catgggaaat ggttgcttca  1500
agatctatca taagtgcgac aacgcctgca tcggcagcat tcggaacgaa acctacgacc  1560
acaacgtcta ccgggatgaa gctctgaaca accggttcca gatcaaggga gtggaactca  1620
agtccggcta caaggactgg atcctttgga tctcgtttgc tatgtcctgc ttccttctct  1680
gtatcgccct gctgggcttc attatgtggg cgtgccagaa gggaaacatt aggtgcaata  1740
tctgcatctg ataataggct cgctttcttg ctgtccaatt tctattaaag gttcctttgt  1800
tccctaagtc caactactaa actgggggat attatgaagg gccttgagca tctggattct  1860
gcctaataaa aaacatttat tttcattgca a                                 1891

SEQ ID NO: 915         moltype = AA  length = 582
FEATURE                Location/Qualifiers
source                 1..582
                       mol_type = protein
                       organism = synthetic construct
SEQUENCE: 915
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCASG KSKVIKGSLP  300
```

-continued

```
LIGEADCLHE KYGGLNKSKP YYTGEHAKAI GNCPIWVKTP LKLANGTKYR PPAKLLKERG  360
FFGAIAGFLE GGWEGMIAGW HGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                     582
```